(12) United States Patent
Wang et al.

(10) Patent No.: US 12,297,197 B2
(45) Date of Patent: May 13, 2025

(54) PYRAZOLOPYRIDINE COMPOUND AS RET INHIBITOR AND APPLICATION THEREOF

(71) Applicant: GUANGZHOU BAIYUNSHAN PHARMACEUTICAL HOLDINGS CO., LTD. BAIYUNSHAN PHARMACEUTICAL GENERAL FACTORY, Guangdong (CN)

(72) Inventors: Jiansong Wang, Guangdong (CN); Zhengxia Chen, Shanghai (CN); Zhibo Luo, Guangdong (CN); Meibi Dai, Shanghai (CN); Yang Zhang, Shanghai (CN); Shuhui Chen, Shanghai (CN); Yingxia Bao, Guangdong (CN); Wei Wang, Guangdong (CN); Zhoufan Xie, Guangdong (CN)

(73) Assignee: GUANGZHOU BAIYUNSHAN PHARMACEUTICAL HOLDINGS CO., LTD. BAIYUNSHAN PHARMACEUTICAL GENERAL FACTORY, Guangdong (CN)

( * ) Notice: Subject to any disclaimer, the term of this patent is extended or adjusted under 35 U.S.C. 154(b) by 805 days.

(21) Appl. No.: 17/600,900

(22) PCT Filed: Apr. 3, 2020

(86) PCT No.: PCT/CN2020/083318
§ 371 (c)(1),
(2) Date: Oct. 1, 2021

(87) PCT Pub. No.: WO2020/200316
PCT Pub. Date: Oct. 8, 2020

(65) Prior Publication Data
US 2022/0220104 A1    Jul. 14, 2022

(30) Foreign Application Priority Data

| Apr. 3, 2019 | (CN) | 201910270289.1 |
| May 27, 2019 | (CN) | 201910449629.7 |
| May 27, 2019 | (CN) | 201910449875.2 |
| Jun. 4, 2019 | (CN) | 201910484977.8 |
| Sep. 20, 2019 | (CN) | 201910892514.5 |
| Sep. 20, 2019 | (CN) | 201910892976.7 |
| Sep. 20, 2019 | (CN) | 201910893692.X |
| Nov. 8, 2019 | (CN) | 201911086217.8 |
| Nov. 13, 2019 | (CN) | 201911105397.X |
| Nov. 13, 2019 | (CN) | 201911110201.6 |
| Jan. 9, 2020 | (CN) | 202010023277.1 |

(51) Int. Cl.
| C07D 471/04 | (2006.01) |
| A61K 31/437 | (2006.01) |
| A61P 35/00 | (2006.01) |
| C07D 491/04 | (2006.01) |
| C07D 519/00 | (2006.01) |

(52) U.S. Cl.
CPC ............ C07D 471/04 (2013.01); A61P 35/00 (2018.01); C07D 491/04 (2013.01); C07D 519/00 (2013.01)

(58) Field of Classification Search
CPC ...... C07D 471/04; A61K 31/437; A61P 35/00
See application file for complete search history.

(56) References Cited

FOREIGN PATENT DOCUMENTS

| CN | 108349969 A | 7/2018 |
| WO | 2017/011776 A1 | 1/2017 |
| WO | 2018/049127 A1 | 3/2018 |
| WO | 2018/189553 A1 | 10/2018 |

OTHER PUBLICATIONS

International Search Report issued to International Application No. PCT/CN2020/083318, with a date of mailing of Jul. 8, 2020 (in Chinese and English translation).
Written Opinion issued to International Application No. PCT/CN2020/083318, with a date of mailing of Jul. 8, 2020 (in Chinese and English translation).

*Primary Examiner* — Bruck Kifle
(74) *Attorney, Agent, or Firm* — Hoffmann & Baron, LLP

(57) ABSTRACT

Disclosed is a series of pyrazolopyridine compounds, and application thereof in the preparation of RET kinase inhibitors for treatment. Specifically disclosed is the compound represented by formula (I), or a pharmaceutically acceptable salt thereof.

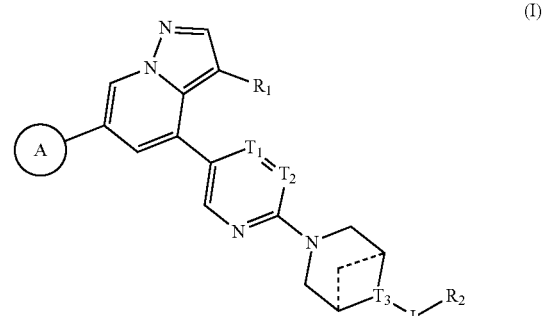

19 Claims, No Drawings

PYRAZOLOPYRIDINE COMPOUND AS RET INHIBITOR AND APPLICATION THEREOF

CROSS-REFERENCE TO RELATED APPLICATIONS

The present application is a national phase entry under 35 USC § 371 of International Application PCT/CN2020/083318, filed Apr. 3, 2020, which claims the benefits of the following priorities:
CN201910449629.7, the filing date is May 27, 2019;
CN201910892514.5, the filing date is Sep. 20, 2019;
CN201911086217.8, the filing date is Nov. 8, 2019;
CN202010023277.1, the filing date is Jan. 9, 2020;
CN201910484977.8, the filing date is Jun. 4, 2019;
CN201910892976.7, the filing date is Sep. 20, 2019;
CN201911110201.6, the filing date is Nov. 13, 2019;
CN201910270289.1, the filing date is Apr. 3, 2019;
CN201910449875.2, the filing date is May 27, 2019;
CN201910893692.X, the filing date is Sep. 20, 2019;
CN201911105397.X, the filing date is Nov. 13, 2019;
the entire disclosures of which are incorporated herein by reference.

TECHNICAL FIELD

The present disclosure relates to a series of pyrazolopyridine compounds and use thereof in the preparation of a RET kinase inhibitor for treatment. Specifically, the present disclosure relates to a compound of formula (I) or a pharmaceutically acceptable salt thereof.

BACKGROUND

A RET protein is a receptor tyrosine kinase (RTK), and is also a transmembrane glycoprotein meanwhile. The RET protein is expressed by a proto-oncogene RET (Rearranged during Transfection), and plays an important role in development of kidney and enteric nervous systems at embryo stage. In addition, the homeostasis of RET protein is crucial in a variety of tissues, such as nerve cells, neuroendocrine cells, hemopotietic tissues and male germ cells. Different from other RTK, RET does not directly bind to ligand molecules, such as GDNF family of ligands (GFLs), including neurodirectin (artemin), glial cell-derived neurotrophic factor (GDNF), neurturin and persephin. These GFLs typically bind to GDNF family receptor α (GFRα) to form GFLs-GFRα composite, which mediates self-dimerization of the RET protein, causes trans-self-phosphorylation reaction of tyrosine in an intracellular domain, recruits relevant linker proteins, and activates signaling cascade reaction such as cell proliferation. Relevant signaling pathways include MAPK, PI3K, JAK-STAT, PKA, PKC and the like.

There are two main carcinogenic activation mechanisms of RET: one mechanism is that rearrangement of chromosome generates new fusion proteins, generally including a kinase domain of RET and a fusion protein containing a self-dimerization domain, the other mechanism is that mutation of RET directly or indirectly activates the kinase activity of RET. Change in the level of these somatic cells or germ cells involves pathogenesis of multiple cancers. RET chromosome rearrangement is found in 5%-10% of patients suffering from papillary thyroid carcinoma; RET point mutation is found in 60% of patients suffering from medullary thyroid medullary carcinoma; and the RET fusions are found in 10-20% of all patients suffering from thyroid cancer, among them, CCDC6 and NCOA4 are the most common fusions. Among all patients suffering from non-small-cell lung cancer (NSCLC), the RET fusion proteins are found in about 1-2% of the patients, in which KIF5B-RET is most common.

To summarize, abnormal RET expression or activation is found in multiple tumors and gastrointestinal tract disorders such as allergic bowel syndrome. Thus, RET inhibitors have potential clinical value in tumors and gastrointestinal tract disorder diseases.

SUMMARY

The present disclosure provides a compound of formula (I) or a pharmaceutically acceptable salt thereof,

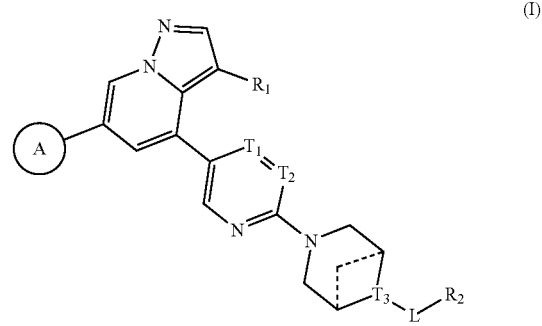

wherein:
$T_1$, $T_2$ and $T_3$ are independently selected from CH and N;
structural unit

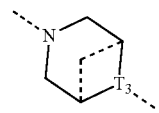

is selected from

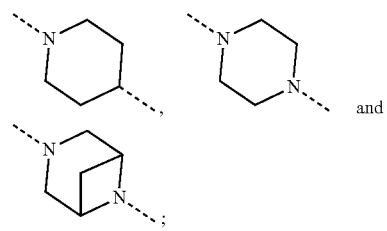

L is selected from —$CH_2$—, —C(=O)—$C_{1-3}$ alkyl-, —C(=O)— and

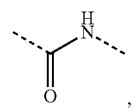

and the —$CH_2$ and —C(=O)—$C_{1-3}$ alkyl- are optionally substituted with 1 or 2 $R_a$;
$R_1$ is selected from H, F, Cl, Br, I, OH, $NH_2$ and CN;
$R_2$ is selected from $C_{1-6}$ alkyl, cyclobutyl, phenyl, pyridyl, pyrazinyl, indolyl,

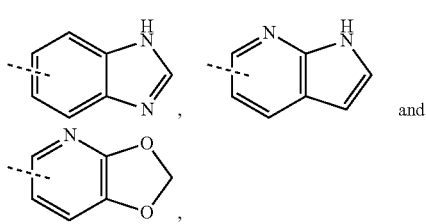

each of which is optionally substituted with 1, 2 or 3 $R_b$,

Ring A is selected from cyclopropyl, tetrahydropyrrolyl,

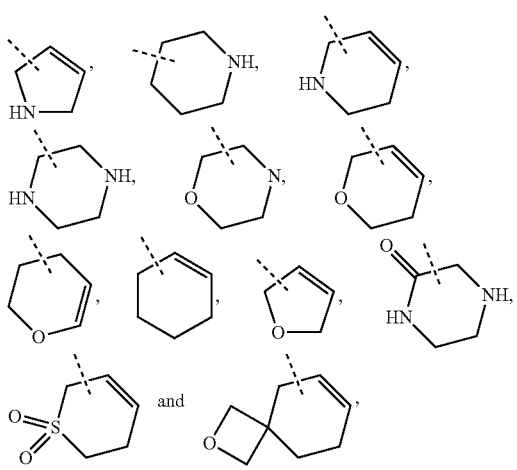

and the cyclopropyl, tetrahydropyrrolyl,

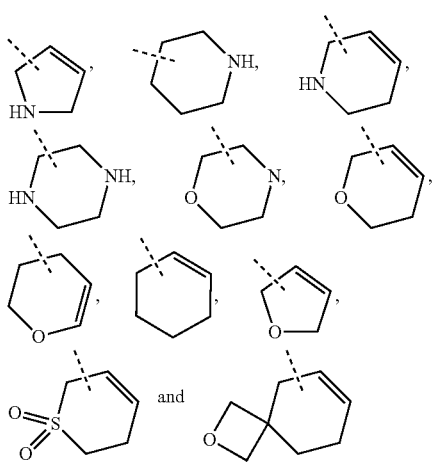

and are optionally substituted with 1, 2 or 3 $R_3$;

$R_3$ is selected from H, F, Cl, Br, I, OH, $NH_2$, CN, $C_{1-3}$ alkyl, C(=O)—$C_{1-3}$ alkyl, $C_{1-3}$ alkylamino and $C_{1-3}$ alkoxy, and the C(=O)—$C_{1-3}$ alkyl, $C_{1-3}$ alkylamino and $C_{1-3}$ alkoxy are optionally substituted with 1, 2 or 3 Rc;

$R_a$ is independently selected from H, F, Cl, Br, I, OH and $CH_3$;

$R_b$ is independently selected from H, F, Cl, Br, I, OH, $NH_2$, CN, $C_{1-3}$ alkyl and $C_{1-3}$ alkoxy, and the $C_{1-3}$ alkyl and $C_{1-3}$ alkoxy are optionally substituted with 1, 2 or 3 R;

$R_c$ is independently selected from H, F, Cl, Br, I, OH and $CH_3$; and

R is independently selected from H, F, Cl, Br and I.

In some embodiments of the present disclosure, the structural unit

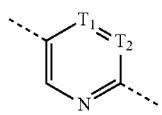

is selected from

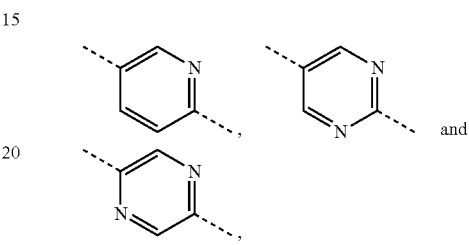

and other variables are as defined herein.

In some embodiments of the present disclosure, $R_1$ is CN, and other variables are as defined herein.

In some embodiments of the present disclosure, L is selected from —$CH_2$—,

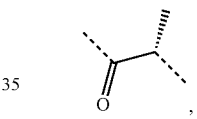

—C(=O)— and

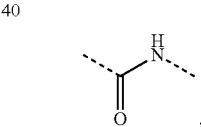

the —$CH_2$— and

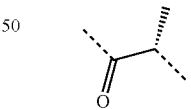

are optionally substituted with 1, 2 or 3 $R_a$, and other variables are as defined herein.

In some embodiments of the present disclosure, L is selected from —$CH_2$—, —C(=O)— and

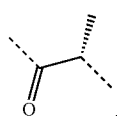

and other variables are as defined herein.

In some embodiments of the present disclosure, $R_b$ is independently selected from H, F, Cl, Br, I, OH, $NH_2$, CN, $CH_3$, and $C_{1-3}$ alkoxy, the $CH_3$ and $C_{1-3}$ alkoxy are optionally substituted with 1, 2 or 3 R, and other variables are as defined herein.

In some embodiments of the present disclosure, $R_b$ is independently selected from H, F, Cl, Br, OH, $NH_2$, $CH_3$, $CHF_2$, $CF_3$, $OCH_3$

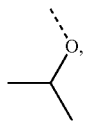

and other variables are as defined herein.

In some embodiments of the present disclosure, the $R_2$ is selected from $C_{1-3}$ alkyl,

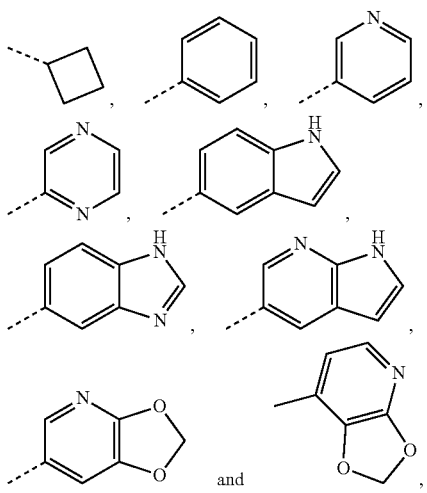

each of which is optionally substituted by 1, 2 or 3 $R_b$, and other variables are as defined herein.

In some embodiments of the present disclosure, $R_2$ is selected from

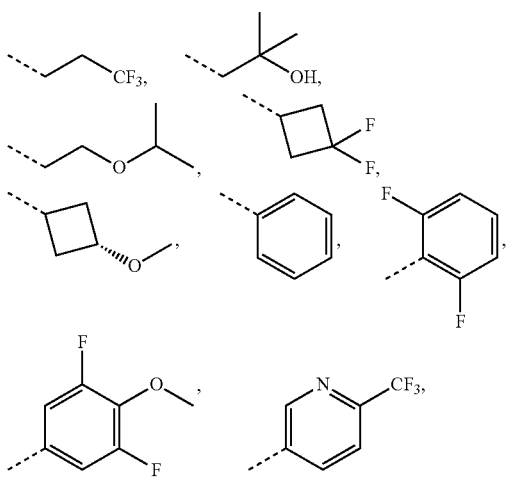

-continued

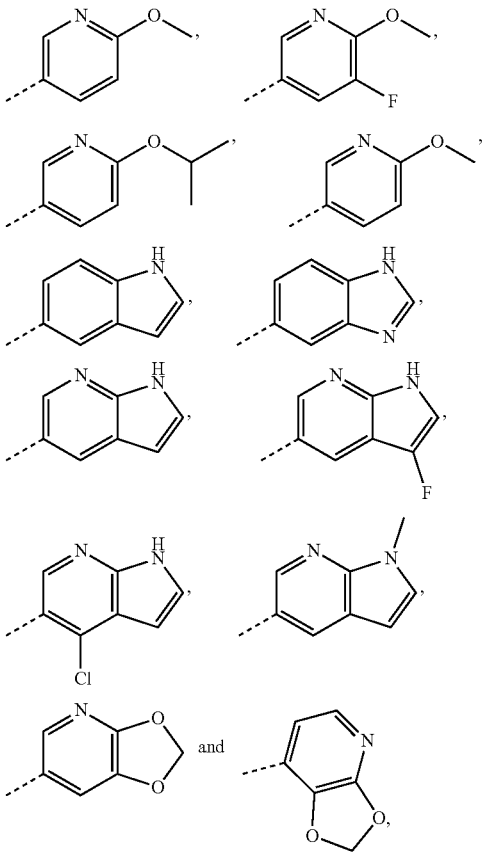

and other variables areas defined herein.

In some embodiments of the present disclosure, the structural unit

is selected from

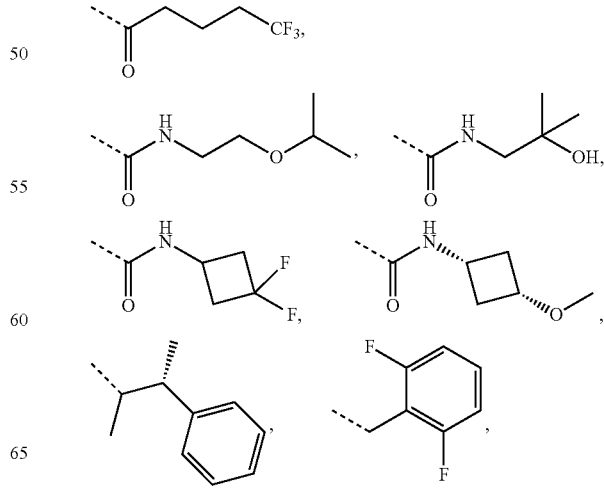

-continued

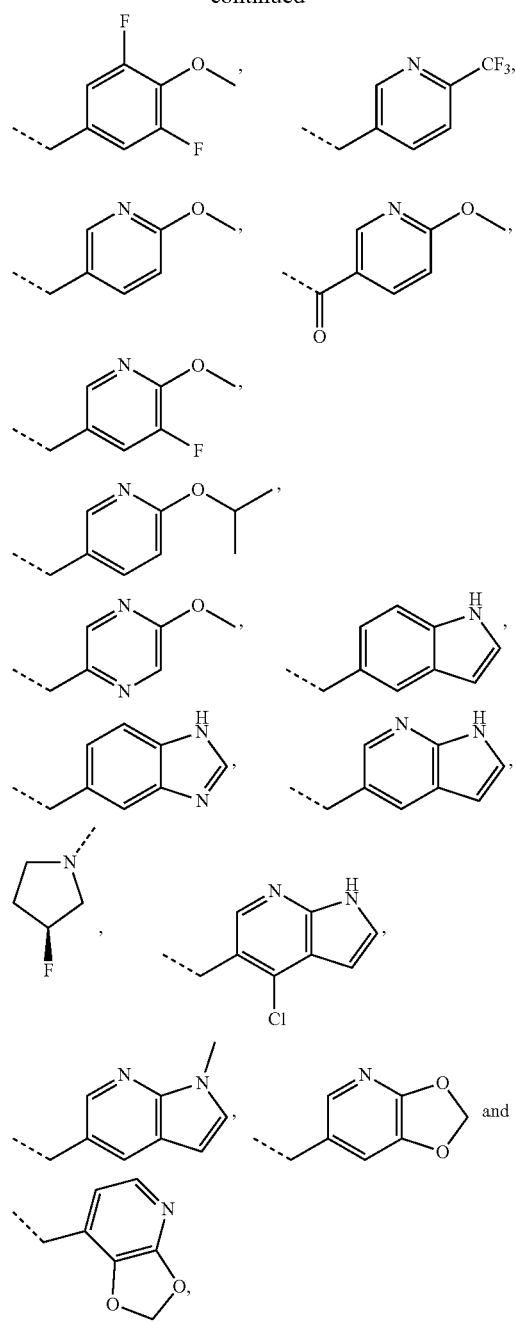

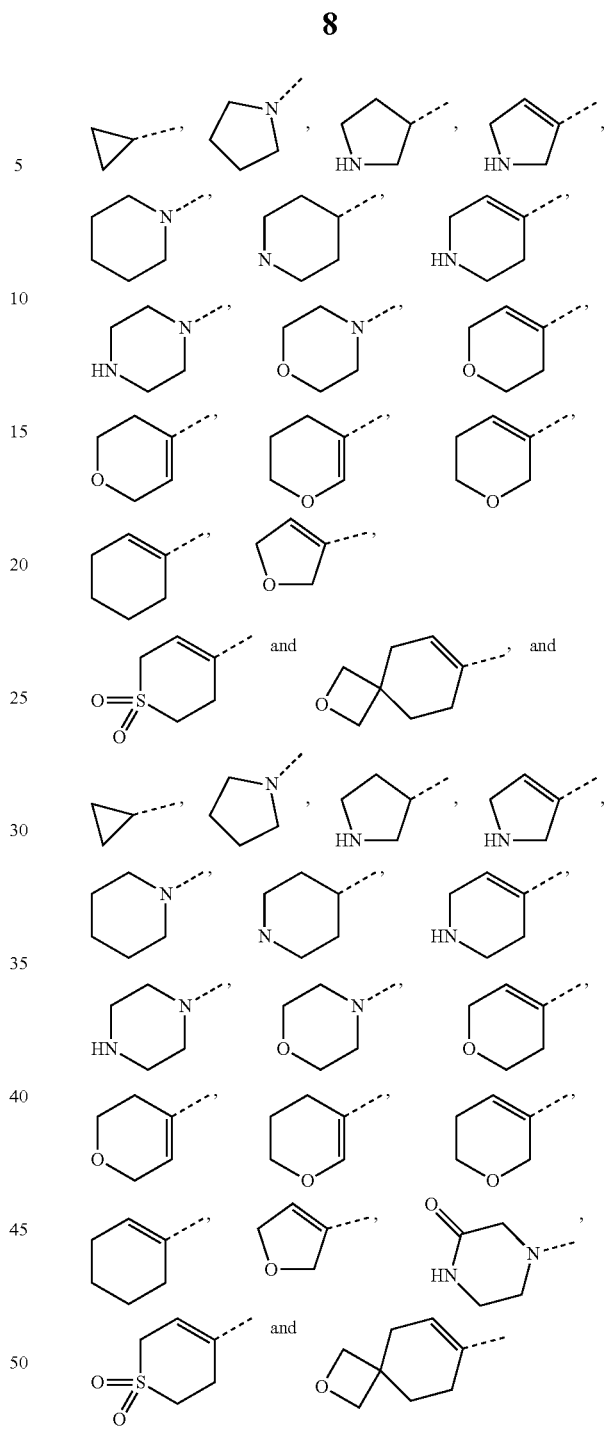

and other variables are as defined herein.

In some embodiments of the present disclosure, $R_3$ is selected from H, F, Cl, Br, I, OH, $NH_2$, CN, $CH_3$, $CH_2CH_3$, $CH(CH_3)$, $C(=O)CH_3$, $N(CH_3)_2$ and $OCH_3$, the $CH_3$, $CH_2CH\ CH(CH_3)_2$, $C(=O)CH_3$, $N(CH_3)_2$ and $OCH_3$ are optionally substituted with 1, 2 or 3 $R_c$, and other variables are as defined herein.

In some embodiments of the present disclosure, $R_3$ is selected from H, F, Cl, Br, I, OH, $NH_2$, $CH_3$, $CHF_2$, $CF_3$, $CH_2CH_3$, $C(=O)CH_3$, $N(CH_3)_2$, $OCH_3$ and $OCF_3$, and other variables are as defined herein.

In some embodiments of the present disclosure, ring A is selected from are optionally substituted with 1, 2 or 3 $R_3$, and other variables are as defined herein.

In some embodiments of the resent disclosure, the ring A is selected from

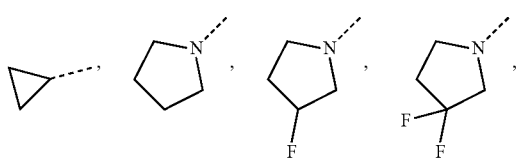

-continued
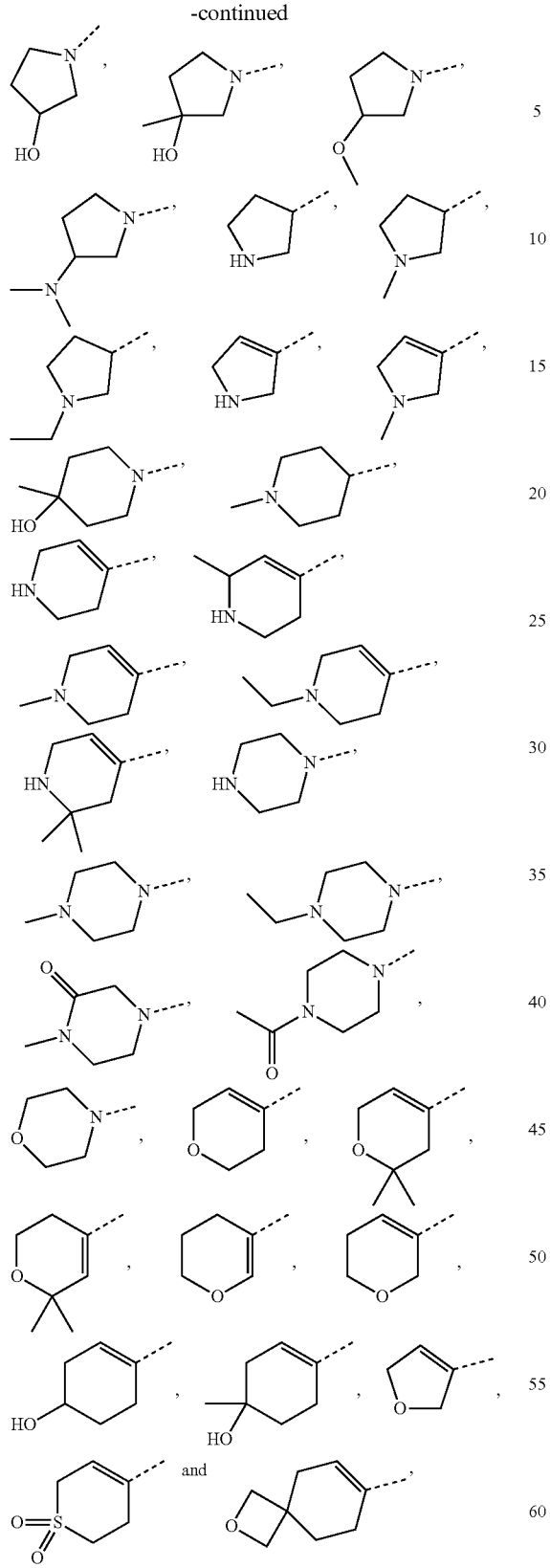
and other variables are as defined herein.
In some embodiments of the present disclosure, the ring A is selected from
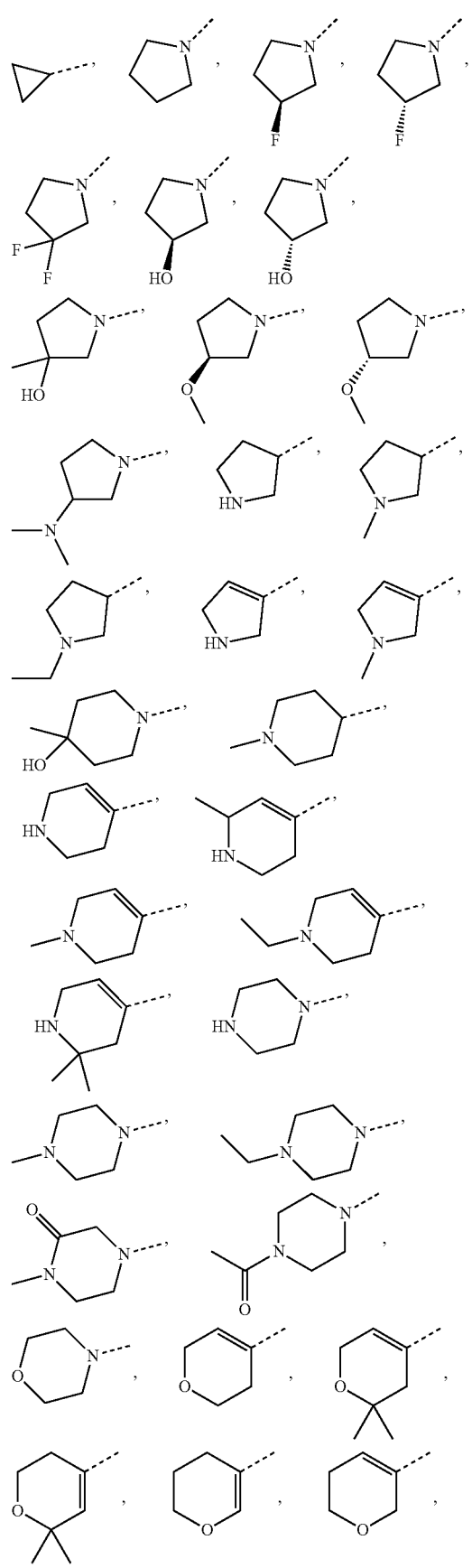

-continued
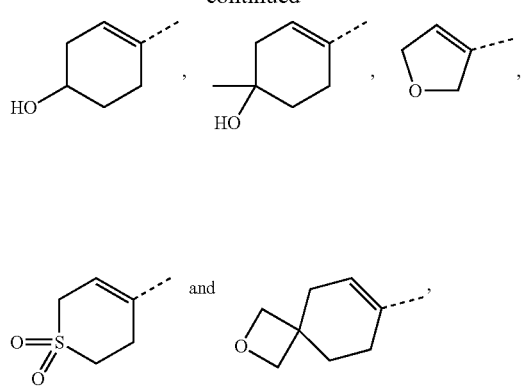
and other variables are as defined herein.
In some embodiments of the present disclosure, the compound or a pharmaceutically acceptable salt thereof is selected from
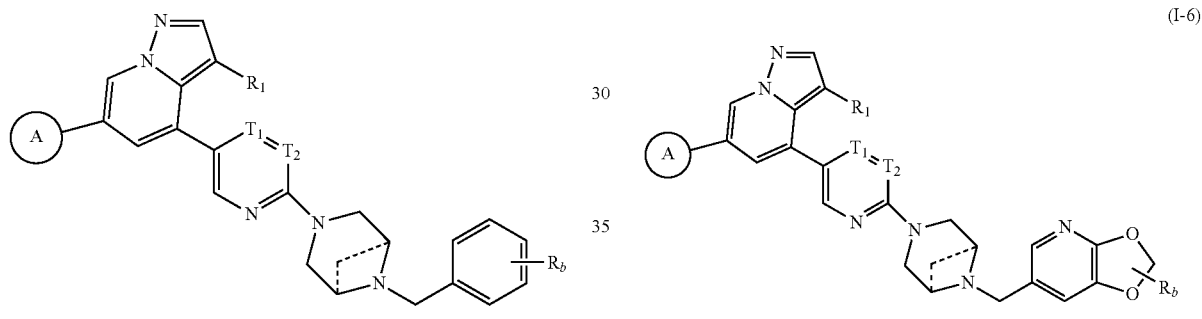
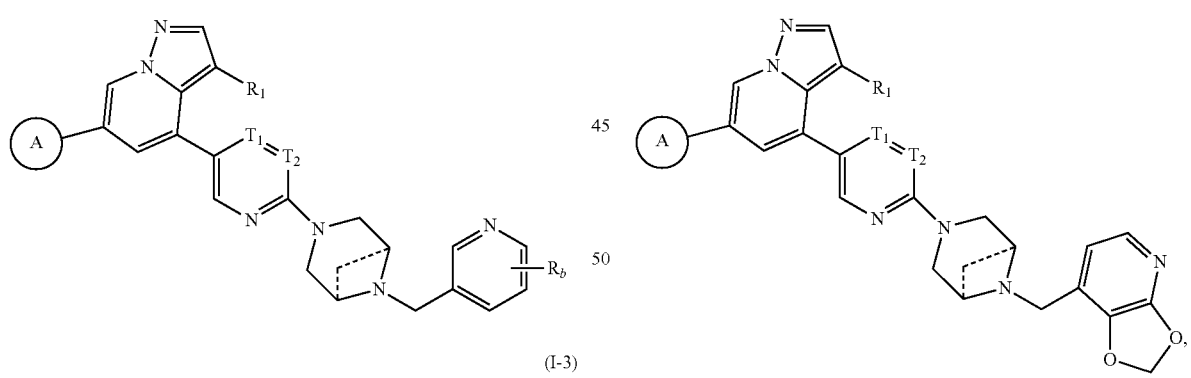
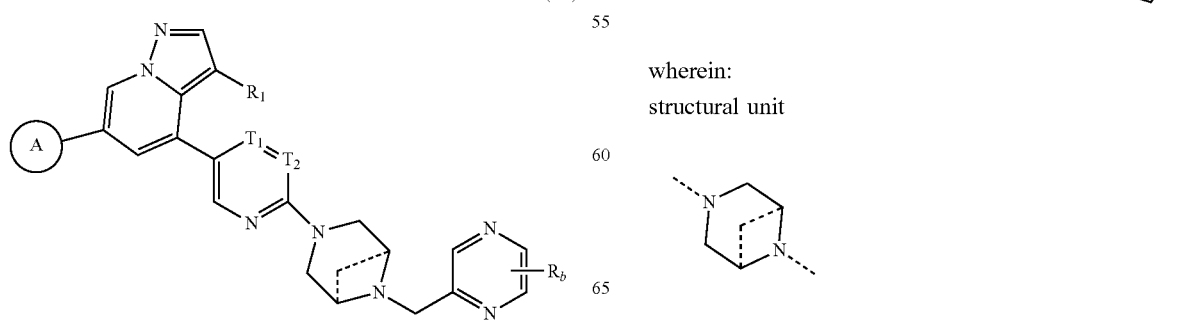
wherein:
structural unit
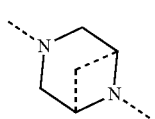
is selected from

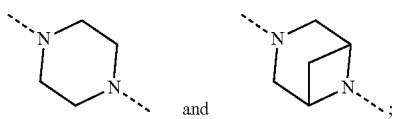 and 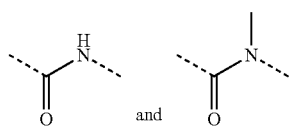

$T_1$, as defined herein.

The present disclosure also provides an embodiment A.

Embodiment A provides a compound of formula (III), an isomer or a pharmaceutically acceptable salt thereof.

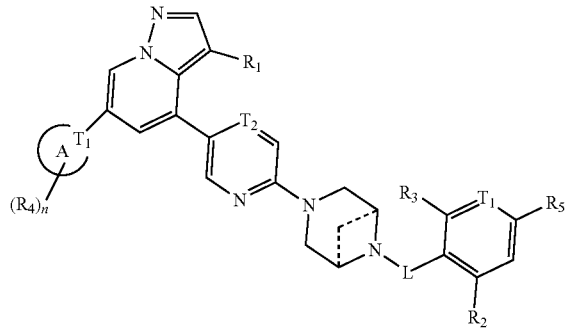
(III)

wherein:

$R_1$ is selected from H, F, Cl, Br, I, OH, $NH_2$ and CN;

$R_2$ is selected from H, F, Cl, Br, I, OH, $NH_2$ and CN;

$R_3$ is selected from H, F, Cl, Br, I, OH, $NH_2$ and CN;

$R_4$ is selected from H, F, Cl, Br, I, OH, $NH_2$, CN, $C_{1-6}$ alkyl and $C_{1-6}$ alkoxy, and the $C_{1-6}$ alkyl or $C_{1-6}$ alkoxy is optionally substituted with 1, 2 or 3 $R_a$;

structural unit

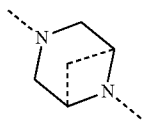

is selected from

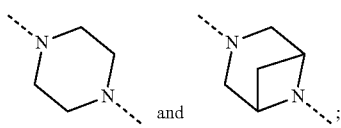

n is selected from 0, 1, 2 and 3;

L is selected from $C_{1-3}$ alkyl,

—C(=O)—$C_{1-3}$ alkyl-, $T_1$ is selected from N and $C(R_5)$;

$T_2$ is selected from N and CH;

$R_5$ is independently selected from H, $C_{1-3}$ alkoxy and $C_{1-3}$ alkyl, and the $C_{1-3}$ alkoxy and $C_{1-3}$ alkyl are optionally substituted with 1, 2 or 3 $R_c$;

ring A is selected from $C_{3-8}$ cycloalkyl and 3-8 membered heterocycloalkyl, and ring A is not pyrrolidinyl when $T_1$ is N;

$R_a$ is independently selected from H, F, Cl, Br, I, OH, $NH_2$ and CN;

$R_b$ is independently selected from H, F, CA. Br, I, OH, $NH_2$, CN and $CH_3$;

$R_c$ is independently selected from H, F, Cl, Br, I, OH, $NH_2$, CN and $CH_3$;

"hetero" in the 3-8 membered heterocycloalkyl is independently selected from: N, O, S and NH; and the number of the heteroatoms or heteroatom groups is independently selected from 1, 2, 3, and 4.

Embodiment A provides a compound of formula (II), an isomer or a pharmaceutically acceptable salt thereof,

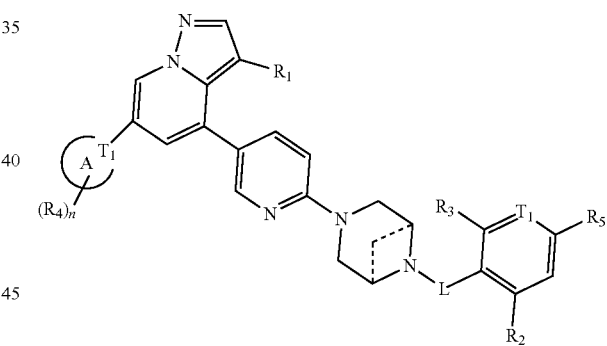
(II)

wherein:

$R_1$ is selected from H, F, Cl, Br, I, OH, $NH_2$ and CN;

$R_2$ is selected from H, F, Cl, Br, I, OH, $NH_2$ and CN;

$R_3$ is selected from H, F, Cl, Br, I, OH, $NH_2$ and CN;

$R_4$ is selected from H, F, Cl, Br, I, OH, $NH_2$, CN, $C_{1-6}$ alkyl and $C_{1-6}$ alkoxy, and the $C_{1-6}$ alkyl or $C_{1-6}$ alkoxy is optionally substituted with 1, 2 or 3 $R_a$;

structural unit

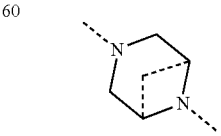

is selected from

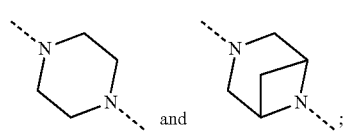

n is selected from 0, 1, 2 and 3;
L is selected from C$_{1-3}$ alkyl,

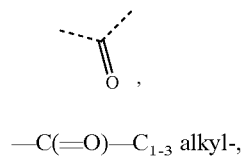

—C(=O)—C$_{1-3}$ alkyl-,

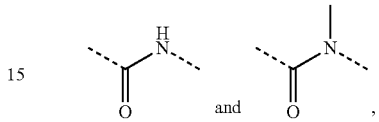

each of which is optionally substituted with 1, 2 or 3 R$_b$;
T$_1$ is selected from N and C(R$_5$);
R$_5$ is selected from H and —O—CH$_3$ alkyl;
ring A is selected from C$_{3-8}$ cycloalkyl and 3-8 membered heterocycloalkyl, and ring A is not pyrrolidinyl when T$_1$ is N;
R$_a$ is independently selected from H, F, Cl, Br, I, OH, NH$_2$ and CN;
R$_b$ is independently selected from H, F, Cl, Br, I, OH, NH$_2$, CN and CH$_3$;
R$_c$ is independently selected from H, F, Cl, Br, I, OH, NH$_2$, CN and CH$_3$;
"hetero" in the 3-8 membered heterocycloalkyl is independently selected from: N, O, S and NH; and
the number of the heteroatoms or heteroatom groups is independently selected from 1, 2, 3, and 4.

Embodiment A provides a compound of formula (I), an isomer or a pharmaceutically acceptable salt thereof,

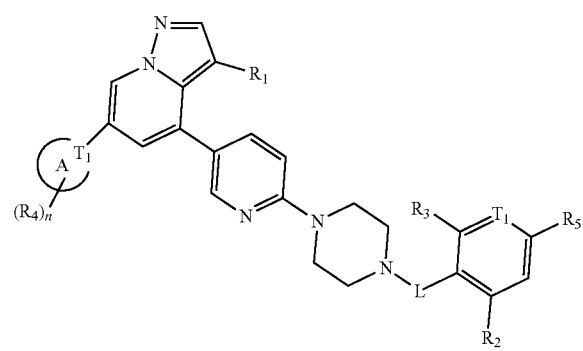

(I)

wherein:
R$_1$ is selected from H, F, Cl, Br, I, OH, NH$_2$ and CN;
R$_2$ is selected from H, F, Cl, Br, I, OH, NH$_2$ and CN;
R$_3$ is selected from H, F, Cl, Br, I, OH, NH$_2$ and CN;
R$_4$ is selected from H, F, Cl, Br, I, OH, NH$_2$, CN, C$_{1-6}$ alkyl and C$_{1-6}$ alkoxy, and the C$_{1-6}$ alkyl or C$_{1-6}$ alkoxy is optionally substituted with 1, 2 or 3 R$_a$;

n is selected from 0, 1, 2 and 3;
L is selected from C$_{1-3}$ alkyl,

—C(=O)—C$_{1-3}$ alkyl-m

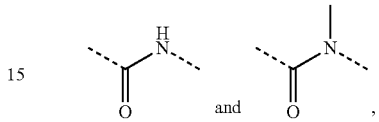

each of which is optionally substituted with 1, 2 or 3 R$_b$,
T$_1$ is selected from N and C(R$_5$);
R$_5$ is selected from H and —O—CH$_3$ alkyl;
ring A is selected from C$_{3-8}$ cycloalkyl and 3-8 membered heterocycloalkyl, and ring A is not pyrrolidinyl when T$_1$ is N;
R$_a$ is independently selected from H, F, Cl, Br, I, OH, NH$_2$ and CN;
R$_b$ is independently selected from H, F, Cl, Br, I, OH, NH$_2$, CN and CH$_3$;
R$_c$ is independently selected from H, F, Cl, Br, I, OH, NH$_2$, CN and CH$_3$;
"hetero" of the 3-8 membered heterocycloalkyl is independently selected from: N, O, S and NH; and
the number of the heteroatoms or heteroatom groups is independently selected from 1, 2, 3, and 4.

In some embodiments of the present disclosure, R$_1$ is CN, and other variables are as defined herein.

In some embodiments of the present disclosure, R$_2$ is selected from H and F, and other variables are as defined herein.

In some embodiments of the present disclosure, R$_2$ is F, and other variables are as defined herein.

In some embodiments of the present disclosure, R$_3$ is selected from H and F, and other variables are as defined herein.

In some embodiments of the present disclosure, R$_3$ is F, and other variables are as defined herein.

In some embodiments of the present disclosure, R$_4$ is selected from H, F, Cl, Br, I, OH, NH$_2$, CN and C$_{1-3}$ alkyl, the C$_{1-3}$ alkyl is optionally substituted with 1, 2 or 3 R$_a$, and other variables are as defined herein.

In some embodiments of the present disclosure, R$_4$ is selected from H, F, Cl, Br, I, OH, NH$_2$, CN, CH$_3$, CHF$_2$, CH$_2$F, CF$_3$, CH$_2$CH$_3$, CH$_2$CHF$_2$, CH$_2$CH$_2$F, CH$_2$CF$_3$ and

and other variables are as defined herein.

In some embodiments of the present disclosure, R$_4$ is selected from H, CH and CH$_2$CH$_3$ and other variables are as defined herein.

In some embodiments of the present disclosure, the structural unit

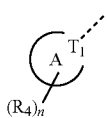

is selected from

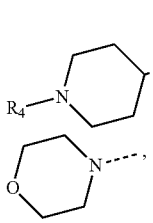 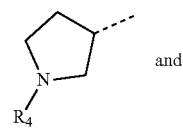 and

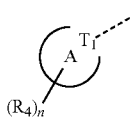

and other variables are as defined herein.

In some embodiments of the present disclosure, the structural unit

is selected from

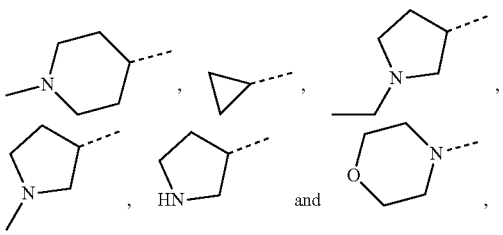 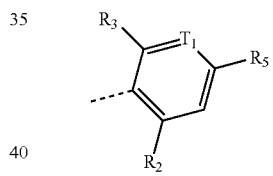

and other variables are as defined herein.

In some embodiments of the present disclosure, L is selected from —CH$_2$—, —CF$_2$—, —CHF—, —CH(CH$_3$)—, —CH(CH$_2$F)—, —CH(CHF$_2$)— and —CH(CF$_3$)—.

In some embodiments of the present disclosure, L is selected from —CH$_2$—, and other variables are as defined herein.

In some embodiments of the present disclosure, L is selected from —CH$_2$—, —CF$_2$—, —CHF—, —CH(CH$_3$)—, —CH(CH$_2$F)—, —CH(CHF$_2$)—, —CH(CF$_3$)—,

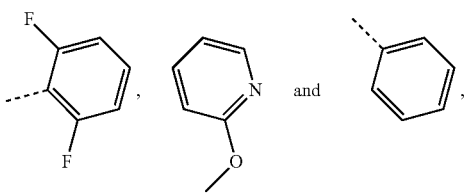

and other variables are as defined herein.

In some embodiments of the present disclosure, L is selected from —CH$_2$— and

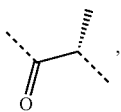

and other variables are as defined herein.

In some embodiments of the present disclosure, R$_5$ is selected from H and C$_{1-3}$ alkyl, the C$_{1-3}$ alkyl is optionally substituted with 1, 2 or 3 R$_C$, and other variables are as defined herein.

In some embodiments of the present disclosure, R$_5$ is selected from H, CH$_3$, CH$_2$F, CHF$_2$, CF$_3$, CH$_2$CH$_3$, CH$_2$CH$_2$F, CH$_2$CHF$_2$, CH$_2$CF$_3$ and

and other variables are as defined herein.

In some embodiments of the present disclosure, R$_5$ is H, and other variables are as defined herein.

In some embodiments of the present disclosure, R$_5$ is selected from H and —OCH$_3$, and other variables are as defined herein.

In some embodiments of the present disclosure, structural unit

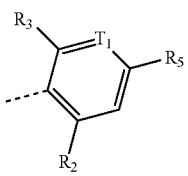

is selected from

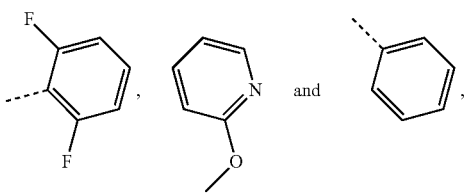

and other variables are as defined herein.

In some embodiments of the present disclosure, structural unit

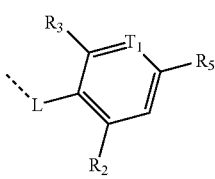

selected from

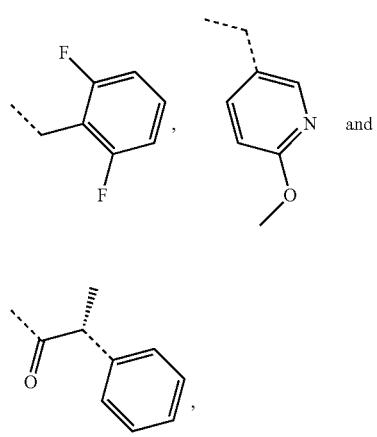
and other variables are as defined herein.
In some embodiments of the present disclosure, a compound or a pharmaceutically acceptable salt thereof is selected from
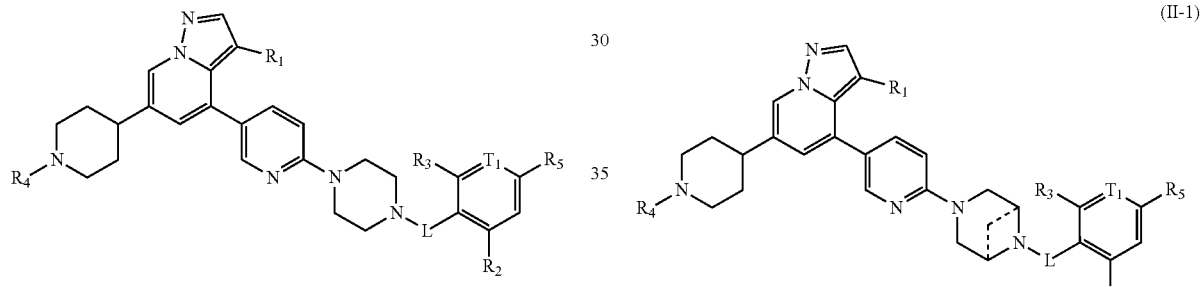
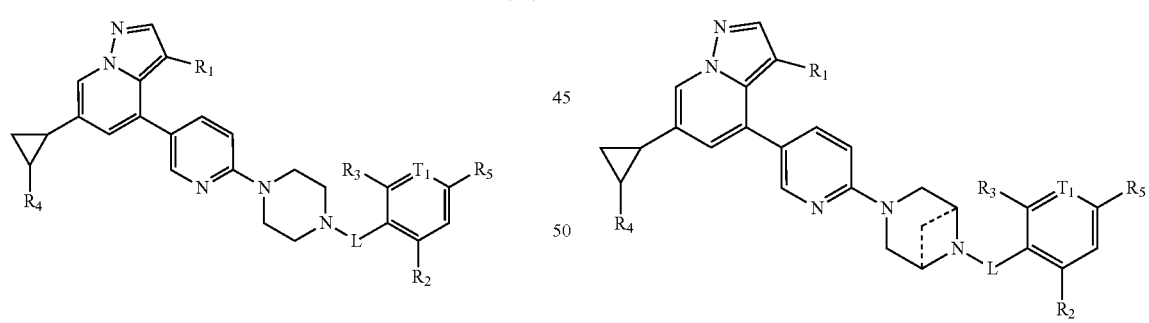
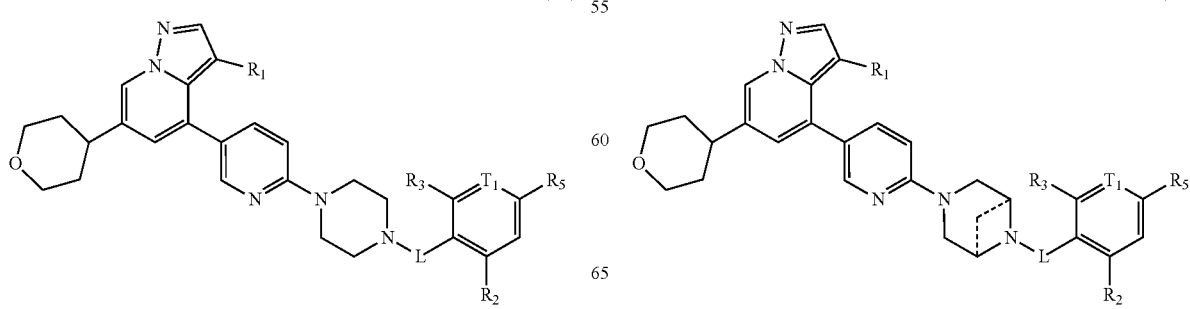
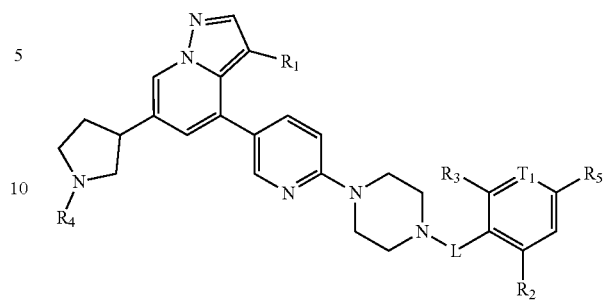
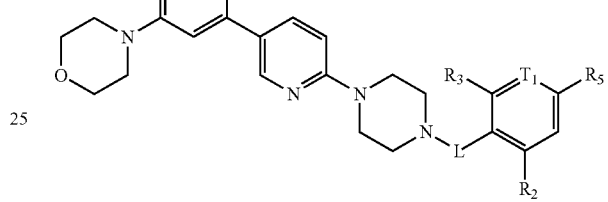

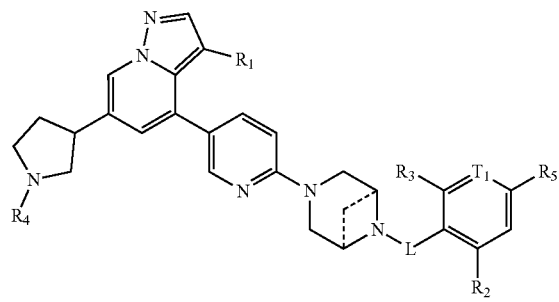
(II-4)

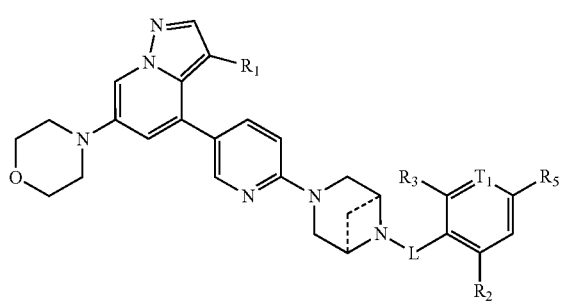
(II-5)

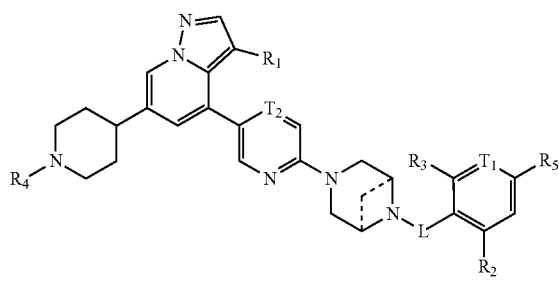
(III-1)

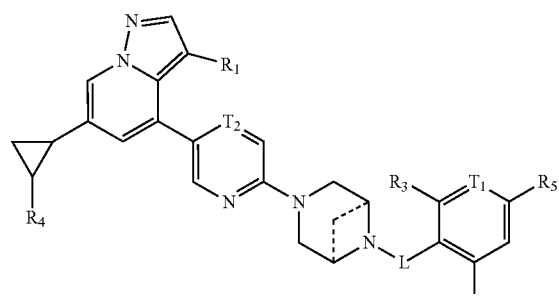
(III-2)

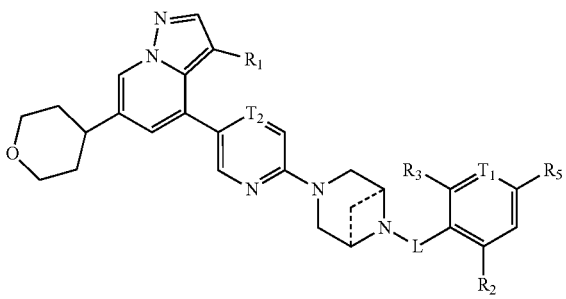
(III-3)

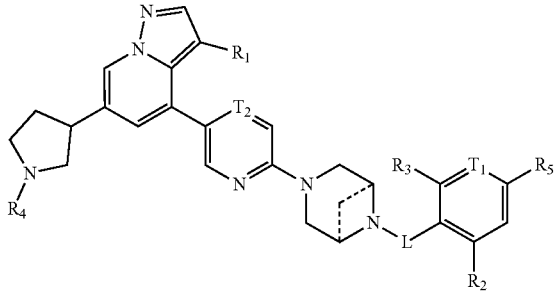
(III-4)

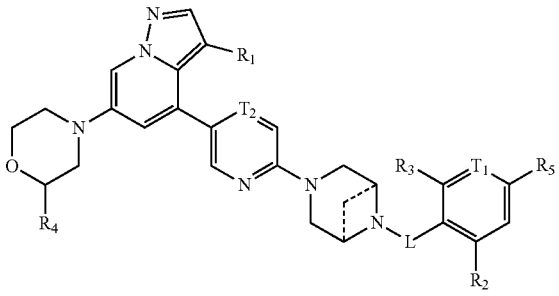
(III-5)

wherein, $R_1$, $R_2$, $R_3$, $R_5$, $T_1$, $T_2$, L and

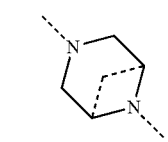

are as defined herein.

The present disclosure also provides an embodiment B.

Embodiment B provides a compound of formula (VI), an isomer or a pharmaceutically acceptable salt thereof,

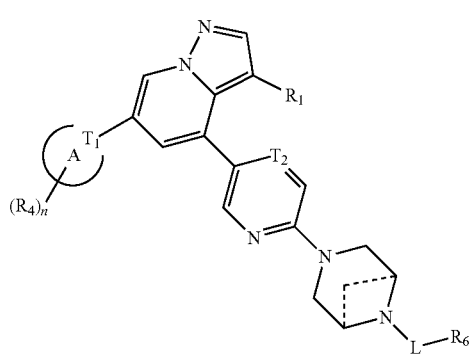
(VI)

wherein:
$R_1$ is selected from H, F, Cl, Br, I, ON, $NH_2$ and CN;
$R_4$ is independently selected from H, F, Cl, Br, I, OH, $NH_2$, CN, $C_{1-6}$ alkyl and $C_{1-6}$ alkoxy, and the $C_{1-6}$ alkyl or $C_{1-6}$ alkoxy is optionally substituted with 1, 2 or 3 $R_a$;
$R_6$ is selected from 5-10 membered heteroaryl and 1,3-dioxolo[4,5-B]pyridyl, each of which is optionally substituted with 1, 2 or 3 $R_d$;

structural unit

[structure]

is selected from

[structures] and [structure];

n is selected from 0, 1, 2 and 3;
L is selected from C$_{1-3}$ alkyl,

[structure],

C(=O)—C$_{1-3}$ alkyl-,

[structures] and [structure], and C$_{1-3}$ alkyl, —C(=O)—C$_{1-3}$ alkyl-,

[structures] and [structure], are optionally substituted with 1, 2 or 3 R$_b$;
T$_1$ is selected from N and CH;
T$_2$ is selected from N and CH;
ring A is selected from C$_{3-8}$ cycloalkyl and 3-8 membered heterocycloalkyl, and ring A is not pyrrolidinyl when T$_1$ is N;
R$_a$ is independently selected from H, F, Cl, Br, I, OH, NH$_2$ and CN;
R$_b$ is independently selected from H, F, Cl, Br, I, OH, NH$_2$, CN and CH$_3$;
R$_d$ is independently selected from H, F, Cl, Br, I, OH, NH$_2$, CN, C$_{1-3}$ alkyl and C$_{1-3}$ alkoxy;
the 3-8 membered heterocycloalkyl and 5-10 membered heteroaryl comprise 1, 2 or 3 heteroatoms or heteroatom groups independently selected from —O—, —NH—, —S— and N.

In some embodiments of the present disclosure, R$_4$ is independently selected from H, F, Cl, Br, I, OH, NH$_2$, CN, and C$_{1-3}$ alkyl, the C$_{1-3}$ alkyl is optionally substituted with 1, 2, or 3 R$_a$, and other variables are as defined herein.

In some embodiments of the present disclosure, R$_4$ is independently selected from H, F, Cl, Br, I, OH, NH$_2$, CN, CH$_3$, CHF$_2$, CH$_2$F, CF$_3$, CH$_2$CH$_3$, CH$_2$CHF$_2$, CH$_2$CH$_2$F, CH$_2$CF$_3$ and

[structure], and other variables are as defined herein.

In some embodiments of the present disclosure, R$_4$ is selected from H, CH$_3$ and CH$_2$CH$_3$, and other variables are as defined herein.

In some embodiments of the present disclosure, structural unit

[structure]

is selected from

[structures]

and other variables are as defined herein.

In some embodiments of the present disclosure, structural unit

[structure]

is selected from

[structures]

and other variables are as defined herein.

In some embodiments of the present disclosure, L is selected from —CH₂—, —CF₂—, —CHF—, —CH(CH₃)—, —CH(CH₂F)—, —CH(CHF₂)—, —CH(CF₃),

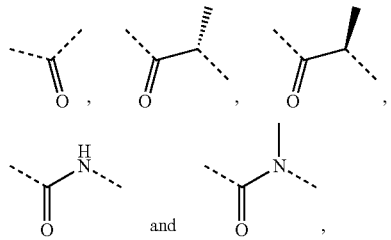

and other variables are as defined herein.

In some embodiments of the present disclosure, L is selected from —CH₂— and

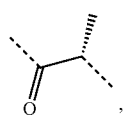

and other variables are as defined herein.

In some embodiments of the present disclosure, $R_d$ is selected from H, F, CH₃,

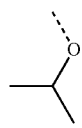

and —OCH₃, and other variables are as defined herein.

In some embodiments of the present disclosure, $R_6$ is selected from phenyl, pyridyl, pyrazinyl, pyridazinyl, 1H-pyrrole-[2,3-b]pyridyl and 1,3-dioxolo[4,5-B]pyridyl, the phenyl, pyridyl, pyrazinyl, pyridazinyl, 1H-pyrrole-[2, 3-b]pyridyl and 1,3-dioxo[4,5-B]pyridyl are optionally substituted with 1, 2 or 3 $R_d$, and other variables are as defined herein.

In some embodiments of the present disclosure, $R_6$ is selected from

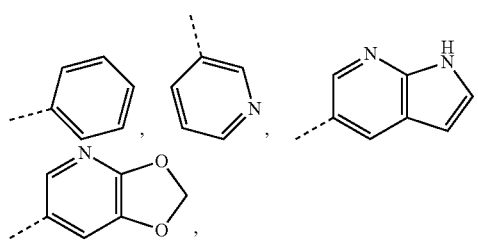

each of which is optionally substituted with 1, 2 or 3 $R_d$, and other variables are as defined herein.

In some embodiments of the present disclosure, $R_6$ is selected from

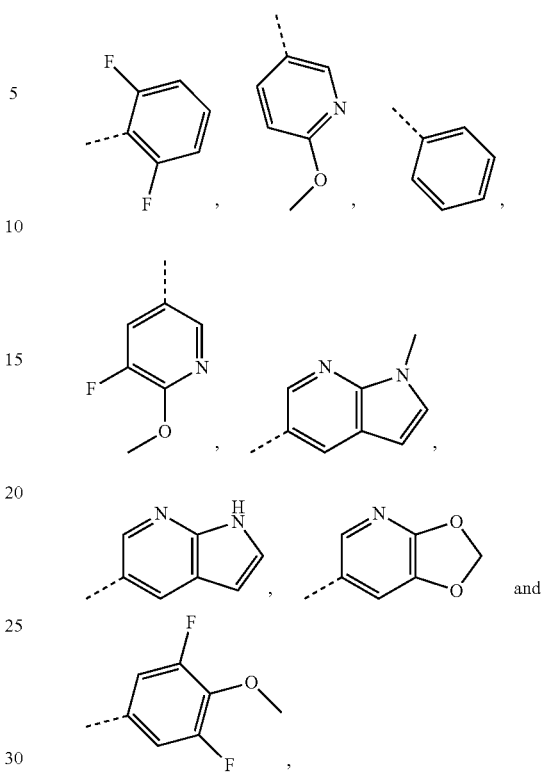

and other variables are as defined herein.

In some embodiments of the present disclosure, the structural unit

is selected from

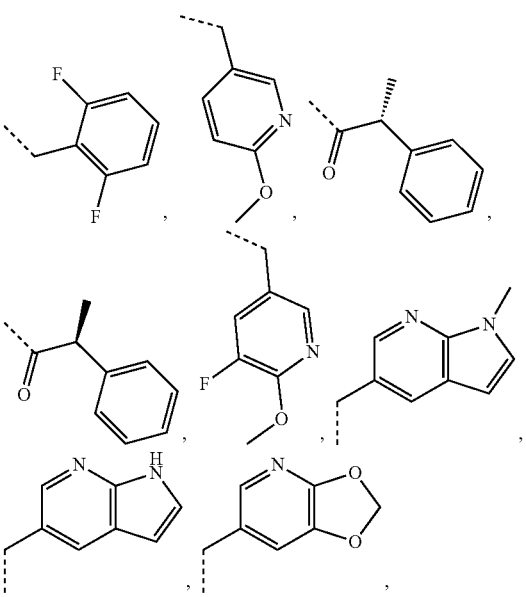

-continued

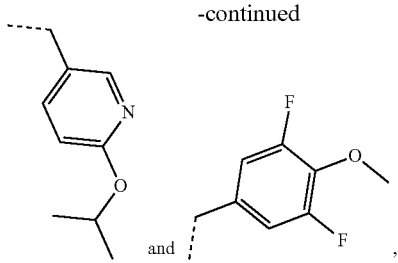

and other variables are as defined herein.

In some embodiments of the present disclosure, a compound, an isomer or a pharmaceutically acceptable salt thereof is selected from (VI-1)

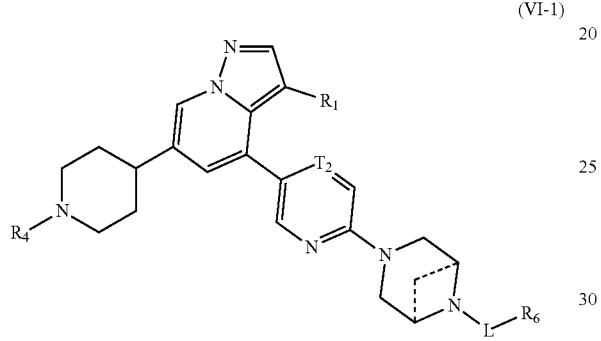

(VI-2)

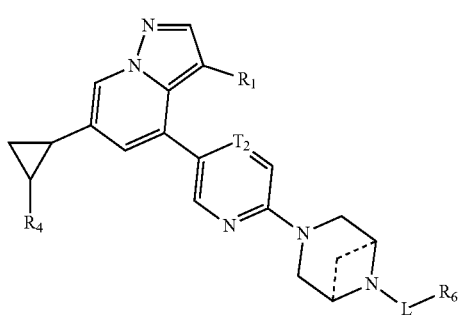

(VI-3)

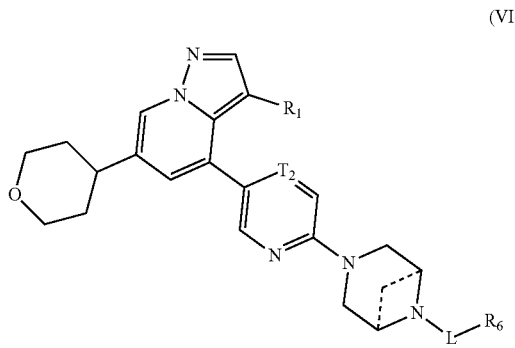

(VI-4)

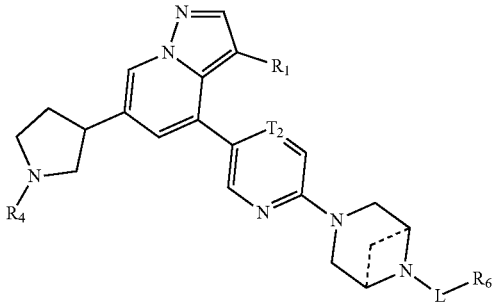

(VI-5)

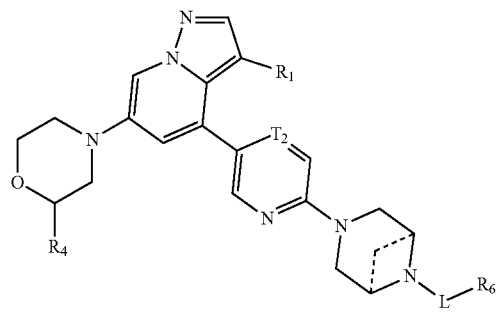

(VI-6)

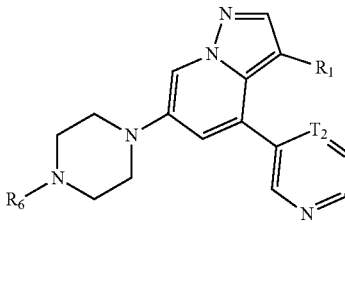

wherein, $R_1$, $R_6$, $T_2$, L and

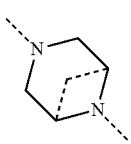

are as defined herein.

The present disclosure also provides an embodiment C.

Embodiment C provides a compound of formula (VII), an isomer or a pharmaceutically acceptable salt thereof, (VII)

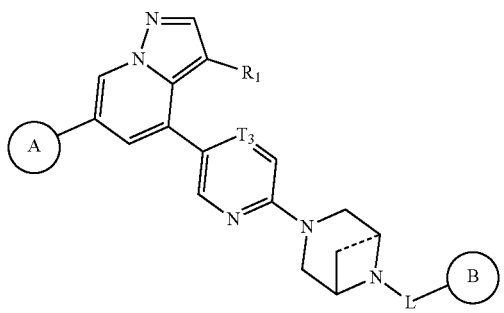

wherein
ring A is selected from

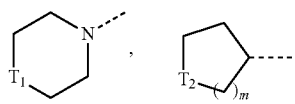

and cyclopropyl, each of which is optionally substituted with 1, 2 or 3 $R_2$;

$T_1$ is selected from NH, $CH_2$ and O;
$T_2$ is selected from NH and $CH_2$;
$T_3$ is selected from N and CH;
m is selected from 0, 1 and 2;
structural unit

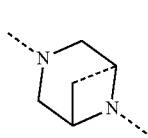

is selected from

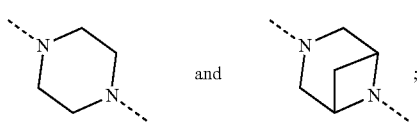

L is selected from $C_{1-3}$ alkyl,

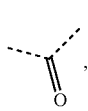

—C(=O)—$C_{1-3}$ alkyl-,

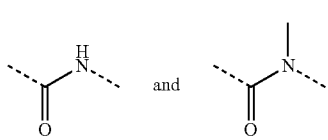

$C_{1-3}$ alkyl, —C(=O)—$C_{1-3}$ alkyl-,

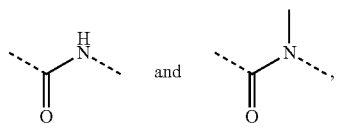

are optionally substituted with 1 $R_a$;
ring B is selected from phenyl, pyridyl, pyrazinyl, pyridazinyl, 1H-pyrrole-[2,3-b]pyridyl and 1,3-dioxolo[4,5-b]pyridyl, and each of which is optionally substituted with 1, 2 or 3 $R_b$;
$R_1$ is selected from H, F, Cl, Br, I, OH, $NH_2$ and CN;
$R_2$ is independently selected from H, F, Cl, Br, I, OH, $NH_2$, CN, $C_{1-6}$ alkyl and $C_{1-6}$ alkoxy, and the $C_{1-6}$ alkyl or $C_{1-6}$ alkoxy is optionally substituted with 1, 2 or 3 $R_c$;
$R_a$ is independently selected from H, F, Cl, Br, I, OH, $NH_2$, CN and $CH_3$;
$R_b$ is independently selected from H, F, Cl, Br, I, OH, $NH_2$, CN, $C_{1-3}$ alkyl and $C_{1-3}$ alkoxy; and
$R_c$ is independently selected from H, F, Cl, Br, I, OH, $NH_2$ and CN.

In some embodiments of the present disclosure, $R_2$ is independently selected from H, F, Cl, Br, I, OH, $NH_2$, CN, and $C_{1-3}$ alkyl, the $C_{1-3}$ alkyl is optionally substituted with 1, 2 or 3 $R_c$, and other variables are as defined herein.

In some embodiments of the present disclosure, $R_2$ is independently selected from H, F, Cl, Br, I, OH, $NH_2$, CN, $CH_3$, $CHF_2$, $CH_2F$, $CF_3$, $CH_2CH_3$, $CH_2CHF_2$, $CH_2CH_2F$, $CH_2CF_3$ and

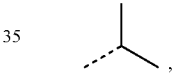

and other variables are as defined herein.

In some embodiments of the present disclosure, $R_2$ is selected from H, $CH_3$ and $CH_2CH_3$, and other variables are as defined herein.

In some embodiments of the present disclosure, ring A is selected from

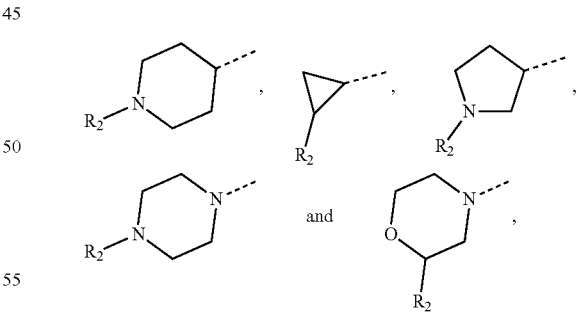

and other variables are as defined herein.

In some embodiments of the present disclosure, ring A is selected from

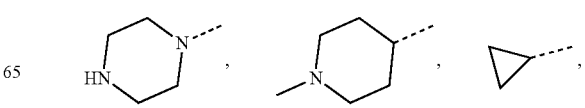

-continued

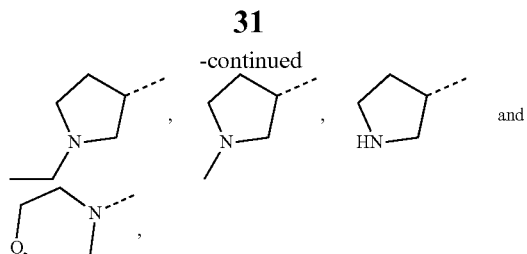

and other variables are as defined herein.

In some embodiments of the present disclosure, L is selected from —CH$_2$—, —CF$_2$—, —CHF—, —CH(CH$_3$)—, —CH(CH$_2$F)—, —CH(CHF$_2$)—, —CH(CF$_3$)—,

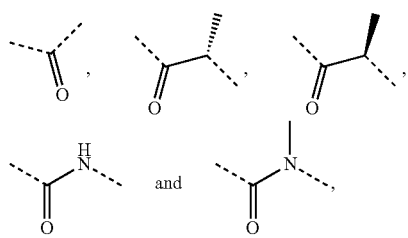

and other variables are as defined herein.

In some embodiments of the present disclosure, L is selected from —CH$_2$— and

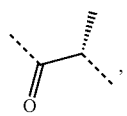

and other variables are as defined herein.

In some embodiments of the present disclosure, R$_b$ is selected from H, F, Cl, CH$_3$,

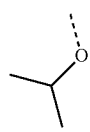

and —OCH$_3$, and other variables are as defined herein.

In some embodiments of the present disclosure, ring B is selected from

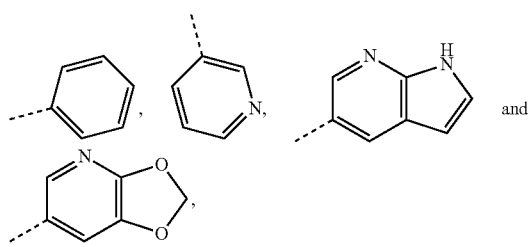

each of which is optionally substituted with 1, 2 or 3 R$_b$, and other variables are as defined herein.

In some embodiments of the present disclosure, ring B is selected from

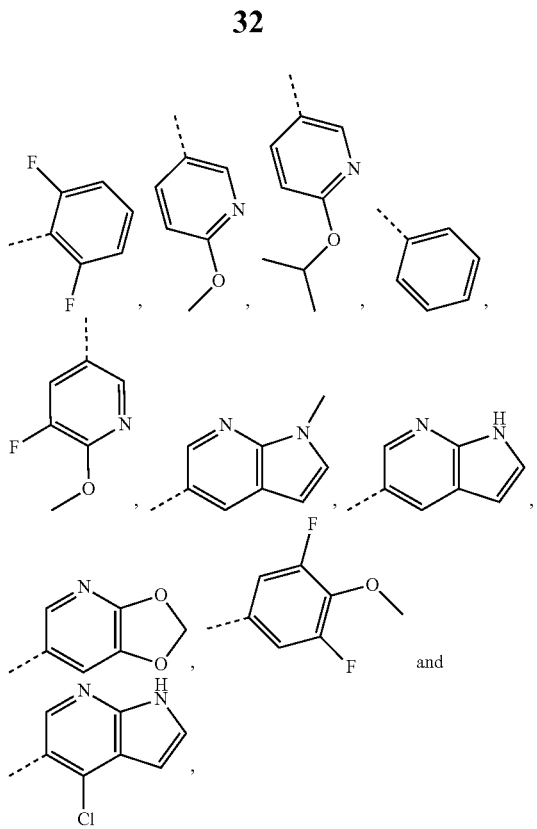

and other variables are as defined herein.

In some embodiments of the present disclosure, structural unit

is selected from

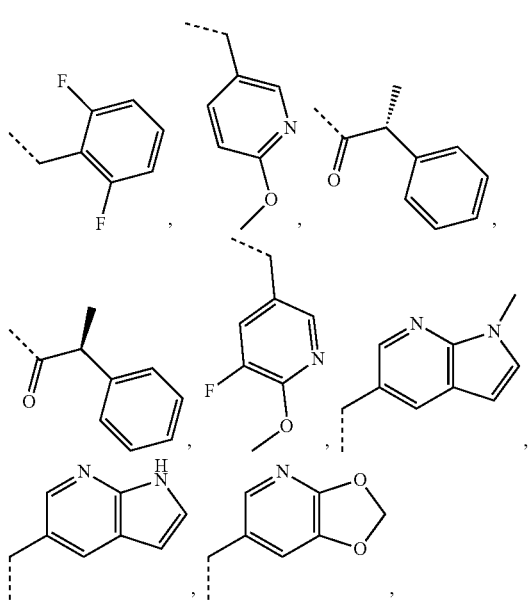

-continued

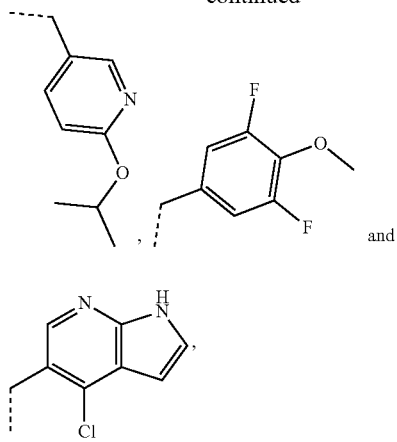

and other variables are as defined herein.

In some embodiments of the present disclosure, a compound, an isomer or a pharmaceutically acceptable salt thereof is selected from (VII-1)

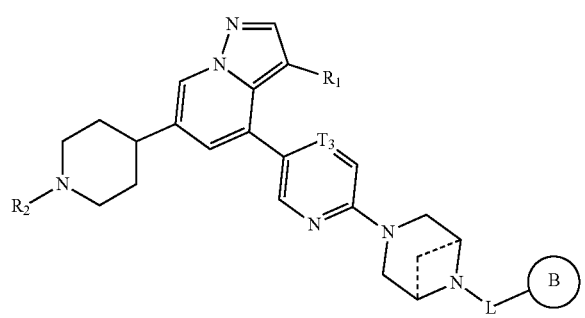

(VII-2)

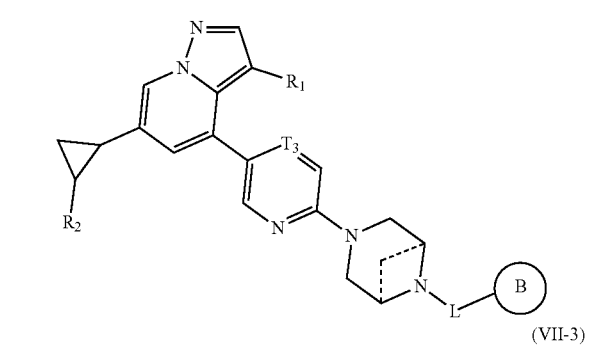

-continued (VII-4)

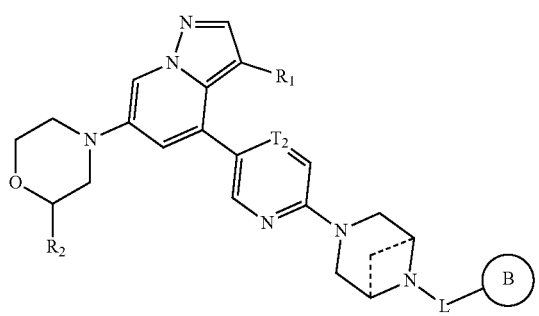

(VII-5)

(VII-6)

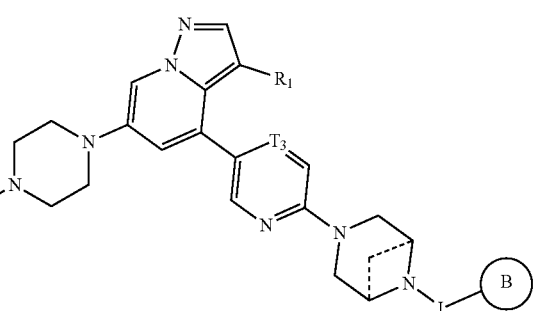

wherein, $R_1$, $R_2$, $T_3$, L,

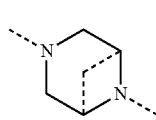

and ring B are as defined herein.

The present disclosure also provides an embodiment D.

Embodiment D provides a compound of formula (VIII), an isomer or a pharmaceutically acceptable salt thereof,

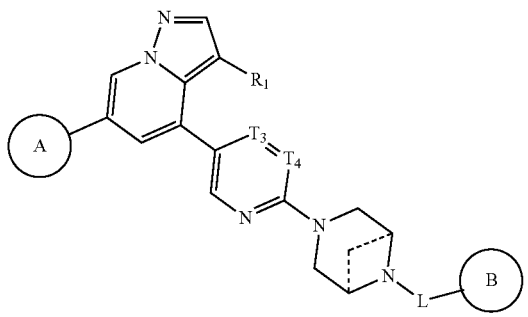

(VIII)

wherein:
ring A is selected from

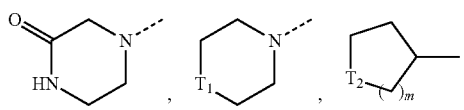

and cyclopropyl, each of which is optionally substituted with 1, 2 or 3 $R_2$;

$T_1$ is selected from NH, $CH_2$ and O;
$T_2$ is selected from NH and $CH_2$;
$T_3$ is selected from N and CH;
$T_4$ is selected from N and $CH_1$;
m is selected from 0, 1 and 2;
structural unit

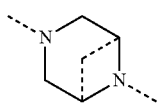

is selected from

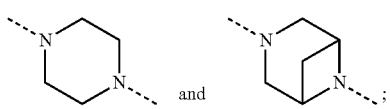

L is selected from $C_{1-3}$ alkyl,

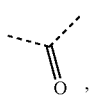

—C(=O)—$C_{1-3}$ alkyl-,

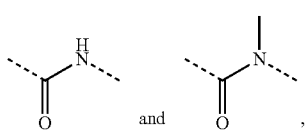

and the $C_{1-3}$ alkyl, —C(=O)—$C_{1-3}$ alkyl-,

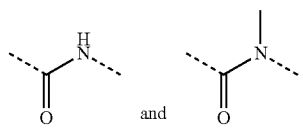

are optionally substituted with 1 $R_a$;

ring B is selected from phenyl, pyridyl, pyrazinyl, pyridazinyl, 1H-pyrrole-[2,3-b]pyridyl and 1,3-dioxolo[4,5-b]pyridyl, and each of which is optionally substituted with 1, 2 or 3 $R_b$;

$R_1$ is selected from H, F, Cl, Br, I, OH, $NH_2$ and CN;

$R_2$ is independently selected from H, F, Cl, Br, I, OH, $NH_2$, CN, $C_{1-6}$ alkyl, $C_{1-6}$ alkoxy and C(=O)$CH_3$, and the $C_{1-6}$ alkyl. $C_{1-6}$ alkoxy and C(=O)$CH_3$ are optionally substituted with 1, 2 or 3 $R_c$;

$R_a$ is independently selected from H, F, Cl, Br, I, OH, $NH_2$, CN and $CH_3$;

$R_b$ is independently selected from H, F, Cl, Br, I, OH, $NH_2$, CN, $C_{1-3}$ alkyl and $C_{1-3}$ alkoxy; and $R_c$ is independently selected from H, F, Cl, Br, I, OH, $NH_2$ and CN.

In some embodiments of the present disclosure, $R_2$ is independently selected from H, F, Cl, Br, I, OH, $NH_2$, CN, $C_{1-3}$ alkyl and C(=O)$CH_3$, the $C_{1-3}$ alkyl and C(=O) $CH_3$ are optionally substituted with 1, 2 or 3 $R_c$, and other variables are as defined herein.

In some embodiments of the present disclosure, $R_2$ is independently selected from H, F, Cl, Br, I, OH, $NH_2$, CN, $CH_3$, $CHF_2$, $CH_2F$, $CF_3$, $CH_2CH_3$, $CH_2CHF_2$, $CH_2CH_2F$, $CH_2CF_3$, and C(=O)$CH_3$, and other variables are as defined herein.

In some embodiments of the present disclosure, $R_2$ is selected from H, OH, $CH_3$, $CH_2CH_3$ and C(=O)$CH_3$, and other variables are as defined herein.

In some embodiments of the present disclosure, ring A is selected from

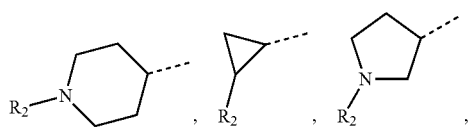

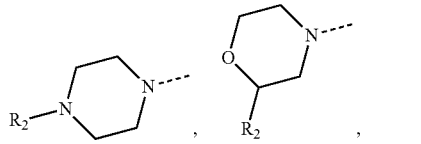

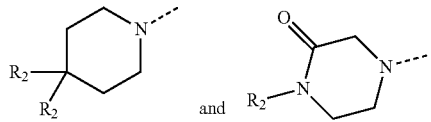

and other variables are as defined herein.

In some embodiments of the present disclosure, ring A is selected from

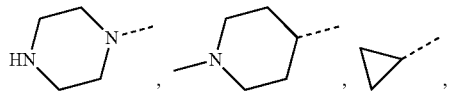

-continued

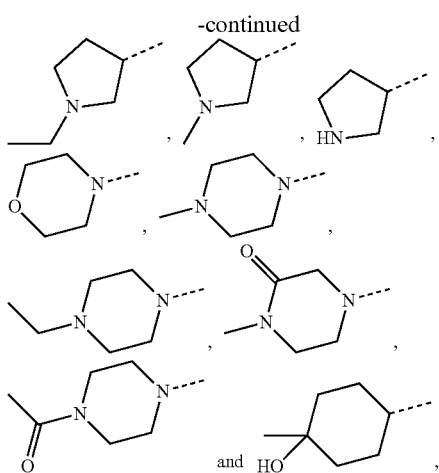

and other variables are as defined herein.

In some embodiments of the present disclosure, L is selected from —CH₂—, —CF₂—, —CHF—, —CH(CH₃)—, —CH(CH₂F)—, —CH(CHF₂)—, —CH(CH₂)—,

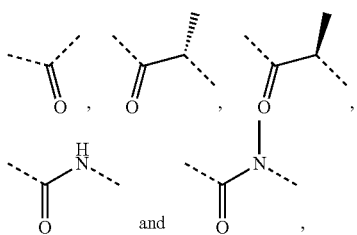

and other variables are as defined herein.

In some embodiments of the present disclosure, L is selected from —CH₂— and

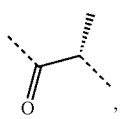

and other variables are as defined herein.

In some embodiments of the present disclosure, R$_b$ is selected from H, F, Cl, CH₃,

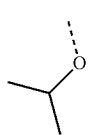

and —OCH₃, and other variables are as defined herein.

In some embodiments of the present disclosure, ring B is selected from

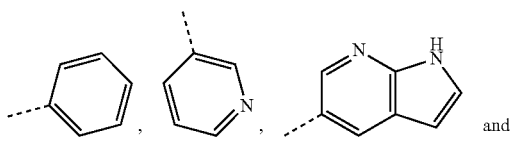

-continued

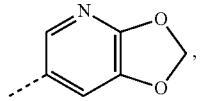

each of which is optionally substituted with 1, 2 or 3 R$_b$, and other variables are as defined herein.

In some embodiments of the present disclosure, ring B is selected from

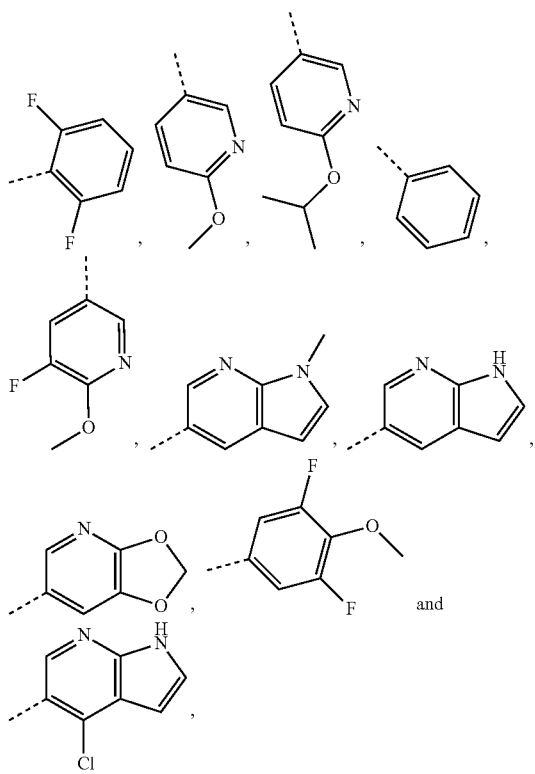

and other variables are as defined herein.

In some embodiments of the present disclosure, structural unit

is selected from

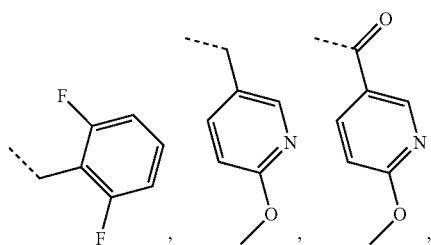

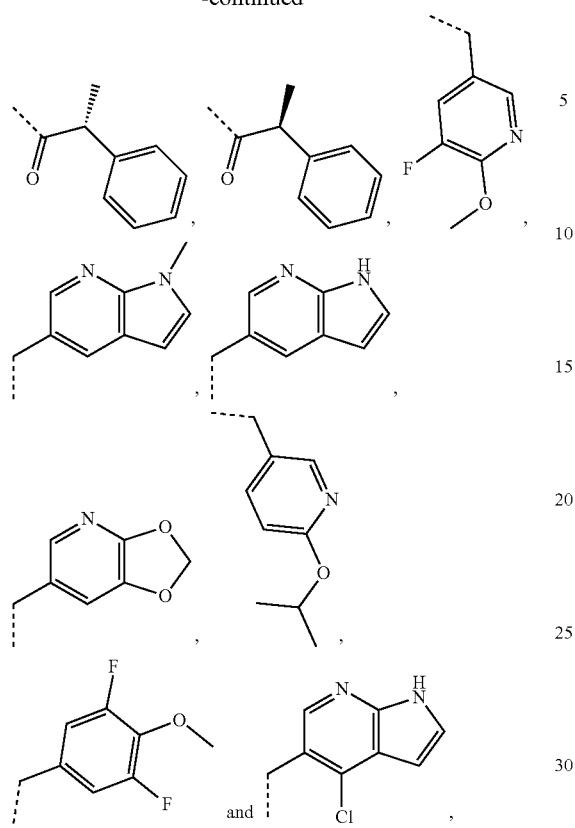
and other variables are as defined herein.
In some embodiments of the present disclosure, a compound, an isomer or a pharmaceutically acceptable salt thereof is selected from

-continued (VIII-2)

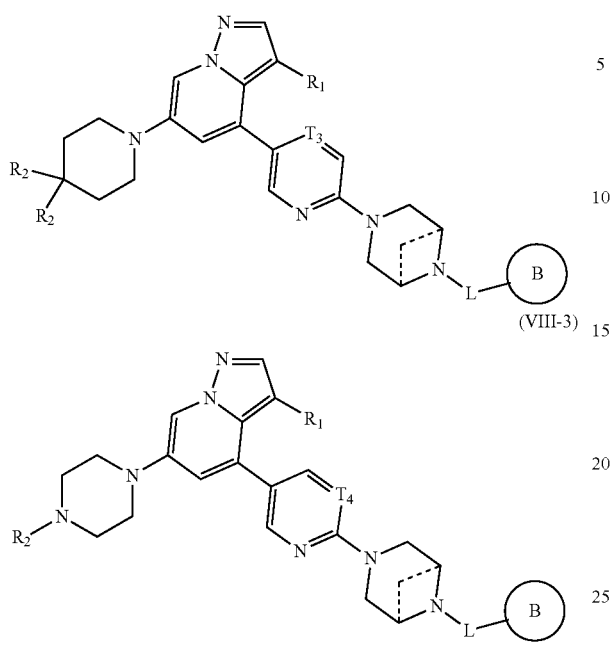

(VIII-3)

wherein, R₁, R₂, T₃, T₄, L,

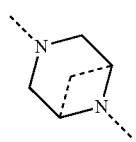

and ring B are as defined herein.

The present disclosure also provides an embodiment E.

Embodiment E provides a compound of formula (III), an isomer or a pharmaceutically acceptable salt thereof, (III)

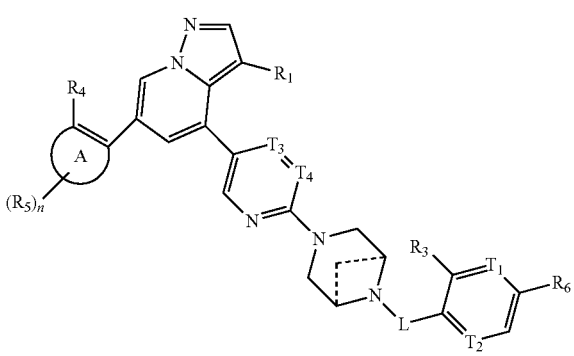

wherein:
$R_1$ is selected from H, F, Cl, Br, I, OH, NH₂ and CN;
$R_3$ is selected from H, F, Cl, Br, I, OH, NH₂ and CN;
$R_4$ is selected from H, F, Cl, Br, I, OH, NH₂ and CN;
$R_5$ is selected from H, F, Cl, Br, I, OH, NH₂, CN, $C_{1-6}$ alkyl and $C_{1-6}$ alkoxy, and the $C_{1-6}$ alkyl or $C_{1-6}$ alkoxy is optionally substituted with 1, 2 or 3 $R_c$;

$R_6$ is selected from H, H, F, Cl, Br, I, OH, NH₂, CN, $C_{1-6}$ alkoxy, and $C_{1-6}$ alkyl, and the $C_{1-6}$ alkoxy and $C_{1-6}$ alkyl are optionally substituted with 1, 2 or 3 $R_c$;
structural unit

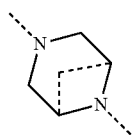

is selected from

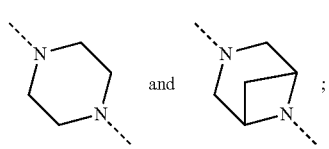

$T_1$ is selected from CH and N;
$T_2$ is selected from $CR_2$ and N;
$T_3$ is selected from CH and N;
$T_4$ is selected from CH and N;
$R_2$ is selected from H, F, Cl, Br, I, OH, NH₂ and CN;
n is selected from 0, 1, 2 and 3;
L is selected from $C_{1-3}$ alkyl,

—C(=O)—$C_{1-3}$ alkyl-,

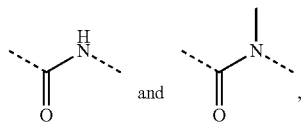

each of which is optionally substituted with 1, 2 or 3 $R_b$;
ring A is selected from 5-8 membered heterocycloalkenyl and $C_{5-8}$ cycloalkenyl;
$R_a$ is independently selected from H, F, Cl, Br, I, OH, NH₂ and CN;
$R_b$ is independently selected from H, F, Cl, Br, I, OH, NH₂, CN and CH₃;
$R_c$ is independently selected from H, F, Cl, Br, I and CH₃;
"hetero" of the 5-8 membered heterocycloalkenyl is independently selected from: N, O, S, NH, —S(=O)—, —S(=O)₂—, —C(=O)—, —C(=O)O— and —C(=O)NH—; and
the number of the heteroatoms or heteroatom groups is independently selected from 1, 2, 3, and 4.

In some embodiments of the present disclosure, structural unit

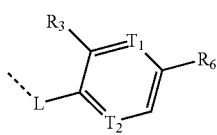

is selected from

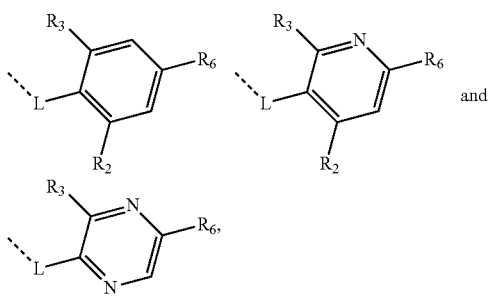

and other variables are as defined herein.

In some embodiments of the present disclosure, structural unit

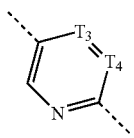

is selected from

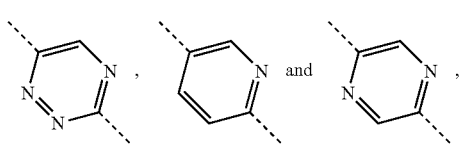

and other variables are as defined herein.

Embodiment E provides a compound of formula (II), an isomer or a pharmaceutically acceptable salt thereof,

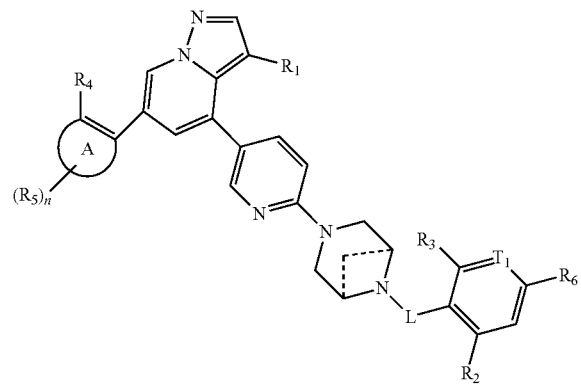

(II)

wherein:
R$_1$ is selected from H, F, Cl, Br, I, OH, NH$_2$ and CN;
R$_2$ is selected from H, F, Cl, Br, I, OH, NH$_2$ and CN;
R$_3$ is selected from H, F, Cl, Br, I, OH, NH$_2$ and CN;
R$_4$ is selected from H, F, Cl, Br, I, OH, NH$_2$ and CN;
R$_5$ is selected from H, F, Cl, Br, I, OH, NH$_2$, CN, C$_{1-6}$ alkyl and C$_{1-6}$ alkoxy, and the C$_{1-6}$ alkyl or C$_{1-6}$ alkoxy is optionally substituted with 1, 2 or 3 R$_a$;

structural unit

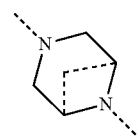

is selected from

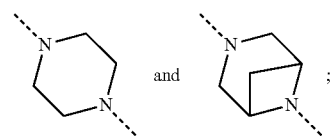

T$_1$ is selected from CH and N;
R$_6$ is selected from H and —OCH$_3$;
n is selected from 0, 1, 2 and 3;
L is selected from C$_{1-3}$ alkyl,

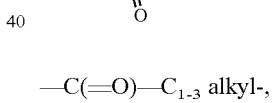

—C(=O)—C$_{1-3}$ alkyl-,

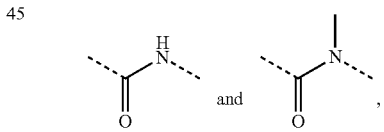

each of which is optionally substituted with 1, 2 or 3 R$_b$, ring A is selected from 5-8 membered heterocycloalkenyl and C$_{5-8}$ cycloalkenyl;
R$_a$ is independently selected from H, F, Cl, Br, I, OH, NH$_2$ and CN;
R$_b$ is independently selected from H, F, Cl, Br, I, OH, NH$_2$, CN and CH$_3$;
"hetero" of the 5-8 membered heterocycloalkenyl is independently selected from N, O, S, NH, —C(=O)—, —C(=O)O— and —C(=O)NH—; and
the number of the heteroatoms or heteroatom groups is independently selected from 1, 2, 3, and 4.

Embodiment E provides a compound of formula (I), an isomer or a pharmaceutically acceptable salt thereof,

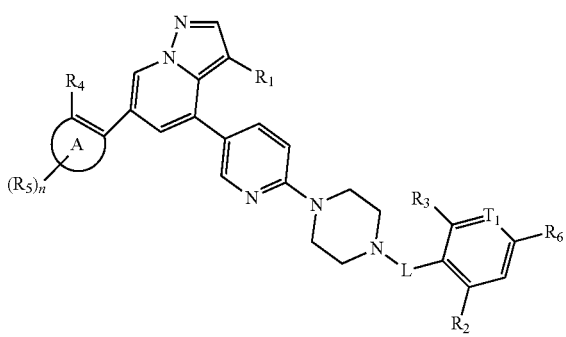
(I)

wherein:
$R_1$ is selected from H, F, Cl, Br, I, OH, $NH_2$ and CN;
$R_2$ is selected from H, F, Cl, Br, I, OH, $NH_2$ and CN;
$R_3$ is selected from H, F, Cl, Br, I, OH, $NH_2$ and CN;
$R_4$ is selected from H, F, Cl, Br, I, OH, $NH_2$ and CN;
$R_5$ is selected from H, F, Cl, Br, I, OH, $NH_2$, CN, $C_{1-6}$ alkyl and $C_{1-6}$ alkoxy, and the $C_{1-6}$ alkyl or $C_{1-6}$ alkoxy is optionally substituted with 1, 2 or 3 $R_a$;
$T_1$ is selected from CH and N;
$R_6$ is selected from H and $-OCH_3$;
n is selected from 0, 1, 2 and 3;
L is selected from $C_{1-3}$ alkyl,

$-C(=O)-C_{1-3}$ alkyl-,

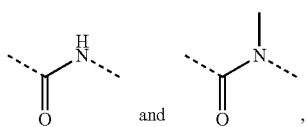

each of which is optionally substituted with 1, 2 or 3 $R_b$;
ring A is selected from 5-8 membered heterocycloalkenyl and $C_{5-8}$ cycloalkenyl;
$R_a$ is independently selected from H, F, Cl, Br, I, OH, $NH_2$ and CN;
$R_b$ is independently selected from H, F, Cl, Br, I, OH, $NH_2$, CN and $CH_3$;
"hetero" of the 5-8 membered heterocycloalkenyl is independently selected from: N, O, S, NH, $-C(=O)-$, $-C(=O)O-$ and $-C(=O)NH-$; and
the number of the heteroatoms or heteroatom groups is independently selected from 1, 2, 3, and 4.

In some embodiments of the present disclosure, $R_1$ is CN, and other variables are as defined herein.

In some embodiments of the present disclosure, $R_2$ is F, and other variables are as defined herein.

In some embodiments of the present disclosure, $R_3$ is F, and other variables are as defined herein.

In some embodiments of the present disclosure, $R_2$ is selected from H and F, and other variables are as defined herein.

In some embodiments of the present disclosure, $R_3$ is selected from H and F, and other variables are as defined herein.

In some embodiments of the present disclosure, $R_5$ is selected from H and $C_{1-3}$ alkyl, the $C_{1-3}$ alkyl is optionally substituted with 1, 2, or 3 $R_a$, and other variables are as defined herein.

In some embodiments of the present disclosure, $R_5$ is selected from H, $CH_3$, $CH_2F$, $CHF_2$, $CF_3$, $CH_2CH_3$, $CH_2CH_3F$, $CH_2CHF_2$, $CH_2CF$ and

other variables are as defined herein.

In some embodiments of the present disclosure, $R_5$ is selected from H, $CH_3$ and $CH_2CH_3$, and other variables are as defined herein.

In some embodiments of the present disclosure, ring A is selected from 3,6-dihydropyranyl, 3-pyrrolinyl, 1,2,5,6-tetrahydropyridyl, 1H-pyridin-2-one and α-pyrone, and other variables are as defined herein.

In some embodiments of the present disclosure, the structural unit

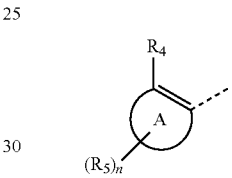

is selected from

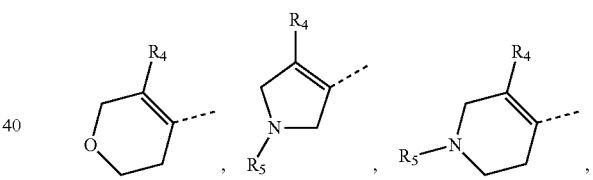

and other variables are as defined herein.

In some embodiments of the present disclosure, structural unit

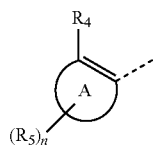

is selected from

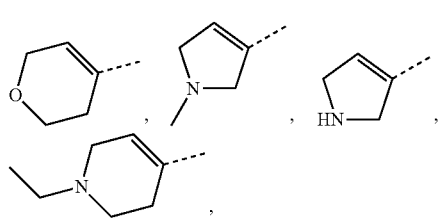

and other variables are as defined herein.

In some embodiments of the present disclosure, L is selected from —CH$_2$—, —CF$_2$—, —CHF—, —CH(CH$_3$)—, —CH(CH$_2$F)—, —CH(CHF$_2$)— and —CH(CF$_3$)—, and other variables are as defined herein.

In some embodiments of the present disclosure, L is —CH$_2$—, and other variables are as defined herein.

In some embodiments of the present disclosure, L is selected from —CH$_2$—, —CH(CH$_3$)—,

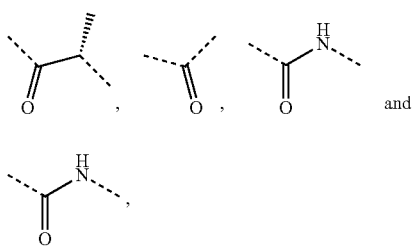

and the —CH$_2$—, —CH(CH$_3$)— and

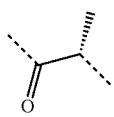

are optionally substituted with 1, 2 or 3 R$_b$, and other variables are as defined herein.

In some embodiments of the present disclosure, L is selected from —CH$_2$— and

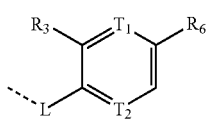

and other variables are as defined herein.

In some embodiments of the present disclosure, R$_6$ is selected from H, F, Cl, Br, I, OH, NH$_2$, CN, C$_{1-3}$ alkoxy and C$_{1-3}$ alkyl, the C$_{1-3}$ alkoxy and C$_{1-3}$ alkyl are optionally substituted with 1, 2 or 3 R$_c$, and other variables are as defined herein.

In some embodiments of the present disclosure, R$_6$ is selected from H and —OCH$_3$, and other variables are as defined herein.

In some embodiments of the resent disclosure, structural unit

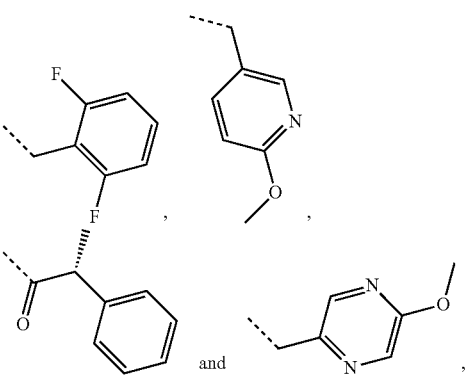

is selected from and other variables are as defined herein.

In some embodiments of the present disclosure, a compound, an isomer or a pharmaceutically acceptable salt thereof are selected from

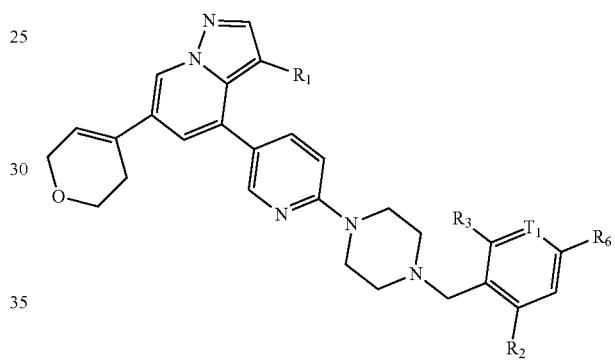

(I-1)

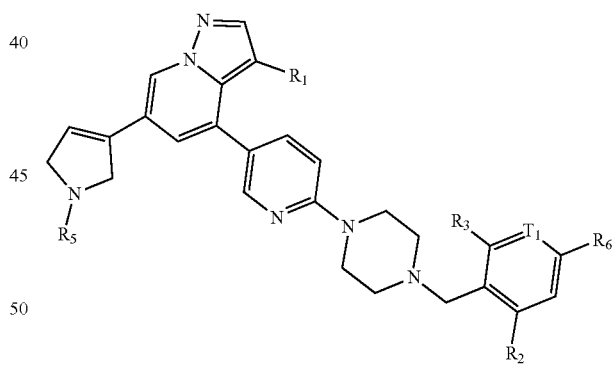

(I-2)

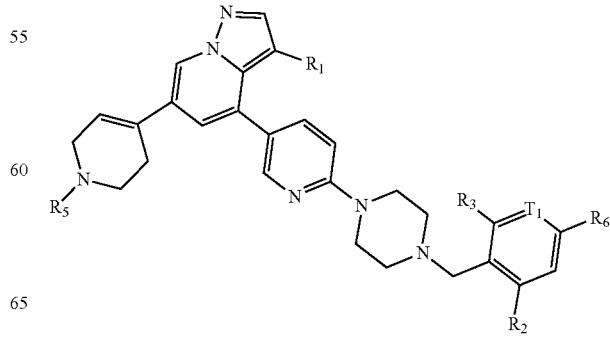

(I-3)

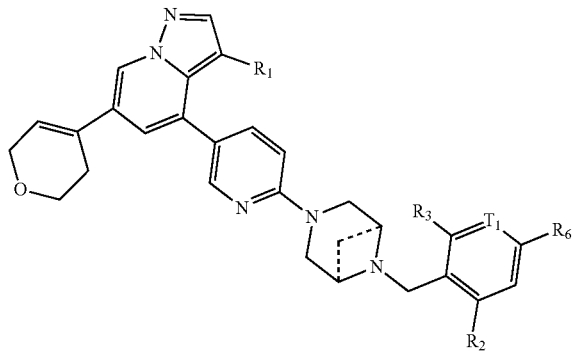
(II-1)
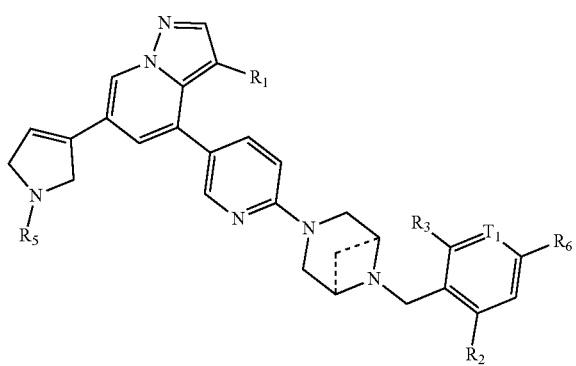
(II-2)
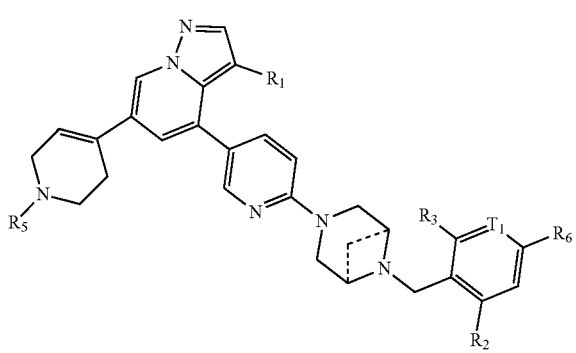
(II-3)
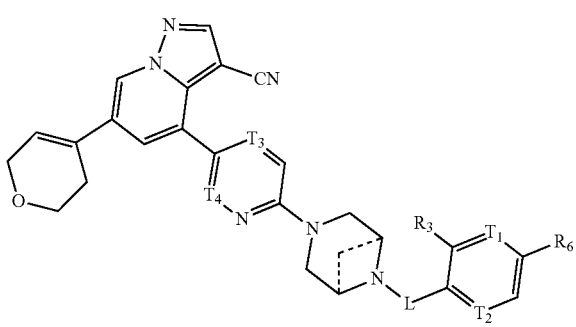
(III-1)
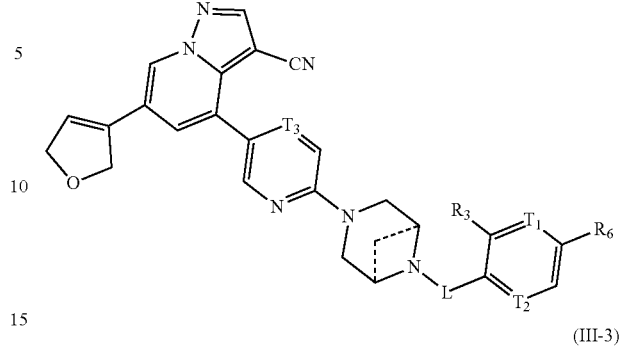
(III-2)
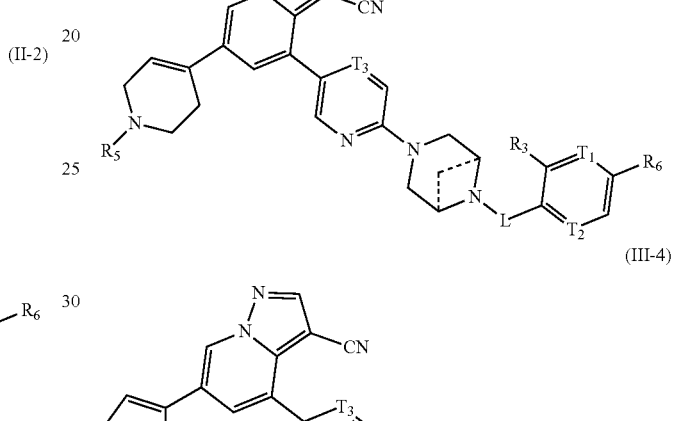
(III-3)
(III-4)
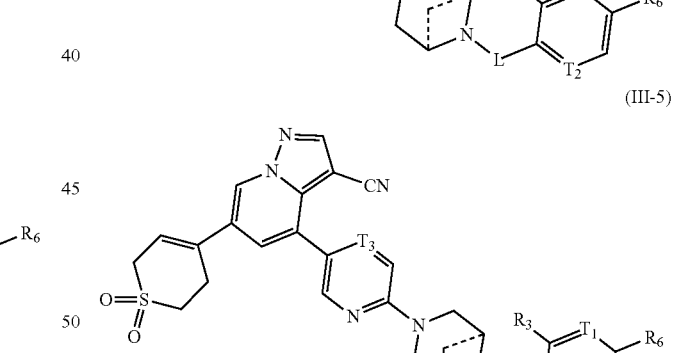
(III-5)
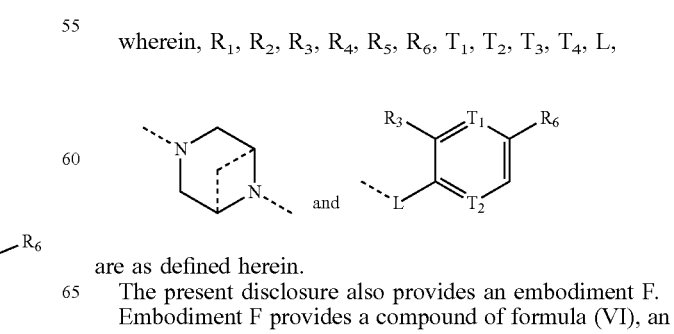
wherein, $R_1$, $R_2$, $R_3$, $R_4$, $R_5$, $R_6$, $T_1$, $T_2$, $T_3$, $T_4$, L,
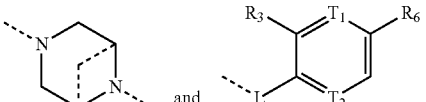 and
are as defined herein.
The present disclosure also provides an embodiment F. Embodiment F provides a compound of formula (VI), an isomer or a pharmaceutically acceptable salt thereof,

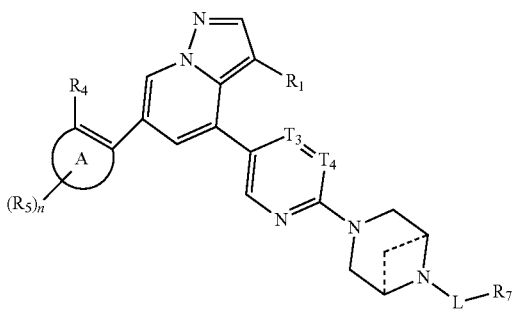
(VI)

wherein:
$R_1$ is selected from H, F, Cl, Br, I, OH, $NH_2$ and CN;
$R_4$ is selected from H, F, Cl, Br, I, OH, $NH_2$ and CN;
$R_5$ is selected from H, F, Cl, Br, I, OH, $NH_2$, CN, $C_{1-6}$ alkyl and $C_{1-6}$ alkoxy, and the $C_{1-6}$ alkyl and $C_{1-6}$ alkoxy are optionally substituted with 1, 2 or 3 $R_a$;
$R_7$ is selected from phenyl, 5-10 membered heteroaryl and 1,3-dioxolo[4,5-B]pyridyl, and each of which is optionally substituted by 1, 2 or 3 $R_d$;
structural unit

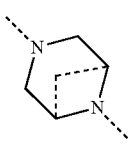

is selected from

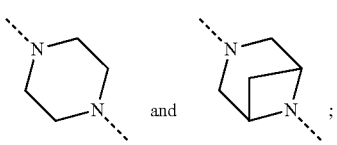

$T_3$ is selected from CH and N;
$T_4$ is selected from CH and N;
n is selected from 0, 1, 2, 3 and 4;
L is selected from $C_{1-3}$ alkyl,

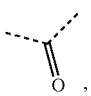

—C(=O)—$C_{1-3}$ alkyl-,

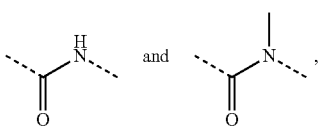

each of which is optionally substituted with 1, 2 or 3 $R_b$;
ring A is selected from 5-10 membered heterocycloalkenyl and $C_{5-8}$ cycloalkenyl;
$R_a$ is independently selected from H, F, Cl, Br, I, OH, $NH_2$ and CN;

$R_b$ is independently selected from H, F, Cl, Br, I, OH, $NH_2$, CN and $CH_3$;
$R_d$ is independently selected from H, F, Cl, Br, I, OH, $NH_2$, CN, $C_{1-4}$ alkoxy and $C_{1-4}$ alkyl, and the $C_{1-4}$ alkoxy and $C_{1-4}$ alkyl are optionally substituted with 1, 2 or 3 halogens; and
the 5-10 membered heterocycloalkenyl and 5-10 membered heteroaryl comprise 1, 2 or 3 heteroatoms or heteroatom groups independently selected from —N, O, S, NH, —S(=O)—, —S(=O)$_2$—, —C(=O)—, —C(=O)O— and —C(=O)NH.

In some embodiments of the present disclosure, structural unit

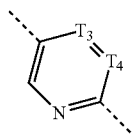

is selected from

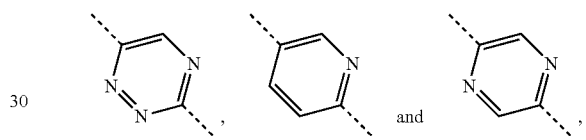

and other variables are as defined herein.

In some embodiments of the present disclosure, $R_1$ is CN, and other variables are as defined herein.

In some embodiments of the present disclosure, $R_4$ is selected from H, and other variables are as defined herein.

In some embodiments of the present disclosure, $R_5$ is selected from H, OH and $C_{1-3}$ alkyl, and the $C_{1-3}$ alkyl is optionally substituted with 1, 2, or 3 $R_a$, and other variables are as defined herein.

In some embodiments of the present disclosure, $R_5$ is selected from H, OH, $CH_3$, $CH_2F$, $CHF_2$, $CF_3$, $CH_2CH_3$, $CH_2CH_2F$, $CH_2CHF_2$, $CH_2CF_3$ and

and other variables are as defined herein.

In some embodiments of the present disclosure, $R_5$ is selected from H, OH, $CH_3$ and $CH_2CH_3$, and other variables are as defined herein.

In some embodiments of the present disclosure, ring A is selected from 3,6-dihydro-2H-pyranyl, 3,4-dihydro-2H-pyranyl, 3-pyrrolinyl, 1,2,5,6-tetrahydropyridyl, 1,2,3,6-tetrahydropyridyl, 1H-pyridin-2-one, α-pyrone, 2,5-dihydrofuranyl, 2,5-dihydro-1H-pyrrolyl, 3,6-dihydro-2H-thiopyran-1,1-dioxy, cyclohexenyl and 2-oxaspiro[3,5]non-6ene, and other variables are as defined herein.

In some embodiments of the present disclosure, structural unit

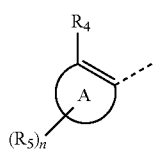

is selected from

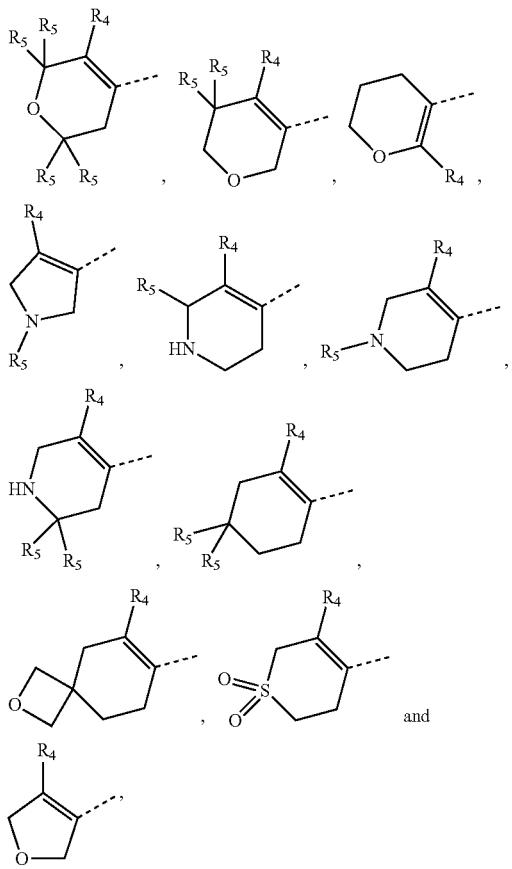

and other variables are as defined herein.

In some embodiments of the present disclosure, structural unit

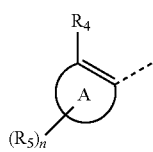

is selected from

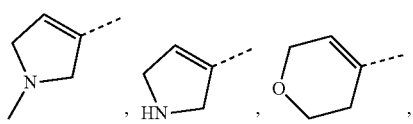

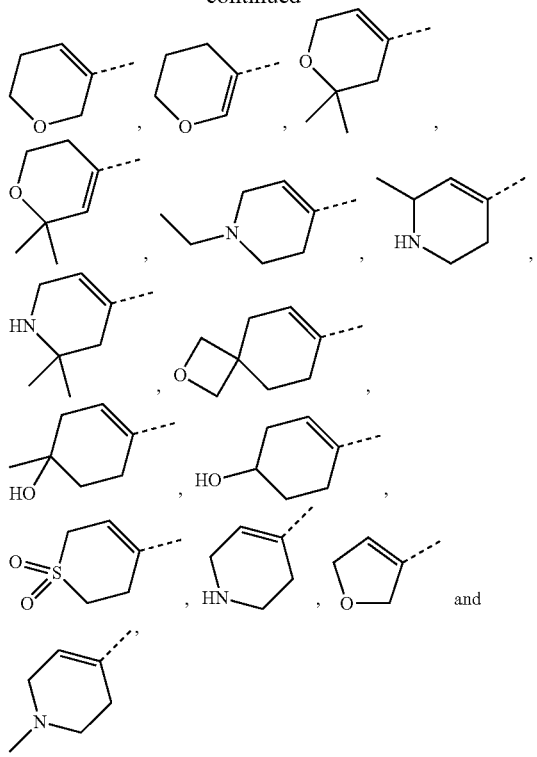

and other variables are as defined herein.

In some embodiments of the present disclosure, L is selected from —CH$_2$—, —CH(CH$_3$)—,

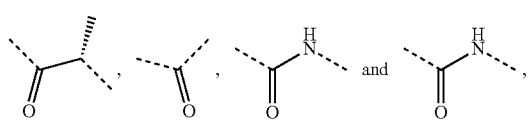

the —CH$_2$—, —CH(CH$_3$)— and

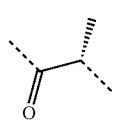

are optionally substituted with 1, 2 or 3 R$_b$, and other variables are as defined herein.

In some embodiments of the present disclosure, L is selected from —CH$_2$— and

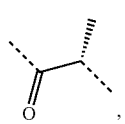

and other variables are as defined herein.

In some embodiments of the present disclosure, R$_d$ is selected from H, F and —OCH$_3$, and other variables are as defined herein.

In some embodiments of the present disclosure, R$_7$ is selected from phenyl, pyridyl, pyrazinyl, pyridazine, 1H-pyrrole-[2,3-b]pyridyl, 1,3-dioxolo[4,5-B]pyridyl and indolyl, each of which is optionally substituted with 1, 2 or 3 $R_d$, and other variables are as defined herein.

In some embodiments of the present disclosure, $R_7$ is selected from

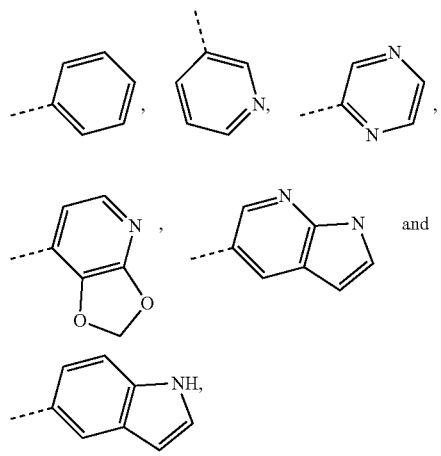

each of which is optionally substituted with 1, 2 or 3 $R_d$, and other variables are as defined herein.

In some embodiments of the present disclosure, $R_7$ is selected from

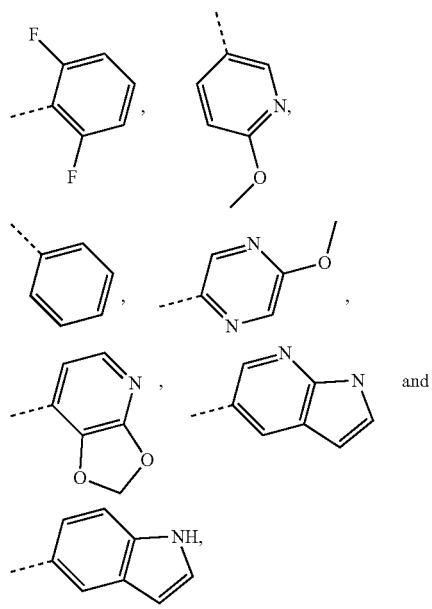

and other variables are as defined herein.

In some embodiments of the present disclosure, structural unit

is selected from

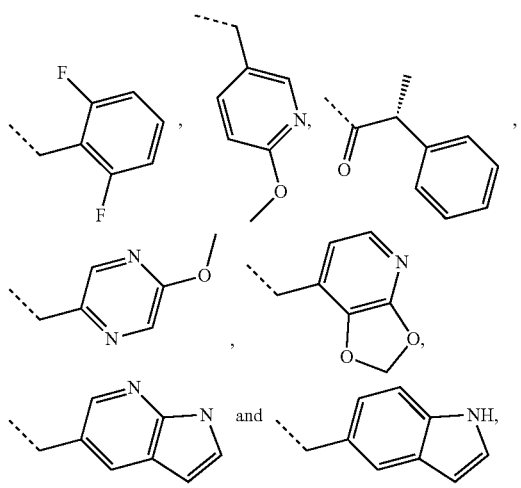

and other variables are as defined herein.

In some embodiments of the present disclosure, a compound, an isomer or a pharmaceutically acceptable salt thereof is selected from

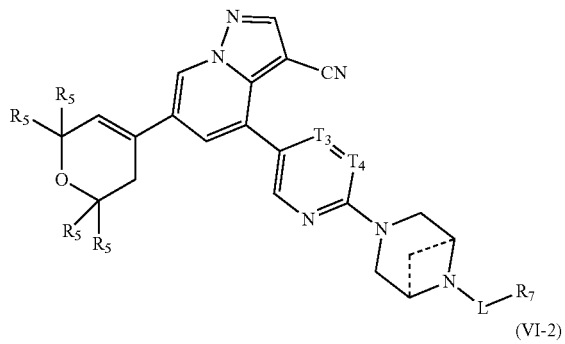
(VI-1)

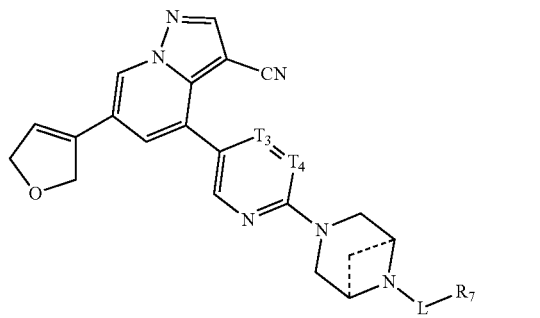
(VI-2)

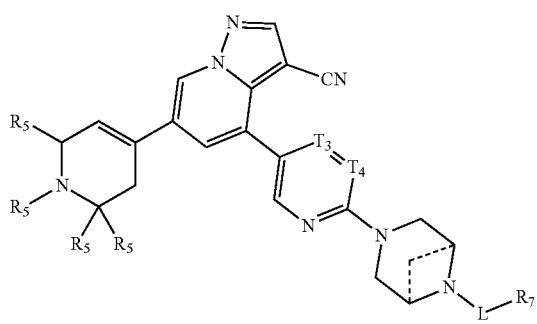
(III-3)

(VI-4)
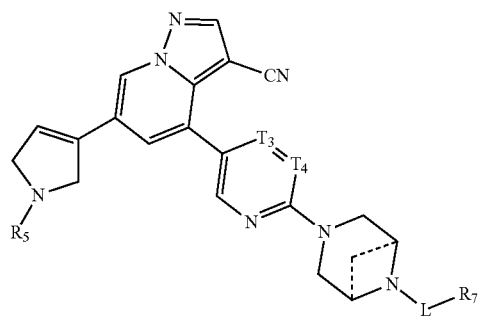
(VI-5)
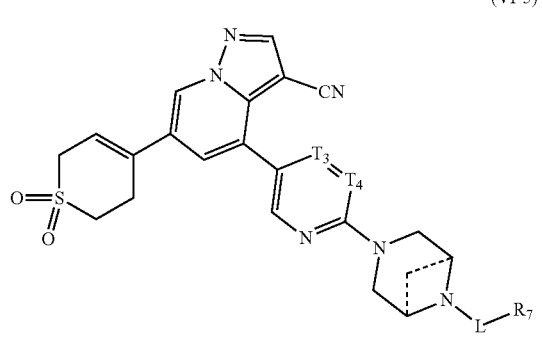
(VI-6)
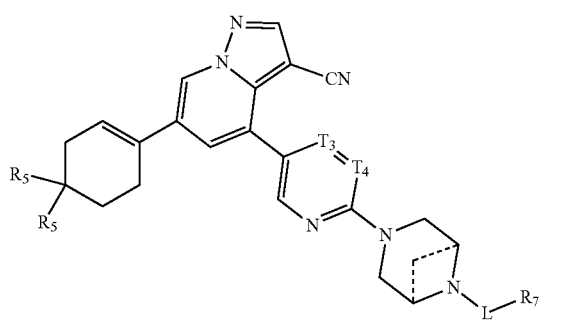
(VI-7)
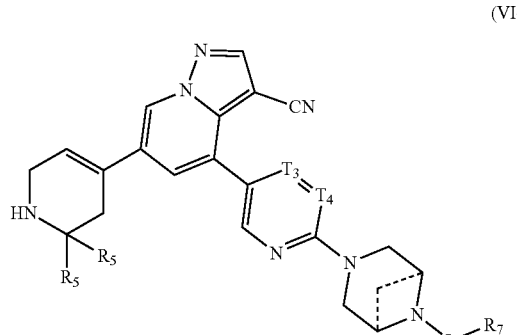
(VI-8)
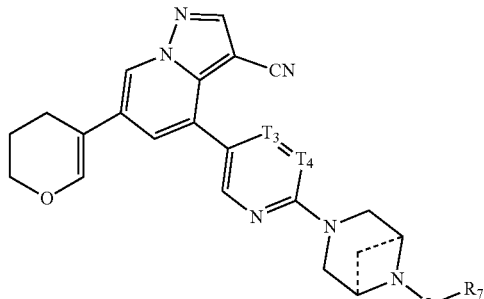
(VI-9)
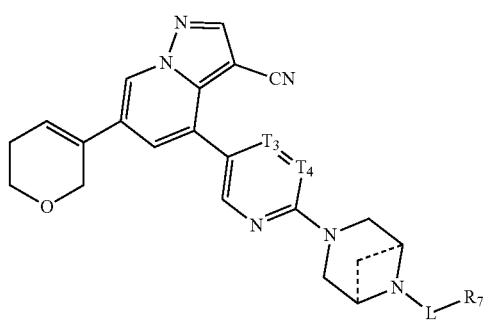
(VI-10)
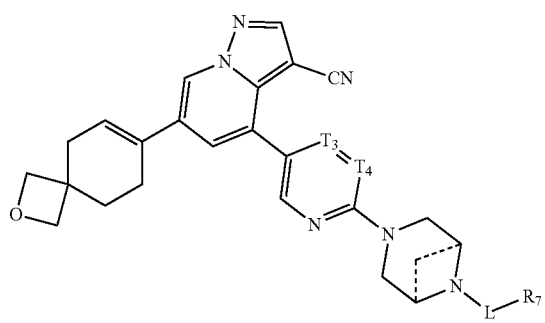
wherein, $R_7$, $T_3$, $T_4$, L and
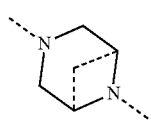
are as defined herein.
The present disclosure also provides an embodiment G.
Embodiment G provides a compound of formula (VII) or a pharmaceutically acceptable salt thereof,

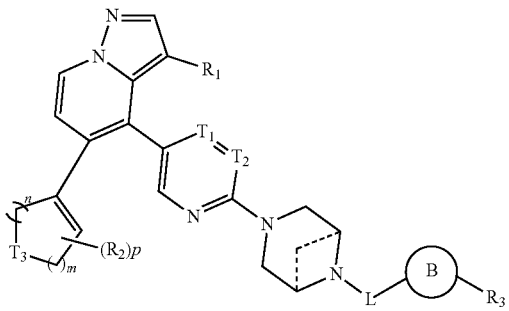
(VII)

wherein:
$R_1$ is selected from H, F, Cl, Br, I, OH, $NH_2$ and CN;
$R_2$ is selected from H, F, Cl, Br, I, OH, $NH_2$, CN, $C_{1-3}$ alkyl and $C_{1-3}$ alkoxy, and the $C_{1-3}$ alkyl and $C_{1-3}$ alkoxy are optionally substituted with 1, 2 or 3 $R_a$;
$R_3$ is selected from H, F, Cl, Br, I, OH, $NH_2$, CN, $C_{1-3}$ alkyl and $C_{1-3}$ alkoxy, and the $C_{1-3}$ alkyl and $C_{1-3}$ alkoxy are optionally substituted with 1, 2 or 3 $R_b$;
structural unit

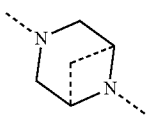

is selected from is selected from

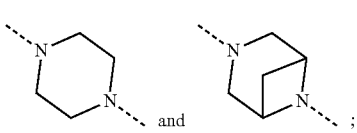

ring B is selected from phenyl, pyridyl, pyrazinyl, pyridazine, 1H-pyrrole-[2,3-b]pyridyl, 1,3-dioxolo[4,5-b]pyridyl, indolyl and benzimidazolyl;
$T_1$ is selected from CH and N;
$T_2$ is selected from CH and N;
$T_3$ is selected from $CH_2$, NH, O, $S(=O)_2$ and $C(R_cR_d)$;
m is selected from 0, 1 and 2;
n is selected from 1, 2 and 3;
p is selected from 0, 1 and 2;
L is selected from $C_{1-3}$alkyl,

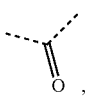

—C(=O)—$C_{1-3}$ alkyl-,

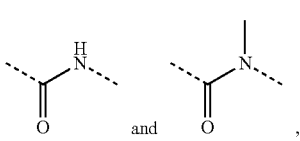

each of which is optionally substituted with 1, 2 or 3 $R_e$;

$R_a$ and $R_b$ are independently selected from H, F, Cl, Br, I, OH and NH;
$R_c$ and $R_d$ are independently selected from $C_{1-3}$ alkyl and $C_{1-3}$ alkoxy, and $R_c$ and $R_d$ are connected to form heterooxycyclobutyl; and
$R_e$ is independently selected from H, F, Cl, Br, I, OH and $NH_2$.

In some embodiments of the present disclosure, structural unit

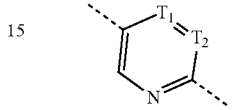

is selected from

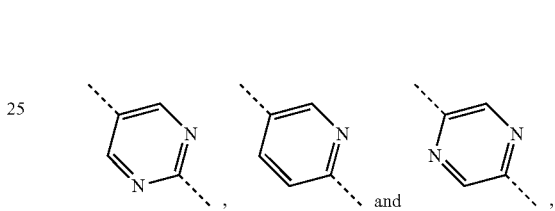

and other variables are as defined herein.

In some embodiments of the present disclosure, $R_1$ is CN, and other variables are as defined herein.

In some embodiments of the present disclosure, $R_2$ is selected from H, OH and $C_{1-3}$ alkyl, and the $C_{1-3}$ alkyl is optionally substituted with 1, 2 or 3 $R_a$, and other variables are as defined herein.

In some embodiments of the present disclosure, $R_2$ is selected from H, OH, $CH_3$, $CH_2F$, $CHF_2$, $CF_3$, $CH_2CH_3$, $CH_2CH_2F$, $CH_2CHF_2$, $CH_2CF_3$ and

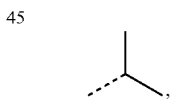

and other variables are as defined herein.

In some embodiments of the present disclosure, $R_2$ is selected from H, OH, $CH_3$ and $CH_2CH_3$, and other variables are as defined herein.

In some embodiments of the present disclosure, structural unit

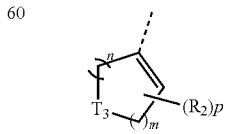

is selected from

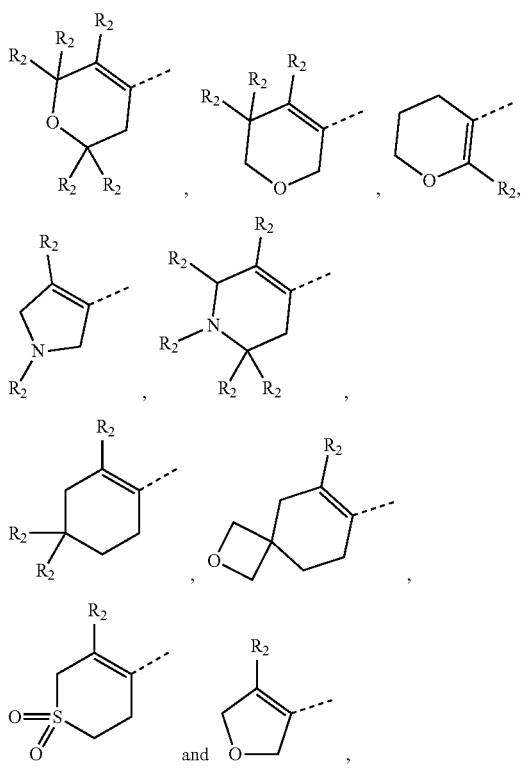

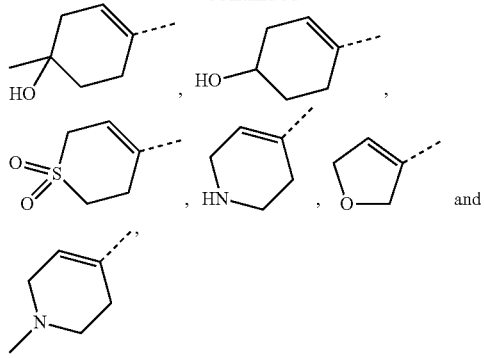

and other variables are as defined herein.

In some embodiments of the present disclosure, the structural unit

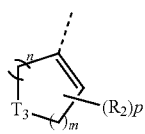

is selected from

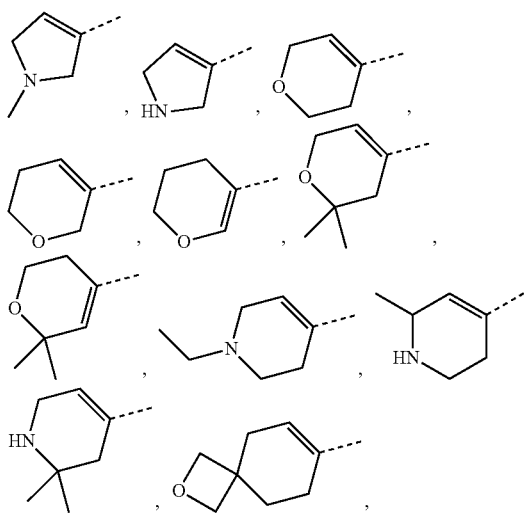

and other variables are as defined herein.

In some embodiments of the present disclosure, L is selected from —CH$_2$—, —CH(CH$_3$)—,

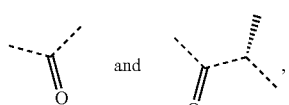

the —CH$_2$—, —CH(CH$_3$)— and

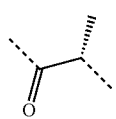

are optionally substituted with 1, 2 or 3 R$_e$, and other variables are as defined herein.

In some embodiments of the present disclosure, L is selected from —CH$_2$— and

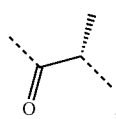

and other variables are as defined herein.

In some embodiments of the present disclosure, R$_3$ is selected from H, F, CH$_3$, CF$_3$ and —OCH$_3$, and other variables are as defined herein.

In some embodiments of the present disclosure, ring B is selected from

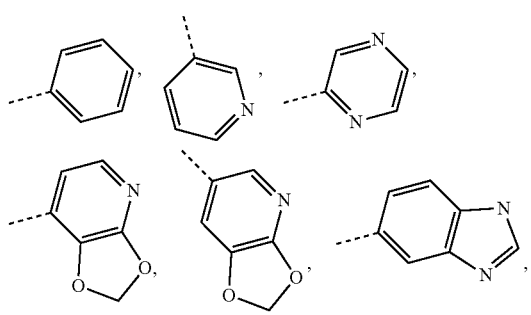

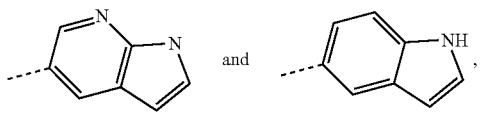 and 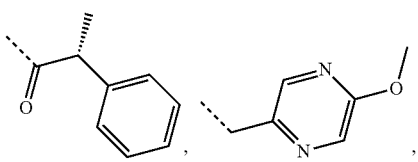

and other variables are as defined herein.

In some embodiments of the present disclosure, the structural unit

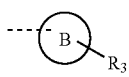

is selected from

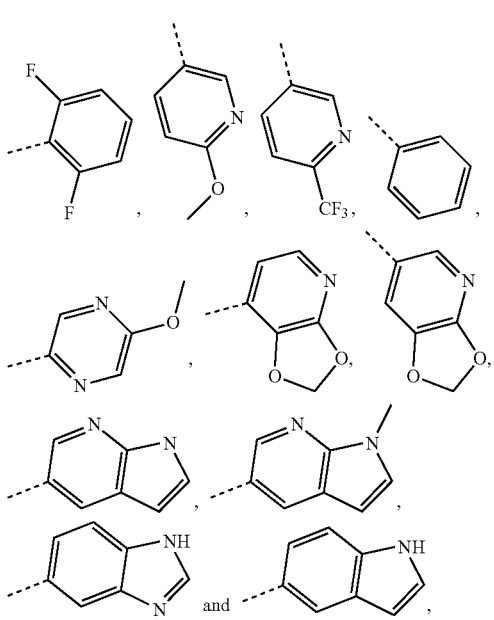

and other variables are as defined herein.

In some embodiments of the present disclosure, the structural unit

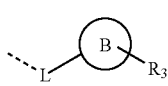

is selected from

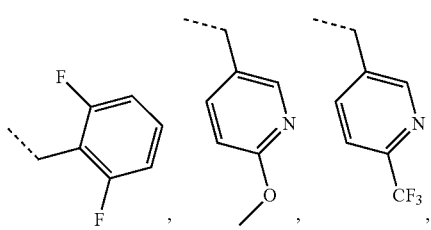

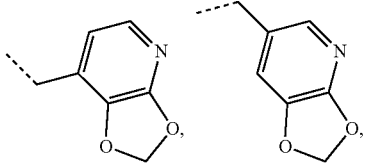

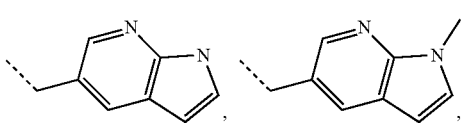

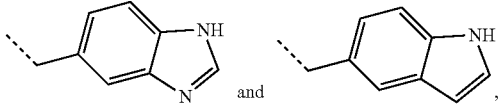

and other variables are as defined herein.

In some embodiments of the present disclosure, a compound or a pharmaceutically acceptable salt thereof is selected from

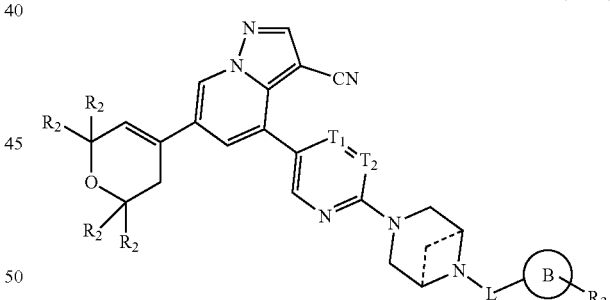

(VII-1)

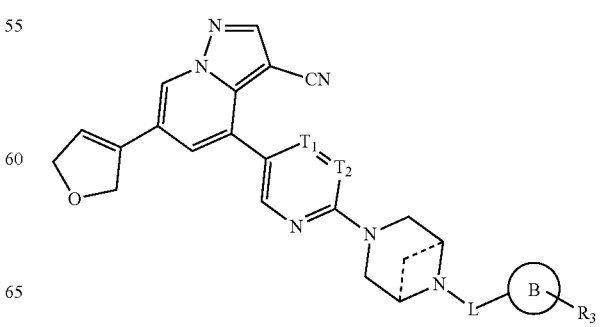

(VII-2)

(VII-3)

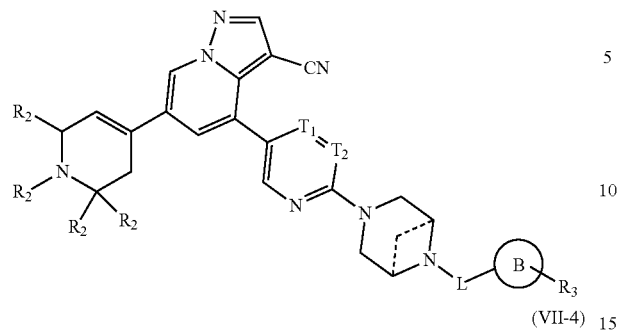

(VII-4)

(VII-8)

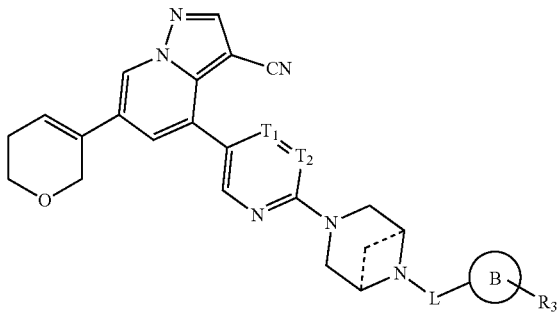

(VII-9)

Wherein, R₂, R₃, T₁, T₂, L,

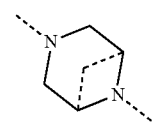

and ring B are as defined herein.

The present disclosure also provides an embodiment H.

Embodiment H provides a compound of formula (I), an isomer or a pharmaceutically acceptable salt thereof, (VII-5)

(VII-6)

(VII-7)

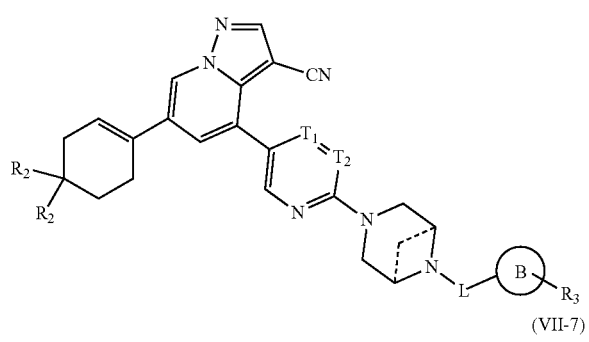

(I)

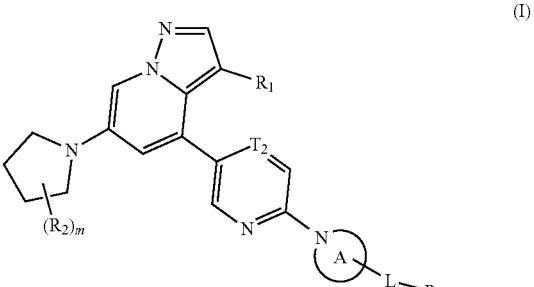

wherein.

R₁ is selected from H, F, Cl, Br, I, OH, NH₂ and CN;

R₂ is independently selected from H, F, Cl, Br, I, OH, NH₂, CN, and C₁₋₃ alkyl, and the C₁₋₃ alkyl is optionally substituted with 1, 2 or 3 Rₐ;

n is selected from 0, 1, 2, 3, 4, 5 and 6;
T$_2$ is selected from CH and N;
structural unit

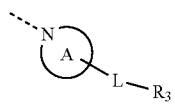

is selected from

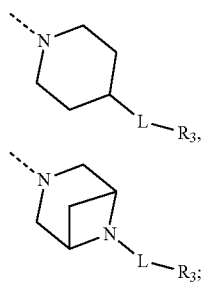

L is selected from —CH$_2$— and

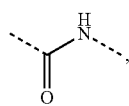

and the —CH$_2$— is optionally substituted with 1 or 2 R$_b$;
R$_3$ is selected from phenyl, 5-6 membered heteroaryl, C$_{3-8}$ cycloalkyl, C$_{1-8}$ alkyl and C$_{1-6}$ alkoxy, each of which is independently optionally substituted with 1, 2 or 3 R$_c$.
R$_a$ is independently selected from H, F, Cl, Br, I, OH, NH$_2$ and CN;
R$_b$ is independently selected from H, F, Cl, Br, I, OH, NH$_2$, CN and CH$_3$;
R$_c$ is independently selected from H, F, Cl, Br, I, OH, NH$_3$, CN, C$_{1-3}$ alkoxy and C$_{1-3}$ alkoxy, and the C$_{1-3}$ alkoxy and C$_1$-alkoxy are independently optionally substituted with 1, 2 or 3 R;
R is independently selected from H, F, Cl, Br and I; and
"hetero" of the 5-6 membered heteroaryl is independently selected from: N, O, S, NH, and the number of the heteroatoms or heteroatom groups is independently selected from 1, 2, 3, and 4.

In some embodiments of the present disclosure, R$_1$ is CN, and other variables are as defined herein.

In some embodiments of the present disclosure R$_1$ is selected from H, F, Cl, Br, I, OH, CH$_3$, CHF$_2$, CH$_2$F, CF$_3$, CH$_2$CH$_3$, CH$_2$CHF$_2$, CH$_2$CH$_2$F, CH$_2$CF$_3$ and

and other variables are as defined herein.

In some embodiments of the present disclosure, R$_2$ is selected from H, F, Cl, Br, I and OH, and other variables are as defined herein.

In some embodiments of the present disclosure, R$_2$ is selected from 0, 1 and 2, and other variables are as defined herein.

In some embodiments of the present disclosure, structural unit

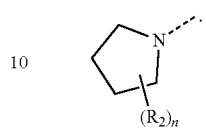

is selected from

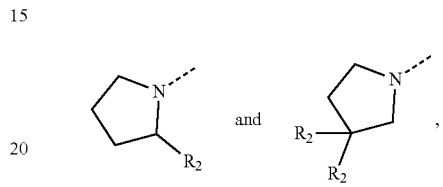

and other variables are as defined herein.

In some embodiments of the present disclosure, structural unit

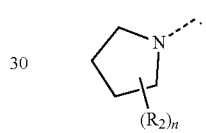

is selected from

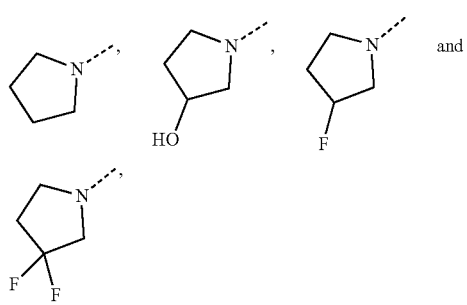

and other variables are as defined herein.

In some embodiments of the present disclosure, the structural unit

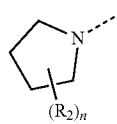

is selected from

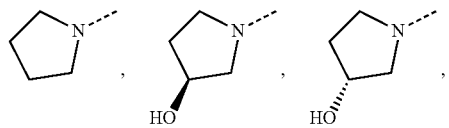

-continued

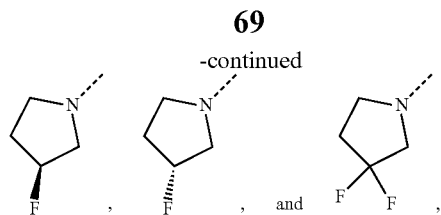

and other variables are as defined herein.

In some embodiments of the present disclosure, L is selected from —CH₂— and

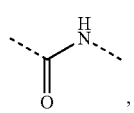

and other variables are as defined herein.

In some embodiments of the present disclosure, $R_c$ is selected from H, F, Cl, Br, I, OH, NH₂, CN, CH₃, CHF₂, CH₂F, CF₃, CH₂CH₃, CH₂CHF₂, CH₂CH₂F₃, CH₂CF₃,

—OCH₃ and

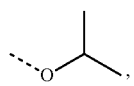

and other variables are as defined herein.

In some embodiments of the present disclosure, $R_3$ is selected from phenyl, pyridyl, —CH₃,

and cyclobutyl each of which is independently optionally substituted with 1, 2 or 3 k, and other variables are as defined herein.

In some embodiments of the present disclosure, $R_3$ is selected from

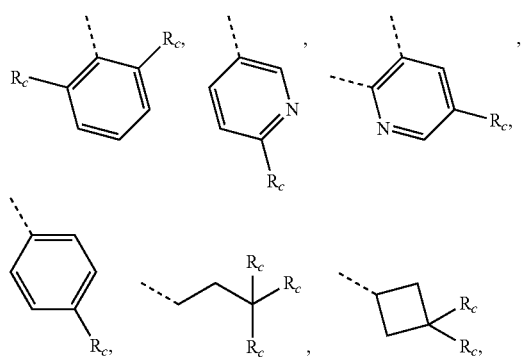

-continued

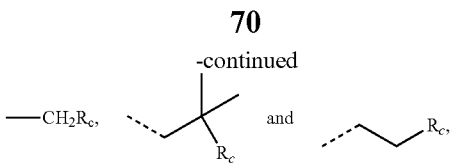

and other variables are as defined herein.

In some embodiments of the present disclosure, $R_3$ is selected from

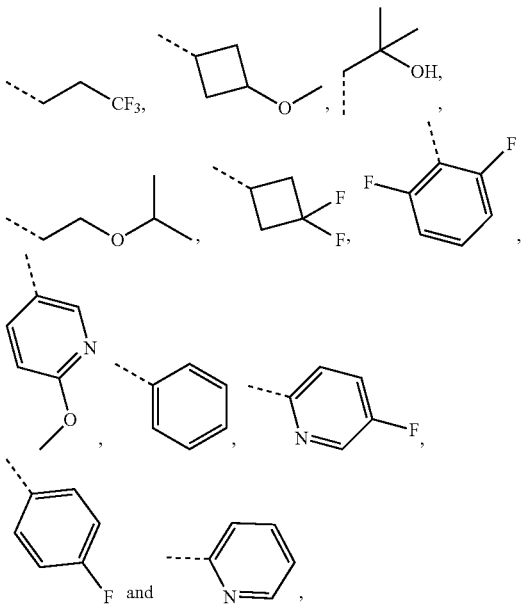

and other variables are as defined herein.

In some embodiments of the present disclosure, structural unit -L-R₃ is selected from

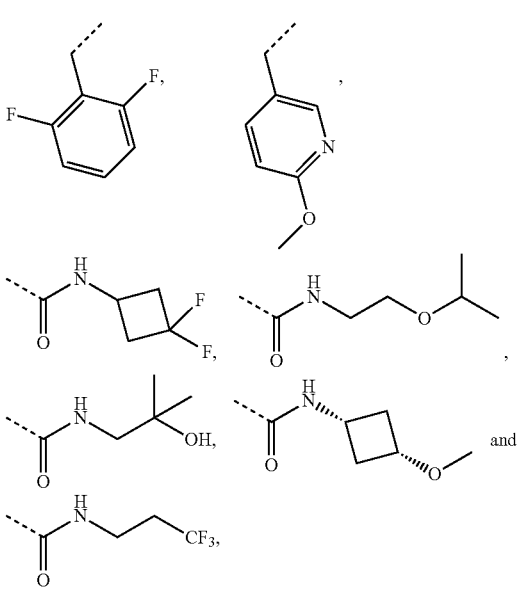

and other variables are as defined herein.

In some embodiments of the present disclosure, a compound, an isomer or a pharmaceutically acceptable salt thereof are selected from wherein, R₁, R₂, n, T₂, L and R₃ are as defined herein.

The present disclosure also provides an embodiment I.

Embodiment I provides a compound of formula (I), an isomer or a pharmaceutically acceptable salt thereof.

wherein;

R$_1$ is selected from H, F, Cl, Br, I, OH, NH$_2$ and CN;

R$_2$ is independently selected from H, F, Cl, Br, I, OH, NH$_2$, CN, and C$_{1-3}$ alkyl, and the C$_{1-3}$ alkyl is optionally substituted with 1, 2 or 3 R$_a$;

n is selected from 0, 1, 2, 3, 4, 5 and 6;

T$_2$ is selected from CH and N;

structural unit is selected from

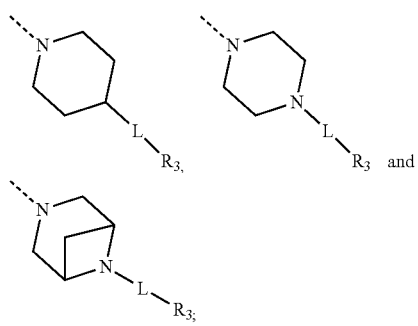

L is selected from —CH$_2$— and

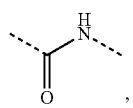

and the —CH$_2$— is optionally substituted with 1 or 2 R$_b$;

R$_3$ is selected from phenyl, 5-6 membered heteroaryl, C$_{3-8}$ cycloalkyl, C$_{1-8}$ alkyl and C$_{1-6}$ alkoxy, each of which is independently optionally substituted with 1, 2 or 3 R$_c$;

R$_a$ is independently selected from H, F, Cl, Br, I, OH, NH$_2$ and CN;

R$_b$ is independently selected from H, F, Cl, Br, I, OH, NH$_2$, CN and CH$_3$;

R$_c$ is independently selected from H, F, Cl, Br, I, OH, NH$_2$, CN, C$_{1-3}$ alkoxy and C$_{1-3}$ alkoxy, and the C$_{1-3}$ alkoxy and C$_1$-alkoxy are independently optionally substituted with 1, 2 or 3 R;

R is independently selected from H, F, Cl, Br and I; and

"hetero" of the 5-6 membered heteroaryl is independently selected from: N, O, S, NH, and the number of the heteroatoms or heteroatom groups is independently selected from 1, 2, 3, and 4.

In some embodiments of the present disclosure, R$_1$ is CN, and other variables are as defined herein.

In some embodiments of the present disclosure, R$_2$ is selected from H, F, Cl, Br, I, OH, CH$_3$, CHF$_2$, CH$_2$F, CF$_3$, CH$_2$CH$_3$, CH$_2$CHF$_2$, CH$_2$CH$_2$F, CH$_2$CF$_3$ and

and other variables are as defined herein.

In some embodiments of the present disclosure, R$_2$ is selected from H, F, Cl, Br, I and OH.

In some embodiments of the present disclosure, n is selected from 0, 1 and 2, and other variables are as defined herein.

In some embodiments of the present disclosure, structural unit

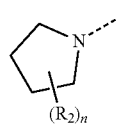

is selected from

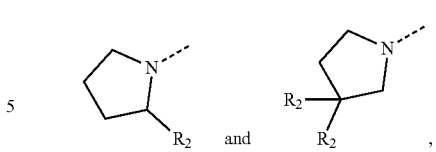

and other variables are as defined herein.

In some embodiments of the present disclosure, the structural unit

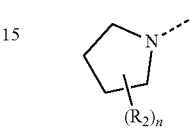

is selected from

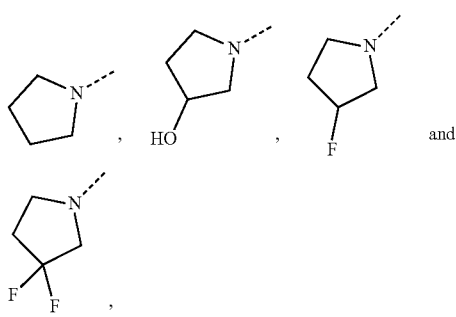

and other variables are herein.

In some embodiments of the present disclosure, structural unit

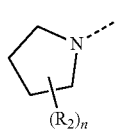

is selected from

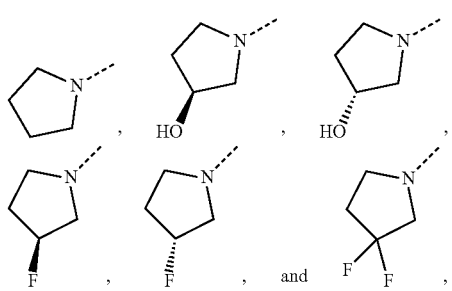

and other variables are as defined herein.

In some embodiments of the present disclosure, L is selected from —CH$_2$— and

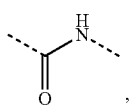

and other variables are as defined herein.

In some embodiments of the present disclosure, $R_c$ is selected from H, F, Cl, Br, I, OH, $NH_2$, CN, $CH_3$, $CHF_2$, $CH_2F$, $CF_3$, $CH_2CH_3$, $CH_2CHF_2$, $CH_2CH_2F$, $CH_2CF_3$,

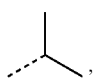

—$OCH_3$ and

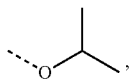

other variables are as defined herein.

In some embodiments of the present disclosure, $R_3$ is selected from phenyl, pyridyl, —$CH_3$,

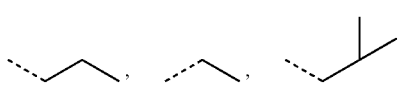

and cyclobutyl, each of which is independently optionally substituted with 1, 2 or 3 $R_c$, and other variables are as defined herein.

In some embodiments of the present disclosure, $R_3$ is selected from

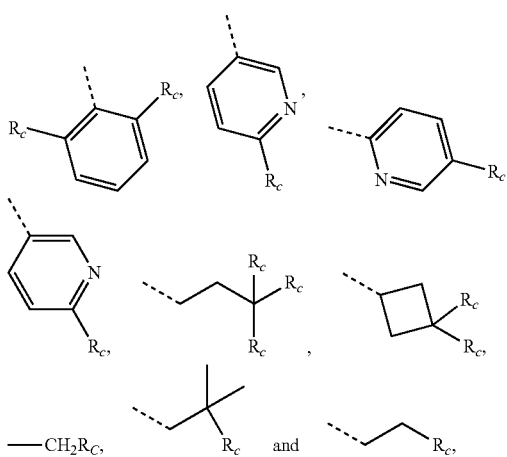

and other variables are as defined herein.

In some embodiments of the present disclosure, $R_3$ is selected from

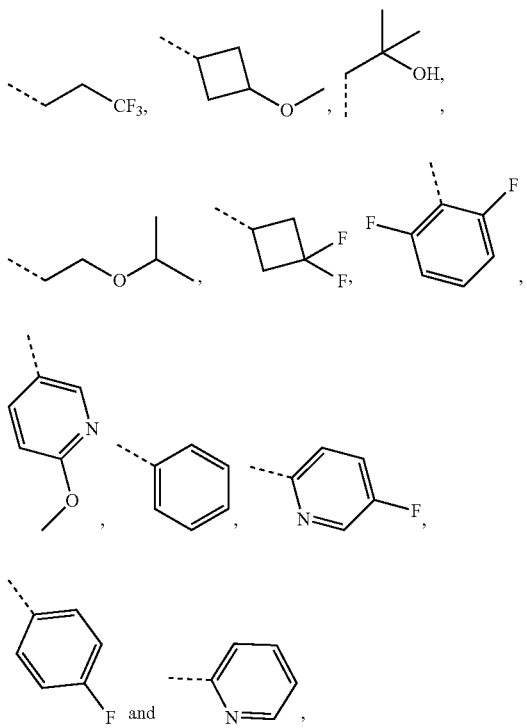

and other variables are as defined herein.

In some embodiments of the present disclosure, the structural unit -L-$R_3$ is selected from

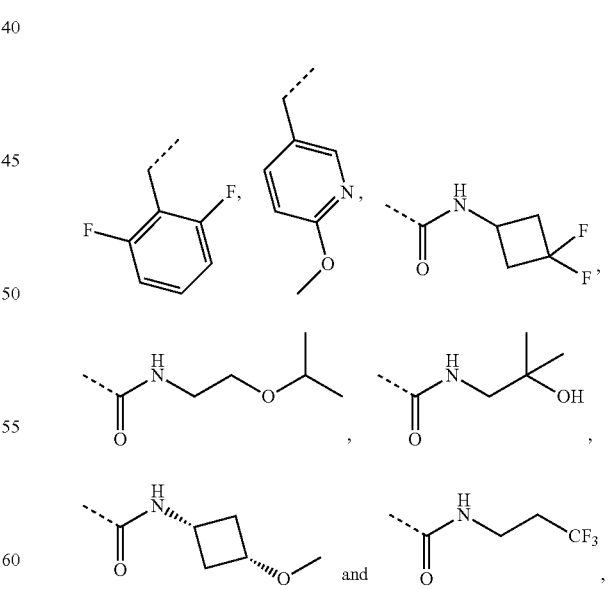

and other variables are as defined herein.

In some embodiments of the present disclosure, a compound, an isomer or a pharmaceutically acceptable salt thereof is selected from (I-1)
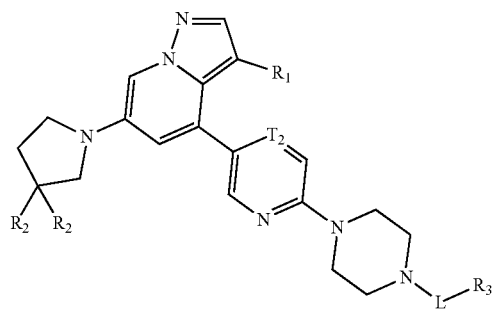

(I-2)
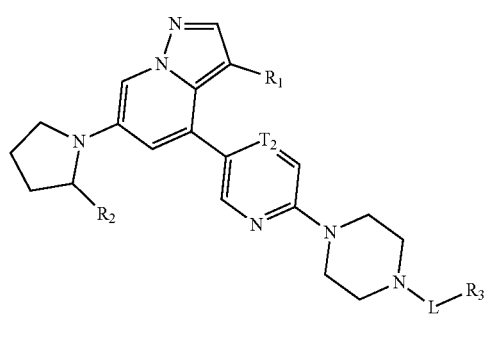

(I-3)
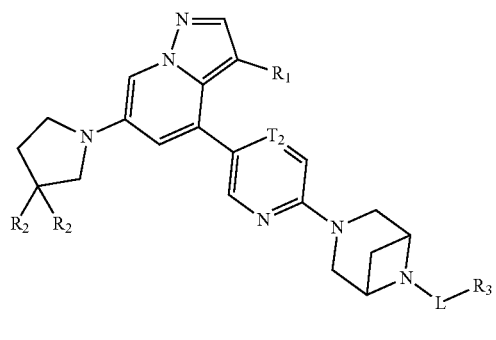

(I-4)
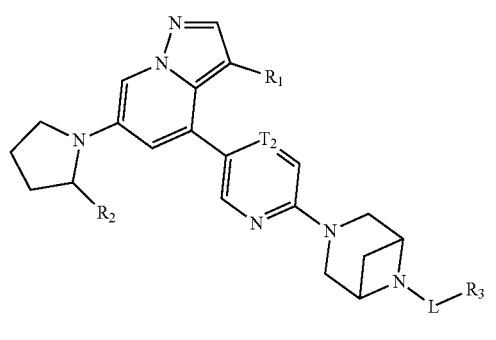

(I-5)
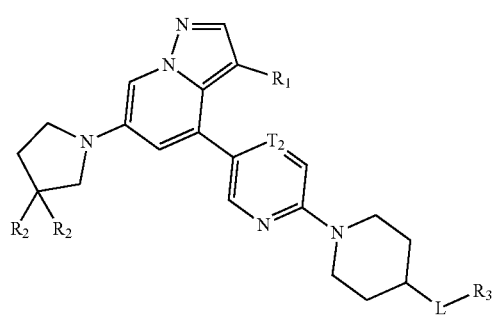

(I-6)
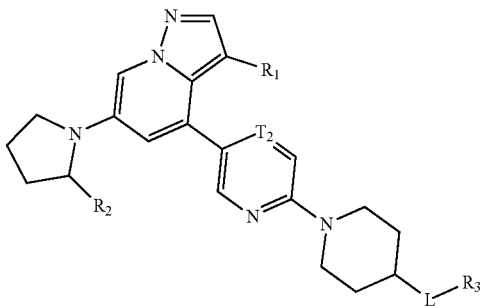

wherein, $R_1$, $R_2$, n, $T_2$. L and R are as defined herein.

The present disclosure also provides an embodiment J. Embodiment J provides a compound of formula (I), an isomer or a pharmaceutically acceptable salt thereof.

(I)
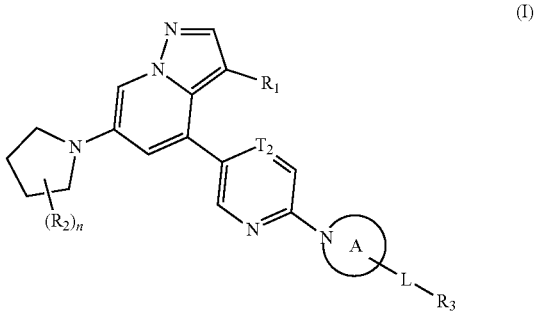

wherein:
$R_1$ is selected from H, F, Cl, Br, I, OH, $NH_2$ and CN;
$R_2$ is independently selected from H, F, Cl, Br, I, OH, $NH_2$, CN, $C_{1-3}$ alkyl and $C_{1-3}$ alkylamino, and the $C_{1-3}$ alkyl and $C_{1-3}$ alkylamino are optionally substituted with 1, 2 or 3 $R_a$;
n is selected from (0, 1, 2, 3, 4, 5 and 6;
$T_2$ is selected from CH and N;
structural unit

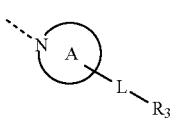

is selected from

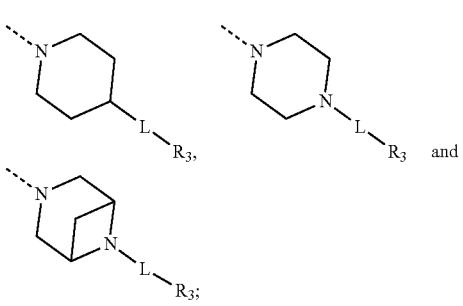

L is selected from —CH$_2$— and

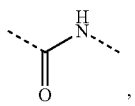, and the —CH$_2$— is optionally substituted with 1 or 2 R$_b$;
R$_3$ is selected from phenyl, 5-6 membered heteroaryl, C$_{3-8}$ cycloalkyl, C$_{1-8}$ alkyl and C$_{1-6}$ alkoxy, each of which is independently optionally substituted with 1, 2 or 3 R$_c$;
R$_a$ is independently selected from H, F, Cl, Br, I, OH, NH$_2$ and CN;
R$_b$ is independently selected from H, F, Cl, Br, I, OH, NH$_2$, CN and CH$_3$;
R$_c$ is independently selected from H, F, Cl, Br, I, OH, NH$_2$, CN, C$_{1-3}$ alkoxy and C$_{1-3}$ alkoxy, and the C$_{1-3}$ alkoxy and C$_1$-alkoxy are independently optionally substituted with 1, 2 or 3 R;
R is independently selected from H, F, Cl, Br and I, and the 5-6 membered heteroaryl comprises 1, 2, 3, or 4 heteroatoms or heteroatom groups selected from N, O, S, and NH.

In some embodiments of the present disclosure, R$_1$ is CN, and other variables are as defined herein.

In some embodiments of the present disclosure, R$_2$ is selected from H, F, Cl, Br, I, OH, CH$_3$, CHF$_2$, CH$_2$F, CF$_3$, CH$_2$CH$_3$, CH$_2$CHF$_2$, CH$_2$CH$_2$F, CH$_2$CF$_3$,

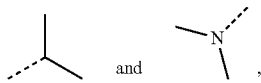, and other variables are as defined herein.

In some embodiments of the present disclosure, R$_2$ is selected from H, F, Cl, Br, I, OH and

, and other variables are as defined herein.

In some embodiments of the present disclosure, n is selected from 0, 1 and 2, and other variables are as defined herein.

In some embodiments of the present disclosure, structural unit

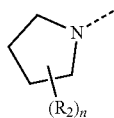

is selected from

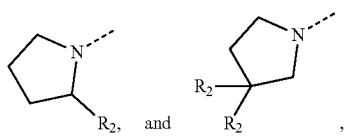, and other variables are as defined herein.

In some embodiments of the present disclosure, structural unit

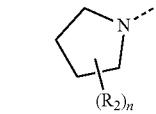

is selected from

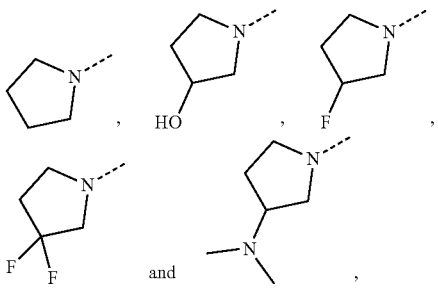, and other variables are as defined herein.

In some embodiments of the present disclosure, structural unit

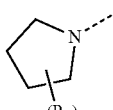

is selected from

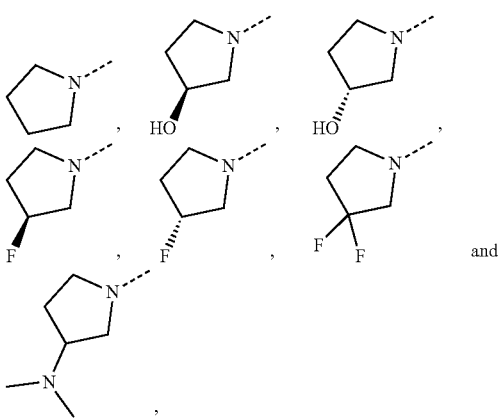, and other variables are as defined herein.

In some embodiments of the present disclosure, L is selected from —CH$_2$— and

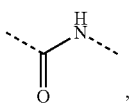, and other variables are as defined herein.

In some embodiments of the present disclosure, R_c is selected from H, F, Cl, Br, I, OH, NH_2, CN, CH_3, CHF_2, CH_2F, CF_3, CH_2CH_3, CH_2CHF_2, CH_2CH_2F, CH_2CF_3,

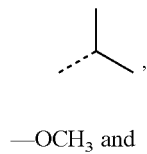

—OCH_3 and

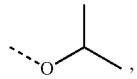

and other variables are as defined herein.

In some embodiments of the present disclosure, R_3 is selected from phenyl, pyridyl, —CH_3,

and cyclobutyl, each of which is independently optionally substituted with 1, 2 or 3 R_c, an other variables are as defined herein.

In some embodiments of the present disclosure, R_3 is selected from

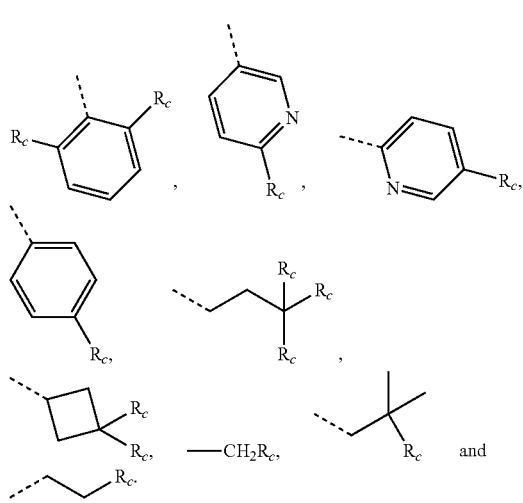

In some embodiments of the present disclosure, R_3 is selected from from

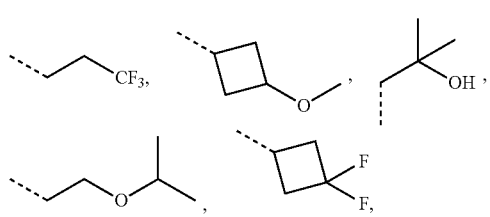

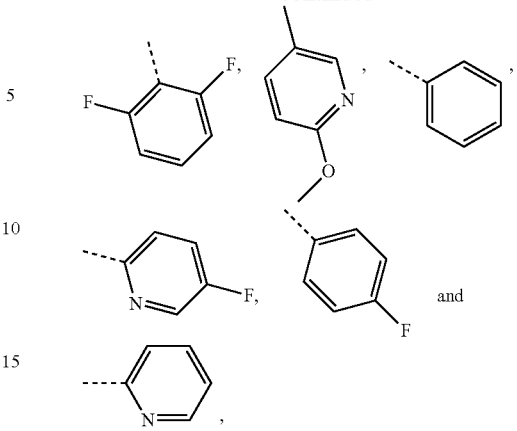

and other variables are as defined herein.

In some embodiments of the present disclosure, the structural unit -L-R_3 is selected from

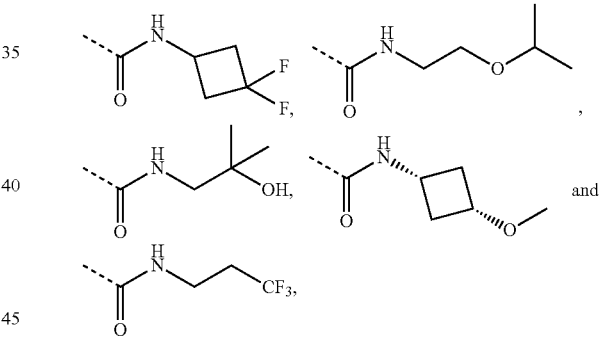

and other variables are as defined in the herein.

In some embodiments of the present disclosure, a compound, an isomer or a pharmaceutically acceptable salt thereof is selected from (I-1)

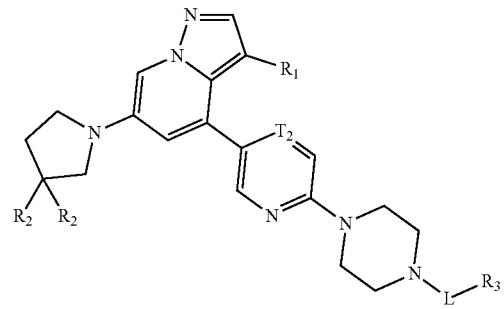

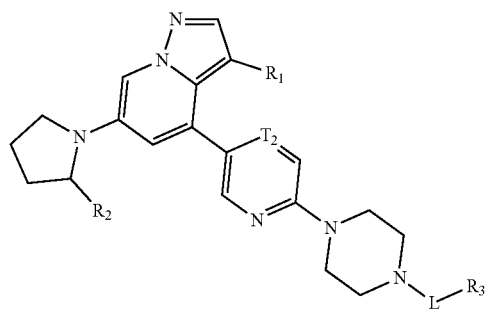
(I-2)

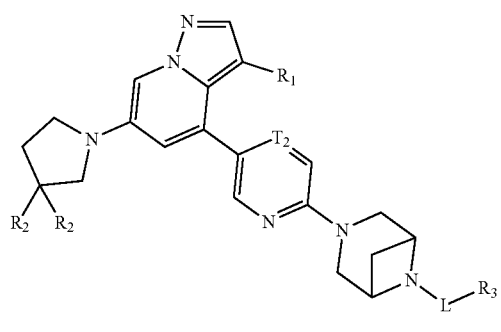
(I-3)

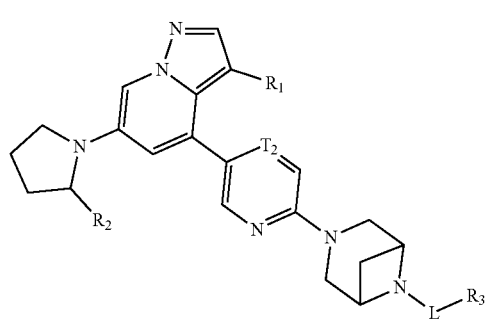
(I-4)

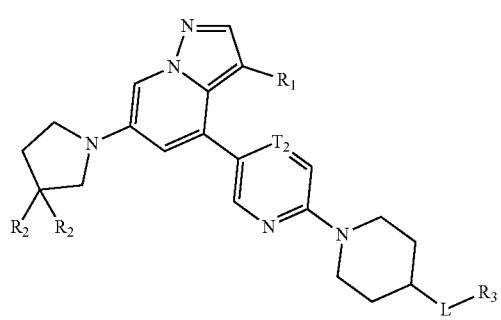
(I-5)

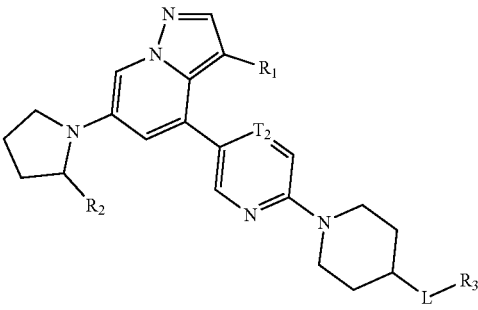
(I-6)

wherein, $R_1$, $R_2$, n, $T_2$, L and $R_3$ are as defined herein.

The present disclosure also provides an embodiment K. Embodiment K provides a compound of formula (I) or a pharmaceutically acceptable salt thereof,

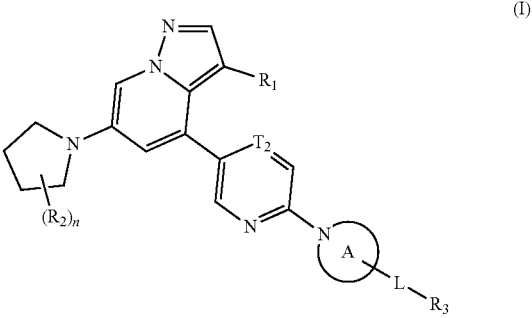
(I)

wherein:
$R_1$ is selected from H, F, Cl, Br, I, OH, $NH_2$ and CN;
$R_2$ is independently selected from H, F, Cl, Br, I, OH, $NH_2$, CN, $C_{1-3}$ alkyl and $C_{1-3}$ alkylamino, and the $C_{1-3}$ alkyl and $C_{1-3}$ alkylamino are optionally substituted with 1, 2 or 3 $R_a$;
n is selected from 0, 1, 2, 3, 4, 5 and 6.
$T_2$ is selected from CH and N;
structural unit

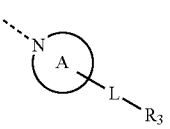

is selected from from

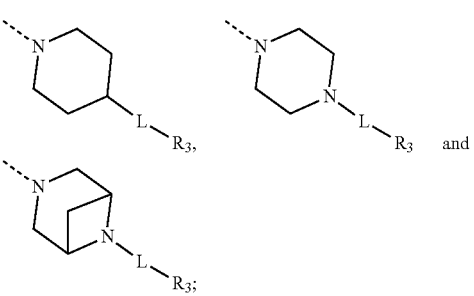

L is selected from —CH$_2$— and

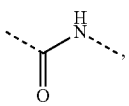

and the —CH$_2$— is optionally substituted with 1 or 2 R$_b$;
R$_3$ is selected from phenyl, pyridyl, azaindolyl, cyclobutyl, C$_{1-8}$ alkyl and C$_{1-6}$ alkoxy, each of which is independently optionally substituted with 1, 2 or 3 R$_c$.
R$_a$ is independently selected from H, F, Cl, Br, I, OH, NH$_2$ and CN;
R$_b$ is independently selected from H, F, Cl, Br, I, OH, NH$_2$, CN and CH$_3$;
R$_c$ is h independently selected from H, F, Cl, Br, I, OH, NH$_2$, CN, C$_{1-3}$ alkoxy and C$_{1-3}$ alkoxy, and the C$_{1-3}$ alkoxy and C$_1$-alkoxy are independently optionally substituted with 1, 2 or 3 R; and
R is independently selected from H, F, Cl, Br and I.

In some embodiments of the present disclosure, R$_1$ is CN, and other variables are as defined herein.

In some embodiments of the present disclosure, R$_2$ is selected from H, F, Cl, Br, I, OH, CH$_3$, CHF$_2$, CH$_2$F, CF$_3$, CH$_2$CH$_3$, CH$_2$CHF$_2$, CH$_2$CH$_2$F, CH$_2$CF$_3$,

and OCH$_3$, and other variables are as defined herein.

In some embodiments of the present disclosure, R$_2$ is selected from H, F, Cl, Br, I, OH,

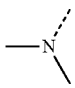

and OCH$_3$, and other variables are as defined herein.

In some embodiments of the present disclosure, n is selected from 0, 1 and 2, and other variables are as defined herein.

In some embodiments of the present disclosure, structural unit

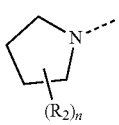

is selected from

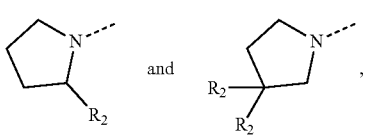

and other variables are as defined herein.

In some embodiments of the present disclosure, structural unit

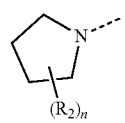

is selected

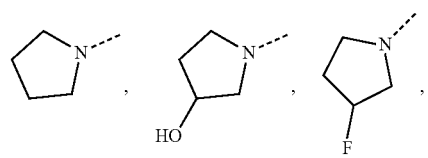

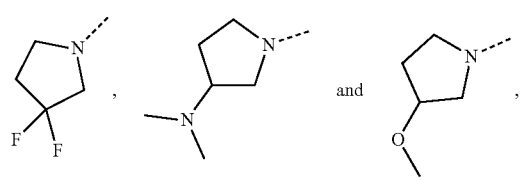

and other variables are as defined herein.

In some embodiments of the present disclosure, structural unit

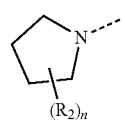

is selected from

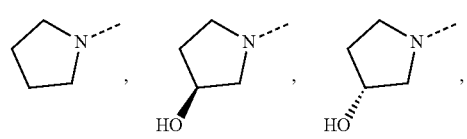

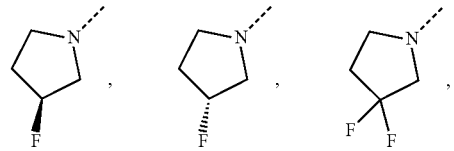

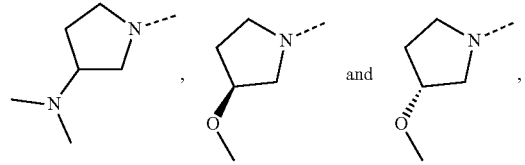

and other variables are as defined herein.

In some embodiments of the present disclosure, L is selected from —CH$_2$— and

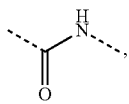

and other variables are as defined herein.

In some embodiments of the present disclosure, $R_e$ is selected from H, F, Cl, Br, I, OH, $NH_2$, CN, $CH_2$, $CHF_2$, $CH_2F$, $CF_3$, $CH_2CH_3$, $CH_2CHF_2$, $CH_2CH_2F$, $CH_2CF_3$,

—OCH— and

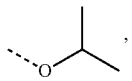

and other variables are as defined herein.

In some embodiments of the present disclosure, $R_3$ is selected from phenyl, pyridyl, 7-azaindolyl, —$CH_3$,

and cyclobutyl, each of which is independently optionally substituted with 1, 2 or 3 $R_c$, and other variables are as defined herein.

In some embodiments of the present disclosure, $R_3$ is selected from

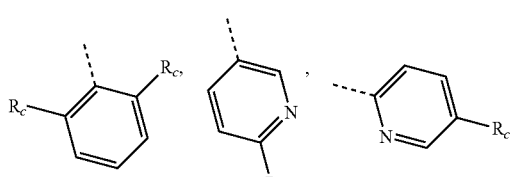

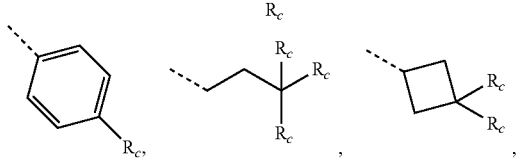

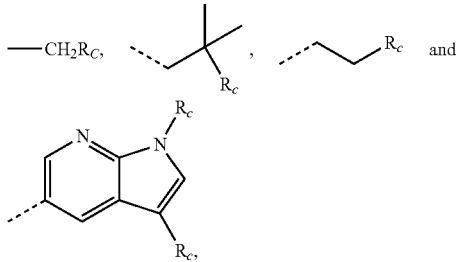

and other variables are as defined herein.

In some embodiments of the present disclosure, $R_3$ is selected from

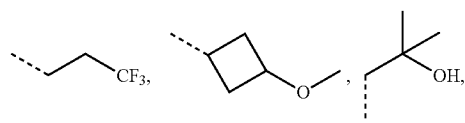

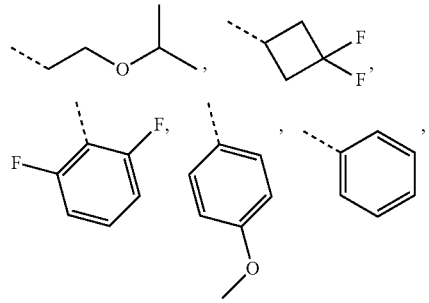

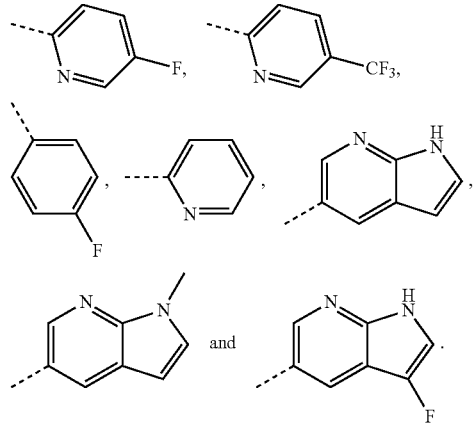

and other variables are as defined herein.

In some embodiments of the present disclosure, the structural unit -L-$R_3$ is selected from

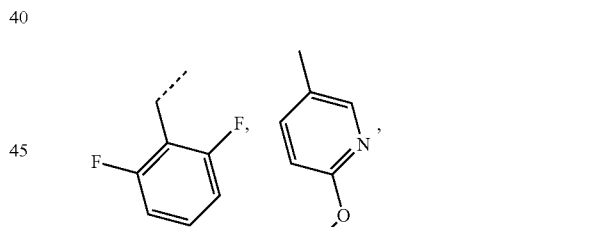

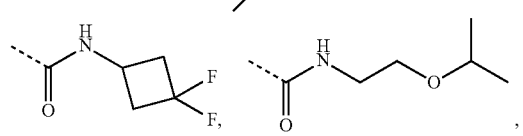

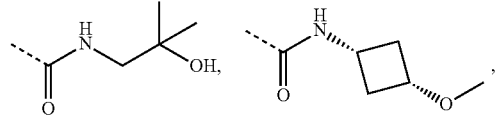

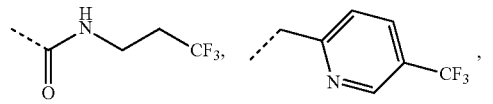

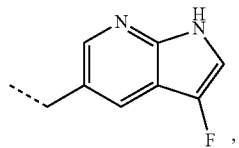

and other variables are as defined herein.

In some embodiments of the present disclosure, a compound or a pharmaceutically acceptable salt thereof is selected from

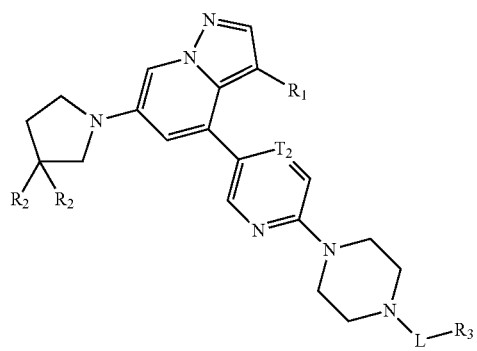
(I-1)

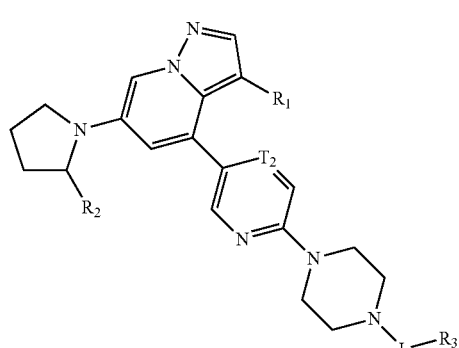
(I-2)

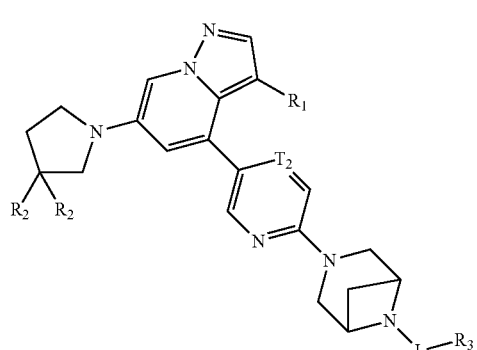
(I-3)

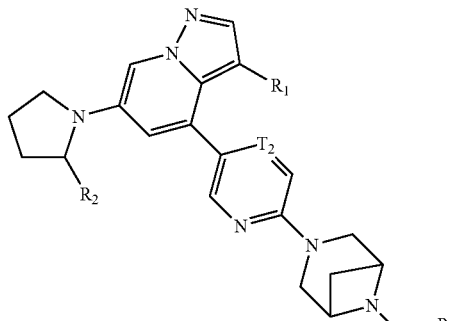
(I-4)

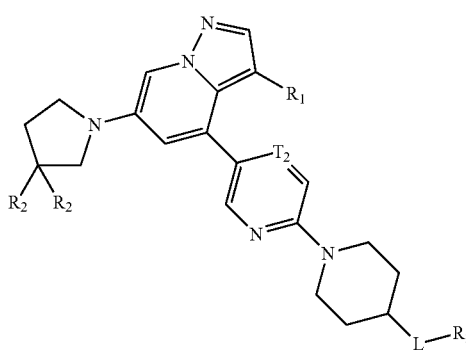
(I-5)

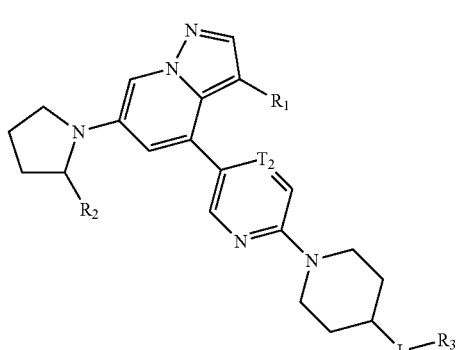
(I-6)

wherein, $R_1$, $R_2$, $T_2$, L and $R_3$ are as defined herein.

Some other embodiments of the present disclosure are obtained from any combination of the above-mentioned variables.

The present disclosure also provides the following compound, an isomer or a pharmaceutically acceptable salt thereof,

91
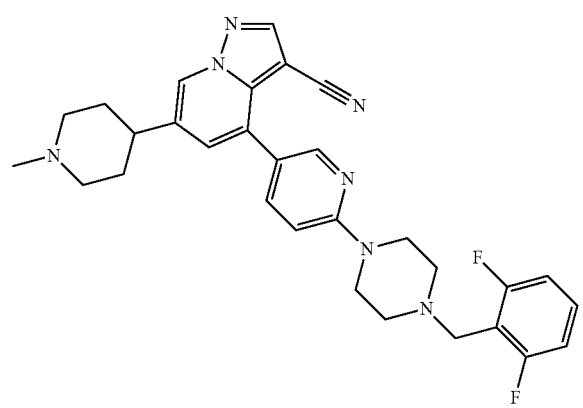
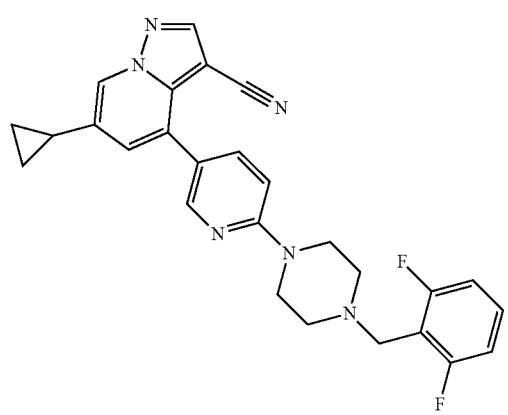
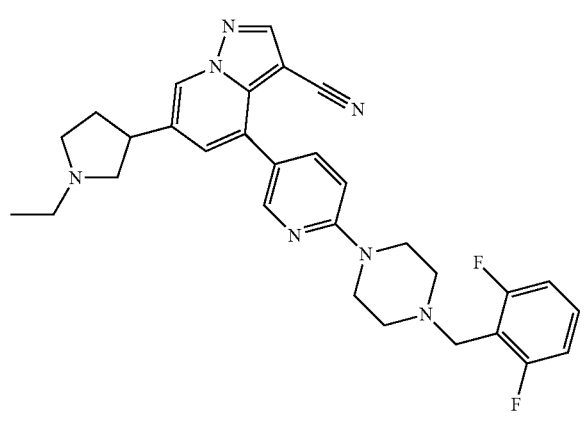
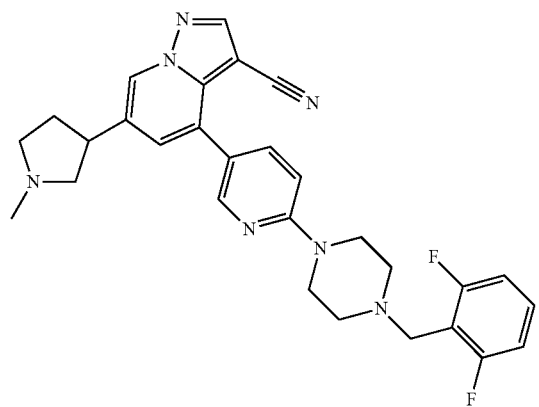
92
-continued
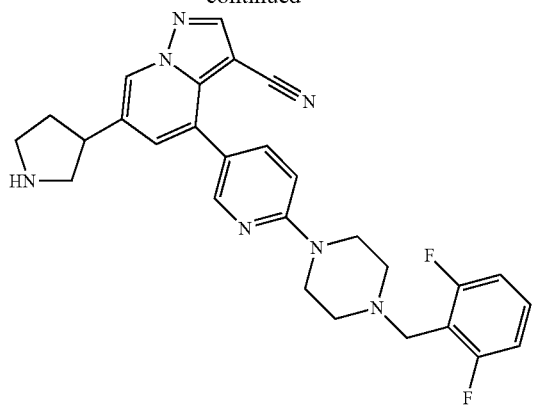
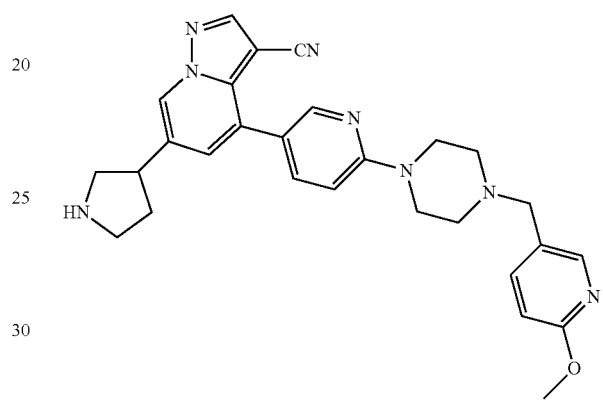
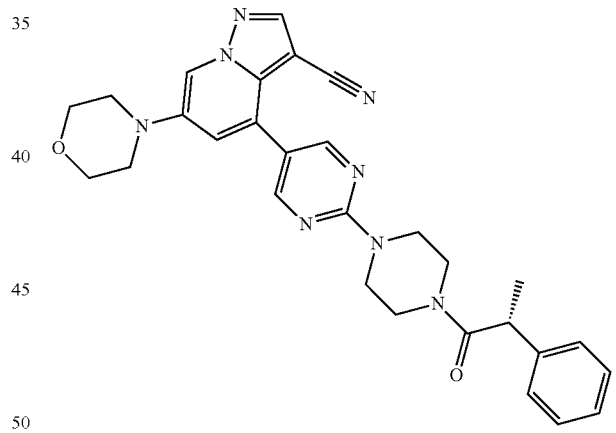
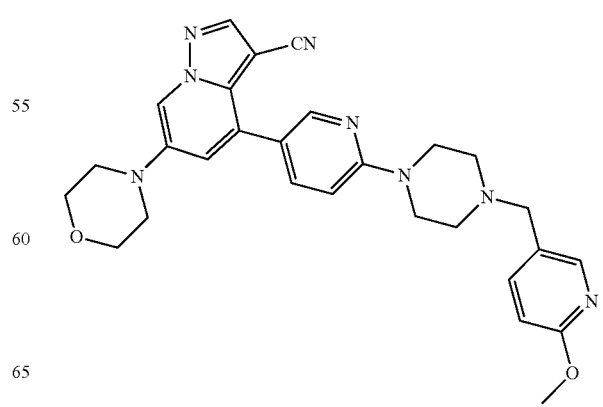

-continued
93
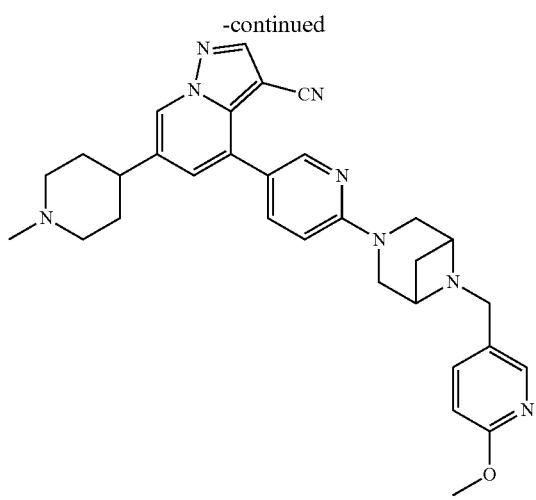
94
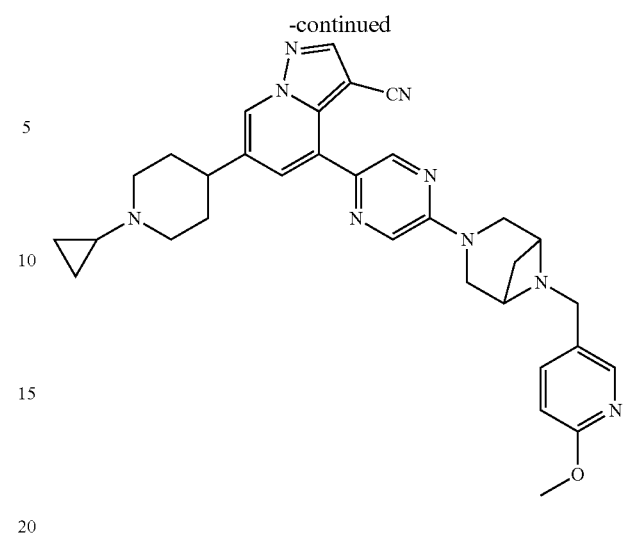
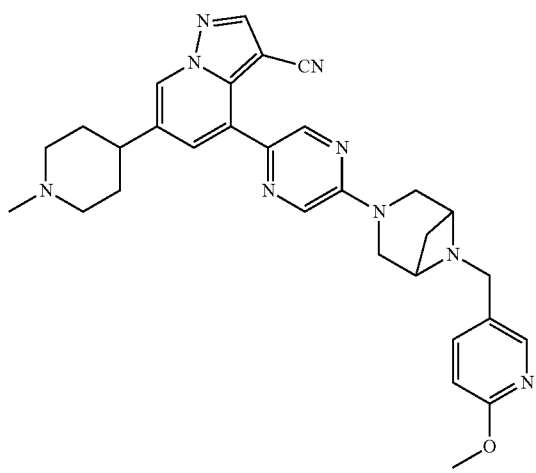
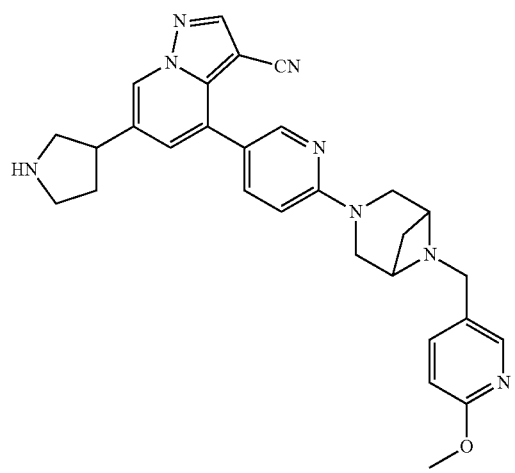
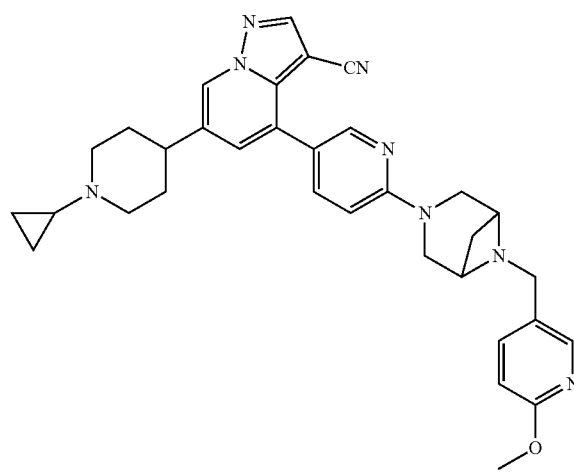
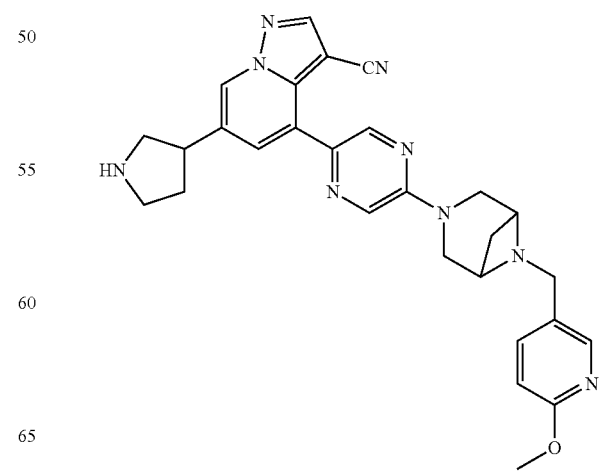

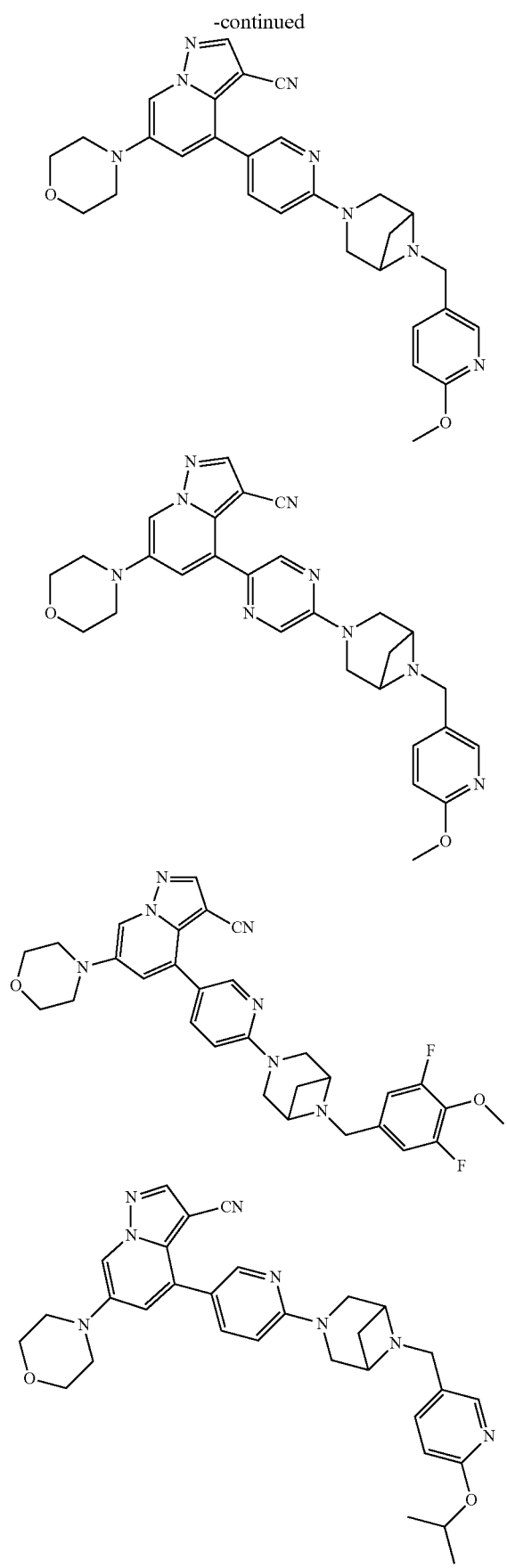
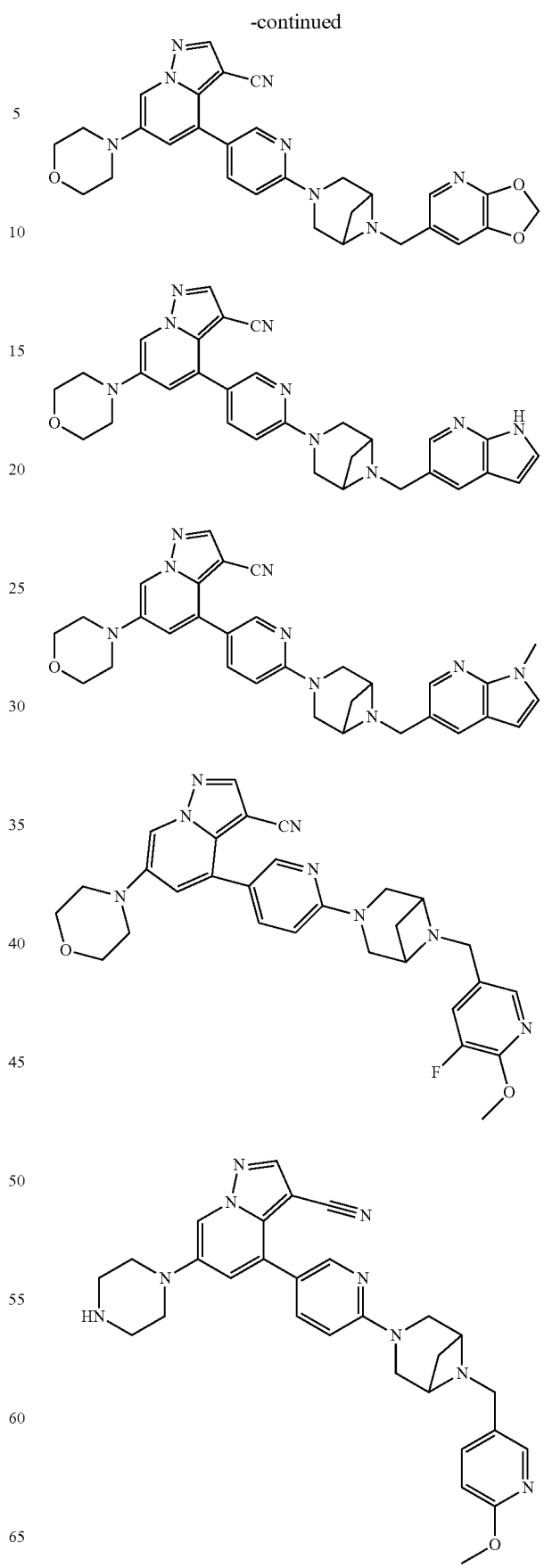

97
-continued
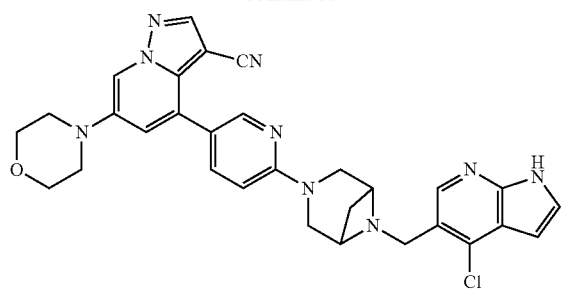 [SMILES: N#Cc1cnn2cc(N3CCOCC3)cc(-c3ccc(N4CC5CC(C4)N5Cc4cnc5[nH]ccc5c4Cl)nc3)c12]
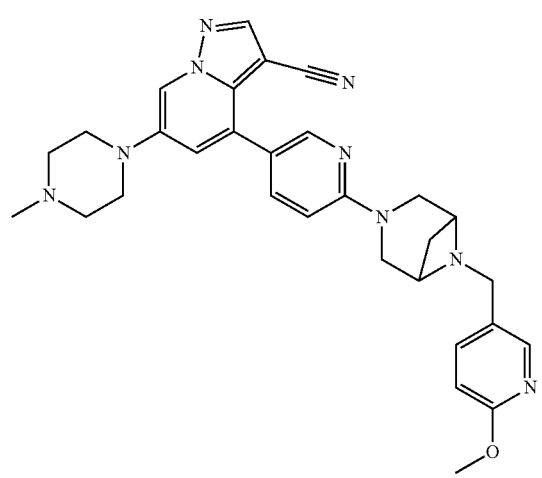
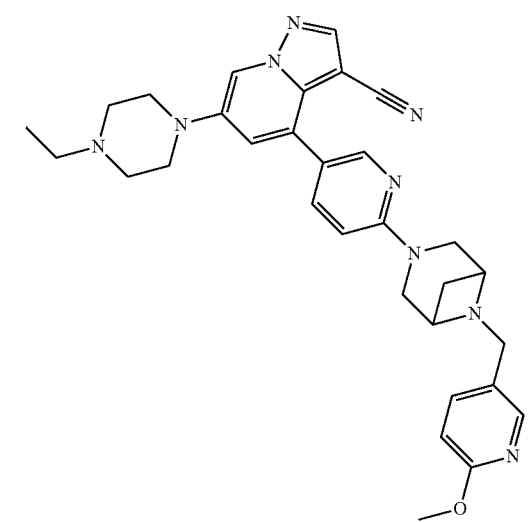
98
-continued
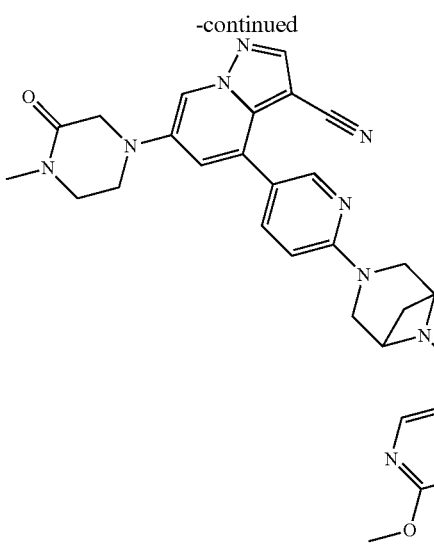
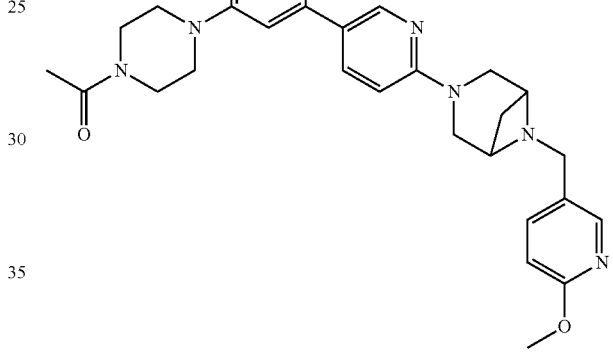
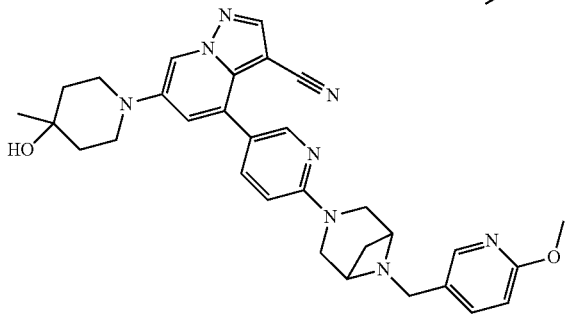
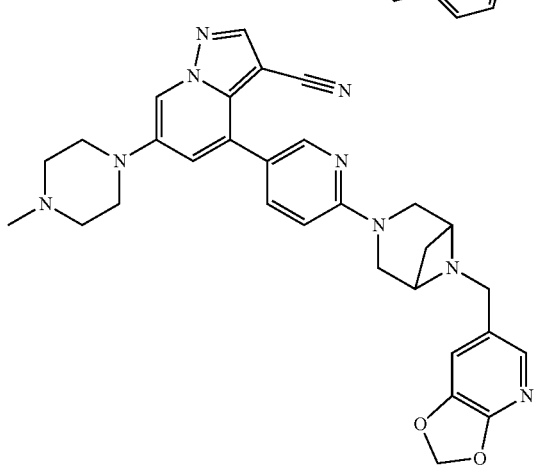

99
-continued
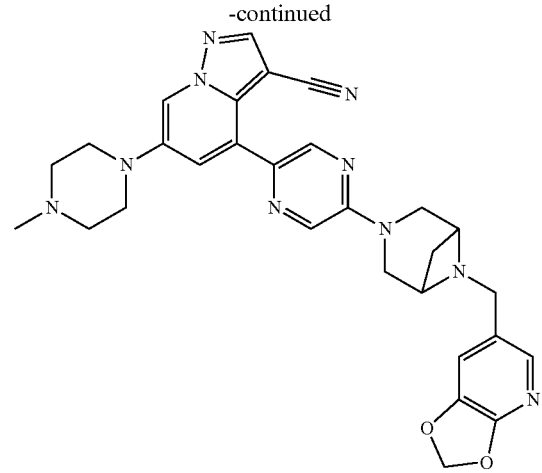
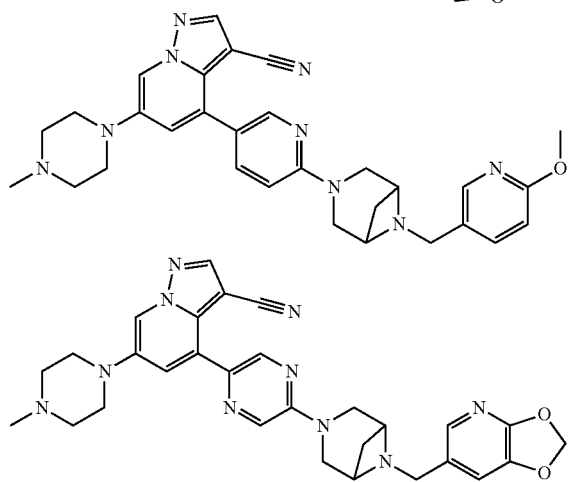
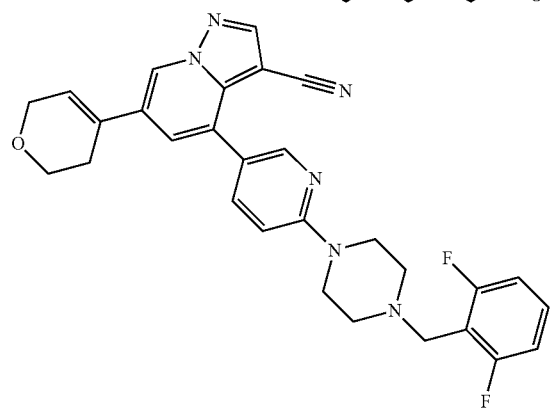
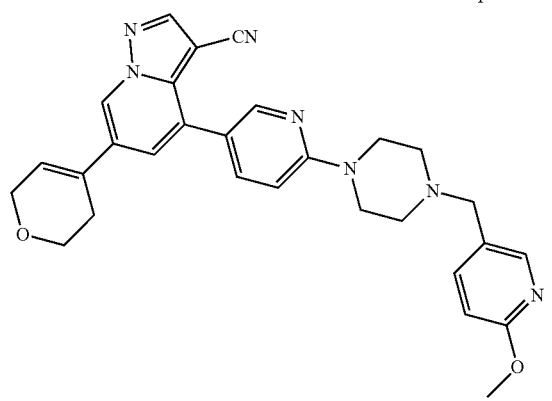
100
-continued
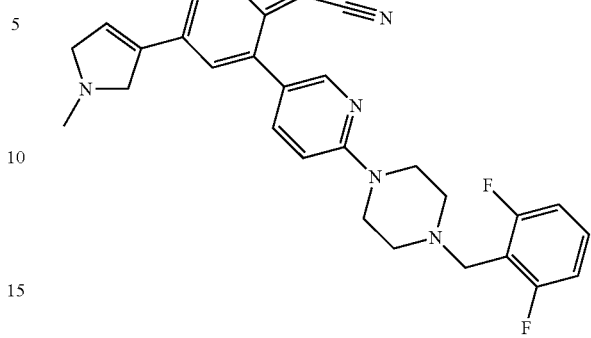
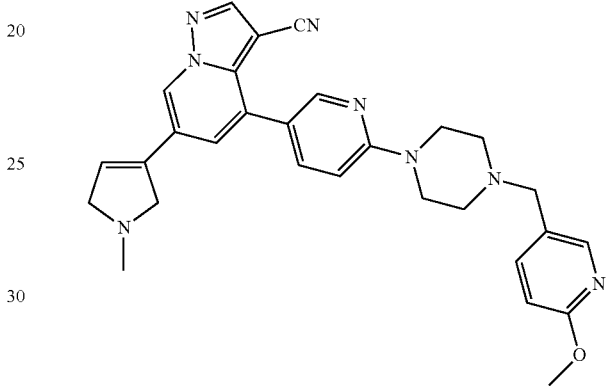
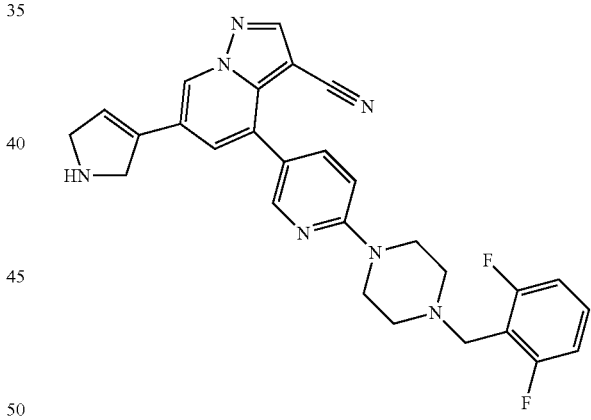
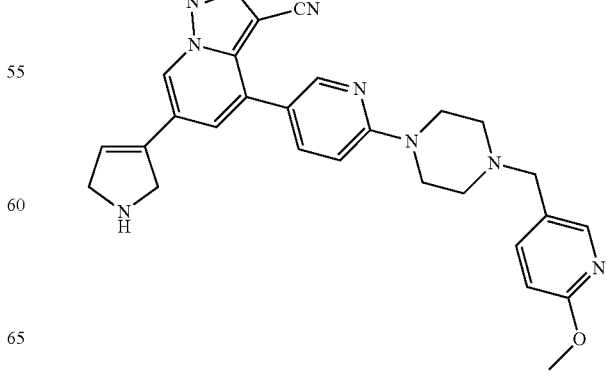

101
-continued
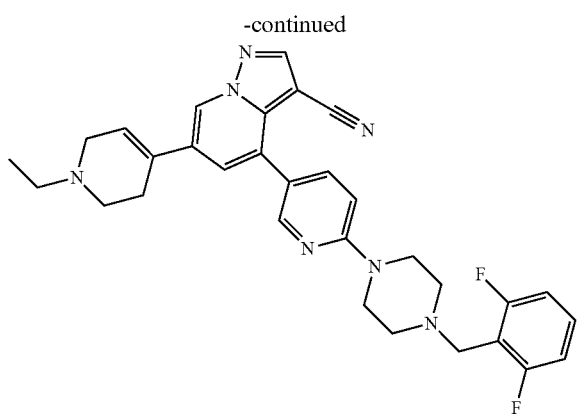
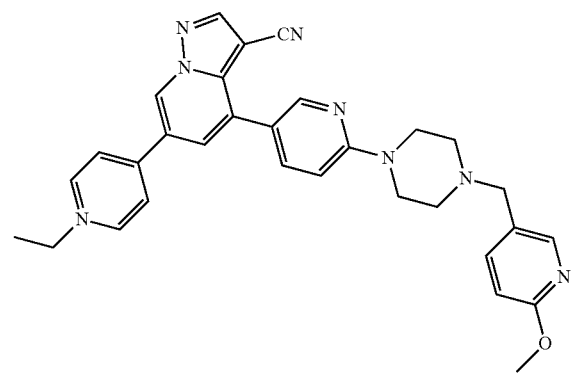
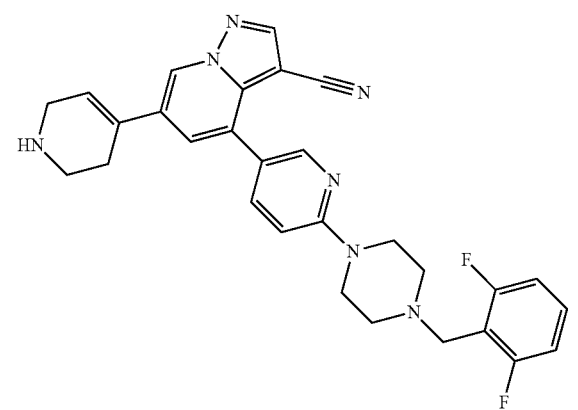
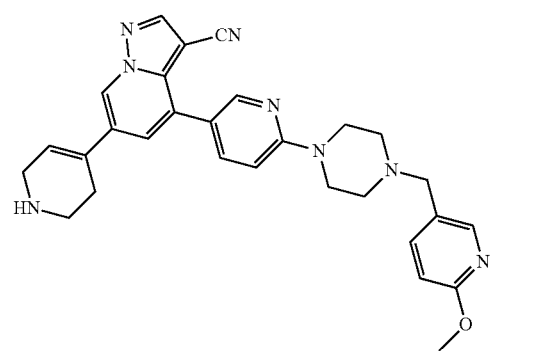
102
-continued
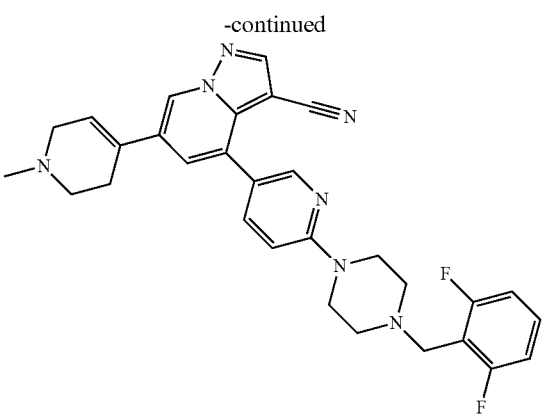
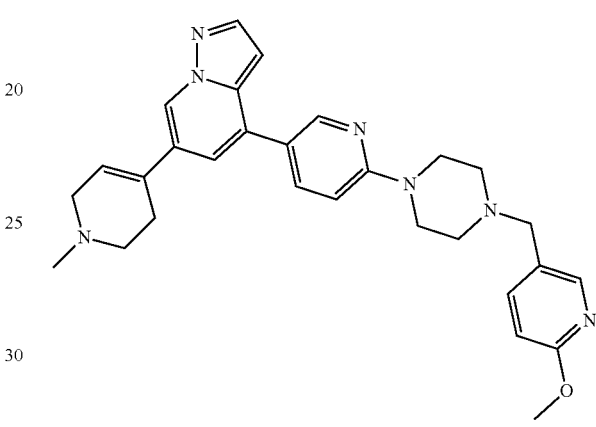
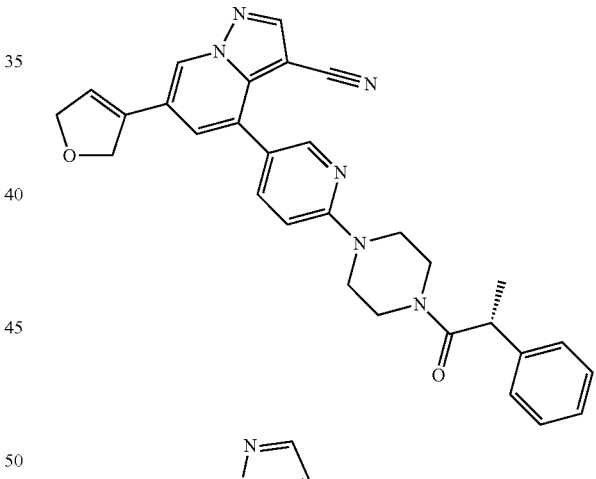
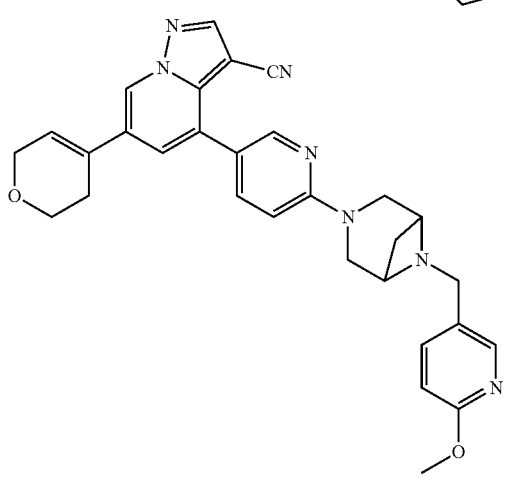

103
-continued
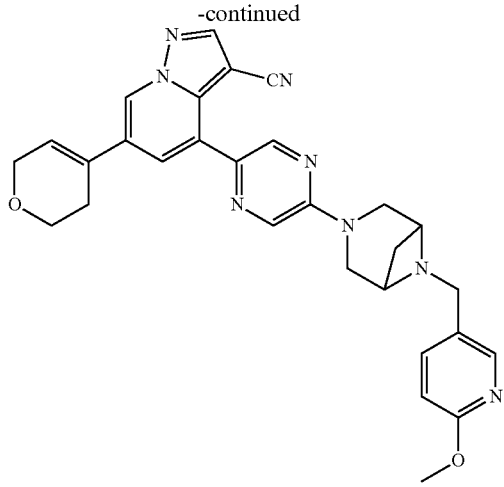
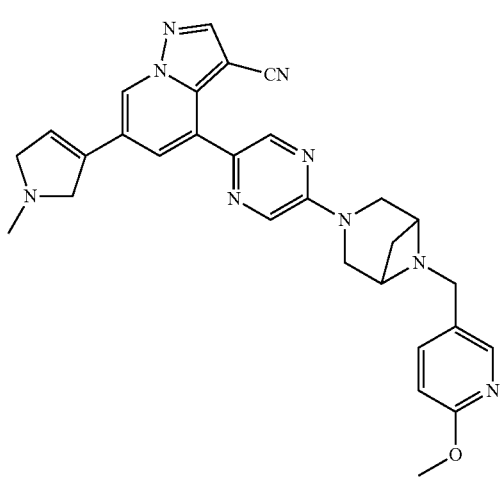
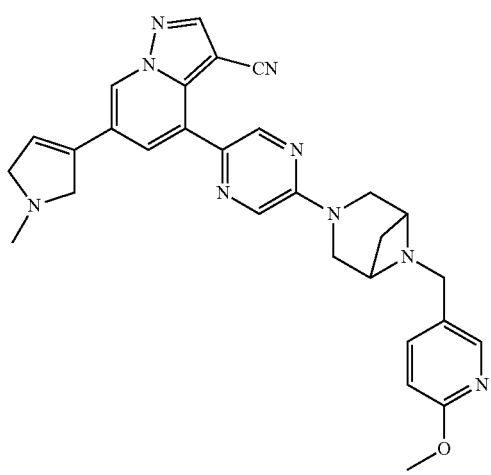
104
-continued
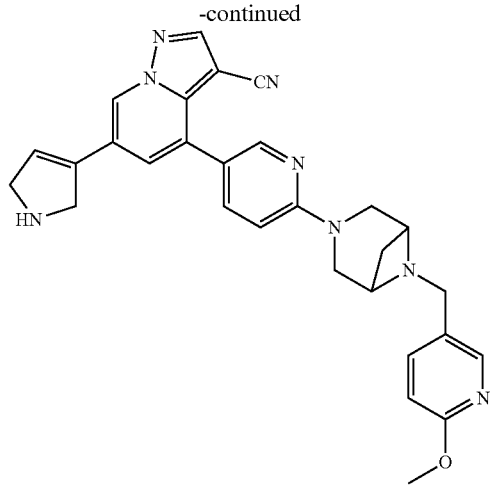
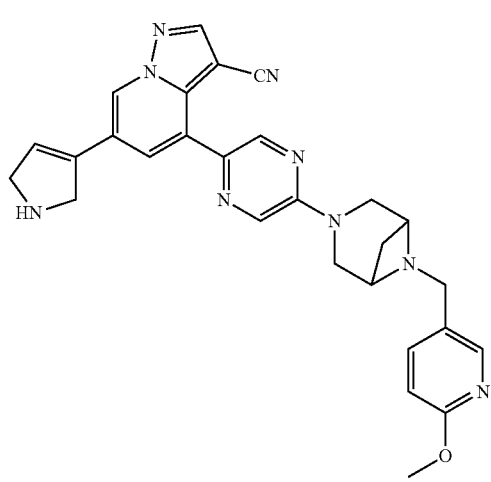
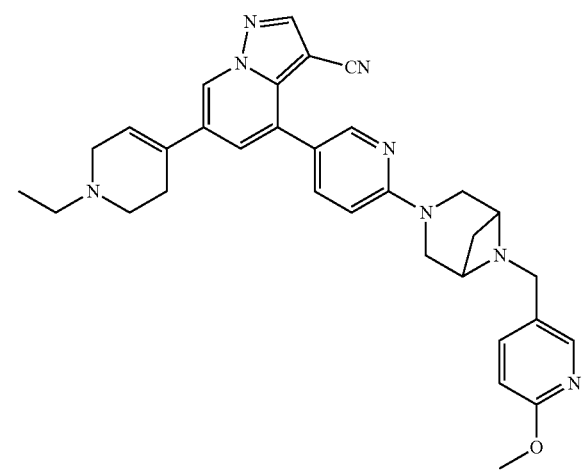

105
-continued
106
-continued
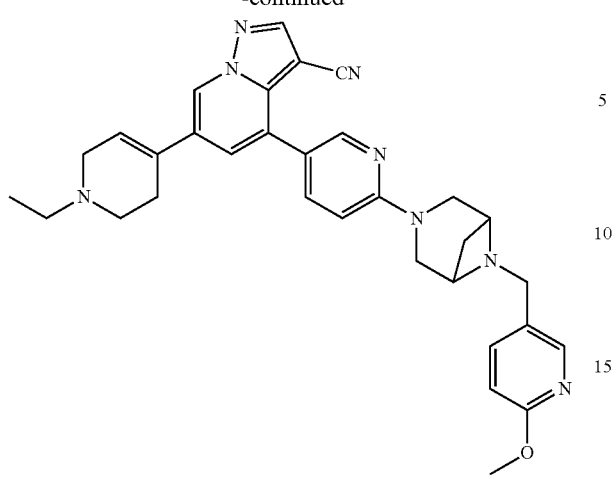
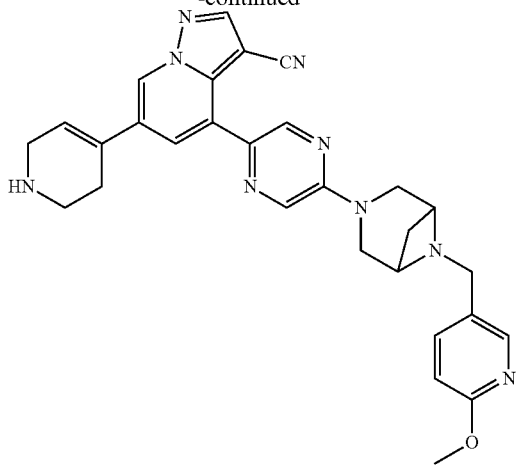
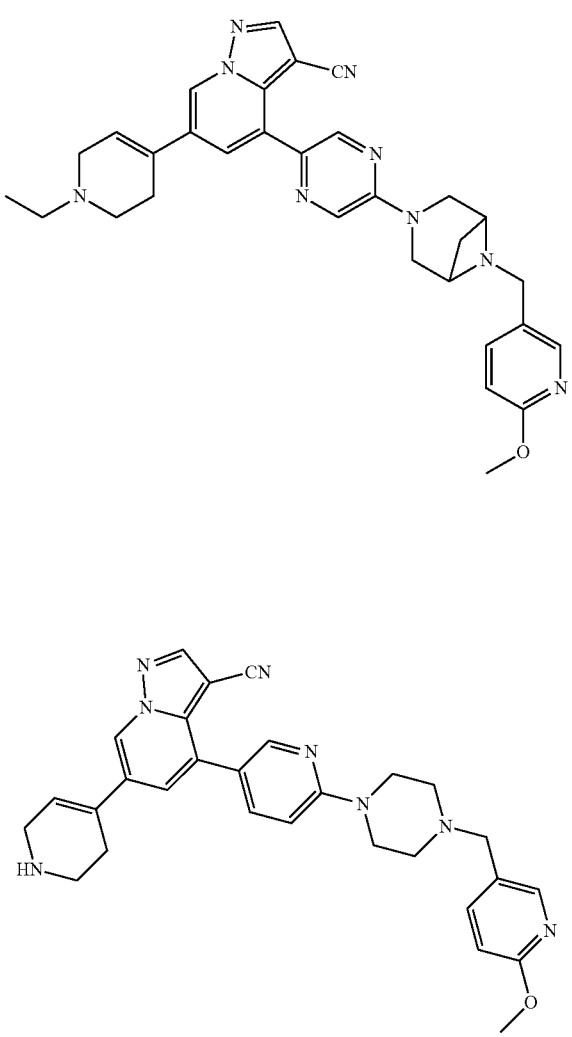
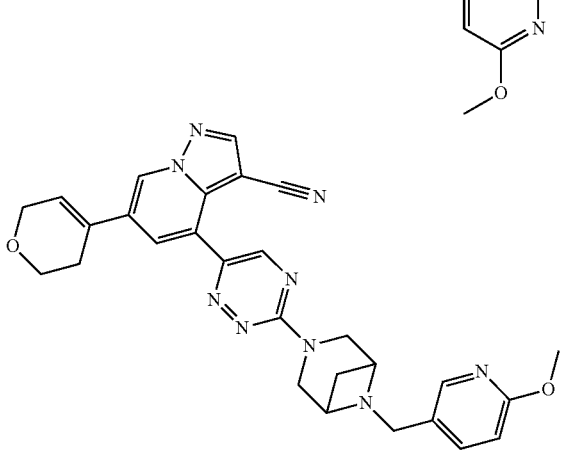

107
-continued
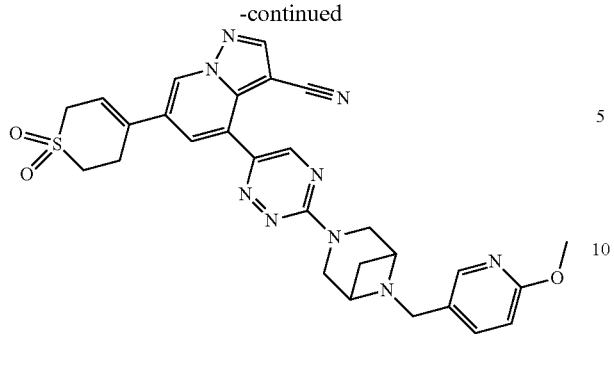
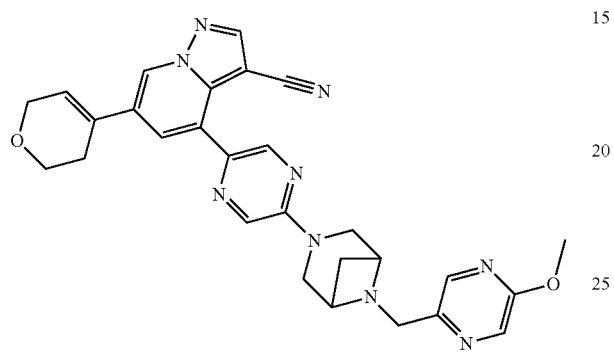
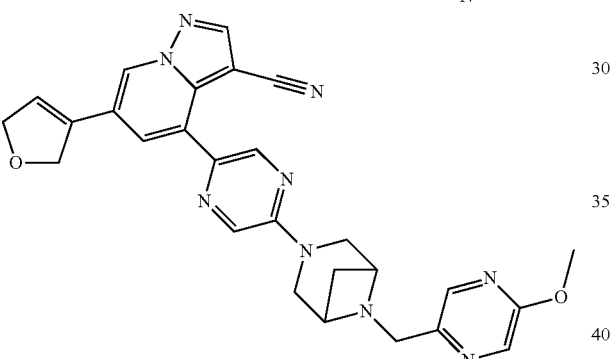
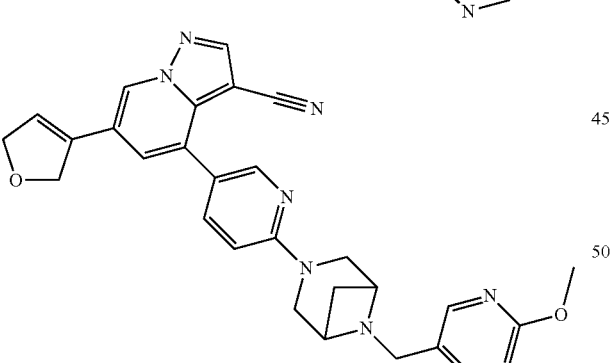
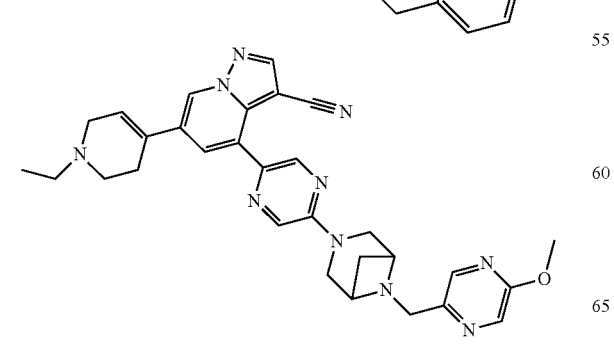
108
-continued
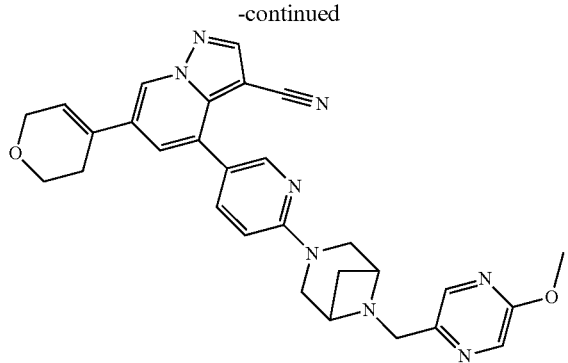
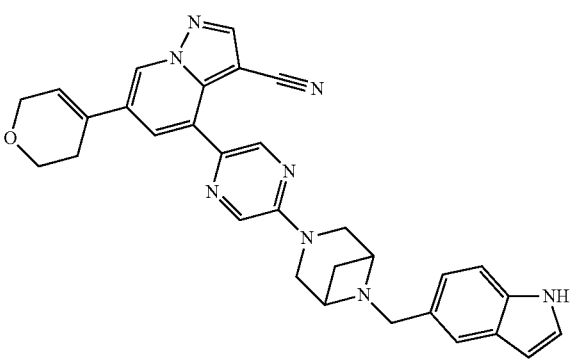
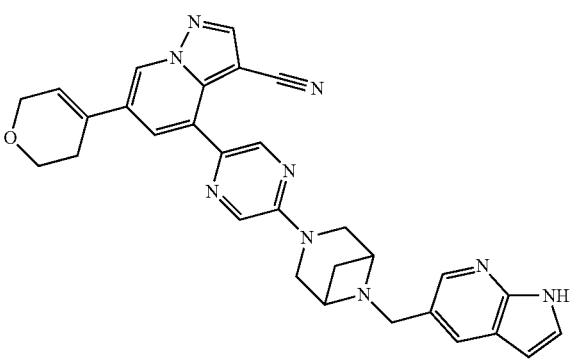
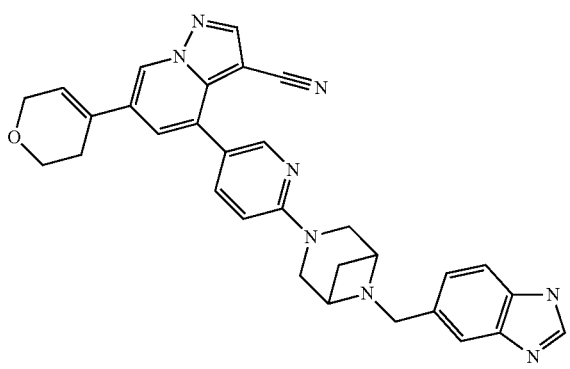

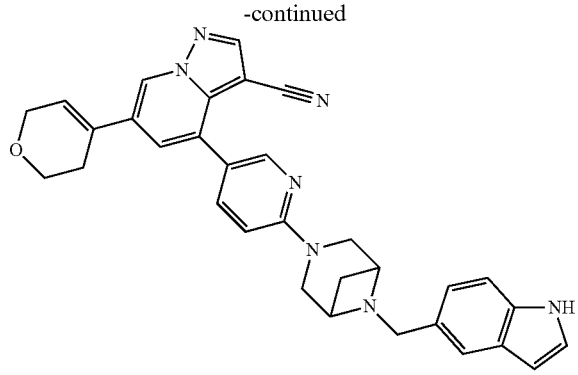
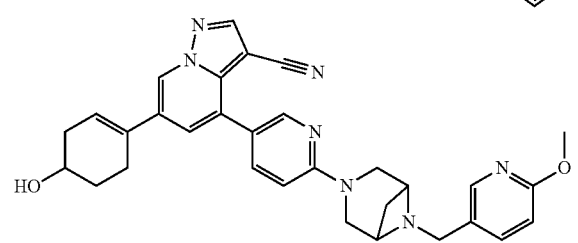
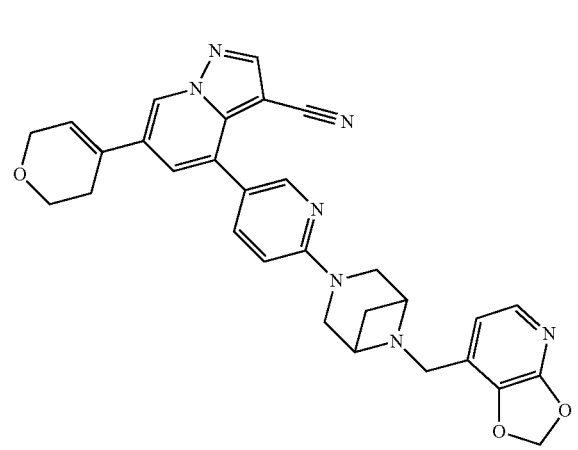
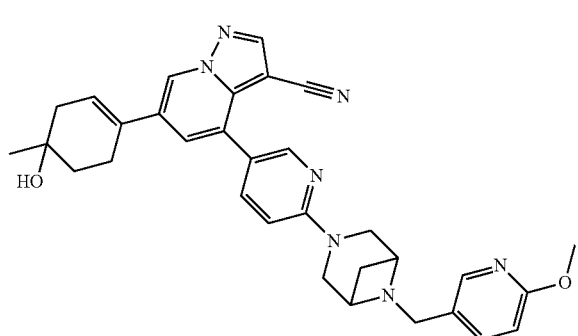
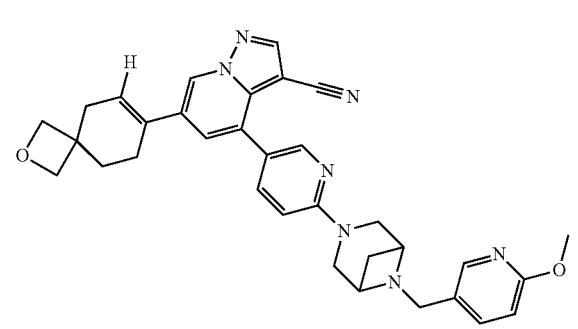
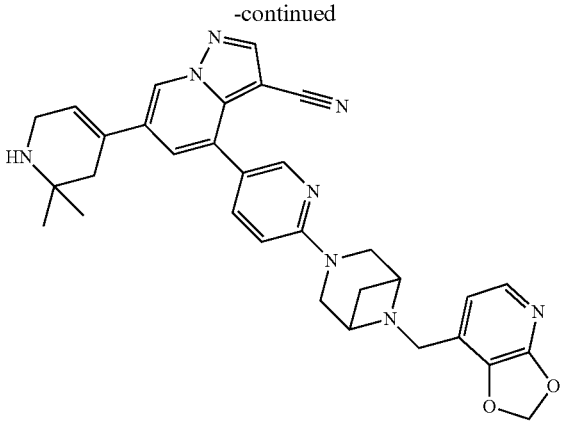
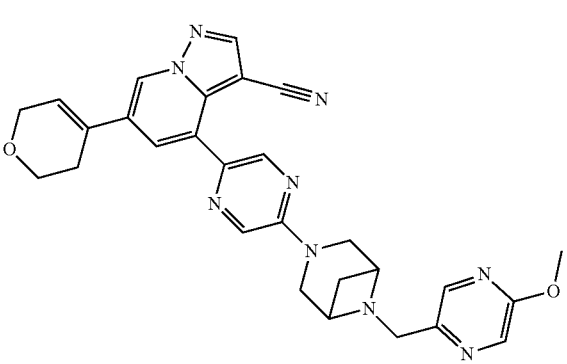
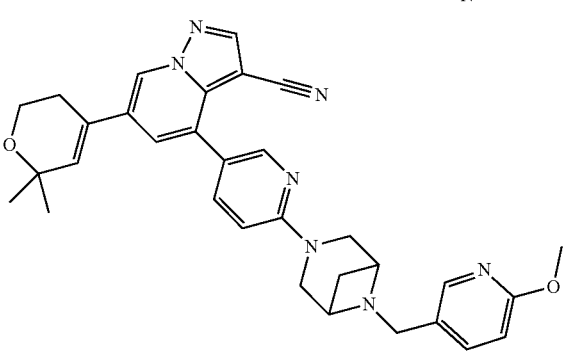
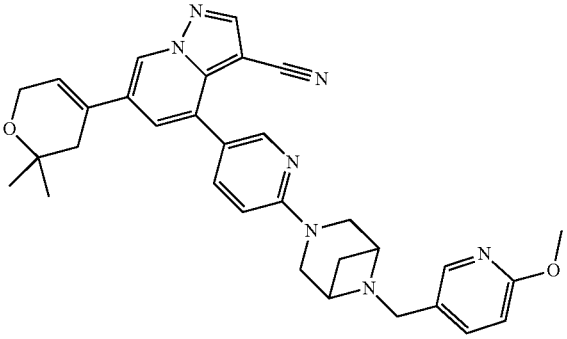
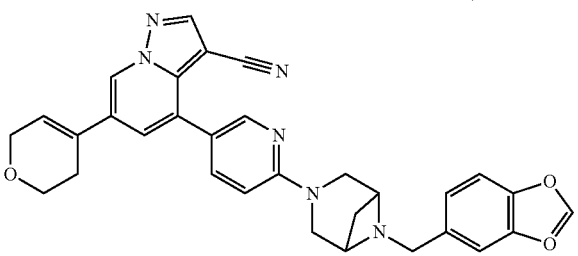

111
-continued
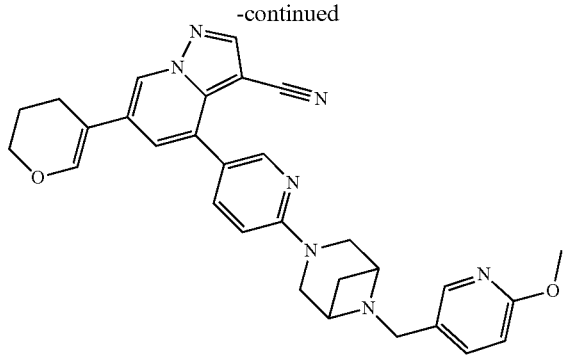
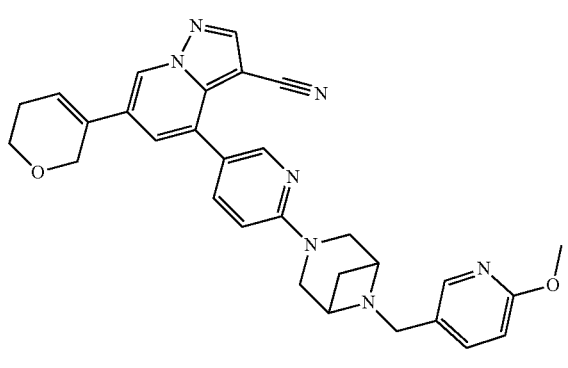
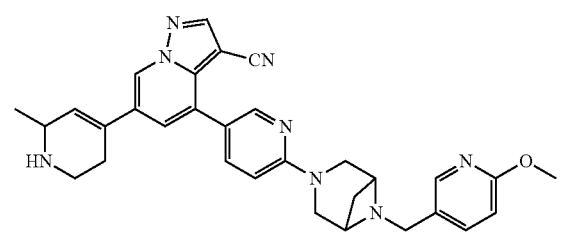
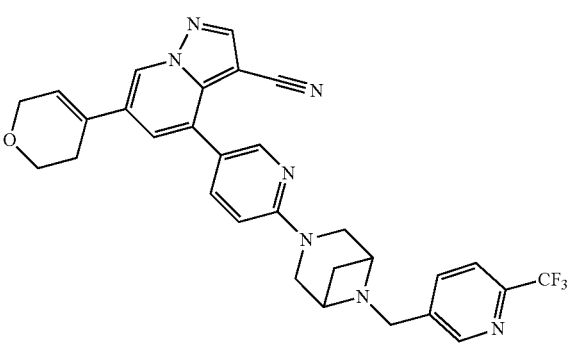
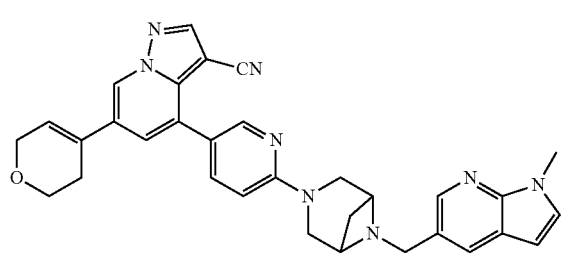
112
-continued
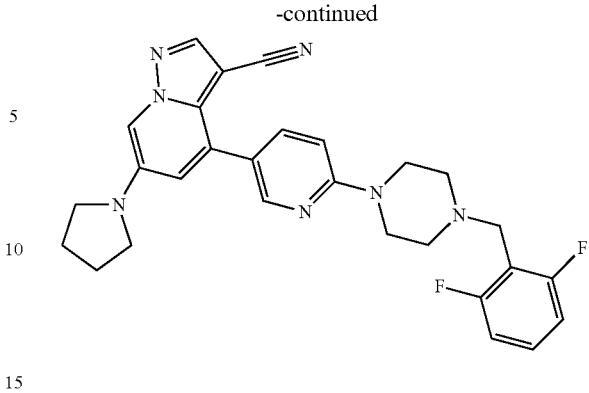
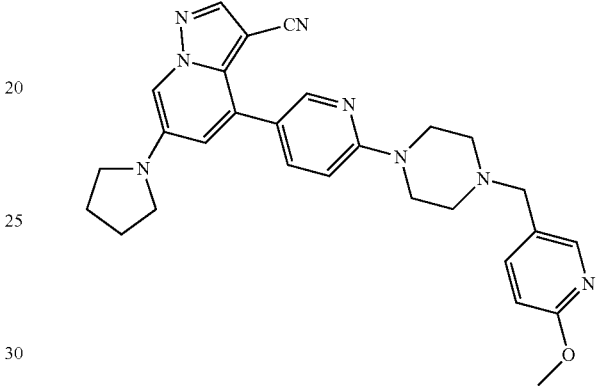
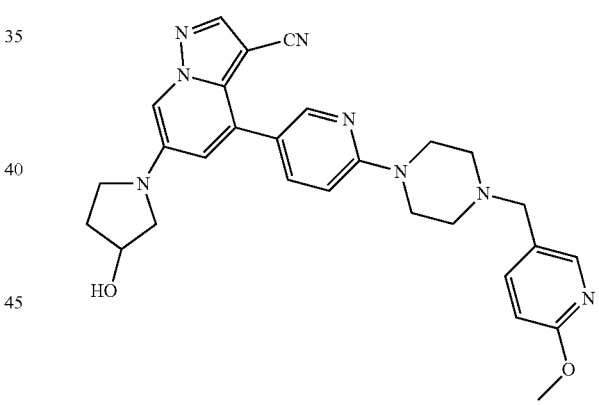
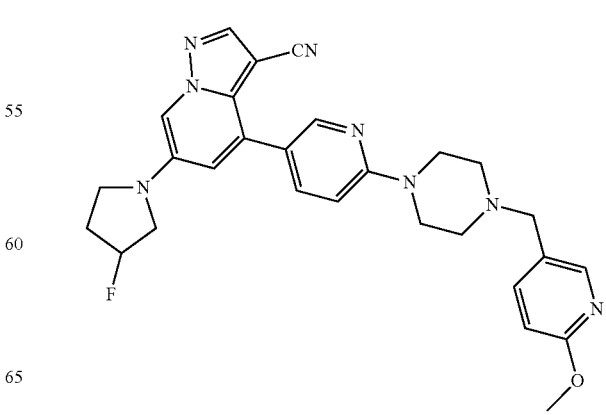

113
-continued
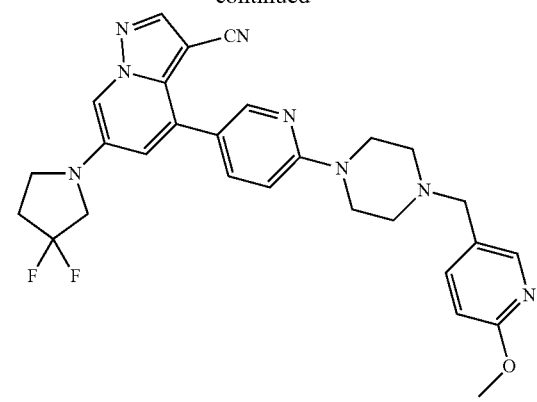
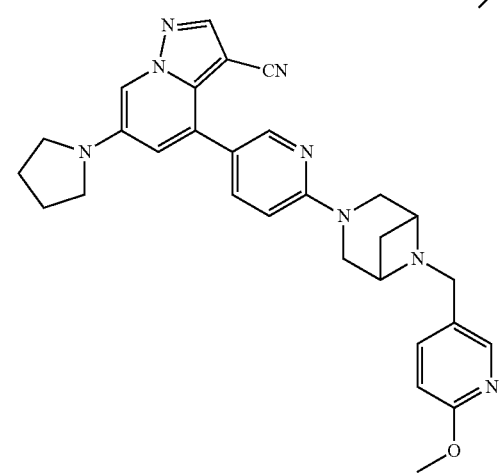
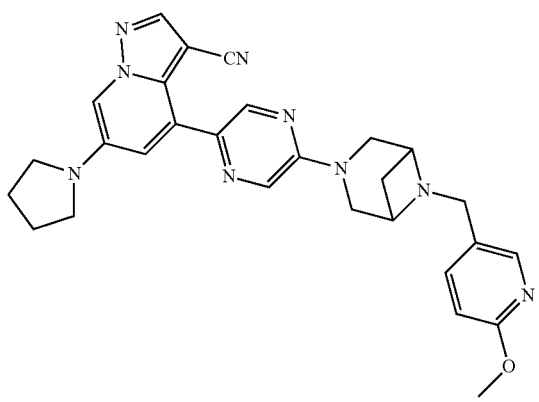
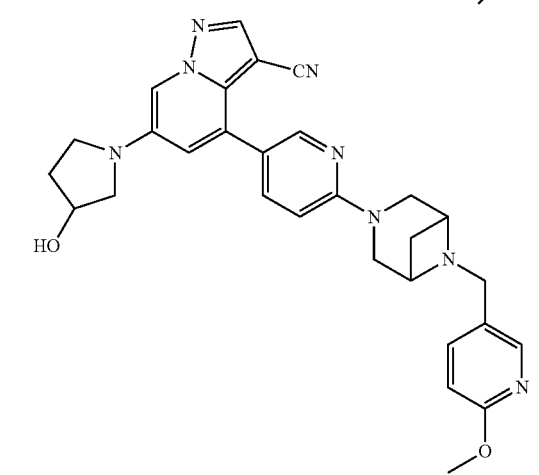
114
-continued
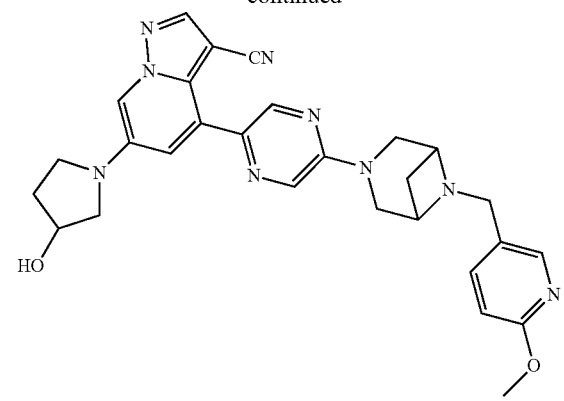
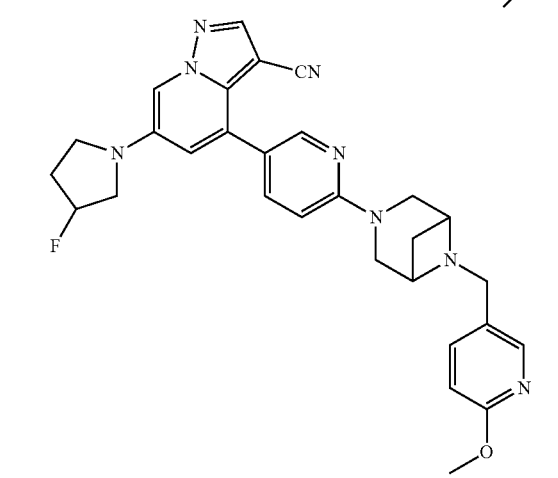
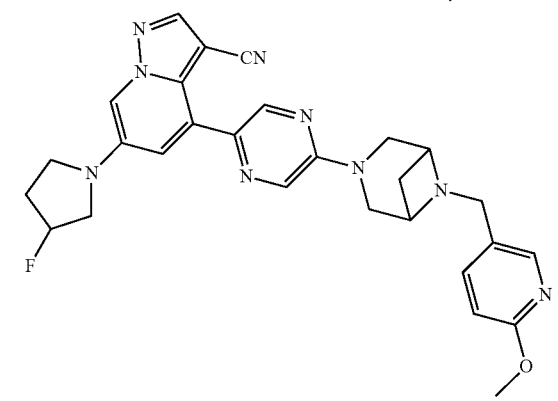
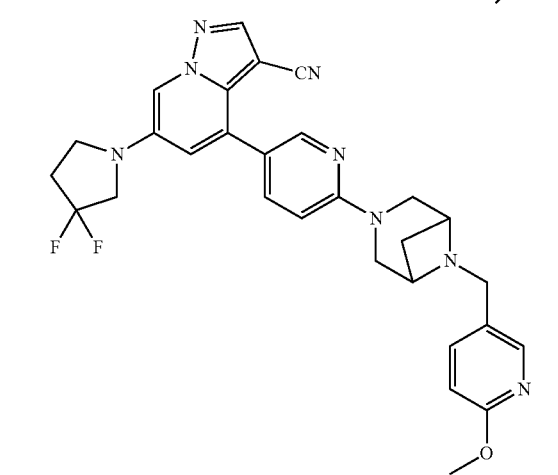

115
-continued
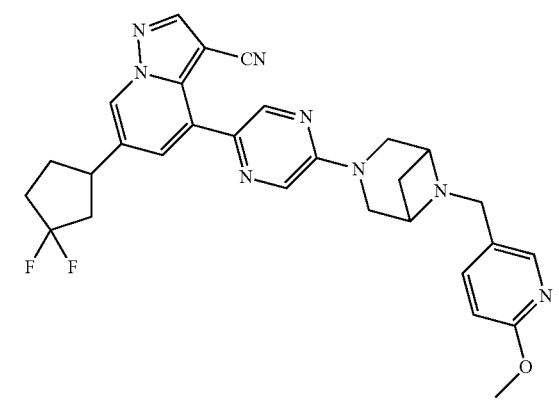
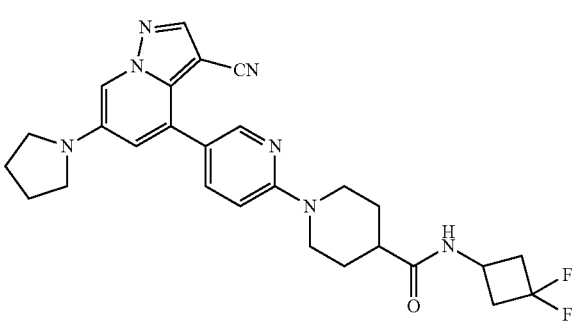
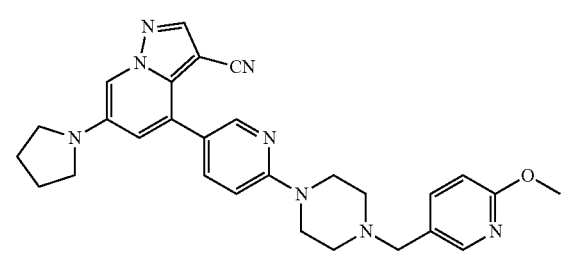
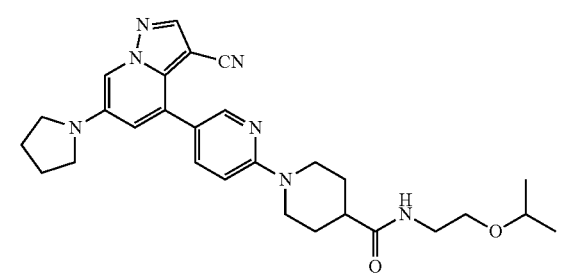 [SMILES: CC(C)OCCNC(=O)C1CCN(c2ccc(-c3cc(N4CCCC4)cn4ncc(C#N)c34)cn2)CC1]
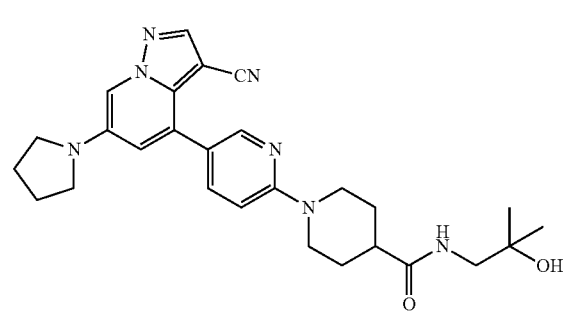 [SMILES: CC(C)(O)CNC(=O)C1CCN(c2ccc(-c3cc(N4CCCC4)cn4ncc(C#N)c34)cn2)CC1]
116
-continued
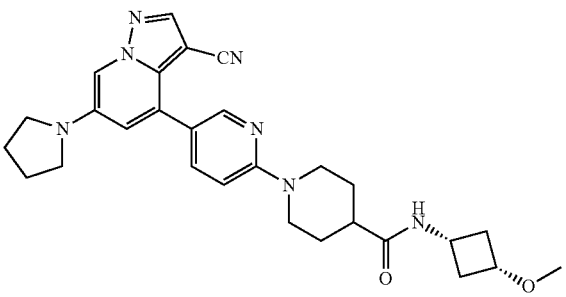 [SMILES: CO[C@H]1C[C@@H](NC(=O)C2CCN(c3ccc(-c4cc(N5CCCC5)cn5ncc(C#N)c45)cn3)CC2)C1]
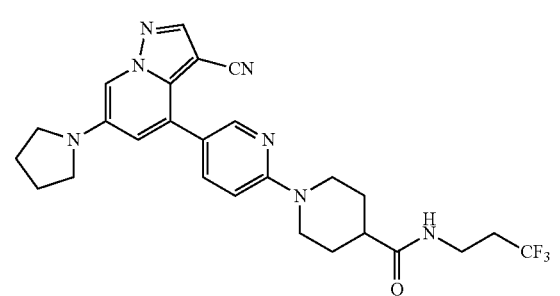 [SMILES: N#Cc1cnn2cc(N3CCCC3)cc(-c3ccc(N4CCC(C(=O)NCCC(F)(F)F)CC4)nc3)c12]
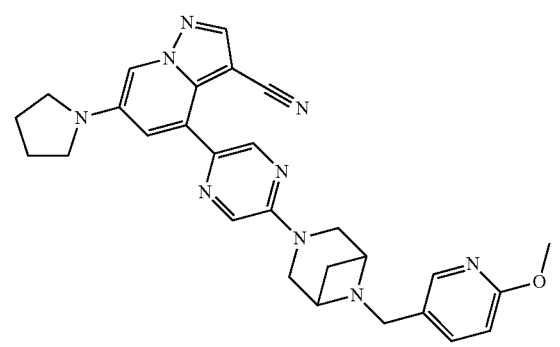
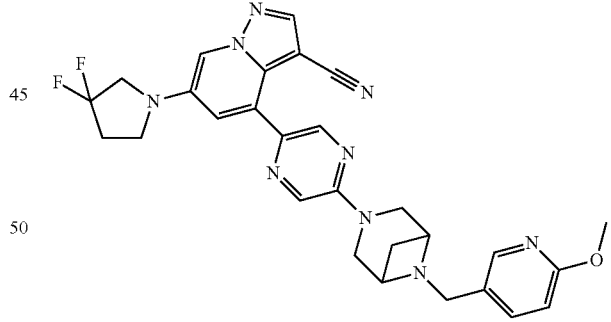
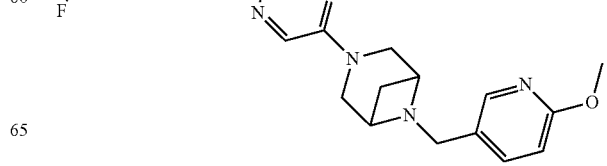

117
-continued
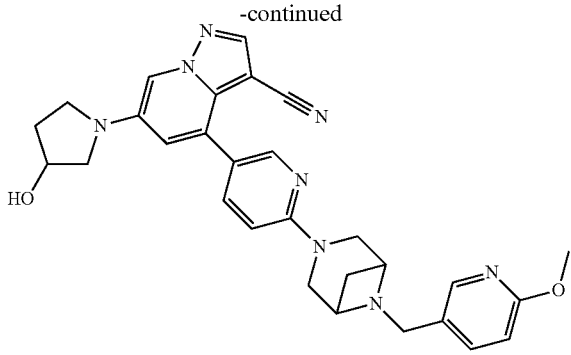
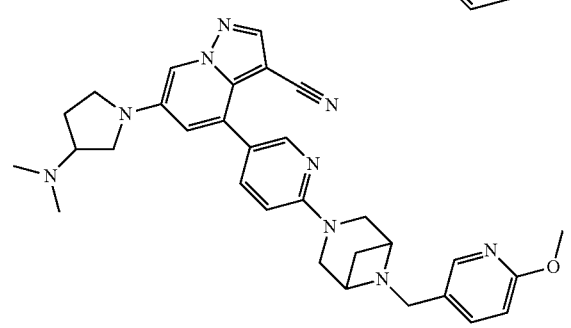
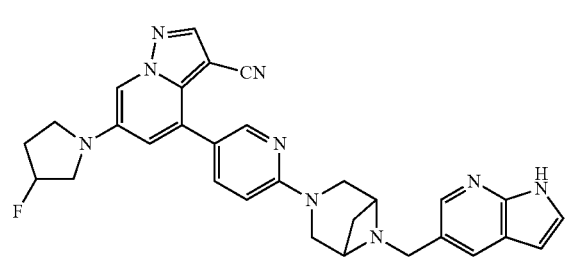
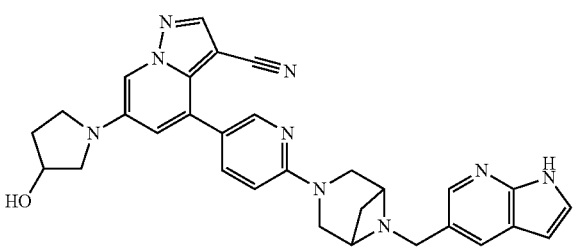
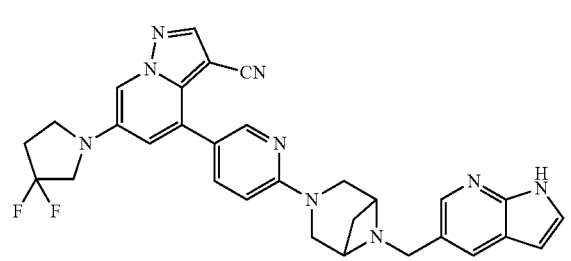
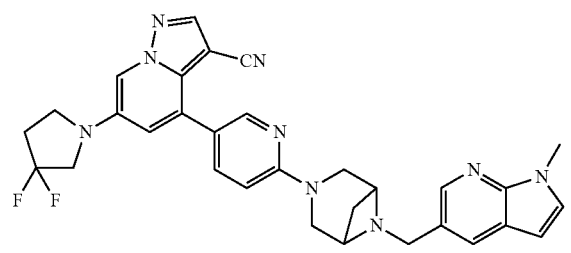
118
-continued
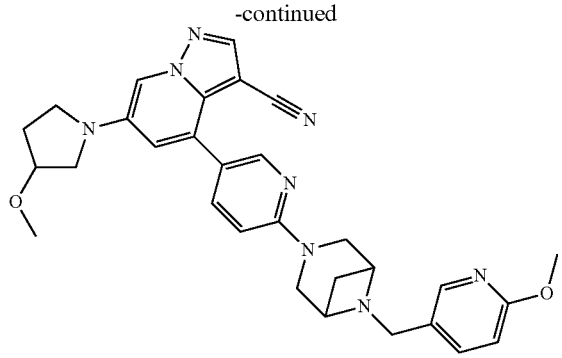
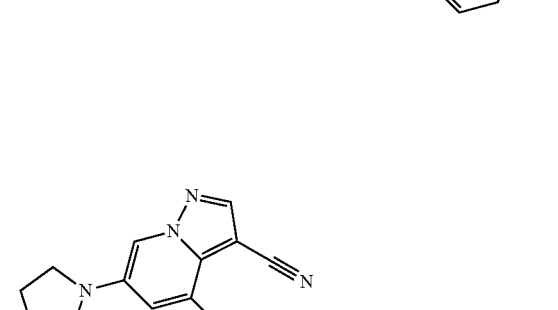
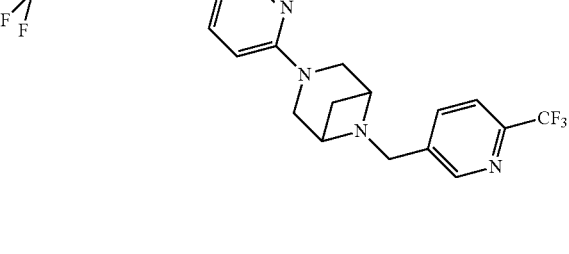
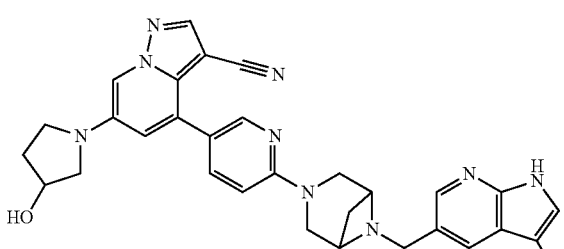
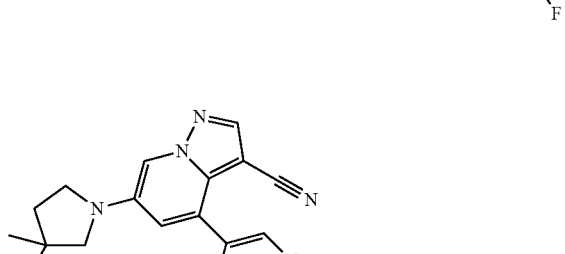
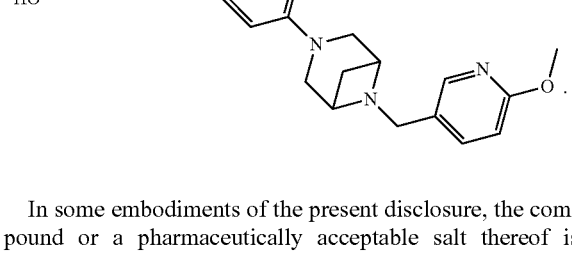
In some embodiments of the present disclosure, the compound or a pharmaceutically acceptable salt thereof is selected from:

119
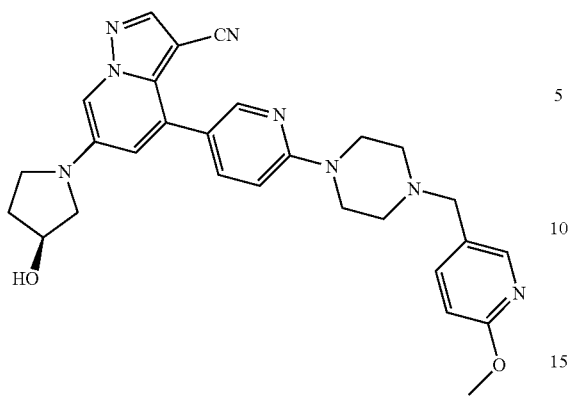
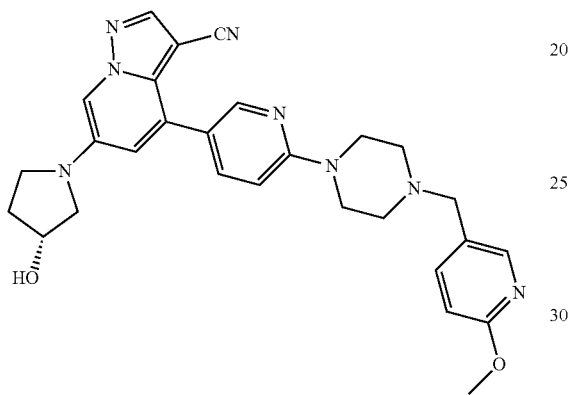
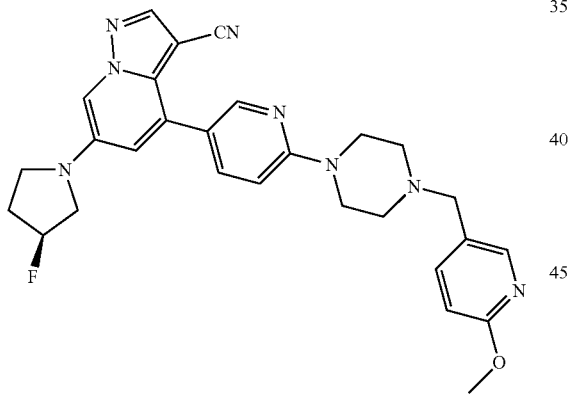
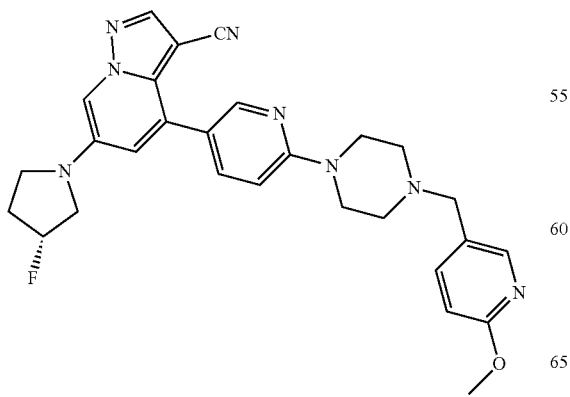
120
-continued
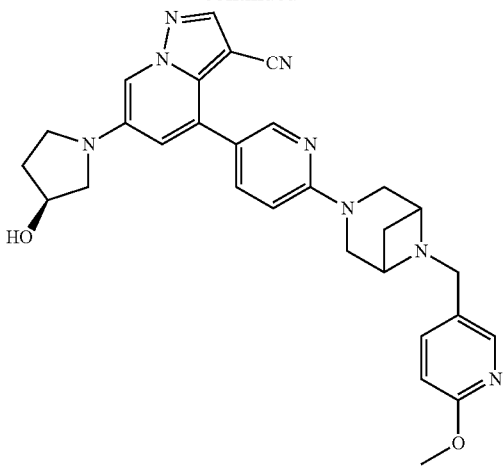
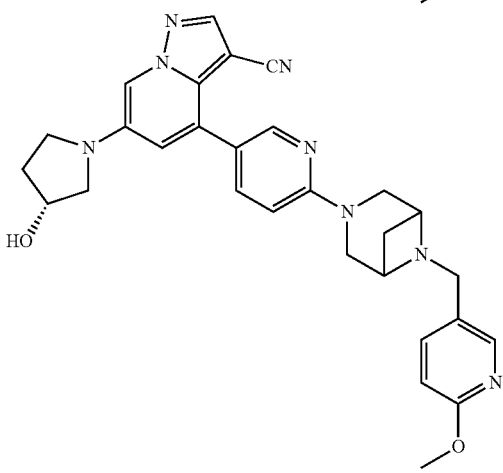
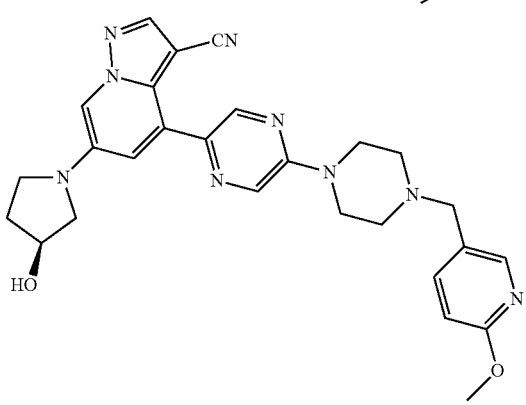
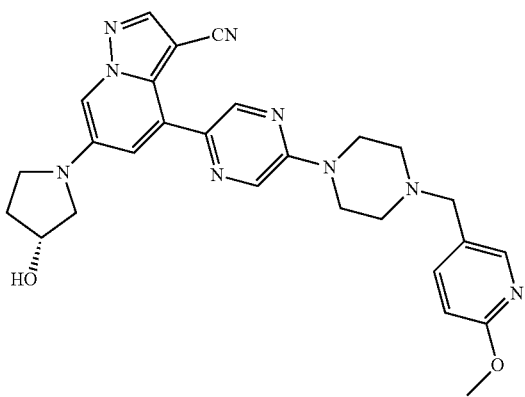

-continued
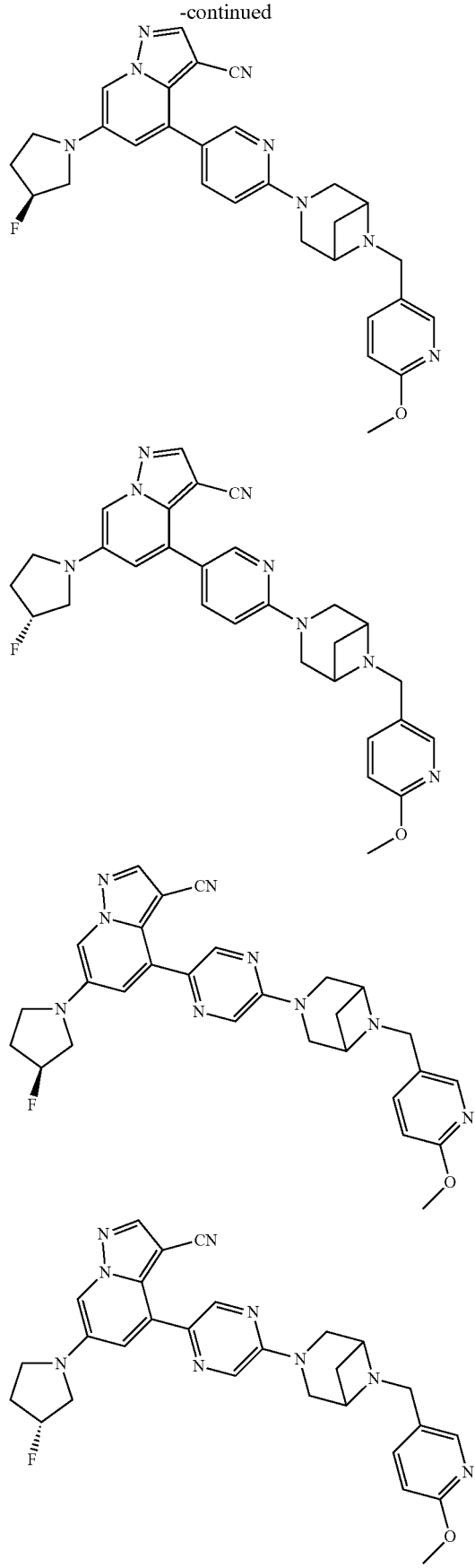
-continued
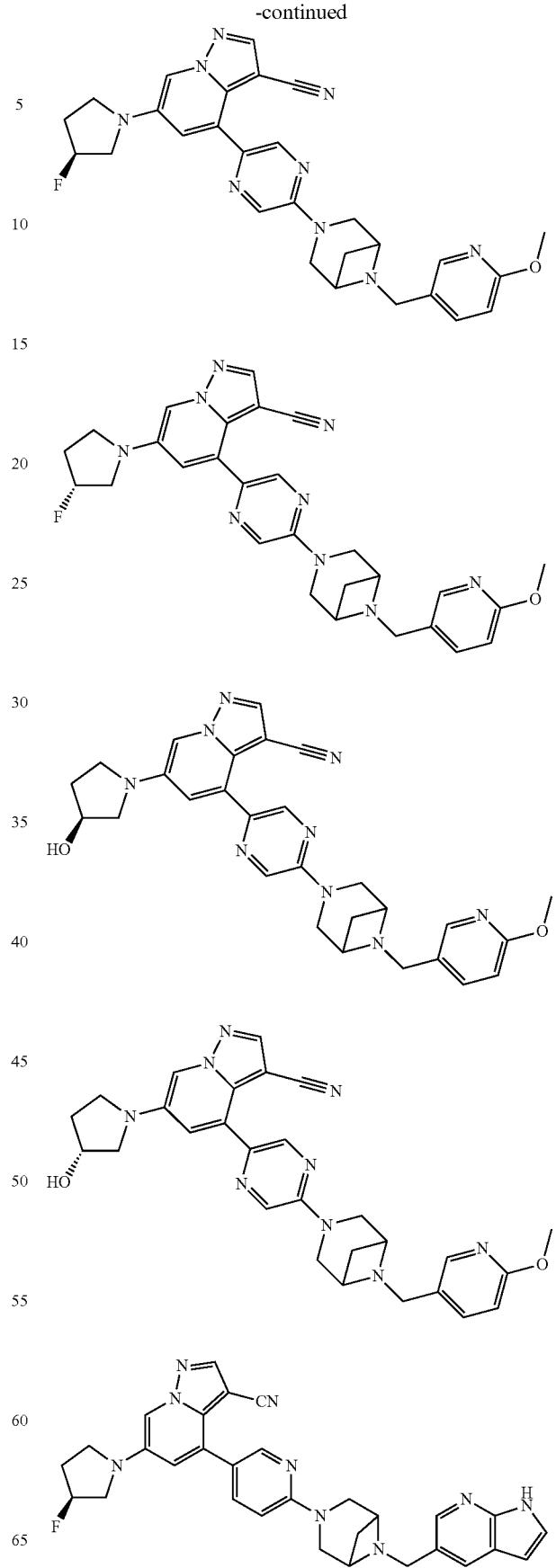

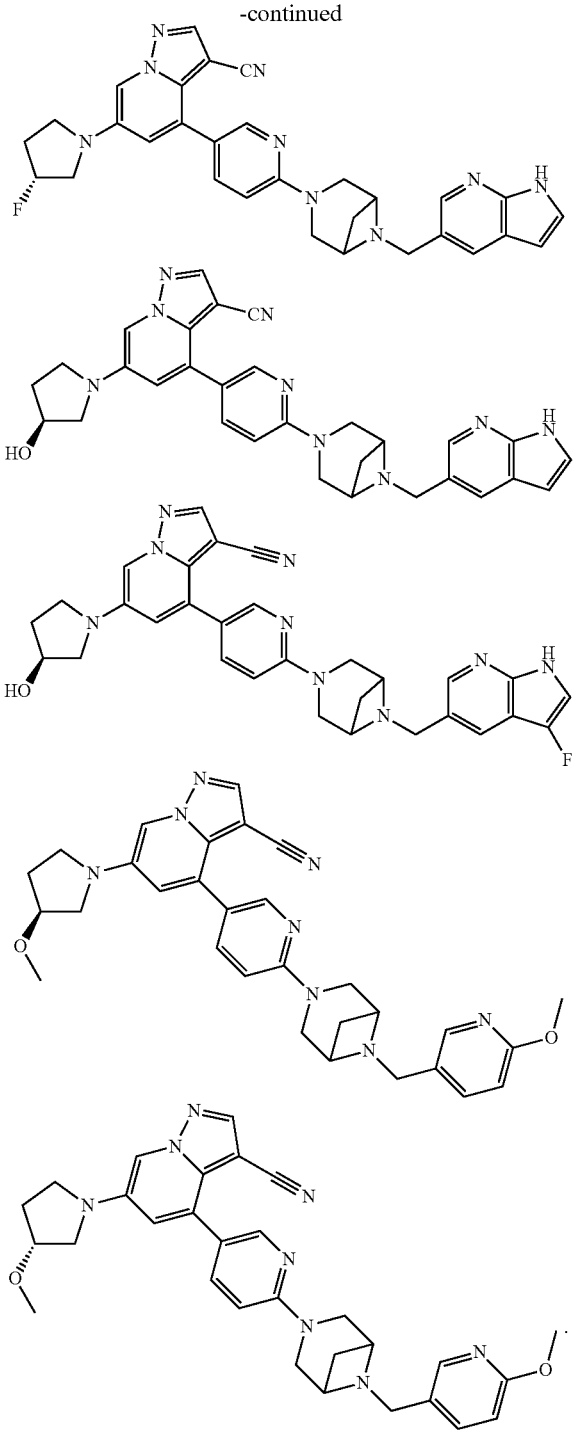

The present disclosure also provides uses of the compound or pharmaceutically acceptable salts thereof in the preparation of a RET kinase inhibitor.

Technical Effects

The compounds of the present disclosure have an excellent inhibitory activity against RET and its mutation RET V804M, and an excellent therapeutic effect on tumor patients with abnormal RET. The compounds of the present disclosure exhibit an excellent tumor suppressive effect in a RET fusion tumor model Ba/F3-CCDC6-RET. The compounds of the present disclosure have good bioavailability.

Definitions

Unless otherwise stated, the following terms and phrases used herein are intended to have the following meanings. A specific term or phrase should not be considered indefinite or unclear without particular definitions, and should be understood according to common meanings. The trade names herein denote its corresponding goods or its active ingredient.

The term "pharmaceutically acceptable" used herein means that compounds, materials, compositions and/or dosage forms are suitable for use in contact with human and animal tissues within the scope of reliable medical judgment, without excessive toxicity, irritation, allergic reactions or other problems or complications, and commensurate with a reasonable benefit/risk ratio.

The term "pharmaceutically acceptable salt" refers to a salt of a compound of the present disclosure, which is prepared from a compound having a specific substituent of the present disclosure and relatively non-toxic acid or alkali. When the compound of the present disclosure contains relatively acidic function groups, an alkali addition salt can be obtained by contacting an enough amount of alkali with such compounds in a pure solution or an appropriate inert solvent.

The pharmaceutically acceptable alkali addition salts include salts of sodium, potassium, calcium, ammonium, organic amine or magnesium, or similar salts. When the compound of the disclosure contains relatively alkaline functional groups, an acid addition salt can be obtained by contacting an enough amount of acids with such compounds in a pure solution or an appropriate inert solvent.

Examples of pharmaceutically acceptable acid addition salts include inorganic acid salts, for example hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid and phosphorous acid, and the like; and organic acid salts, including for example similar acids such as acetic acid, propionic acid, isobutyric acid, maleic acid, malonic acid, benzoic acid, succinic acid, octanedioic acid, fumaric acid, lactic acid, mandelic acid, phthalic acid, benzenesulfonic acid, p-toluenesulfonic acid, citric acid, tartaric acid and methanesulfonic acid, and the like; also include salts of amino acid (such as arginine); and salts of organic acids such as glucuronic acid. Some particular compounds of the present disclosure contain alkaline and acidic functional groups, so as to be converted into any one alkali or acid addition salt.

The pharmaceutically acceptable salt of the present disclosure can be synthesized by parent compounds containing acid radicals or alkaline groups using a conventional chemical method. In general, the preparation method of such salt is as follows: reacting the compounds having free acidic or alkaline form with stoichiometric appropriate alkalis or acids in water or an organic solvent or a mixture of both.

The compound of the present disclosure can have particular geometric or stereoisomer forms. In the present disclosure, it is conceived that all of these compounds include cis and trans isomers, (−)- and (+)-enantiomers, (R)- and (S)-enantiomers, diastereomers, (D)-isomers, (L)-isomers, and their racemic mixtures and other mixtures, for example an enriched mixture of enantiomers or diastereomers, all of these mixtures fall into the scope of the present disclosure, Substituents such as alkyl can have additional unsymmetrical carbon atoms. All of these isomers and their mixtures are all included within the scope of the present disclosure.

Unless otherwise stated, the term "enantiomers" or "optical isomers" refer to stereoisomers which are in a mutual mirror-image relation.

Unless otherwise stated, the term "cis-trans-isomer" or "geometrical isomer" is caused by a fact that a double bond or a ring-forming carbon atom single bond cannot freely rotate.

Unless otherwise stated, the term "diastereoisomer" refers to a stereoisomer in which the molecule has two or more chiral centers, and the relationship between the molecules is non-mirror image.

Unless otherwise stated, "(+) represents dextrorotation, or "(−) represents levorotation, and "(±)" represents racemization.

Unless otherwise stated, a wedge-shaped solid line bond ( ◢ ) and a wedge-shaped dashed line bond ( ⋯ ) are used to represent the absolute configuration of the stereocenter; a straight solid line bond ( ◢ ) and a straight dashed line bond ( ⋯ ) are used to represent the relative configuration of the stereocenter; and a wavy line ( ∿ ) is used to represent a wedge-shaped solid line bond ( ◢ ) or a wedge-shaped dashed line bond ( ⋯ ), or the wave line ( ∿ ) is used to represent the straight solid line bond ( ◢ ) and the straight dashed line bond ( ⋯ ).

Unless otherwise stated, when there is a double bond structure in the compound, such as a carbon-carbon double bond, a carbon-nitrogen double bond, and a nitrogen-nitrogen double bond, and each atom on the double bond is connected to two different substituents (in a double bond containing a nitrogen atom, a lone pair of electrons on the nitrogen atom is regarded as one substituent to which the nitrogen atom is connected), if the atom on the double bond in the compound and its substituent are connected by a wavy line ( ∿ ), it represents a (Z) isomer, an (E) isomer or a mixture of the two of the compound. For example, the following formula (A) represents that the compound exists in a form of a single isomer of formula (A-1) or formula (A-2) or a mixture of the two isomers of the formula (A-1) and formula (A-2). The following formula (B) represents that the compound exists in a form of a single isomer of formula (B-1) or formula (B-2) or a mixture of the two isomers of the formula (B-1) and formula (B-2). The following formula (C) represents that the compound exists in a form of a single isomer of formula (C-1) or formula (C-2) or a mixture of the two isomers of the formula (C-1) and formula (C-2).

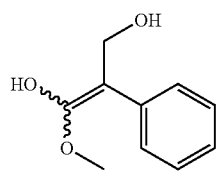

(A)

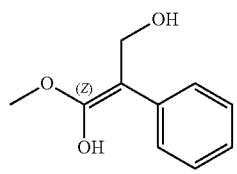

(A-1)

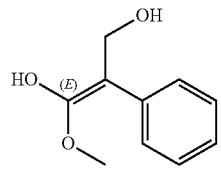

(A-2)

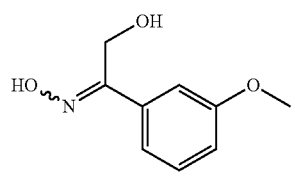

(B)

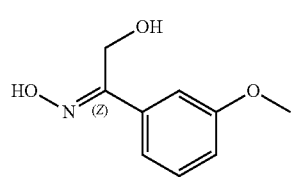

(B-1)

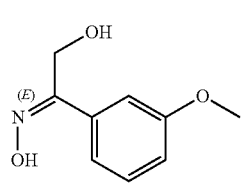

(B-2)

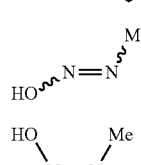

(C)

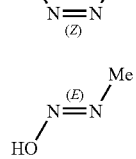

(C-1)

(C-2)

Unless otherwise stated, the term "tautomer" or "tautomer form" means that different functional isomers are in dynamic balance at room temperature and can be rapidly transformed mutually. If the tautomer is possible (for example, in solution), the chemical balance of the tautomer can be achieved. For example, a proton tautomer (also referred as prototropic tautomer) includes mutual transformation via proton migration, such as keto-enol isomerization and imine-enamine isomerization. A valence tautomer includes mutual transformation performed by recombination of some bonding electrons. The specific example of the keto-enol isomerization is mutual transformation between two tautomers namely pentane-2,4-dione and 4-hydroxypent-3-en-2-one.

Unless otherwise stated, the term "enriching an isomer", "isomer enrichment", "enriching an enantiomer" or "enantiomer enrichment" means that the content of one isomer or enantiomer is less than 100%, and the content of the isomer or enantiomer is more than or equal to 60%, or more than or equal to 70%, or more than or equal to 80%, or more than or equal to 90%, or more than or equal to 95%, or more than or equal to 96%, or more than or equal to 97%, or more than or equal to 98%, or more than or equal to 99%, or more than or equal to 99.5%, or more than or equal to 99.6%, or more than or equal to 99.7%, or more than or equal to 99.8%, or more than or equal to 99.9%.

Unless otherwise stated, the term "isomeric excess" or "enantiomeric excess" refers to a difference between relative percentages of two isomers or two enantiomers. For example, if the content of one isomer or enantiomer is 90%, and the content of the other isomer or enantiomer is 10%, the value of isomeric or enantiomeric excess (ee value) is 80%.

The optically active (R)- and (S)-isomers and D and L isomers can be prepared by chiral synthesis or chiral reagents or other conventional techniques. If it is desired to obtain an enantiomer of a compound of the present disclosure, the enantiomer can be prepared by asymmetric synthesis or derivatization with chiral auxiliary agents, comprising separating the resulting diastereomeric mixture, and cleaving the auxiliary group to obtain the pure desired enantiomer. Alternatively, when the molecule contains an alkaline functional group (such as amino) or an acidic functional group (such as carboxyl), it together with an appropriate optically active acid or alkali forms a diastereomeric salt, the diastereoisomers are resolved through a conventional method known in the art, and the pure enantiomers are recovered and obtained. In addition, the separation of enantiomers and diastereomers is usually accomplished by using chromatography with a chiral stationary phase, and optionally combined with a chemical derivatization method (for example, carbaminate is formed from amine).

The compound of the present disclosure can contain non-natural proportions of atomic isotopes on one or more atoms constituting this compound. For example, compounds can be labeled with radioisotopes, such as tritium ($^3$H), iodine-125 ($^{125}$I), or C-14 ($^{14}$C). Again, for example, hydrogen can be substituted by heavy hydrogen to form a deuterated drug. The bond consisting of deuterium and carbon is firmer than the bond formed by ordinary hydrogen and carbon. Compared with an undeuterated drug, the deuterated drug has the advantages of reduced toxic and side effects, increased drug stability, enhanced curative efficacy and prolonged biological half-life. Transformations in all the isotopes of the compound of the present disclosure, whether radioactive or not, are included in the scope of the present disclosure.

"Optional" or "optionally" means that the subsequently described events or conditions possibly but unnecessarily occur, and this description includes a situation in which the event or condition occurs and a situation in which the event or condition does not occur.

The term "substituted" means that any one or more hydrogen atoms on a particular atom are substituted by substituents, and deuterium and hydrogen variants can be included, as long as the valence of the particular atom is normal and the substituted compound is stable. When the substituent is oxygen (namely, =O), it means that two hydrogen atoms are substituted. Oxygen substitution does not occur on aromatic groups. The term "optionally substituted" means that it can be substituted or not substituted. Unless otherwise specified, the type and number of substituents may vary randomly as long as they are chemically achievable.

When any variable (for example R) occurs more than once in the composition or structure of a compound, its definition is independent in each case. Thus, for example, if one group is substituted with 0-2 R, the group may be optionally substituted with at most two R, and the substituent R is independently selected in each case. In addition, combinations of substituents and/or variants thereof are allowable only if such combinations can generate stable compounds.

When the number of a linking group is 0, such as —(CRR)$_0$—, it means that this linking group is a single bond.

When one of the variables is selected from a single bond, it means that the two groups linked thereby are directly linked. For example, when L in A-L-Z represents the single bond, this structure is actually A-Z.

When one substituent is absent, it means that the substituent does not exist. For example, when X in A-X is absent, it means that the structure is actually A. When the listed substituents do not indicate it is connected to the substituted group through which atom, such substituents can be bonded by any atoms. For example, as a substituent, pyridyl can be connected to the substituted group through any one carbon atom of a pyridine ring.

When the linking group listed does not indicate its linking direction, the linking direction is arbitrary, for example, when the linking group L in

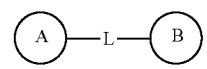

is -M-W—, -M-W— can link ring A and ring B in the direction same as the reading sequence from left to right to form

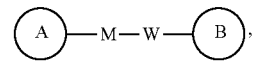, or link ring A and ring B in the direction opposite to the reading sequence from left to right to form

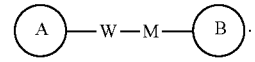.

The combination of the linking groups, substituents and/or variants thereof can be allowable only if such the combination can generate a stable compound.

Unless otherwise stated, when a group has one or more linkable sites, any one or more sites of the group can be connected to other groups through chemical bonds. The chemical bonds ⟋ between the sites and other groups can be represented by a straight solid line bond ( ⟋ ), a straight dashed line bond ( ⟋ ) or a wavy line ( ⟿ ). For example, the straight solid line bond in —OCH$_3$ indicates that the group is connected to other group through an oxygen atom; the straight dashed line bond in

indicates that the group is connected to other groups through two ends of the nitrogen atom; the wavy line in the

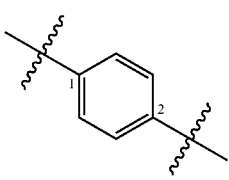

indicates that the phenyl group is connected to other groups through 1- and 2-position carbon atoms.

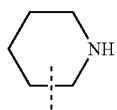

indicates that any linkable site on the piperidinyl can be connected to other groups through one chemical bond, including at least four connection ways

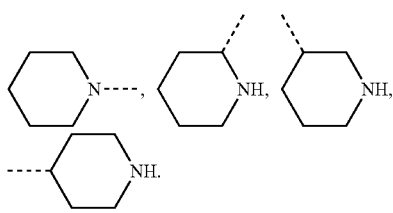

Even if a H atom is drawn on —N—,

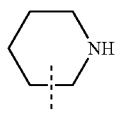

still comprises the group in the connection way of

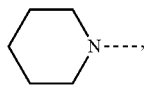

but when one chemical bond is linked, the H at the site will be reduced by one and a corresponding monovalent piperidinyl is formed.

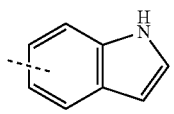

indicates that any linkable site on the indolyl can be connected to other groups through one chemical bond, including at least

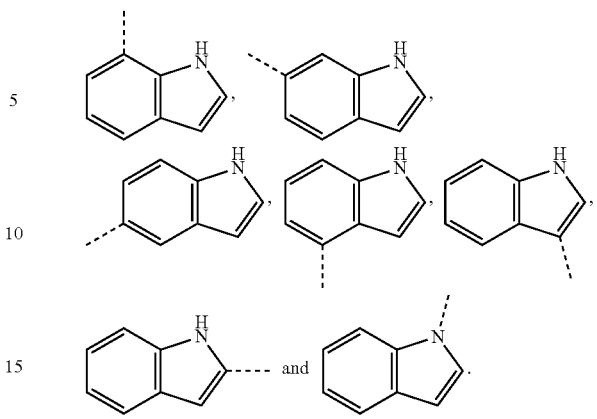

Unless otherwise stated, the term "$C_{1-8}$ alkyl" is used to represent a linear or branched saturated hydrocarbon group composed of 1 to 8 carbon atoms. The $C_{1-8}$ alkyl includes $C_{1-6}$ alkyl, $C_{1-5}$ alkyl, $C_{1-4}$ alkyl, $C_{1-3}$ alkyl, $C_{1-2}$ alkyl, $C_{2-6}$ alkyl, $C_{2-4}$ alkyl, $C_8$ alkyl, $C_7$ alkyl, $C_6$ alkyl $C_5$ alkyl, and so on. The $C_{1-8}$ alkyl may be monovalent (such as methyl), divalent (such as methylene) or multivalent (such as methine). Examples of the $C_{1-8}$ alkyl include, but are not limited to, methyl (Me), ethyl (Et), propyl (including n-propyl and isopropyl), butyl (including n-butyl, isobutyl, s-butyl and t-butyl), pentyl (including n-pentyl, isopentyl and neopentyl), hexyl, heptyl, octyl, and the like.

Unless otherwise stated, the term "$C_{1-6}$ alkyl" is used to represent a linear or branched saturated hydrocarbon group composed of 1 to 6 carbon atoms. The $C_{1-4}$ alkyl includes $C_{1-5}$ alkyl, $C_{1-4}$ alkyl, $C_{1-3}$ alkyl, $C_{1-2}$ alkyl, $C_{2-6}$ alkyl, $C_{2-4}$ alkyl, $C_6$ alkyl, $C_5$ alkyl, and so on. The $C_{1-6}$ alkyl may be monovalent (such as methyl), divalent (such as methylene) or multivalent (such as methine). Examples of the $C_{1-6}$ alkyl include, but are not limited to, methyl (Me), ethyl (Et), propyl (including n-propyl and isopropyl), butyl (including n-butyl, isobutyl, s-butyl and t-butyl), pentyl (including n-pentyl, isopentyl and neopentyl), hexyl, and the like.

Unless otherwise stated, the term "$C_{1-6}$ alkyl" is used to represent a linear or branched saturated hydrocarbon group composed of 1 to 3 carbon atoms. The $C_{1-3}$ alkyl includes $C_{1-2}$ alkyl, $C_{2-3}$ alkyl, and so on. The $C_{1-3}$ alkyl may be monovalent (such as methyl), divalent (such as methylene) or multivalent (such as methine). Examples of the $C_{1-3}$ alkyl include, but are not limited to, methyl (Me), ethyl (Et), propyl (including n-propyl and isopropyl), and the like.

Unless otherwise stated, "$C_{2-8}$ alkenyl" is used to represent a linear or branched hydrocarbon group composed of 2 to 8 carbon atoms containing at least one carbon-carbon double bond, and the carbon-carbon double bond can be located in any position of the group. The $C_{2-8}$ alkenyl includes $C_{2-6}$ alkenyl, $C_{2-4}$ alkenyl, $C_{2-3}$ alkenyl, $C_4$ alkenyl, $C_3$ alkenyl, $C_2$ alkenyl, and so on, and can be monovalent, divalent or multivalent. Examples of the $C_{2-8}$ alkenyl include, but are not limited to, vinyl, propenyl, butenyl, pentenyl, hexenyl, butadienyl, pentadienyl, hexadienyl, and the like.

Unless otherwise stated, the term "$C_{1-6}$ alkoxy" represents an alkyl group containing 1 to 6 carbon atoms connected to the rest of the molecule through an oxygen atom. The $C_{1-6}$ alkoxy includes $C_{1-4}$ alkoxy, $C_{1-3}$ alkoxy, $C_{1-2}$ alkoxy, $C_{2-4}$ alkoxy, $C_{2-3}$ alkoxy, $C_6$ alkoxy, $C_5$ alkoxy, $C_4$ alkoxy, $C_3$ alkoxy, and so on. Examples of the $C_{1-6}$ alkoxy include, but are not limited to, methoxy, ethoxy, propoxy (including n-propoxy and isopropoxy), butoxy (including n-butoxy, isobutoxy, s-butoxy and t-butoxy), pentoxy (including n-pentoxy, isopentoxy and neopentoxy), hexoxy, and the like.

Unless otherwise stated, the term "$C_{1-3}$ alkoxy" represents an alkyl group containing 1 to 3 carbon atoms connected to the rest of the molecule through an oxygen atom. The $C_{1-3}$ alkoxy includes $C_{1-2}$ alkoxy, $C_{2-3}$ alkoxy, $C_3$ alkoxy, $C_2$ alkoxy, and so on. Examples of the $C_{1-3}$ alkoxy include, but are not limited to, methoxy, ethoxy, propoxy (including n-propoxy and isopropoxy), and the like.

Unless otherwise stated, the term "$C_{1-3}$ alkylamino" represents an alkyl group containing 1 to 3 carbon atoms connected to the rest of the molecule through an amino group. The $C_{1-3}$ alkylamino includes $C_{1-2}$ alkylamino, $C_3$ alkylamino, $C_2$ alkylamino and so on. Examples of the $C_{1-3}$ alkylamino include, but are not limited to, —NHCH$_3$, —N(CH)$_2$, —NHCH$_2$CH$_3$, —N(CH$_3$)CH$_2$CH$_3$, —NHCH$_2$CH$_2$CH$_3$, —NHCH$_2$ (CH)$_2$, and the like.

Unless otherwise stated, "$C_{3-8}$ cycloalkyl" represents a saturated cyclic hydrocarbon group composed of 3 to 8 carbon atoms, which comprises monocyclic and bicyclic ring systems, wherein the bicyclic ring system comprises spiro, fused, and bridged rings. The $C_{3-8}$ cycloalkyl includes $C_{3-6}$ cycloalkyl. $C_{3-5}$ cycloalkyl. $C_{4-8}$ cycloalkyl, $C_{4-6}$ cycloalkyl, $C_{4-5}$ cycloalkyl. $C_{5-8}$ cycloalkyl or $C_{5-6}$ cycloalkyl and so on, and may be monovalent, divalent or multivalent. Examples of the $C_{3-8}$ cycloalkyl include, but are not limited to, cyclopropyl, cyclobutyl, cyclopentyl, cyclohexyl, cycloheptyl, norbornyl, [2.2.2] bicyclooctane, and the like.

Unless otherwise stated, the term "3-8 membered heterocycloalkyl" by itself or in combination with other terms respectively represents a saturated cyclic group composed of 3 to 8 ring atoms, wherein 1, 2, 3 or 4 ring atoms are heteroatoms independently selected from O, S and N, and the rest are carbon atoms, wherein the nitrogen atom is optionally quaternized, and the nitrogen and sulfur heteroatoms can be optionally oxidized (i.e., NO and S(O)$_p$, p is 1 or 2). The saturated cyclic group comprises monocyclic and bicyclic ring systems, wherein the bicyclic ring system comprises spiro, fused, and bridged rings. In addition, for the "3-8 membered heterocycloalkyl", a heteroatom may occupy a linking position of the heterocycloalkyl with the rest of the molecule. The 3-8 membered heterocycloalkyl includes 3-6 membered heterocycloalkyl, 3-5 membered heterocycloalkyl, 4-6 membered heterocycloalkyl, 5-6 membered heterocycloalkyl, 4 membered heterocycloalkyl, 5 membered heterocycloalkyl, 6 membered heterocycloalkyl, and so on Examples of the 3-8 membered heterocycloalkyl include, but are not limited to, azetidinyl, oxetanyl, thietanyl, pyrrolidinyl, pyrazolidinyl, imidazolidinyl, tetrahydrothienyl (including tetrahydrothiophen-2-yl and tetrahydrothiophen-3-yl, and so on), tetrahydrofuranyl (including tetrahydrofuran-2-yl, and so on), tetrahydropyranyl, piperidinyl (including 1-piperidinyl, 2-piperidinyl, 3-piperidinyl, and so on), piperazinyl (including 1-piperazinyl, 2-piperazinyl, and so on), morpholinyl (including 3-morpholinyl, 4-morpholinyl, and so on), dioxanyl, dithianyl, isoxazolidinyl, isothiazolidinyl, 1,2-oxazinyl, 1,2-thiazinyl, hexahydropyridazinyl, homopiperazinyl, homopiperidinyl or dioxepanyl, and the like.

Unless otherwise stated, the terms "5-10 membered heteroaryl ring" and "5-10 membered heteroaryl" can be used interchangeably in the present disclosure. The term "5-10 membered heteroaryl" represents a ring group which is composed of 5 to 10 ring atoms and has a conjugated π-electron system, wherein 1, 2, 3 or 4 ring atoms are heteroatoms independently selected from O, S and N, and the rest are carbon atoms. The ring group can be monocyclic, fused bicyclic or fused tricyclic systems, wherein each ring is aromatic, wherein the nitrogen atom is optionally quaternized, the nitrogen and sulfur heteroatoms can be optionally oxidized (i.e. NO and S(O)$_p$, p is 1 or 2). The 5-10 membered heteroaryl group can be connected to the rest of the molecule through a heteroatom or a carbon atom. The 5-10 membered heteroaryl group includes 5-8 membered heteroaryl, 5-7 membered heteroaryl, 5-6 membered heteroaryl, 5 membered heteroaryl, 6 membered heteroaryl, and so on. Examples of the 5-10 membered heteroaryl include, but are not limited to, pyrrolyl (including N-pyrrolyl, 2-pyrrolyl, 3-pyrrolyl, and so on), pyrazolyl (including 2-pyrazolyl, 3-pyrrolyl, and so on), imidazolyl (including N-imidazolyl, 2-imidazolyl, 4-imidazolyl, 5-imidazolyl, and so on), oxazolyl (including 2-oxazolyl, 4-oxazolyl, 5-oxazolyl, and so on), triazolyl (1H-1,2,3-triazolyl, 2H-1,2,3-triazolyl, 1H-1,2,4-triazolyl, 4H-1,2,4-triazolyl, and so on), tetrazolyl, isoxazolyl (3-isoxazolyl, 4-isoxazolyl, 5-isoxazolyl, and so on), thiazolyl (including 2-thiazolyl, 4-thiazolyl, 5-thiazolyl, and so on), furyl (including 2-furyl, 3-furyl, and so on), thienyl (including 2-thienyl, 3-thienyl, and so on), pyridyl (including 2-pyridyl, 3-pyridyl, 4-pyridyl, and so on), pyrazinyl, pyrimidinyl (including 2-pyrimidinyl, 4-pyrimidinyl, and so on), benzothiazolyl (including 5-benzothiazolyl, and so on), purinyl, benzimidazolyl (including 2-benzimidazolyl, and so on), benzoxazolyl, indolyl (including 5-indolyl, and so on), isoquinolyl (including 1-isoquinolyl, 5-isoquinolyl, and so on), quinoxalinyl (including 2-quinoxalinyl, 5-quinoxalinyl, and so on) or quinolyl (including 3-quinolyl, 6-quinolyl, and so on).

Unless otherwise stated, the terms "5-6 membered heteroaryl ring" and "5-6 membered heteroaryl" can be used interchangeably in the present disclosure. The term "5-6 membered heteroaryl" represents a monocyclic group which is composed of 5 to 6 ring atoms and has a conjugated n-electron system, wherein 1, 2, 3 or 4 ring atoms are heteroatoms independently selected from O, S and N, and the rest are carbon atoms, wherein the nitrogen atom is optionally quaternized, and the nitrogen and sulfur heteroatoms can be optionally oxidized (i.e. NO and S(O)$_p$, p is 1 or 2). The 5-6 membered heteroaryl can be connected to the rest of the molecule through a heteroatom or a carbon atom. The 5-6 membered heteroaryl comprises 5-membered heteroaryl and 6-membered heteroaryl. Examples of the 5-6 membered heteroaryl include, but are not limited to, pyrrolyl (including N-pyrrolyl, 2-pyrrolyl, 3-pyrrolyl, and so on), pyrazolyl (including 2-pyrazolyl, 3-pyrrolyl, and so on), imidazolyl (including N-imidazolyl, 2-imidazolyl, 4-imidazolyl, 5-imidazolyl, and so on), oxazolyl (including 2-oxazolyl, 4-oxazolyl, 5-oxazolyl, and so on), triazolyl (1H-1,2,3-triazolyl, 2H-1,2,3-triazolyl, 1H-1,2,4-triazolyl, 4H-1,2,4-triazolyl, and so on), tetrazolyl, isoxazolyl (3-isoxazolyl, 4-isoxazolyl, 5-isoxazolyl, and so on), thiazolyl (including 2-thiazolyl, 4-thiazolyl, 5-thiazolyl, and so on), furyl (including 2-furyl, 3-furyl, and so on), thienyl (including 2-thienyl, 3-thienyl, and so on), pyridyl (including 2-pyridyl, 3-pyridyl, 4-pyridyl, and so on), pyrazinyl or pyrimidinyl (including 2-pyrimidinyl, 4-pyrimidyl, and so on).

Unless otherwise specified, the term "5-8 membered heterocycloalkenyl" by itself or in combination with other terms respectively represents a partially unsaturated ring group which is composed of 5 to 8 ring atoms and contains at least one carbon-carbon double bond, wherein 1, 2, 3 or 4 ring atoms are heteroatoms independently selected from 0.

S and N and the rest are carbon atoms, wherein the nitrogen atom is optionally quaternized, and the nitrogen and sulfur heteroatoms can be optionally oxidated (i.e. NO and S(O)$_p$, p is 1 or 2). The partially unsaturated ring group comprises monocyclic, bicyclic, and tricyclic systems, wherein the bicyclic and tricyclic systems comprise spiro, fused, and bridged rings, and any ring in these systems is non-aromatic. In addition, for the "5-8 membered heterocycloalkenyl", a heteroatom can occupy a linking position of the heterocycloalkenyl with the rest of the molecule. The 5-8 membered heterocycloalkenyl comprises 5-7 membered heterocycloalkenyl, 5-6 membered heterocycloalkenyl, 4-5 membered heterocycloalkenyl, 4 membered heterocycloalkenyl, 5 membered heterocycloalkenyl, 6 membered heterocycloalkenyl, and so on. Examples of the 5-8 membered heterocycloalkenyl include, but are not limited to

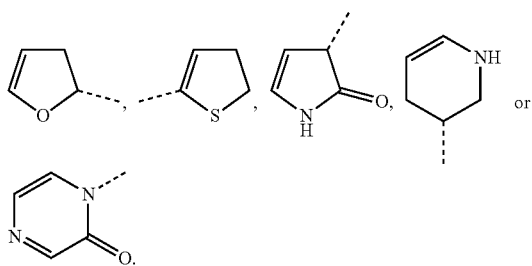

Unless otherwise stated. "$C_{5-8}$ cycloalkenyl" represents a partially unsaturated cyclic hydrocarbon group which is composed of 5 to 8 carbon atoms and contains at least one carbon-carbon double bond. The partially unsaturated cyclic hydrocarbon group comprises monocyclic and bicyclic systems, wherein the bicyclic ring system comprises spiro, fused and bridged rings, and any ring of these systems is non-aromatic. The $C_{5-8}$ cycloalkenyl comprises $C_{5-6}$ cycloalkenyl, $C_{5-7}$ cycloalkenyl, $C_{6-8}$ cycloalkenyl or $C_{6-7}$ cycloalkenyl, and so on, and may be monovalent, divalent or multivalent. Examples of the $C_{5-8}$ cycloalkenyl include, but are not limited to, cyclopentenyl, cyclopentadienyl, cyclohexenyl, cyclohexadienyl, and on the like.

Unless otherwise specified. $C_{n-n+m}$ or $C_n$-$C_{n+m}$ includes any specific condition of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$ and $C_{12}$, also includes any range from n to n+m, for example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$ and $C_{9-12}$. Similarly, n member to n+m member means that the number of atoms in the ring is from n to n+m, for example, 3-12 membered ring includes 3-membered ring, 4-membered ring, 5-membered ring, 6-membered ring, 7-membered ring, 8-membered ring, 9-membered ring, 10 membered ring, 11-membered ring and 12-membered ring, and also includes any range from n to n+m, for example, 3-12 membered ring includes 3-6 membered ring, 3-9 membered ring, 5-6 membered ring, 5-7 membered ring, 6-7 membered ring, 6-8 membered ring and 6-10 membered ring.

The term "leaving group" refers to a functional group or an atom that can be substituted by another functional group or atom through substitution reaction (for example, affinity substitution reaction). For example, representative leaving groups include trifluoromethanesulfonate; chlorine, bromine, and iodine; sulfonate groups such as mesylate, tosylate, p-bromobenzenesulfonate, p-toluenesulfonate; acyloxy groups, such as acetoxy and trifluoroacetoxy.

The term "protecting group" includes but is not limited to "amino protecting group". "hydroxyl protecting group" or "thiol protecting group". The term "amino protecting group" refers to a protecting group suitable for preventing side reaction at a nitrogen position of amino. Representative amino protecting groups include but are not limited to formyl; acyl, such as alkanoyl (such as acetyl, trichloroacetyl or trifluoroacetyl); alkoxycarbonyl, such as tert-butoxycarbonyl (Boc); arylmethyloxycarbonyl, such as benzyloxycarbonyl (Cbz) and 9-fluorenylmethyloxycarbonyl (Fmoc); arylmethyl, such as benzyl (Bn), trityl (Tr), 1,1-di-(4'-methoxyphenyl) methyl; silyl, such as trimethylsilyl (TMS) and tert-butyldimethylsilyl (TBS), and the like. The term "hydroxyl protecting group" refers to a protecting group suitable for preventing side reaction of hydroxyl. Representative hydroxyl protecting groups include but are not limited to alkyl, such as methyl, ethyl and tert-butyl; acyl, such as alkanoyl (such as acetyl); arylmethyl, such as benzyl (Bn), p-methoxybenzyl (PMB), 9-fluorenylmethyl (Fm) and diphenylmethyl (DPM); silyl, such as trimethylsilyl (TMS) and tert-butyl dimethylsilyl (TBS), and the like.

The compound of the present disclosure can be prepared by various synthetic methods well known to those skilled in the art, including specific embodiments listed below, embodiments formed by combining the specific embodiments listed below with other chemical synthesis methods, and equivalent replacement manners well known to those skilled in the art. The preferred embodiments include but are not limited to the embodiments of the present disclosure.

The structure of the compound of the present disclosure can be confirmed by conventional methods known by those skilled in the art. If the present disclosure relates to an absolute configuration of a compound, the absolute configuration can be confirmed by conventional technical means in the art. For example single crystal X-ray diffraction (SXRD), the diffraction intensity data of cultured single crystal is collected by a Bruker D8 venture diffraction instrument, the light source is CuKα radiation, the scanning manner is φ/ω scanning, and after relevant data is collected, the crystal structure is analyzed using a direct method (SheIxs97) so as to confirm the absolute configuration.

The solvents used in the present disclosure are commercially available. The following abbreviations are used in the present disclosure: Pd(PPh$_3$)$_4$ means tetrakistriphenylphosphine palladium; DIPEA means N,N-diisopropylethylamine; Boc means tert-butoxycarbonyl; NaBH(OAc)$_3$ means sodium triacetoxyborohydride; K$_3$PO$_4$ means potassium phosphate; Pd(dppf)Cl$_2$ means [1,1'-bis(diphenylphosphino) ferrocene] palladium dichloride; K$_2$CO$_3$ means potassium carbonate; DCM means dichloromethane; MeOH means methanol; DMF means N,N-dimethylformamide, H$_2$O means water; Na$_2$CO$_3$ means sodium carbonate, EtOH means ethanol; Pd/C means palladium/carbon; NaBH$_3$CN means sodium cyanoborohydride; HCl means hydrochloric acid; EtOAc means ethyl acetate; HATU means 2-(7-azabenzotriazol)-N,N,N',N'-tetramethyl uronium hexafluorophosphate; BINAP means 1,1'-binaphthyl-2,2'-diphemyl phosphine, ACN means acetonitrile; NMP means acetonitrile N-methylpyrrolidone; TFA means trifluoroacetic acid; Pd$_2$ (dba)$_3$ means; t-BuONa means sodium tert-butoxide; KOAc means potassium acetate; Pd(dppf)Cl$_2$CH$_2$Cl$_2$ means a [1,1'-bis(diphenylphosphino)ferrocene]dichloropalladium dichloromethane complex; N$_2$ means nitrogen; DMSO means dimethyl sulfoxide; THF means tetrahydrofuran, LiHMDS means lithium bistrimethylsilylamide; AcOH means acetic acid; and Na$_3$VO$_4$ means sodium vanadate.

Compounds are named according to conventional naming principles in the art or using ChemDraw® software, and commercially available compounds are named based on the supplier's catalog name.

DETAILED DESCRIPTION

The present disclosure will be described in detail through examples below, but it is not intended to adversely limit the present disclosure. The present disclosure has been described in detail herein, in which the specific embodiments thereof have also been disclosed. For those skilled in the art, it will be obvious to make various variations and improvements to the specific embodiments of the present disclosure without departing from the spirits and scope of the present disclosure.

Example 1

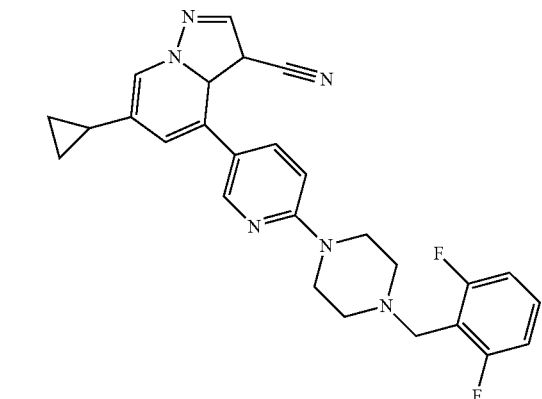

1

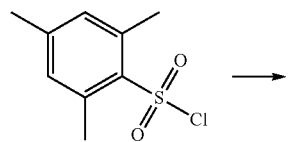

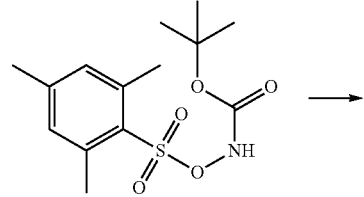

1a

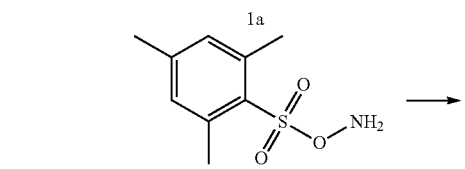

1b

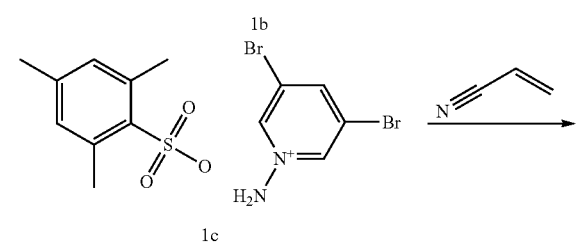

1c

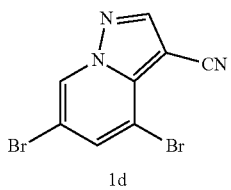

1d

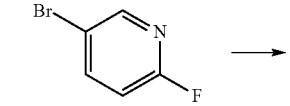

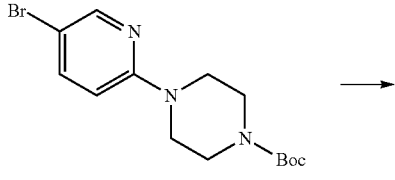

1e

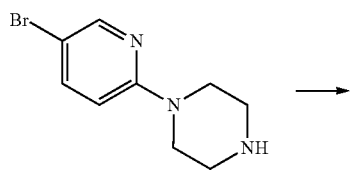

1f

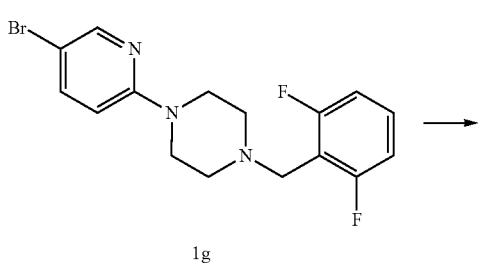

1g

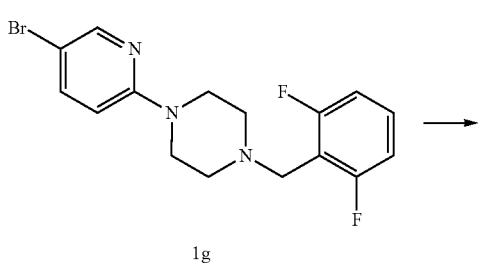

1h

-continued

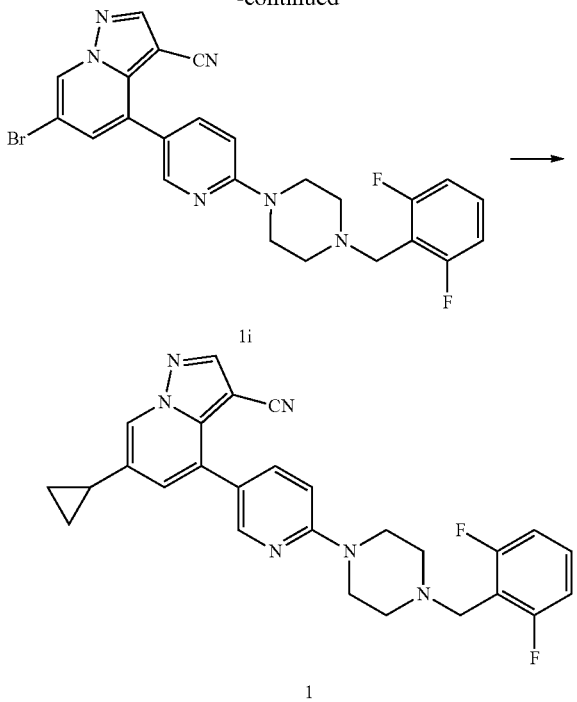

1i

1

Step 1

2,4,6-trimethyl-benzenesulfonyl chloride (100 g, 457.25 mmol) and N-Boc-hydroxylamine (73.06 g, 548.70 mmol) were added to methyl tert-butyl ether (1 L), triethylamine (55.52 g, 548.70 mmol) was then slowly dropped into the reaction solution, and the reaction was conducted at 0° C. for 2 hours under stirring. The reaction solution was filtered to obtain a filtrate, the filtrate was dried by a spinning method to ⅓ of the original volume to which 5% methyl tert-butyl ether (MTBE) (54.5 mL) and 95% n-heptane (1,040 mL) were added, stirred for 10 mm, and filtrated to collect compound 1a.

$^1$H NMR (400 MHz, CDCl$_3$) δ7.62 (s, 1H), 6.99 (s, 2H), 2.68 (s, 6H), 2.32 (s, 3H), 1.32 (s, 9H).

Step 2

Compound 1a (70 g, 221.95 mmol) was added in portions to trifluoroacetic acid (25.31 g, 221.95 mmol) within 30 min, and the reaction was conducted at 0° C. for 2 hours under stirring, 115 mL of ice water was added to the reaction solution, then 230 mL of broken ice was added, a white solid was precipitated out, then 340 mL of ice water was added. The reaction solution was stirred for 10 min, and filtrated to obtain 1b. The 1b was dissolved in dichloromethane (950 mL), dried with anhydrous sodium sulfate, and filtrated to a obtain filtrate. The filtrate was stored in dichloromethane (950 mL) for later use Step 3

3,5-dibromopyridine (52.58 g, 221.95 mmol) was added in portions into the dichloromethane (950 mL) solution of compound 1b, and the reaction was conducted at 0° C. for 3 hours under stirring. Methyl tert-butyl ether (1 L) was added to the reaction solution, the reaction solution was stirred for 10 min, a white solid was precipitated out. The reaction solution was filtrated to collect a solid, and the solid was dried by a spinning method to obtain 1c for direct use in the next reaction.

$^1$H NMR (400 MHz, DMSO-d$_6$) δ 9.10 (s, 2H), 8.94 (s, 1H), 8.66 (s, 2H), 6.75 (s, 2H), 2.45 (s, 6H), 2.17 (s, 3H).

Step 4

Compound 1c (48 g, 106.16 mmol) was dissolved in 1,4-dioxane (100 mL), acrylonitrile (12.96 g, 244.16 mmol) and N,N-diisopropylethylamine (109.76 g, 849.26 mmol, 147.92 mL) were added and the reaction solution was stirred for 3 hours at 30° C., 2,3-dichloro-5,6-dicyano-p-benzoquinone (DDQ) (50.12 g, 220.81 mmol) was then added to the reaction solution, and the reaction solution was continued to stir for 3 hours at 30° C. Water (1,920 mL) was added to the reaction solution, a solid was precipitated out. The reaction solution was filtrated, and dried by a spinning method to obtain compound 1d.

LCMS (ESI) m/z: 303.9 [M+1]$^+$ $^1$H NMR (400 MHz, CDCl$_3$) δ 8.71 (s, 1H), 8.29 (s, 1H), 7.75 (s, 1H).

Step 5

5-bromo-2-fluoropyridine (5 g, 28.41 mmol) and N-Boc-piperazine (5.29 g, 28.41 mmol) were added to DMSO (150 mL). K$_2$CO$_3$ (7.85 g, 56.82 mmol) was added to the reaction solution under stirring, and reaction was conducted for 2 hours at 120° C. The reaction solution was cooled to room temperature to which 50 mL of water was added, and extracted with ethyl acetate (30 mL×3). Organic phases were combined, dried with anhydrous sodium sulfate, dried by a spinning method under reduced pressure at 40-50° C. to obtain a crude product which was purified by column chromatography (PE/EA=10/1 to 1/1) to obtain compound 1e.

LCMS (ESI) m/z: 342.1[M+1]$^+$, 344.1 [M+3]$^+$ $^1$H NMR (400 MHz, CDCl$_3$) δ8.21 (d, J=2.4 Hz, 1H), 7.56 (dd, J=9.2, 2.8 Hz, 1H), 6.56 (d, J=4.0 Hz, 1H), 3.51-3.56 (m, 8H), 1.64 (s, 9H).

Step 6

Compound 1e (4 g, 11.69 mmol) was added to DCM (100 mL), trifluoroacetic acid (13.33 g, 116.88 mmol, 8.65 mL) was added to the reaction solution under stirring, and the reaction was conducted for 2 hours at 25-30° C. The reaction solution was directly dried by a spinning method under reduced pressure at 40-50° C. to obtain compound 1f.

LCMS (ESI) m/z: 242.1[M+1]$^+$, 244.1 [M+3]$^+$

Step 7

Compound 1e (1.5 g, 4.21 mmol) and N,N-diisopropylethylamine (1.63 g, 12.64 mmol, 2.20 mL) were dissolved in 1,2-dichloroethane (30 mL), 2,6-difluoro-benzaldehyde (718.22 mg, 5.05 mmol) and acetic acid (25.29 mg, 421.18 μmol) were added to the reaction solution, the pH of the solution was adjusted to 5-6, and the reaction solution was stirred at 20-25° C. for 2 hours. NaBH(OAc)$_3$ (1.79 g, 8.42 mmol) was then added in portions to the reaction solution, and the reaction was continued to stir for 2 hours, 15 mL of water was added to the reaction solution, and organic phases were combined with dichloromethane (30 mL/3), dried with anhydrous sodium sulfate, filtered and dried by a spinning method under reduced pressure to obtain a crude product which was purified by column chromatography (DCM/MeOH=10/1) to obtain 1 g.

LCMS (ESI) m/z: 368.1[M+1]$^+$. 370.1 [M+3]$^+$

Step 8

Compound 1g (1 g, 2.72 mmol), bis(pinacolato)diboron (1.03 g, 4.07 mmol) was added to 1,4-dioxane (10 mL), K$_3$PO$_4$ (1.73 g, 8.15 mmol) and Pd(dppf)Cl$_2$ (99.36 mg, 135.79 μmol) were added to the reaction solution under stirring, replacement with nitrogen was conducted for three times. The reaction solution was subjected to a microwave reaction at 100° C. for 15 min, and filtrated to obtain a filtrate. The filtrate was concentrated under reduced pressure at 40-50° C. to obtain a crude product which was purified by column chromatography (PE/EA=10/1 to 2/1) to obtain compound 1h.

Step 9

To the DMF (40 mL) and H$_2$O (4 mL) solution of compound 1d (1.30 g, 4.32 mmol) and compound 1h (1.61 g, 3.89 mmol), Na$_2$CO$_3$ (2 M, 5.40 mL) and Pd(PPh$_3$)$_4$ (124.80 mg, 108.00 μmol) were added, and then under nitrogen protection, the reaction solution was directly placed in an oil bath pot at 60° C., and stirred for 16 hours. Anhydrous sodium sulfate was added to the reaction solution for drying, and the reaction solution was filtrated, and dried by a spinning method to obtain a crude product. The crude product was purified by column chromatography (dichloromethane/methanol=20:1 to 10:1) to obtain a crude finished product which was further purified to obtain compound 1i.

LCMS (ESI) m/z: 509.2[M+1]$^+$, 511.2[M+3]$^+$ $^1$H NMR (400 MHz, CDCl$_3$) δ 8.69 (d, J=1.61 Hz, 1H), 8.30-8.35 (m, 1H), 8.27 (s, 1H), 7.69 (dd, J=8.92, 2.64 Hz, 1H), 7.38 (d, J=1.6 Hz, 1H), 7.31 (s, 1H), 6.94 (t, J=7.2 Hz, 2H), 6.75 (d, J=8.8 Hz, 1H), 3.82 (s, 2H), 3.70 (br s, 4H), 2.67 (br s, 4H).

Step 10

Compound 1i (0.1 g, 196.33 μmol) and cyclopropylboronic acid (25.30 mg, 294.49 μmol) were added to a mixed solution of 1,4-dioxane (5 mL) and water (1 mL), then potassium phosphate (125.02 mg, 588.99μ (12) and 1,1-bis(diphenylphosphorus)ferrocene palladium chloride (14.37 mg, 19.63 μmol) were added, and the reaction was conducted for 2 hours at 90° C. The reaction solution was added to water (10 mL), extracted with ethyl acetate (10 mL×3). Organic phases were combined, washed with a saturated salt solution (30 mL×3), dried with anhydrous sodium sulfate, and filtrated to obtain a crude product. The crude product is purified by layer chromatography (petroleum ether:ethyl acetate=1:1) to obtain a crude product which was purified with a preparative chromatography column (chromatography column: Xbridge 150×25 5 μm; mobile phase; [water (10 mM ammonium bicarbonate)-acetonitrile]; B (acetonitrile) %: 55%-85%, 10 min) to obtain compound 1.

LCMS (ESI) m/z: 471.3 (M+1)$^+$

1H NMR (400 MHz, CD$_3$OD) δ 8.54 (s, 1H), 8.37 (s, 1H), 8.28 (s, 1H), 7.77 (dd, J=2.4, 8.9 Hz, 1H), 7.48-7.34 (m, 1H), 7.21 (s, 1H), 7.03 (t, J=8.0 Hz, 2H), 6.95 (d, J=9.2 Hz, 1H), 3.79 (s, 2H), 3.70-3.62 (m, 4H), 2.68 (br d, J=4.8 Hz, 4H), 2.09 (br d, J=4.8 Hz, 1H), 1.09 (q, J=6.4 Hz, 2H), 0.87 (q, J=5.21 Hz, 2H).

Example 2

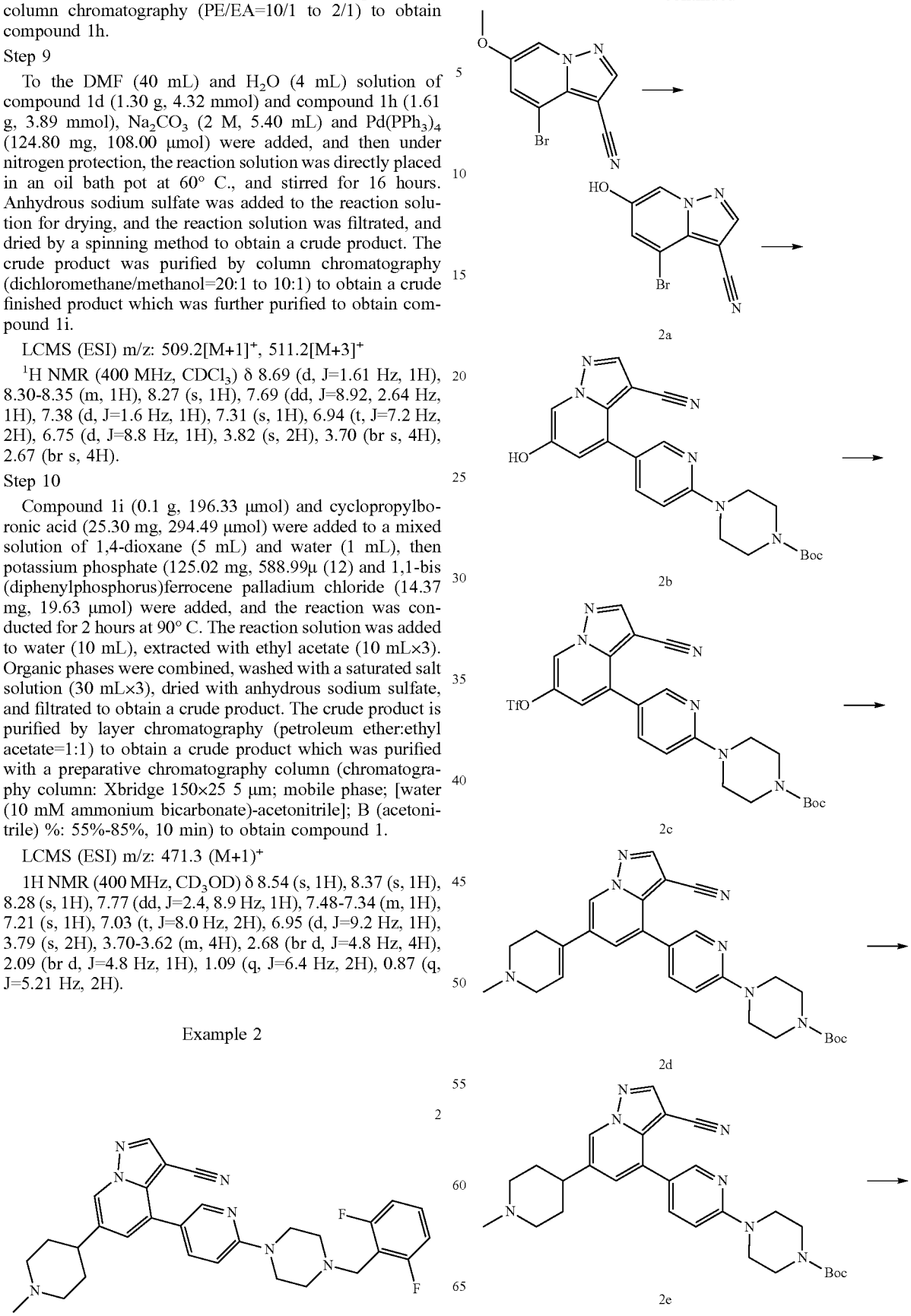

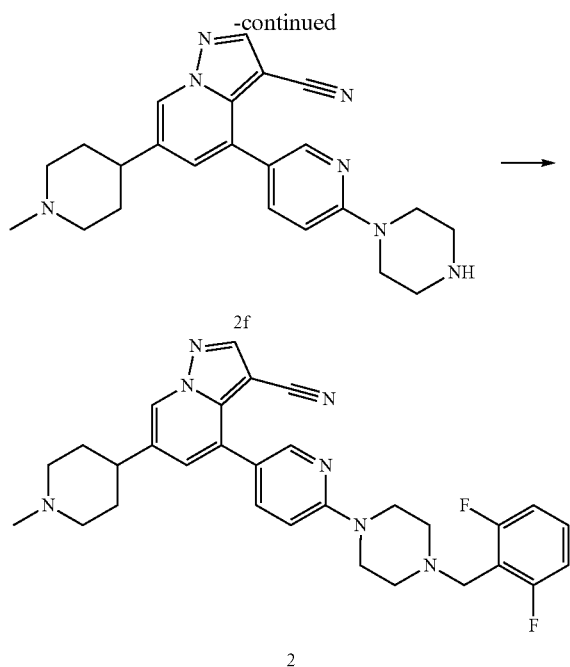

Step 1

3-cyano-4-bromo-6-methoxypyrazoline (50 mg, 198.36 μmol) was added to 1,2-dichloroethane (2 mL), aluminum trichloride (79.35 mg, 595.08 μmol) was added to the reaction solution, and the reaction was conducted at 80° C. under stirring for 16 hours. The reaction solution was cooled to 25-30° C. the reaction was quenched by adding 5 mL of tetrahydrofuran solution containing 100 mg of sodium sulfate decahydrate, and the reaction was conducted at 25-30° C. for 1 hour under stirring. The reaction solution was filtrated under reduced pressure to obtain a filtrate. The filtrate was dried by a spinning method under reduced pressure at 40-50° C. to obtain a crude product 2a.

LCMS (ESI) m/z 237.9[M+1]$^+$ $^1$H NMR (400 MHz, CD$_3$OD) δ10.53 (s, 1H) 8.59 (s, 1H) 8.39 (d, J=1.6 Hz, 1H), 7.66 (d, J=4 Hz, 1H)

Step 2

Compound 2a (25 mg, 105.02 μmol), 1-Boc-4-[5-boronic acid pinacol ester-pyridin-2-yl]piperazine (49.06 mg, 126.03 μmol) and K$_3$PO$_4$ (66.88 mg, 315.07 μmol) were added to 1,4-dioxane (4 mL) and H$_2$O (1 mL), Pd(dppf)Cl$_2$ (3.84 mg, 5.25 μmol) was added to the reaction solution under stirring, replacement with nitrogen was conducted for three times, and the reaction was conducted at 100° C. for 16 hours. The reaction solution was concentrated under reduced pressure at 40-50° C. to obtain a crude product which was purified with a preparative chromatography plate (PE/EA=1/1) to obtain 2b.

LCMS (ESI) m/z: 443.2 [M+23]$^+$

Step 3

Compound 2b (20 mg, 47.57 μmol) was added to DMF (4 mL). N,N-diisopropylethylamine (18.44 mg, 142.70 μmol) and N-phenylbis(trifluoromethanesulfonyl)imine (18.69 mg, 52.32 μmol) were added to the reaction solution under stirring, and the reaction was conducted at 20-25° C. for 2 hours under stirring, 5 mL of water was added to the reaction solution, and then the reaction solution was extracted with ethyl acetate (5 mL×2). Organic phases were combined, washed with a saturated salt solution (5 mL), dried with anhydrous sodium sulfate, and concentrated under reduced pressure at 40-50° C. to obtain compound 2c.

Step 4 Compound 2c (50 mg, 90.49 μmol), 1-methyl-1,2,3,6-tetrahydro-4-boronic acid pinacol ester (24.23 mg, 108.59 μmol), KPO$_4$ (57.63 mg, 271.48 μmol) were added to a mixed solution of 1,4-dioxane (4 mL) and 1120 (1 mL). Pd(dppf)Cl$_2$ (3.31 mg, 4.52 μmol) was added to the reaction solution under stirring, replacement with nitrogen was conducted for three times, and the reaction was conducted at 100° C. for 16 hours. The reaction solution was concentrated under reduced pressure at 40-50° C. to obtain a crude product, and the crude product was purified with a preparative chromatography plate (PE/EA=1/1) to obtain compound 2d.

LCMS (ESI) m/z 522.4 [M+23]$^+$

Step 5

Compound 2d (30 mg, 60.05 μmol) and ammonium formate (30.29 mg, 480.38 μmol) were added to EtOH (6 mL), Pd/C (30 mg) was added to the reaction solution under stirring, replacement with nitrogen was conducted for three times, and the reaction was conducted at 70° C. for 6 hours.

The reaction solution was concentrated under reduced pressure at 40-50° C. to obtain a crude product. The crude product was purified by a preparative chromatography plate (PE/EA=/1) to obtain 2e.

LCMS (ESI) m/z 524.5[M+23]$^+$

Step 6

Compound 2e (25 mg, 49.84 μmol) was added to DCM (4 mL), trifluoroacetic acid (568.27 mg, 4.98 mmol, 369.01 μL) was added to the reaction solution under stirring, and the reaction was conducted at 20-30° C. for 15 min. The reaction solution was concentrated under reduced pressure at 40-50° C. to obtain compound 2f.

LCMS (ESI) m/z 402.3[M+1]$^+$

Step 7

Compound 2f (10 mg, 24.91 μmol) and N,N-diisopropylethylamine (9.66 mg, 74.72 μmol, 13.01 μL) were added to DMF (2 mL), 2,6-difluoro-benzaldehyde (4.25 mg, 29.89 μmol) and acetic acid (149.56 μg, 2.49 μmol) were added to the reaction solution, the reaction was conducted at 20-25° C. for 2 hours under stirring. NaBH$_3$CN (3.13 mg, 49.81 μmol) was then added to the reaction solution, and the reaction was continued for 2 hours under stirring, 5 mL of water was added to the reaction solution, and then the reaction solution was extracted with ethyl acetate (10 mL×3). Organic phases were combined, dried with anhydrous sodium sulfate, and dried by a spinning method under reduced pressure at 40-50° C. to obtain a crude product. The crude product was purified by a preparative chromatography column (chromatography column YMC-Actus Triart C18 100×30 mm×5 μm; mobile phase: [water (0.05% HCl)-acetonitrile]; B (acetonitrile) %: 20%-50%, 10 min), and then purified by a preparative chromatography plate (DCM/MeOH=10/1) to obtain a hydrochloride of compound 2. The hydrochloride of compound 2 was added to a sodium bicarbonate solution, and the obtained solution was extracted with ethyl acetate. Organic phases were dried with anhydrous sodium sulfate, and concentrated under reduced pressure to obtain compound 2.

LCMS (ESI) m/z 528.1[M+1]$^+$ $^1$H NMR (400 MHz, CD$_3$OD) δ 8.67 (s, 1H), 8.42 (s, 1H), 8.31 (d, J=4.0 Hz, 1H), 7.79 (dd, J=8.0, 1H), 7.44 (d, J=4.0 Hz, 1H) 6.99-7.07 (m, 2H) 6.88-6.99 (m, 2H) 3.82 (s, 2H) 3.65-3.70 (m, 5H), 3.15-3.36 (m, 3H), 2.94 (s, 3H), 2.67-2.74 (m, 4H), 2.26 (m, 2H), 2.04-2.15 (m, 2H).

Example 4

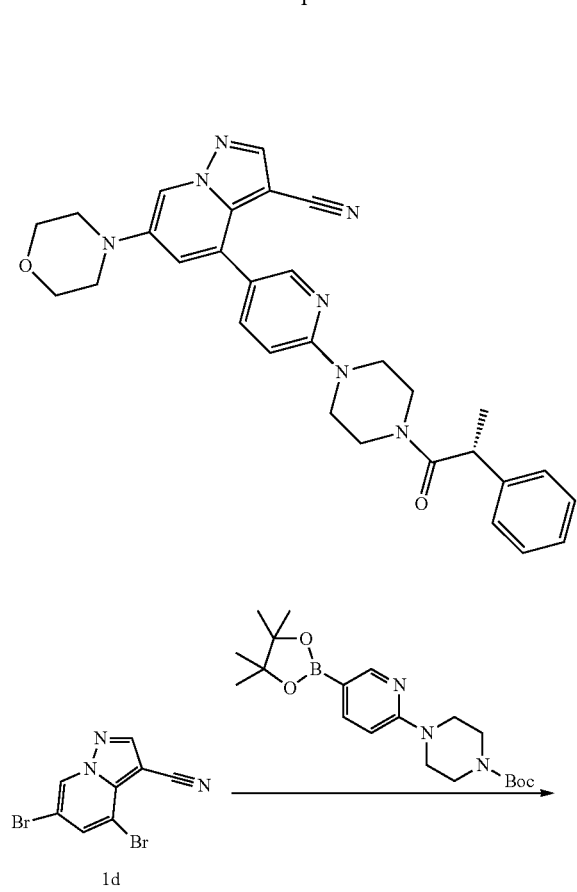

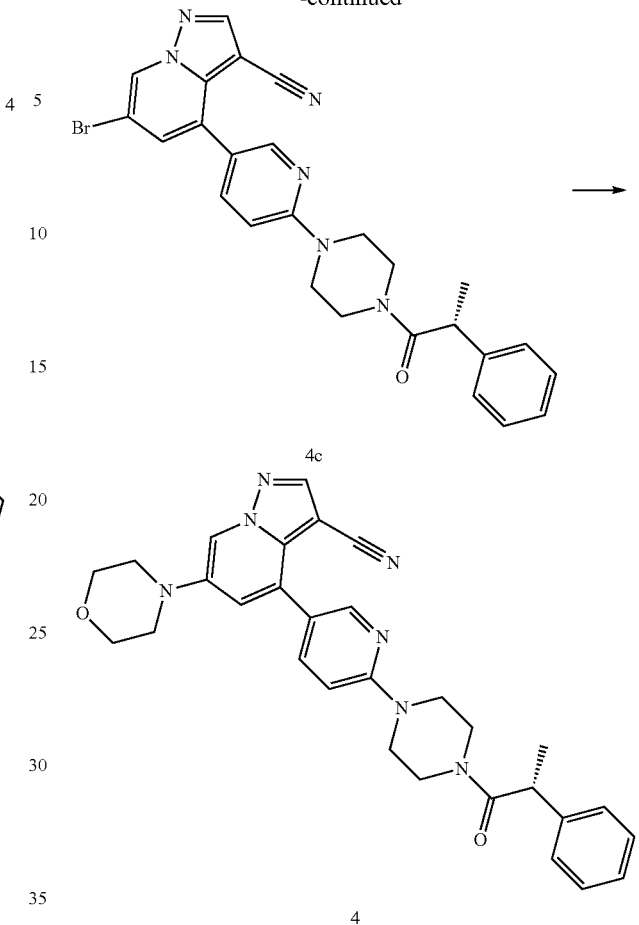

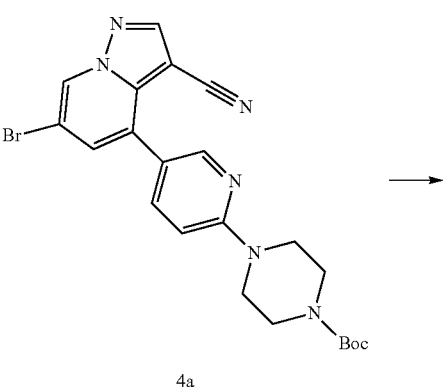

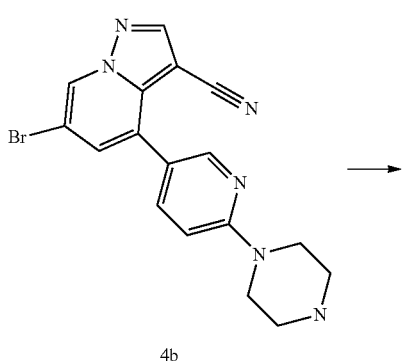

Step 1

1-Boc-4-[5-boronic acid pinacol ester-pyridin-2-yl]piperazine (4.66 g, 11.96 mmol) and compound 1d (3 g, 9.97 mmol) were added to a mixed solution of DMF (60 mL) and H$_2$O (10 mL), Pd(PPh$_3$)$_4$ (1.15 g, 996.89 μmol) and Na$_2$CO$_3$ (3.17 g, 29.91 mmol) were then added, and stirring was conducted at 60° C. for 16 hours under a protection of N$_2$. Solids in the reaction solution were filtered to obtain a filter cake, the filter cake was washed with 10 mL of water for three times, the solids precipitated out from a mother solution were filtered to obtain a filter cake, the filter cake was washed with 10 mL of water for three times, 2 portions of the filter cake were combined and dried under vacuum to obtain a crude product 4a which was directly used in the next step.

LCMS (ESI) m/z: 483.0[M+1]$^+$, 485.0[M+3]$^+$

Step 2

Compound 4a (0.5 g, 1.03 mmol) was added to EtOAc (10 mL). HCl/EtOAc (4 M, 258.61 μL) was added dropwise at 25° C., and the reaction was conducted at 25° C. for 16 hours. Solids were formed in the reaction solution, the reaction solution was filtered to obtain a filter cake, and the filter cake was washed with 5 mL of ethyl acetate for three times and dried to obtain 4b.

LCMS (ESI) m/z: 383.0[M+1]$_+$, 385.0[M+3]$^+$ $^1$H NMR (400 MHz, CD$_3$OD) δ 9.20 (d, J=1.32 Hz, 1H), 8.50 (s, 1H), 8.44 (d, J=2.0 Hz, 1H), 8.33 (dd, J=2.0, 9.32 Hz, 1H), 7.81 (d, J=1.32 Hz, 1H), 7.61 (d, J=9.6 Hz, 1H), 4.18-4.09 (m, 4H), 3.59-3.50 (m, 4H)

Step 3

Compound 4b (0.2 g, 476.52 μmol) was added to DMF (6 mL). HATU (543.57 mg, 1.43 mmol), DIPEA (184.76 mg, 1.43 mmol) and (2R)-2-phenylpropionic acid (71.56 mg, 476.52 μmol) were then added, and the reaction was conducted at 25° C. for 1 hour. The reaction solution was poured into 20 mL of water, a yellow solid was precipitated out, and the reaction solution was filtered to obtain a filter cake. The filter cake was washed with 5 mL of water for three times, and concentrated with an oil pump to obtain compound 4c.

LCMS (ESI) m/z: 514.9[M+1]⁺, 516.9[M+3]⁺

Step 4

Compound 4c (0.02 g, 38.80 μmol) and morpholine (3.38 mg, 38.80 μmol) were added to toluene (1 mL), BINAP (4.83 mg, 7.76 μmol), Pd₂(dba)₃, (3.55 mg, 3.88 μmol) and sodium tert-butoxide (7.46 mg, 77.61 μmol) were then added, stirring was conducted at 90° C. for 2 hours. The reaction solution was directly concentrated to obtain a crude product. The crude product was purified by a preparative chromatography column (chromatography column: Venusil ASB Phenyl 250 mm×50 mm×10 μm; mobile phase: [water (0.05% HCl)-ACN]; B (acetonitrile) %: 35%-65%, 10 min) to obtain a hydrochloride of compound 4. The hydrochloride of compound 4 was added to a sodium bicarbonate solution, and the obtained solution was extracted with ethyl acetate. Organic phases were dried with anhydrous sodium sulfate and concentrated under reduced pressure to obtain compound 4.

LCMS (ESI) m/z: 522.4[M+1]⁺

¹H NMR (400 MHz, CD₃OD) δ 8.35 (d, J=4.6 Hz, 1H), 8.29-8.23 (m, 1H), 7.62 (s, 1H), 7.50 (br d, J=9.8 Hz, 1H), 7.41-7.31 (m, 2H), 7.31-7.24 (m, 1H), 4.21-4.12 (m, 1H), 4.06-3.67 (m, 12H), 3.27-3.20 (m, 4H), 1.45 (d, J=6.8 Hz, 3H).

Examples 5 and 23

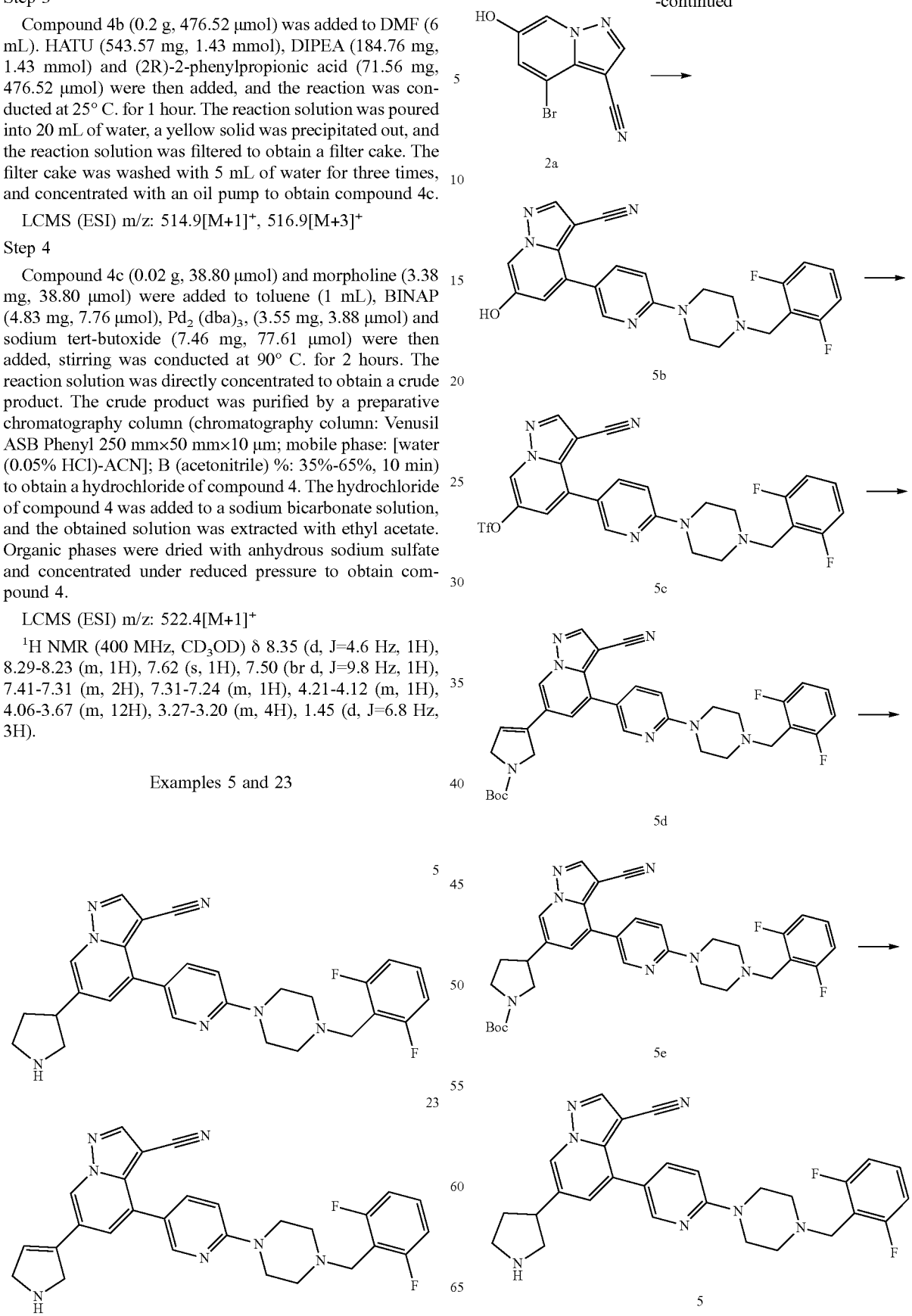

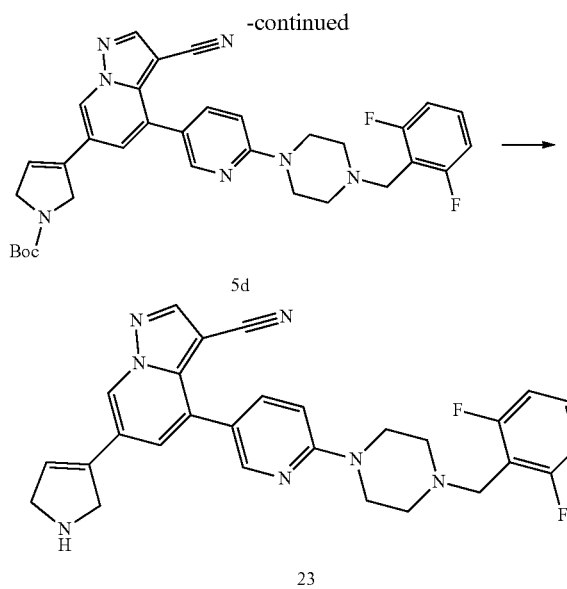

Step 1

Compound 2a (0.5 g, 2.10 mmol), potassium phosphate (1.34 g, 6.30 mmol) and 1,1-bis(diphenylphosphorus)ferrocene palladium chloride (153.69 mg, 210.05 µmol) were added to a mixed solution of 1,4-dioxane (8 mL) and water (2 mL), compound 1h (87229 mg, 2.10 mmol) was then added, and the reaction was conducted at 100° C. for 5 hours. The reaction solution was added to water (10 mL), and extracted with ethyl acetate (10 mL×3). Organic phases were combined, washed with a saturated salt solution (20 mL×3) for three times, dried with anhydrous sodium sulfate, filtered, and concentrated to obtain a crude product. The crude product was purified by a flash silica gel column (petroleum ether/ethyl acetate=10/1 to 1:1) to obtain 5b.

LCMS (ESI) m/z: 447.0[M+1]$^+$

Step 2

At 25° C., 2b (0.545 g, 1.22 mmol) was added to anhydrous DMF (5 mL). N,N-diisopropylethylamine (473.30 mg, 3.66 mmol, 637.88 µL) and N-phenylbis(trifluoromethanesulfonyl)imine (654.16 mg, 1.83 mmol) were added to the reaction solution under stirring, the reaction was conducted at 25° C. for 2 hours under stirring. The reaction solution was added to water (50 mL), and extracted with ethyl acetate (30 mL×3). Organic phases were combined, washed with a saturated salt solution (50 mL×3), and dried with anhydrous sodium sulfate, filtrated to obtain a filtrate. The filtrate was dried by a spinning method in vacuum to obtain a crude product, and the crude product was purified by a flash silica gel column (petroleum ether/ethyl acetate=10/1 to 3:1) to obtain 5c.

Step 3

5c (0.3 g, 518.57 µmol) and N-Boc-2,5-dihydro-1H-pyrrole-1-boronic acid pinacol ester (229.61 mg, 777.86 µmol) were added to a mixed solution of 1,4-dioxane (4 mL) and water (1 mL), then 1,1-bis(diphenylphosphorus)ferrocene palladium chloride (37.94 mg, 51.86 µmol) and potassium phosphate (330.23 mg, 1.56 mmol) were added, and the reaction was conducted at 90° C. for 2 hours. The reaction solution was added to water (50 mL), and extracted with ethyl acetate (30 mL×3). Organic phases were combined, washed with a saturated salt solution (90 mL×3), and dried with anhydrous sodium sulfate, filtrated to obtain a filtrate. The filtrate was dried by a spinning method in vacuum to obtain a crude product, and the crude product was purified by a flash silica gel column (petroleum ether/ethyl acetate=10/1 to 0:1) to obtain 5d.

LCMS (ESI) m/z: 598.2[M+1]$^+$

Step 4

Compound 5d (0.06 g, 100.39 µmol) was dissolved in absolute ethanol (6 mL), ammonium formate (6.33 mg, 100.39 µmol) and Pd/C (0.1 g, 10%) were added at 25° C., stirring was conducted at 50° C. for 0.5 hour. The reaction solution was filtered through diatomite and washed with methanol (5 mL×3) to obtain a filtrate, and the filtrate was concentrated to obtain a crude product. The crude product was purified with a preparative chromatography plate (petroleum ether/ethyl acetate=1/1) to obtain compound 5e.

LCMS (ESI) m/z: 600.1 [M+1]$^+$ $^1$H NMR (40) MHz, CD$_3$OD) δ 8.96 (s, 1H), 8.53 (s, 11-1), 8.47 (d, J=2.4 Hz, 1H), 8.33 (dd, J=2.4, 9.2 Hz, 1H), 7.98 (d, J=1.2 Hz, 1H), 7.75-7.63 (m, 1H), 7.57 (d, J=9.2 Hz, 1H), 7.25 (t, J=8.4 Hz, 2H), 6.72 (d, J=2.0 Hz, 1H), 4.65 (s, 2H), 4.6 (br d, J=2.0 Hz, 2H), 4.42-3.88 (m, 6H), 3.69 (br s, 4H).

Step 5

5e (0.04 g, 66.70 µmol) was dissolved in ethyl acetate (I mL), hydrochloric acid-ethyl acetate (4 M, 166.76 µL) was added at 25° C., and stirring was conducted at 25° C. for 0.5 hour. The reaction solution was filtered to obtain residue, the residue was purified to obtain a hydrochloride of compound 5. The hydrochloride of compound 5 was added to dichloromethane containing excess sodium bicarbonate solid, stirred for 1 hour, and filtrated to obtain a filtrate. The filtrate was concentrated under reduced pressure to obtain compound 5.

LCMS (ESI) m/z: 500.4[M+1]$^+$ $^1$H NMR (400 MHz, CD$_3$OD) δ 8.87 (s, 1H), 8.49 (s, 1H), 8.45 (d, J=2.4 Hz, 1H), 820 (dd, J=2.4, 9.2H, 1H), 7.74-7.64 (m, 2H), 7.43 (d, J=9.2 Hz, 1H), 7.25 (t, J=8.4 Hz, 2H), 4.63 (s, 2H), 3.91-3.72 (m, 3H), 3.71-3.59 (m, 5H), 3.51-3.38 (n, 2H), 3.34 (br s, 4H), 2.66-2.52 (m, 1H).

Step 6

5d (0.1 g, 167.32 µmol) was dissolved in ethyl acetate (1 mL), hydrogen chloride-ethyl acetate (4 M, 4 mL) was added at 25° C., and stirring was conducted at 25° C. for 1 hour. The reaction solution was filtered to obtain a hydrochloride of compound 23. The hydrochloride of compound 23 was added to a sodium bicarbonate solution, and the obtained solution was extracted with ethyl acetate. Organic phases were dried with anhydrous sodium sulfate, and concentrated under reduced pressure to obtain compound 23.

LCMS (ESI) m/z: 498.3[M+1]$^+$ $^1$H NMR (400 MHz, d4-MeOH) δ 8.96 (s, 1H), 8.53 (s, 1H), 8.47 (d, J=2.4 Hz, 1H), 8.33 (dd, J=2.4, 92 Hz, 1H), 7.98 (d, J=1.2 Hz, 1H), 7.75-7.63 (m, 1H), 7.57 (d, J=9.2 Hz, 1H), 7.25 (t, J=8.4 Hz, 2H), 6.72 (d, J=2.0 Hz, 1H), 4.65 (s, 2H), 4.64) (br d, J=2.0 Hz, 2H), 4.42-3.88 (m, 6H), 3.69 (br s, 4H).

Example 6

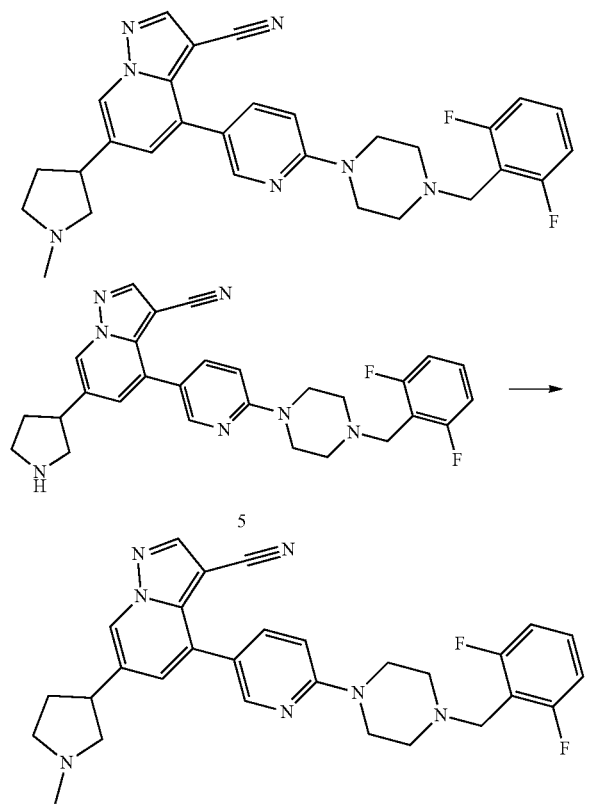

Step 1

A hydrochloride of compound 5 (0.02 g, 37.31 μmol, HCl) was dissolved in a mixed solution of anhydrous methanol (1 mL) and anhydrous dichloromethane (2 mL), N,N-diisopropylethylamine (14.47 mg, 111.94 μmol, 19.50 μL) was added under 25° C., stirring was conducted for 10 min, glacial acetic acid (17.92 mg, 298.50 μmol, 17.07 μL) and formaldehyde (2.24 mg, 74.62 μmol, 2.06 μL) aqueous solution were added, stirring was conducted for 20 min, then triacetyl sodium borohydride (23.72 mg, 111.94 μmol) was added, and stirring was conducted at 25° C. for 10 min. The reaction solution was directly concentrated to obtain a crude product. The crude product was purified by a preparative chromatography column (chromatography column: Boston Green ODS 150×30 mm 5 μm; mobile phase: [water (0.075% trifluoroacetic acid)-acetonitrile]; B (acetonitrile) %: 20%-50%, 7 min) to obtain a trifluoroacetate of compound 6. The trifluoroacetate of compound 6 was added to a sodium bicarbonate solution, and the obtained solution was extracted with ethyl acetate. Organic phases were dried with anhydrous sodium sulfate, and concentrated under reduced pressure to obtain compound 6.

LCMS (ESI) m/z: 514.5[M+1]$^+$ $^1$H NMR (400 MHz, CD$_3$OD) δ 8 81 (br s, 1H), 8.45 (s, 1H), 8.43 (d, J=2.4 Hz, 1H), 7.93 (dd, J=2.4, 8.8 Hz, 1H), 7.71-7.62 (m, 1H), 7.58 (br s, 1H), 7.22 (t, J=8.8 Hz, 2H), 7.15 (d, J=8.8 Hz, 1H), 4.58 (s, 2H), 4.16-3.82 (m, 6H), 3.55 (br t, J=4.4 Hz, 4H), 3.06 (s, 3H), 2.73-2.28 (m, 2H), 1.42-1.33 (m, 1H).

Example 7

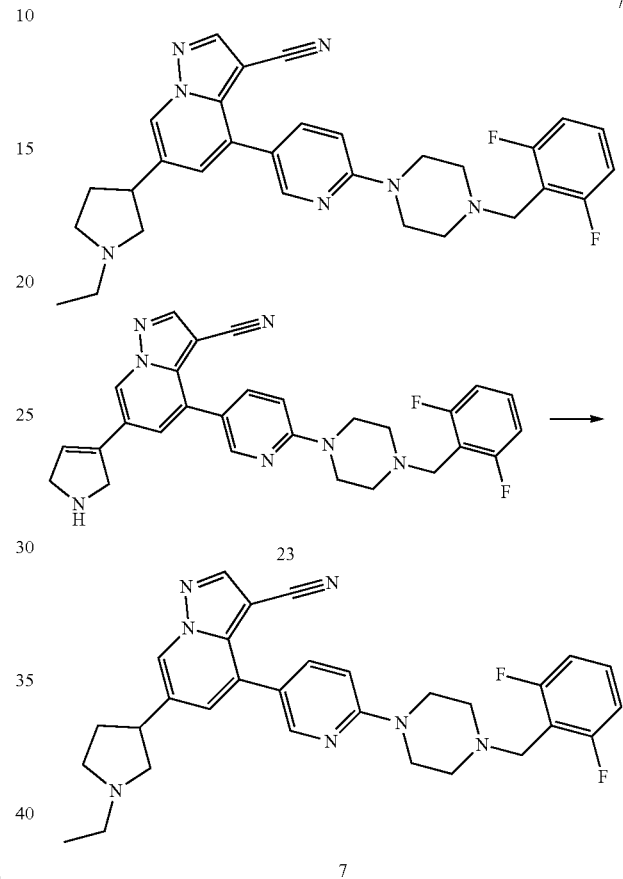

Step 1

A hydrochloride of compound 23 (0.05 g, 93.63 μmol, HCl) was dissolved in absolute ethanol (5 mL), ammonium formate (590.07 mg, 9.36 mmol) and Pd/C (465.86 mg, 437.76 μmol, 10% purity) were added at 25° C., and stirring was conducted at 50° C. for 0.5 hour. The reaction solution was filtered through diatomite, washed with methanol (5 mL×3), and concentrated to obtain a crude product. The crude product was purified by a preparative chromatography column (chromatography column: Boston Green ODS 150× 30 mm 5 μm, mobile phase: [water (0.075% trifluoroacetic acid)-acetonitrile]; B (acetonitrile) %: 20%-50%, 7 min) to obtain a trifluoroacetate of compound 7. The trifluoroacetate of compound 7 was added to a sodium bicarbonate solution, and the obtained solution was extracted with ethyl acetate. Organic phases were dried with anhydrous sodium sulfate, and concentrated under reduced pressure to obtain compound 7.

LCMS (ESI) m/z: 528.5[M+1]$^+$ $^1$H NMR (400 MHz, CD$_3$OD) δ8.86-8.76 (m, 1H), 8.50-8.39 (m, 2H), 7.90 (dd, J=2.4, 8.8 Hz, 1H), 7.72-7.60 (m, 1H), 7.56 (br d, J=15.6 Hz, 1H), 7.24 (t, J=8.4 Hz, 2H), 7.12

(d, J=8.8 Hz, 1H'), 4.58 (s, 2H), 4.18-3.66 (m, 6H), 3.54 (br s, 4H), 3.39 (br d, J=7.3H z, 2H), 2.74-2.22 (m, 2H), 1.45-1.36 (m, 3H).

Example 8

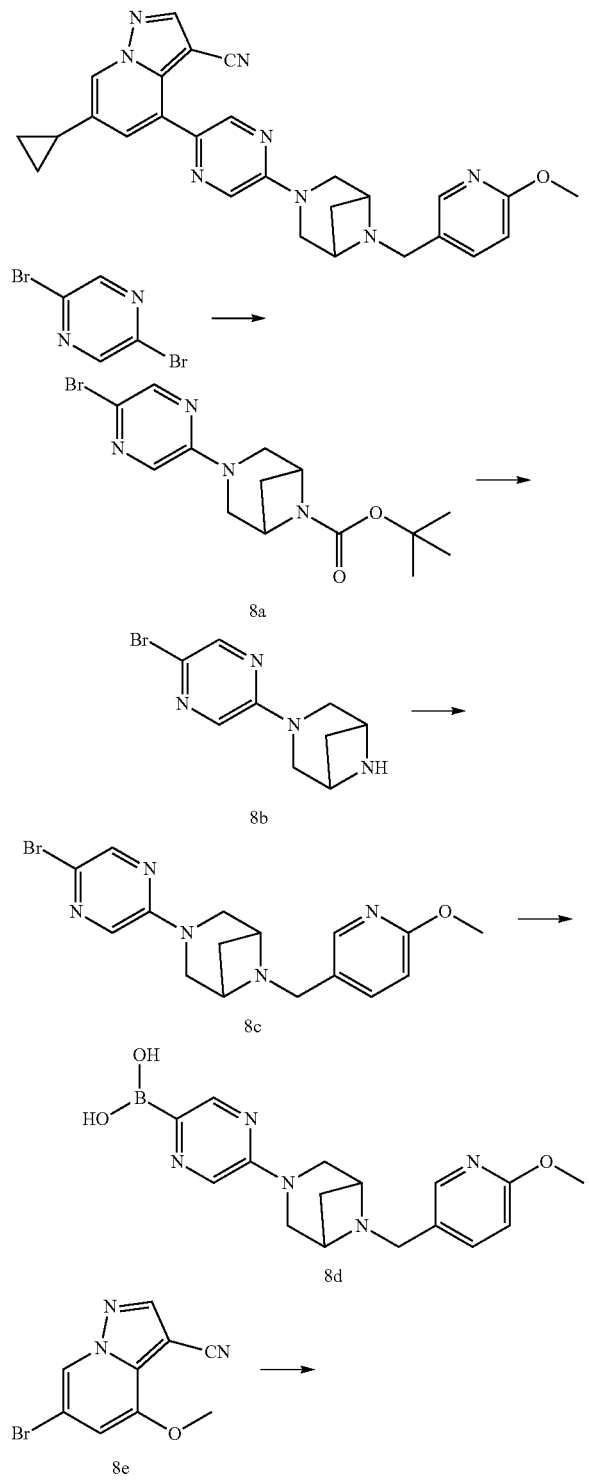

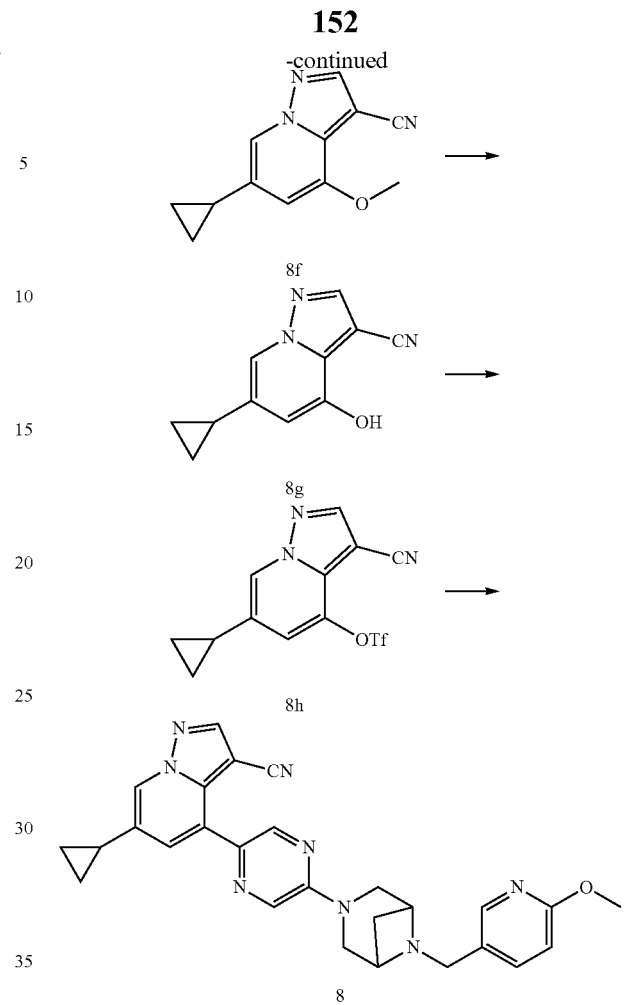

Step 1

2,5-dibromopyrazine (4 g, 16.82 mmol) and 6-Boc-3,6-diazabicyclo[3.1.1]-heptane (4.00 g, 20.18 mmol) were dissolved in NMP (50 mL). DIPEA (6.52 g, 50.45 mmol, 8.79 mL) was added, and stirring was conducted at 100° C. for 16 hours, 60 mL of water was added, and then the reaction solution was extracted with ethyl acetate (100 mL×3). Organic phases were combined, washed with water (050 mL×5), washed with a saturated sodium chloride solution (150 mL×1), and dried with anhydrous sodium sulfate, and finally dried by a spinning method to obtain a crude product. The crude product was purified by an automatic column passing machine (petroleum ether:ethyl acetate=4.1) to obtain compound 8a.

LCMS (ESI) m/z: 354.9[M+1]$^+$. 356.9[M+3]$^+$ $^1$H NMR (400 MHz, CDCl$_3$) δ8.15 (d, J=1.2 Hz, 1H), 7.77 (s, 1H), 4.28-4.31 (m, 2H), 3.90-4.12 (m, 2H), 3.42 (d, J=12.0 Hz, 2H), 2.64-2.72 (m, 1H), 1.50 (d, J=12.4 Hz, 1H), 1.38 (s, 9H).

Step 2

Compound 8a (3 g, 8.45 mmol) was dissolved in ethyl acetate (15 mL), hydrogen chloride/ethyl acetate (4 M, 20 mL) was added, and stirring was conducted at 16° C. for 3 hours. The solvent was dried by a spinning method to obtain a crude product 8b which was directly put into the next reaction without purification.

LCMS (ESI) m/z: 254.9[M+1]$^+$, 256.9[M+3]$^{30}$

Step 3

Compound 8b (2.45 g, 8.40 mmol) and 6-methoxy-3-pyridinecarbaldehyde (2.30 g, 16.81 mmol) were added to DCM (50 mL), NaBH(OAc)₃ (5.34 g, 25.21 mmol) was then added, stirring was conducted at 16'C for 1.5 hours, the reaction solution became clear, 50 mL of water was added to the reaction solution, and then the reaction solution was extracted with dichloromethane (50 mL×3). Organic phases were combined, washed with a saturated sodium chloride solution (100 mL×1), and dried with anhydrous sodium sulfate, and finally dried by a spinning method to obtain a crude product. The crude product was purified by an automatic column passing machine (petroleum ether:ethyl acetate=1:3 to dichloromethane:methanol=10:1) to obtain compound 8c.

LCMS (ESI) m/z: 376.0[M+1]⁺, 378.0[M+3]⁺

Step 4

Compound 8c (1.8 g, 4.78 mmol) and bis(pinacolato)diboron (1.82 g, 7.18 mmol) were dissolved in 1,4-dioxane (15 mL). Pd(dppf)Cl₂ (350.05 mg, 478.40 μmol) and KOAc (1.41 g, 14.35 mmol) were added, and stirring was conducted at 80° C. for 16 hours under nitrogen protection. Some dehalogenation side products were produced during the reaction. The reaction solution was directly filtered, and washed with ethyl acetate twice to obtain a filtrate. The filtrate was dried by a spinning method to obtain a crude product 8d which was directly used in the next step.

LCMS (ESI) m/z: 342, [M+1]³⁰

Step 5

Cyclopropylboronic acid (153.35 mg, 1.79 mmol), compound 8e (300 mg, 1.19 mmol), Pd(dppf)Cl₂ (87 mg, 119 mol) and K₂PO₄ (758 mg, 3.57 mmol) were added to a mixed solution of 1,4-dioxane (4 mL) and 1-120 (2 mL), t heated to 90° C. wider nitrogen protection, and reacted for 8 hours under stirring. The insoluble material was removed by filtration, a filter residue was washed with ethyl acetate. Filtrates were combined, and dried by a spinning method to obtain a crude product. The crude product was purified by an automatic column passing machine (petroleum ether/ethyl acetate=3:1) to obtain compound 8f.

LCMS (ESI) m/z: 213.9[M+1]⁺

Step 6

A pyridine hydrochloride (840 mg, 7.27 mmol) was added to compound 8f (155 mg, 0.73 mmol), heated to 180° C. by microwave under nitrogen protection, and reacted for 30 minutes wider stirring. The reactant was added to 10 mL saturated sodium bicarbonate solution for quenching, and the reaction solution was extracted with ethyl acetate (20 mL×4). Organic phases were combined, washed with a saturated sodium chloride solution, dried with anhydrous sodium sulfate, and finally dried by a spinning method to obtain a crude product 8g. The crude product was used directly in the next step without further purification.

Step 7

Compound 8g (100 mg, 0.50 mmol), N-phenylbis(trifluoromethanesulfonyl imine (269 mg, 0.75 mmol) and DIPEA (195 mg, 1.5 mmol) were added to DMF (1 mL), and reaction was conducted under nitrogen protection at 10-20° C. for 1 hour under stirring. The reaction solution was directly subjected to rotary evaporation to remove the solvent to obtain a crude product. The crude product was purified by an automatic column passing machine (petroleum ether/ethyl acetate=4:1) to obtain compound 8h.

LCMS (ESI) m/z: 331.9[M+1]⁺

Step 8

Compound 8h (100 mg, 0.30 mmol), compound 8d (154.48 mg, 0.45 mmol), Pd(dppf)Cl₂ (22.1 mg, 30.19 μmol) and K₃PO₄ (192.23 mg, 0.90 mmol) were added to a mixed solution of 1,4-dioxane (1 mL) and H₂O (0.5 mL), heated to 90° C. under nitrogen protection, and reacted for 1 hour wider stirring. The insoluble material was removed by filtration, a filter residue was washed with ethyl acetate. Filtrates were combined, and dried by a spinning method to obtain a crude product. The crude product was separated and purified by a preparative chromatography column (chromatography column: YMC-Triart Prep C18 150×40 mm×7 μm; mobile phase: [water (0.075% TFA)-ACN]; B (acetonitrile) %: 35%-65%, 7 min) to obtain a trifluoroacetate of compound 8. The trifluoroacetate of compound 8 was added to a sodium bicarbonate solution, and the obtained solution was extracted with ethyl acetate. Organic phases were dried with anhydrous sodium sulfate, and concentrated under reduced pressure to obtain compound 8.

LCMS (ESI) m/z: 479.2 [M+1]⁺

¹H NMR (400 MHz, CD₃OD) δ 8.78-8.63 (m, 2H), 8.45-8.31 (m, 3H), 7.92-7.89 (m, 2H), 6.93 (d, J=8 Hz, 1H), 6.57-6.52 (m, 2H), 4.71-4.61 (m, 3H), 4.33-4.31 (m, 4H), 4.10-4.05 (m, 1H), 3.97 (s, 3H), 3.65-3.62 (m, 1H), 3.07-3.03 (m, 1H), 2.25-2.22 (m, 1H), 1.98-1.97 (m, 4H).

Example 9

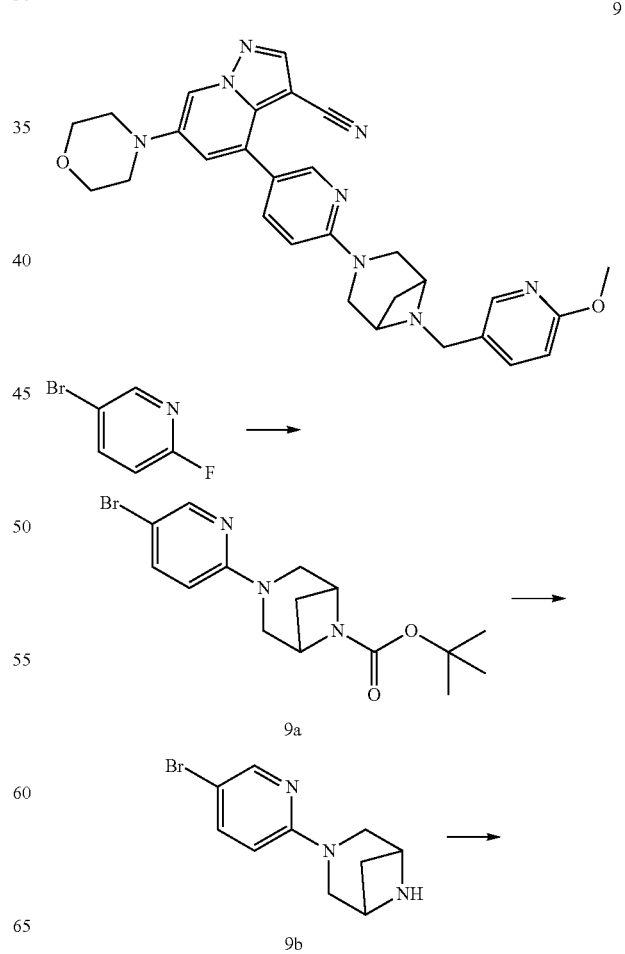

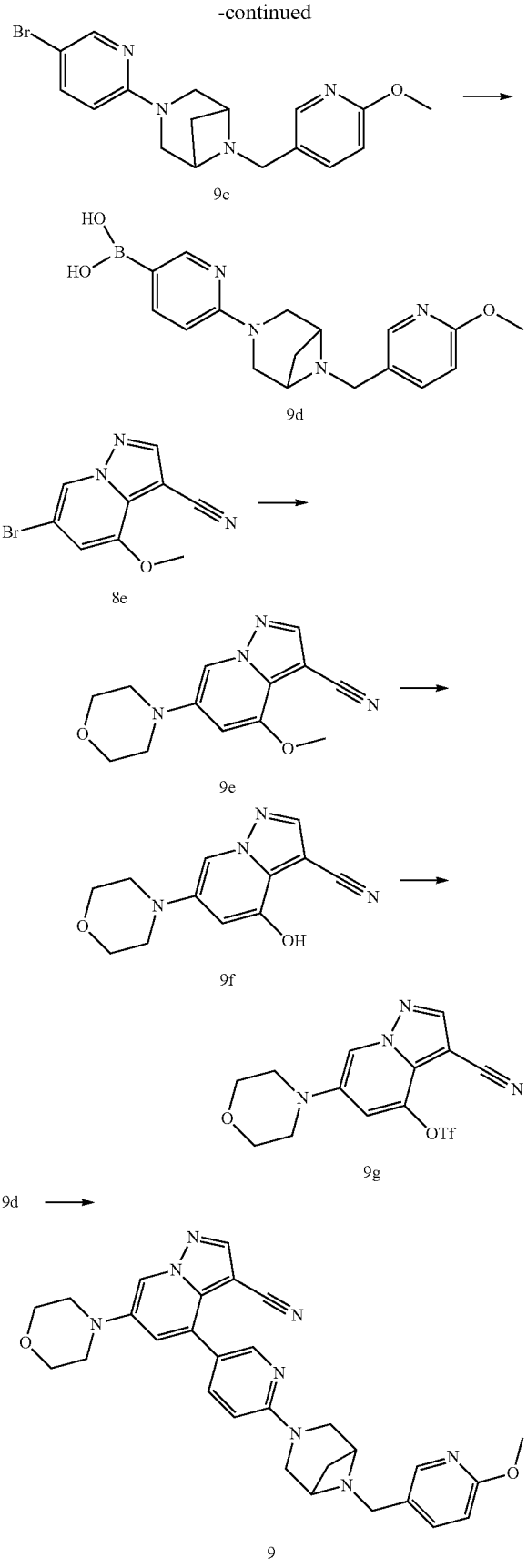

Step 1

5-bromo-2-fluoropyridine (4.5 g, 25.57 mmol), 6-Boc-3,6-diazabicyclo[3.1.1]-heptane (6.08 g, 30.68 mmol) were dissolved in NMP (70 mL), DIPEA (9.91 g, 76.71 mmol, 13.36 mL) was added, stirring was conducted at 100° C. for 16 hours, 70) mL of water was added, and then the reaction solution was extracted with ethyl acetate (70 mL×3). Organic phases were combined, washed with water (100 mL×5), washed with a saturated sodium chloride solution (100 mL×1), dried with anhydrous sodium sulfate, and dried by a spinning method to obtain a crude product. The crude product was purified by an automatic column passing machine (petroleum ether:ethyl acetate=3:1) to obtain compound 9a.

$^1$H NMR (400 MHz, CDCl$_3$) δ8.21 (d, J=6.8 Hz, 1H), 7.53-7.56 (m, 1H), 6.41 (d, J=8.8 Hz, 1H), 4.27 (d, J=5.2 Hz, 2H), 4.05 (d, J=6.0 Hz, 2H), 3.41 (br s, 2H), 2.62-2.68 (m, 2H), 1.47 (d, J=8.0 Hz, 1H), 1.38 (s, 9H)

Step 2

Compound 9a (3 g, 8.47 mmol) was dissolved in EtOAc (20 mL), hydrogen chloride/ethyl acetate (4 M, 10 mL) was added, stirring was conducted at 16° C. for 8 hours. A large quantity of solids were generated, the solvent was directly dried by a spinning method to obtain a crude compound 9b which was directly used in the next step without purification.

LCMS (ESI) m/z: 289.8[M+1-56]$^+$, 291.8[M+43-56]$^+$

Step 3

Compound 9b (2.6 g, 8.95 mmol), 6-methoxy-3-pyridinecarbaldehyde (2.45 g, 17.89 mmol) were added to DCM (50 mL), NaBH(OAc) (5.69 g, 26.84 mmol) was then added in portions, stirring was conducted at 16° C. for 1.5 hours, and the reaction solution became clear, 50 mL of water was added to the reaction solution for quenching, and then the reaction solution was extracted with dichloromethane (50 mL×3). Organic phases were combined, washed with a saturated sodium chloride solution (000 mL×1), dried with anhydrous sodium sulfate, and finally dried by a spinning method to obtain a crude product. The crude product was then purified by an automatic column passing machine (petroleum ether:ethyl acetate=1.3 to dichloromethane:methanol=10.1) to obtain compound 9c.

LCMS (ESI) m/z: 375.0[M+1]$^+$, 377.0[M+3]$^+$

Step 4

Compound 9c (1.07 g, 2.85 mmol) was dissolved in 1,4-dioxane (25 mL), and bis(pinacolato)diboron (2.17 g, 8.55 mmol). Pd(dppf)Cl$_2$CH$_2$Cl$_2$ (232.85 mg, 285.13 μmol) and potassium acetate (839.49 mg, 8.55 mmol) were added successively. Under the protection of N$_2$, stirring was conducted at 80° C. for 16 hours. The reaction solution was filtered to remove insoluble solids, a filter residue was washed with ethyl acetate (20 mL) to obtain filtrates. The filtrates were combined, and dried by a spinning method to obtain a crude product. The crude product was purified by a flash silica gel column (petroleum ether/ethyl acetate=1:1-dichloromethane/methanol=10:1) to obtain compound 9d which can be directly used in the next step.

LCMS (ESI) m/z: 340.9[M+1]$^+$.

Step 5

Compound 8e (500 mg, 1.98 mmol), morpholine (207.37 mg, 2.38 mmol, 209.47 μL), tris(dibenzylideneacetone)dipalladium (181.64 mg, 198.36 mmol), 2,2-bis(diphenylphosphino)-1,1-binaphthyl (247.03 mg, 396.72 μmol), and sodium tert-butoxide (571.89 mg, 5.95 mmol) were added in toluene (5 mL), and stirring was conducted at 90° C. for 8 hours. After Cooling, the reaction solution was filtrated was to remove insoluble solids to obtain a filtrate, and the filtrate was dried by a spinning method to obtain a crude product. The crude product was purified by a flash silica gel column (petroleum ether/ethyl acetate=1:1, Rf=0.16) to obtain compound 9e.

LCMS (ESI) m/z: 258.9 [M+]+.

$^1$H NMR (400 MHz, CDCl$_3$) δ ppm 8.08 (s, 1H) 7.68 (s, 1H) 6.51 (s, 1H) 4.02 (s, 3H) 3.95-3.82 (m, 4H) 3.17-3.04 (m, 4H).

Step 6

Compound 9e (230 mg, 890.52 μmol) and pyridine hydrochloride (1.03 g, 8.91 mmol) were added to a microwave tube and mixed evenly, and the reaction was conducted at 80° C. for 20 minutes. The reactant was added to 10 mL of a saturated sodium bicarbonate solution, and the obtained solution was extracted with ethyl acetate (10 mL×3). Organic phases were combined, washed with a saturated sodium chloride solution (20 mL), dried with anhydrous sodium sulfate, and finally dried by a spinning method to obtain a crude product compound 9f which was directly used in the next step without purification.

Step 7

Compound 9f (300 mg, 614.13 μmol). N-phenylbis(trifluoromethanesulfonyl) imine (329.10 mg, 921.19 μmol) were dissolved in N,N-dimethylformamide (10 mL). N,N-diisopropylethylamine (238.12 mg, 1.84 mmol, 320.91 μL) was added, and stirring was conducted at 16° C. for 1 hour. The solvent was dried by a spinning method to obtain a crude product which was purified by an automatic column passing machine (petroleum ether/ethyl acetate=1:1) to obtain compound 9g.

LCMS (ESI) m/z: 377.0 [M+1]+.

Step 8

In a microwave tube, compound 9g (80 mg, 212.59 μmol) and compound 9d (269.35 mg, 318.89 μmol) were dissolved in a 1,4-dioxane (2 mL)/water (1 mL) solution, 1,1-bis (diphenylphosphorus)ferrocene palladium chloride (15.56 mg, 21.26 μmol) and potassium acetate (62.59 mg, 637.77 μmol) were added, and a microwave reaction was conducted at 90° C. for 30 minutes under stirring. The reaction solution was filtrated to remove insoluble material, and washed with ethyl acetate. Filtrates were combined, and dried by a spinning method to obtain a crude product. The crude product was separated and purified by a preparative chromatography column (chromatography column: Boston Green ODS 150×30 nm×5 um; mobile phase [water (0.075% trifluoroacetic acid)-acetonitrile]; B (acetonitrile) %: 14%-44%, 10 min) to obtain a trifluoroacetate of compound 9. The trifluoroacetate of compound 9 was added to a sodium bicarbonate solution, and the obtained solution was extracted with ethyl acetate. Organic phases were dried with anhydrous sodium sulfate, and concentrated under reduced pressure to obtain compound 9.

LCMS (ESI) m/z: 523.1[M+1]+.

$^1$H NMR (400 MHz, MeOD) δ ppm 8.49-8.23 (m, 4H) 7.98-7.78 (m, 2H) 7.45 (s, 1H) 6.93 (d, J=8.76 Hz, 2H) 4.84-4.80 (m, 1H) 4.69 (s, 2H) 4.62-4.56 (m, 1H) 4.32-4.20 (m, 3H) 4.03 (s, 1H) 3.97 (s, 3H) 3.89 (s, 4H) 3.59 (s, 1H) 3.27-3.20 (m, 4H) 2.21 (d, J=11.13 Hz, 1H).

Example 10

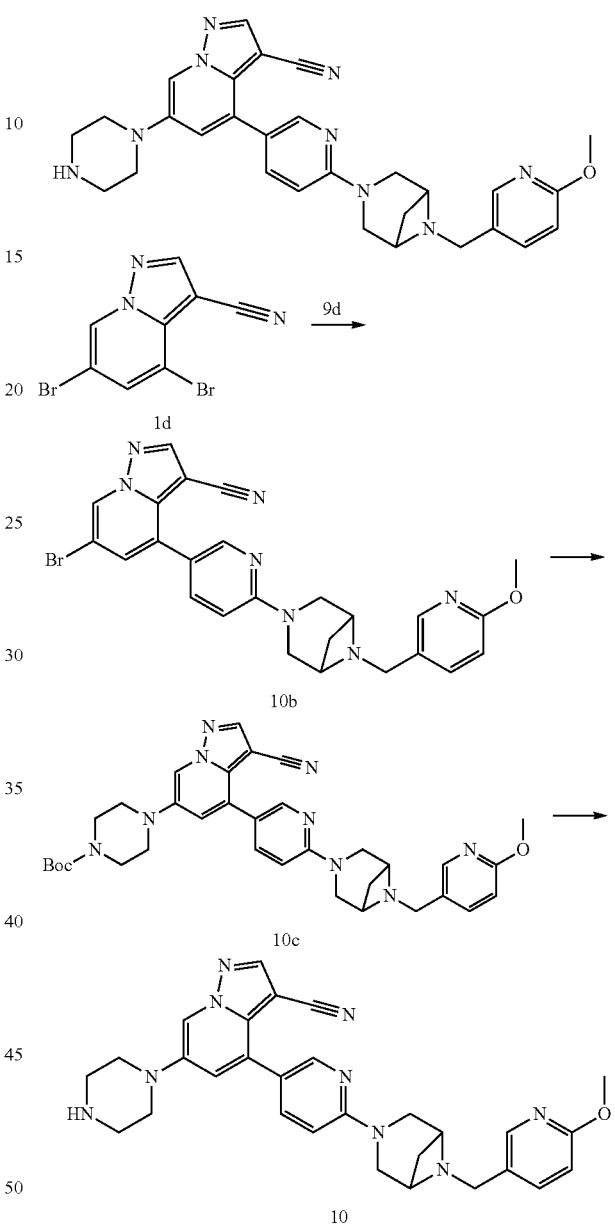

Step 1

Compound 1d (500 mg, 769.55 μmol) and compound 9d (277.90 mg, 923.46 μmol) were dissolved in N,N-dimethylformamide (2 mL), and tetrakistnphenylphosphine palladium (88.93 mg, 76.95 μmol) and potassium carbonate (2 M, 769.55 μL) were added, and stirring was conducted at 60° C. for 16 hours under nitrogen protection. 5 mL of water was added to the reaction solution, and then the reaction solution was extracted with ethyl acetate (10 mL×3). Organic phases were combined, washed with water (15 mL×3), washed with a saturated sodium chloride solution (15 mL×1), dried with anhydrous sodium sulfate, and finally dried by a spinning method to obtain a crude product. The crude product was purified by an automatic column passing machine (PE: EA=1:1-DCM:MeOH=10-1) to obtain compound 10b.

LCMS (ESI) m/z: 516.0 [M+1]+

$^1$H NMR (400) MHz, CDCl$_3$) δ ppm 8.70 (d, J=1.52 Hz, 1H) 8.40 (d, J=2.26 Hz, 1H) 8.28 (s, 1H) 8.11 (d, J=2.04 Hz, 1H) 7.77 (dd, J=8.78, 2.51 Hz, 1H) 7.63 (dd, J=8.52, 2.00 Hz, 1H) 7.41 (d, J=1.52 Hz, 1H) 6.75-6.64 (m, 2H) 3.93-3.91 (m, 5H) 3.80-3.74 (m, 4H) 3.57-3.47 (m, 2H) 2.70 (d, J=7.28 Hz, 1H), 2.25-2.20 (m, 1H).

Step 2

Compound 10b (100 mg, 193.65 μmol) and N-Boc piperazine (36.07 mg, 193.65 μmol) were dissolved in toluene (2 mL) Pd$_2$(dba)$_3$ (8.87 mg, 9.68 mol), BINAP (12.06 mg, 19.37 μmol) and t-BuONa (46.53 mg, 484.13 μm) were added, and reaction was conducted at 90° C. for 16 hours under nitrogen protection under stirring. The reaction solutions directly dried by a spinning method to obtain a crude product. The crude product was purified by a column (PE/EA:=I/1 and DCM/MeOH=10/1) to obtain compound 10c.

LCMS (ESI) m/z: 622.2 [M+1]+.

Step 3

Compound 10c (120 mg, 193.01 μmol) was dissolved in EtOAc (8 mL). HCl/EtOAc (4 M, 2.40 mL, 49.74 eq) was added, and the reaction was conducted at 20° C. for 16 hours under stirring.

The reaction solution was directly dried by a spinning method to obtain a solid crude product. The crude product was dissolved in methanol, and purified by a preparative chromatography column (chromatography column. Boston Green ODS 150×30 mm×5 μm; mobile phase. [water (0.075% TFA)-ACN]; B (acetonitrile) %: 10%-40%, 8 min) to obtain a trifluoroacetate of compound 10. The trifluoroacetate of compound 10 was added to a sodium bicarbonate solution, and the obtained solution was extracted with ethyl acetate. Organic phases were dried with anhydrous sodium sulfate, and concentrated under reduced pressure to obtain compound 10.

LCMS (ESI) m/z: 522.3 [M+1]+

$^1$H NMR (400 MHz, CD$_3$OD) δppm 8.28-8.55 (m, 4H) 8.20 (br s, 1H) 7.85-7.96 (m, 1H) 7.60 (br s, 1H) 7.18-7.46 (m, 11) 6.89-6.96 (m, 1H) 4.60-4.88 (m, 3H) 4.27-4.50 (m, 3H) 4.09-4.26 (m, 1H) 3.96 (s, 3H) 3.68 (br s, 1H) 3.50-3.57 (m, 4H) 3.47 (br d, J=5.02 Hz, 4H) 3.13 (br s, 1H) 2.25 (br d, J=11.04 Hz, 1H).

Examples 17 and 18

Compounds in the examples in Table 1 can be prepared by referring to steps similar to a preparation route of the aforementioned Example 10, with the difference lying in that the raw material used in step 2 is the raw material B in the following table instead of N-Boc piperazine to obtain trifluoroacetate of the corresponding compounds. The obtained trifluoroacetate of the compounds were respectively added to sodium bicarbonate solutions, the obtained solutions were extracted with ethyl acetate, and organic phases were dried with anhydrous sodium sulfate and concentrated under reduced pressure to obtain the corresponding compounds.

TABLE 1

| NO. | Product Structure | Raw Material B | LCMS m/z: [M + 1]+ | Product $^1$H NMR |
|---|---|---|---|---|
| Ex. 17 | 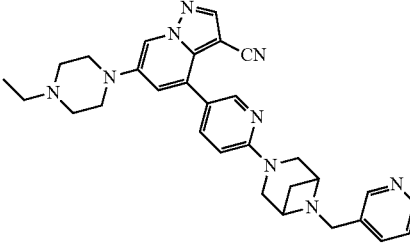 | 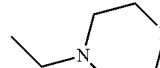 | 550.1 | Trifluoroacetate of compound 17 $^1$H NMR (400 MHz, CD$_3$OD) δ ppm 8.25-8.51 (m, 4 H) 7.77-8.02 (m, 2 H) 7.51 (br s, 1 H) 6.87-7.08 (m, 2 H) 4.89-4.94 (m, 1 H) 4.82 (br d, J = 6.78 Hz, 1 H) 4.70 (br s, 2 H) 4.59 (br s, 1 H) 4.15-4.38 (m, 4 H) 3.88-4.08 (m, 6 H) 3.73 (br s, 2 H) 3.60 (br s, 1 H) 3.36 (br s, 1 H) 3.31 (br s, 1 H) 3.19 (br s, 2 H) 2.21 (br d, J = 11.04 Hz, 1 H) 1.43 (t, J = 7.28 Hz, 3 H) |
| Ex. 18 | 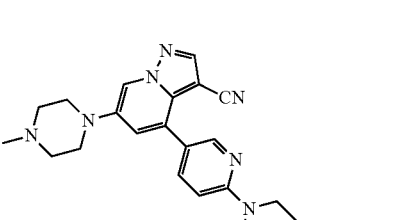 |  | 536.2 | Trifluoroacetate of compound 18 $^1$H MMR (400 MHz, CD$_3$OD) δ ppm 8.34 (s, 1 H) 8.30 (s, 1 H) 8.22 (s, 1 H) 8.10 (br s, 1 H) 7.80-7.86 (m, 1 H) 7.72 (br d, J = 8.52 Hz, 1 H) 7.42 (s, 1 H) 6.87 (br d, J = 8.78 Hz, 1 H) 6.79 (d, J = 8.52 Hz, 1 H) 3.81-3.95 (m, 9 H) 3.62-3.75 (m, 4 H) 2.73 (br s, 5 H) 2.42 (s, 3 H) 1.95 (s, 2 H) 1.74 (br d, J = 8.78 Hz, 1 H) |
| Ex. 19 | 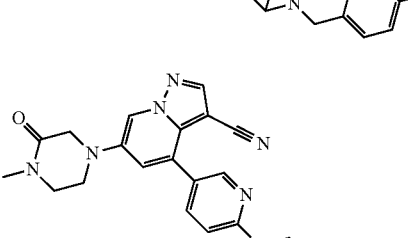 |  | 550.1 | Trifluoroactate of compund 19 $^1$H NMR (400 MHz, CD$_3$OD) δ ppm 8.35-8.53 (m, 2 H) 8.33 (br s, 2 H) 7.77-8.04 (m, 2 H) 7.48 (br s, 1 H) 6.86-7.06 (m, 2 H) 4.84-4.86 (m, 1 H) 4.69 (br s, 2 H) 4.60 (br s, 1 H) 4.20-4.31 (m, 2 H) 4.20-4.21 (m, 1 H) 4.03 (br d, J = 13.02 Hz, 1 H) 3.97 (s, 3 H) 3.92 (s, 2 H) 3.60 (br s, 4 H) 3.32 (br s, 1 H) 3.06 (s, 3 H) 2.21 (br d, J = 11.02 Hz, 1 H) |

TABLE 1-continued

| NO. | Product Structure | Raw Material B | LCMS m/z: [M + 1]+ | Product ¹H NMR |
|---|---|---|---|---|
| Ex. 20 | | | 564.2 | Trifluoroacetate of compound 20<br>¹H NMR (400 MHz, DMSO-d6)<br>δ = 8.53-8.60 (m, 1H), 8.40-8.45 (m, 1H), 8.34-8.38 (m, 1H), 8.06-8.09 (m, 1H), 7.82-7.88 (m, 1H), 7.65-7.72 (m, 1H), 7.53-7.57 (m, 1H), 6.75-6.83 (m, 2H), 3.83 (s, 3H), 3.74 (br d, J = 12.32 Hz, 2H), 3.69 (br d, J = 5.82 Hz, 2H), 3.59-3.65 (m, 4H), 3.56 (br d, J = 11.84 Hz, 2H), 3.51 (s, 2H), 3.23-3.29 (m, 2H), 3.18-3.21 (m, 2H), 2.55 (br s, 1H), 2.07 (s, 3H), 1.60 ppm (d, J = 8.52 Hz, 1H). |
| Ex. 21 | | | 551.2 | Trifluoroacetate of compound 21<br>¹H NMR (400 MHz, CD₃OD)<br>δ ppm 8.5-8.35 (m, 1 H) 8.29 (s, 2 H) 8.08 (s, 1 H) 7.87 (s, 1 H) 7.56-7.40 (m, 2 H) 7.31-7.06 (m, 1 H) 6.90 (d, J = 8.64 Hz, 1 H) 4.78-4.55 (m, 3 H) 4.40-4.21 (m, 3 H) 4.20-4.05 (m, 1 H) 3.94 (s, 3 H) 3.63 (s, 1 H) 3.43-3.33 (m, 4 H) 3.28-3.19 (m, 2 H) 3.16-3.02 (m, 1 H) 2.21 (d, J = 9.26 Hz, 1 H) 1.86-1.72 (m, 3 H) 1.35-1.23 (m, 3 H). |
| Ex. 68 | | | 525.1 | Trifluoroacetate of compound 68<br>¹H NMR (400 MHz, CD₃OD)<br>δ = 8.47-8.26 (m, 3H), 8.02-8.78 (m, 3H), 7.18 (s, 1H), 6.94-6.91 (m, 2H), 5.45 (d, J = 28.2 Hz, 1H), 4.69-4.25 (m, 3H), 4.29-4.21 (m, 4H), 4.04-3.95 (m, 4H), 3.74-3.53 (m, 6H), 2.41-2.19 (m, 2H). |
| Ex. 69 | | | 543.2 | Trifluoroacetate of compound 69<br>¹H NMR (400 MHz, CD₃OD)<br>δ = 8.40 (br d, J = 15.6 Hz, 2H), 8.29 (br s, 1H), 8.06 (br s, 1H), 8.02-7.76 (m, 3H), 7.20 (br s, 1H) 6.93 (br d, J = 8.3 Hz, 1H), 4.69 (br s, 2H), 4.59 (br s, 1H), 4.24 (br d, 13.1 Hz, 4H), 4.02 (br d, J = 12.5 Hz, 1H), 3.97 (s, 3H), 3.87-3.72 (m, 2H), 3.63 (br d, J = 6.0 Hz, 3H), 2.58 (dt, J = 7.5, 13.6 Hz, 2H), 2.21 (br d, J = 11.0 Hz, 1H) |
| Ex. 70 | | | 523.1 | Compound 70 ¹ H NMR (400 MHz, CD₃OD δ ppm 8.37 (d, J = 2.26 Hz, 1 H) 8.25 (s, 1 H) 8.11 (d, J = 2.26 Hz, 1 H) 7.93 (d, J = 2.01 Hz, 1 H) 7.87 (dd, J = 8.78, 2.51 Hz, 1 H) 7.74 (dd, J = 8.53, 2.51 Hz, 1 H) 7.14 (d, J = 1.76 Hz, 1 H) 6.90 (d, J = 9.03 Hz, 1 H) 6.81 (d, J = 8.53 Hz, 1 H) 4.60 (d, J = 2.76 Hz, 1 H) 3.94 (s, 1 H) 3.91 (s, 4 H) 3.82 (d, J = 6.02 Hz, 2 H) 3.64-3.70 (m, 4 H) 3.51-3.63 (m, 3 H) 3.43-3.49 (m, 1 H) 2.72 (s, 1 H) 2.06-2.30 (m, 2 H) 1.73 (d, J = 8.78 Hz, 1H) |

TABLE 1-continued

| NO. | Product Structure | Raw Material B | LCMS m/z: [M + 1]+ | Product ¹H NMR |
|---|---|---|---|---|
| Ex. 71 | | | 523.1 | Compound 71 ¹H NMR (400 MHz, CD₃OD) δ ppm 8.37 (d, J = 2.51 Hz, 1 H) 8.25 (s, 1 H) 8.11 (d, J = 2.01 Hz, 1 H) 7.93 (d, J = 2.01 Hz, 1 H) 7.87 (dd, J = 8.78, 2.51 Hz, 1 H) 7.74 (dd, J = 8.41, 2.38 Hz, 1 H) 7.15 (d, J = 2.01 Hz, 1 H) 6.90 (d, J = 8.53 Hz, 1 H) 6.81 (d, J = 8.78 Hz, 1 H) 4.61 (s, 1 H) 3.91 (s, 5 H) 3.82 (d, J = 5.52 Hz, 2 H) 3.65-3.72 (m, 4 H) 3.54-3.63 (m, 2 H) 3.42-3.63 (m, 2 H) 2.74 (s, 1 H) 2.05-2.30 (m, 2H) 1.73 (d, J = 8.78 Hz, 1 H). |
| Ex. 72 | | | 550.1 | Trifluoroacetate of compound 72 ¹H NMR (400 MHz, CD₃OD) δ ppm 8.70 (s, 1 H) 8.64-8.51 (m, 1 H) 8.44-8.24 (m, 2 H) 8.11 (s, 1 H) 7.87 (s, 1 H) 7.28 (s, 1 H) 7.09-6.85 (m, 2 H) 4.75-4.53 (m, 3 H) 4.34-4.15 (m, 5 H) 4.09-4.00 (m, 1 H) 3.95 (s, 3 H) 3.91-3.74 (m, 2 H) 3.74-3.55 (m, 2 H) 3.22 (q, J = 8.52 Hz, 1 H) 3.01 (s, 6 H) 2.65-2.52 (m, 1 H) 2.41-2.30 (m, 1 H) 2.23-2.13 (m, 1 H) |
| Ex. 77 | | | 537.1 | Trifluoroacetate of compound 77 ¹H NMR (400 MHz, CD₃OD) δ ppm 8.38 (br d, J = 10.04 Hz, 1 H) 8.22 (s, 1 H) 7.99 (br s, 1 H) 7.93 (s, 1 H) 7.86 (br s, 1 H) 7.33-7.57 (m, 1 H) 7.16 (s, 1 H) 6.96-7.11 (m, 1 H) 6.90 (d, J = 8.52 Hz, 1 H) 4.82 (br d, J = 7.28 Hz, 1 H) 4.69 (br s, 2 H) 4.59 (br s, 1 H) 4.28 (br s, 1 H) 4.25 (s, 1 H) 4.22 (s, 1 H) 4.18 (br d, J = 2.26 Hz, 1 H) 4.05 (br d, J = 13.30 Hz, 1 H) 3.95 (s, 3 H) 3.59-3.70 (m, 1 H) 3.54 (br dd, J = 10.28, 4.77 Hz, 1 H) 3.36-3.46 (m, 6 H) 2.15-2.25 (m, 3 H). |
| Ex. 78 | | | 537.1 | Compound 78 ¹H NMR (400 MHz, CD₃OD) δ ppm 8.36 (d, J = 2.26 Hz, 1 H) 8.23 (s, 1 H) 8.11 (s, 1 H) 7.92 (d, J = 1.76 Hz, 1 H) 7.85 (dd, J = 8.92, 2.38 Hz, 1 H) 7.73 (dd, J = 8.52, 2.26 Hz, 1 H) 7.13 (d, J = 1.76 Hz, 1 H) 6.88 (d, J = 8.78 Hz, 1 H) 6.80 (d, J = 8.78 Hz, 1 H) 4.15-4.23 (m, 1 H) 3.93-3.90 (m, 7H) 3.71 (br d, J = 11.28 Hz, 3 H) 3.53-3.57 (m, 1 H) 3.42-3.47 (m, 1 H) 3.40-3.42 (m, 1 H) 3.40-3.46 (m, 1 H) 3.37-3.39 (m, 1 H) 3.39 (s, 2 H) 2.78 (br s, 1 H) 2.13-2.25 (m, 2 H) 1.76 (br d, J = 9.04 Hz, 1 H) 1.25-1.35 (m, 1 H). |

TABLE 1-continued
| NO. | Product Structure | Raw Material B | LCMS m/z: [M + 1]+ | Product 1H NMR |
|---|---|---|---|---|
| Ex. 79 | | | 537.1 | Compound 79 1 H NMR (400 MHz, CD3OD) δ ppm 8.39 (d, J = 2.00 Hz, 1 H) 8.26 (br s, 1 H) 8.22 (s, 1 H) 7.91 (d, J = 1.52 Hz, 1 H) 7.87 (dd, J = 8.78, 2.26 Hz, 1 H) 7.81 (br d, J = 7.28 Hz, 1 H) 7.12 (s, 1 H) 6.88 (br t, J = 9.78 Hz, 2 H) 4.59 (br s, 1 H) 4.37 (br s, 1 H) 4.19-4.23 (m, 1 H) 4.18 (br s, 1 H) 4.04 (br s, 4 H) 3.93 (s, 3 H) 3.54 (dd, J = 10.54, 4.77 Hz, 1 H) 3.40-3.46 (m, 2 H) 3.39 (s, 3 H) 3.35 (br s, 1 H) 2.12-2.26 (m, 2 H) 2.04 (br s, 1 H) 1.29 (s, 1 H) 1.15-1.23 (m, 1 H). |
| Ex. 82 | | | 537.3 | Trifluoroacetate of compound 82 1H NMR (400 MHz, CDCl3) δ ppm 8.36 (d, J = 2.12 Hz, 1 H) 8.26 (d, J = 1.88 Hz, 1 H) 8.24 (s, 1 H), 8.12 (s, 1 H) 7.77-7.79 (m, 1 H) 7.64 (dd, J = 8.68, 2.44 Hz, 1 H) 7.24 (d, J = 7.88 Hz, 1 H) 6.92 (d, J = 2.00 Hz, 1 H) 6.64-6.68 (m, 1 H) 6.51 (dd, J = 13.88, 8.38 Hz, 2 H) 4.32 (br s, 4 H) 3.66 (d, J = 3.63 Hz, 2 H) 3.60 (dd, J = 8.32, 5.69 Hz, 3 H) 3.39 (s, 2 H) 2.01 (s, 1 H) 1.44 (s, 9 H) 1.29-1.36 (m, 1 H) |
Example 11
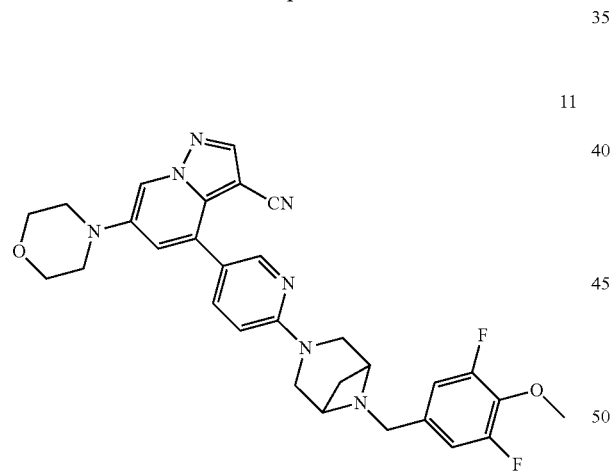
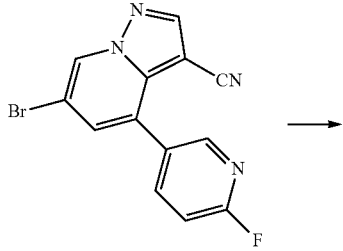
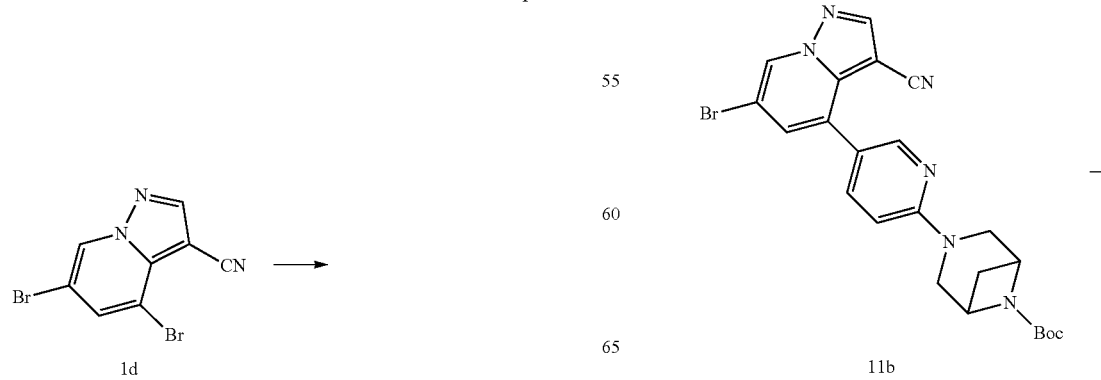

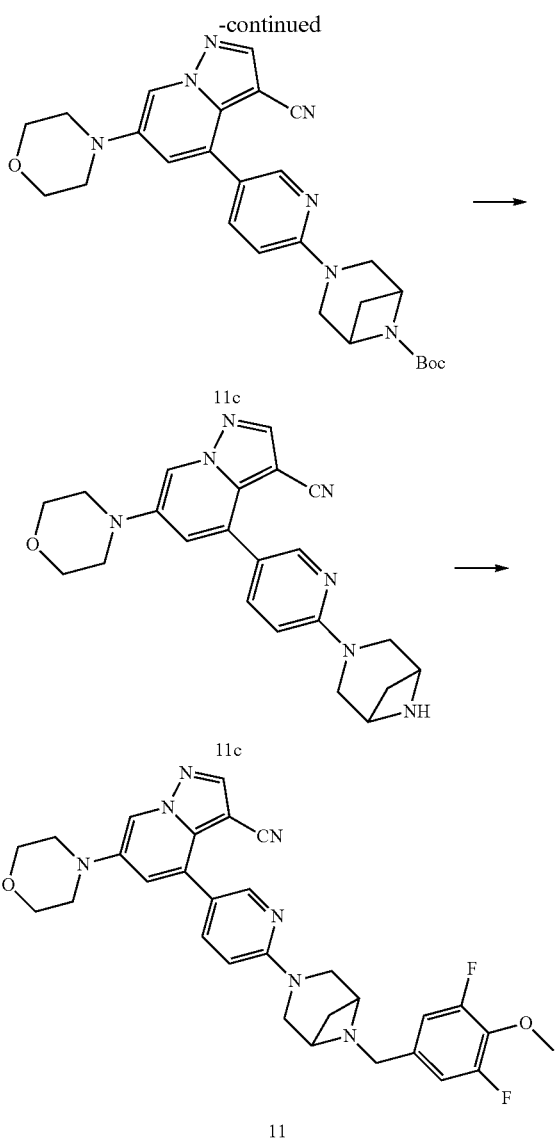

Step 1

Compound 1d (10 g, 33.23 mmol) was dissolved in THF (250 mL), 2-fluoro-5-borate pyridine (7.41 g, 33.23 mmol), KOAc (6.52 g, 66.46 mmol). $H_2O$ (50 mL) and Pd(dppf)$Cl_2CH_2Cl_2$ (814.09 mg, 996.90 μmol) were added, stirring was conducted at 50° C. for 16 hours under nitrogen protection. 45 mL MeOH and 35 mL $H_2O$ were added, the reaction solution was filtrated after stirring for 1 hour to obtain a filter cake. The filter cake was washed with 10 mL MeOH, and was dried by a spinning method to obtain product 11a.

$^1$H NMR (400 MHz, $CD_2OD$) δ ppm 8.80 (s, 1H) 8.41 (s, 1H) 8.29 (s, 1H) 8.01-8.02 (m, 1H) 7.48 (s, 1H) 7.16-7.14 (m, 1H)

Step 2

Compound 11a (6 g, 18.92 mmol) and 6-Boc-3,6-diazabicyclo[3.1.1]-heptane (5.63 g, 28.38 mmol) were added to a DMSO (100 mL) solution. KOAc (3.71 g, 37.84 mmol) was then added to the reaction solution, and stirring was conducted at 75° C. for 16 hours. 10 mL of water was added, then ethyl acetate (10 mL×3) was added. Organic phases were combined, washed twice with a saturated sodium chloride solution, dried with anhydrous sodium sulfate, and dried by a spinning method to obtain a crude product. The crude product was purified by a flash silica gel column (PE:EA=1:1) to obtain compound 11b.

LCMS (ESI) m/z: 439.2 [M+1-56]$^+$. 441.2 [M+3-56]$^+$ $^1$H NMR (400 MHz, $CD_3OD$) δ ppm 8.69 (s, 1H) 8.37 (s, 1H) 8.26 (s, 1H) 8.01-8.02 (m, 1H) 7.74-7.71 (m, 1H) 7.39 (s, 1H) 4.33-4.32 (m, 2H) 4.16-4.12 (m, 2H) 3.55-3.47 (m, 2H) 2.72-2.68 (m, 1H) 1.55-1.53 (m, 1H) 1.39 (s, 9H).

Step 3

Compound 11b (1 g, 2.02 mmol), morpholine (211.04 mg, 2.42 mmol) and $Pd_2(dba)_3$ (184.86 mg, 201.87 μmol) and BINAP (251.40 mg, 403.74 μmol) were added to toluene (30 mL), sodium tert-butoxide (388.01 mg, 4.04 mmol) was then added to the reaction solution, replacement with nitrogen was conducted for three times, and the reaction was conducted for 4 hours at 90° C. 20 mL of water was added to the reaction solution, and then the reaction solution was extracted with ethyl acetate (20 mL×2). Organic phases were combined, dried with anhydrous sodium sulfate, and dried by a spinning method under reduced pressure at 40-50° C. to obtain a crude product. The crude product was was purified by a column chromatography (PE/EA=: 10/1 to 2/1) to obtain compound 11c.

LCMS (ESI) m/z: 502.1 [M+1]$^+$ $^1$H NMR (400 MHz, $CD_3OD$) δ ppm 8.28 (s, 1H) 8.13 (s, 1H) 7.93 (s, 1H) 7.67-7.64 (m, 1H) 6.65 (s, 1H) 6.59-6.52 (m, 1H) 4.24 (d, J=2.8 Hz, 2H) 4.14-4.02 (m, 2H) 3.84-3.82 (m, 4H) 3.49 (br s, 2H) 3.10-3.08 (m, 4H) 2.64-2.58 (m, 1H) 1.47-1.46 (m, 1H) 1.32 (s, 9H).

Step 4

Compound 11c (500 mg, 996.85 μmol) was added to DCM (20 mL), trifluoroacetic acid (1.14 g, 9.97 mmol, 738.08 μL) was then added to the reaction solution, and the reaction was conducted for 30 min at 20-30° C. The reaction solution was directly dried by a spinning method under reduced pressure at 40-50° C. to obtain a crude product compound 11d which was directly used in the next step.

LCMS (ESI) m/z 402.0 [M+1]$^+$

Step 5

Compound 11c (100 mg, 193.99 μmol) was added to 1,2-dichloroethane (4 mL). DIPEA (25.07 mg, 193.99 μmol, 33.79 μL) was added to the reaction solution, and the reaction was conducted at 20-30° C. for 30 minutes under stirring, 3,5-difluoro-4-methoxy-benzaldehyde (36.73 mg, 213.39 μmol) was then added to the reaction solution, the pH of the reaction solution was adjusted to 5-6 with acetic acid (11.65 mg, 193.99 μmol, 11.09 μL), and the reaction was conducted at 20-30° C. for 2 hours under stirring. NaBH(OAc)$_3$ (61.67 mg, 290.99 μmol) was then added to the reaction solution, and the reaction was conducted at 20-30° C. for 4 hours. The reaction solution was dried by a spinning method under reduced pressure to obtain a crude product of brown oil. The crude product is purified by pre-HPLC (chromatography column. Boston Green ODS 150×30 mm×5 μm; mobile phase: [water (0.075% TFA)-ACN]; B (acetonitrile) %: 20%-50%, 12 min) to obtain a trifluoroacetate of compound 11. The trifluoroacetate of compound 11 was added to a sodium bicarbonate solution, and the obtained solution was extracted with ethyl acetate.

Organic phases were dried with anhydrous sodium sulfate, and concentrated under reduced pressure to obtain compound 11.

LCMS (ESI) m/z: 558.1 [M+1]$^+$;

$^1$H NMR (400 MHz, $CD_3OD$) δ ppm 8.18-8.48 (m, 3H) 7.91 (s, 1H) 7.44 (s, 1H) 7.26 (s, 2H) 6.71-6.99 (m, 1H)

4.53-4.71 (m, 3H) 4.14-4.25 (m, 3H) 4.02 (s, 4H) 3.84-3.91 (m, 4H) 3.21 (s, 4H) 2.18 (d, J=1.04 Hz, 1H) 1.43 (s, 2H).

Compounds in the examples in Table 2 can be prepared by referring to steps similar to a preparation route of the aforementioned Example 11, with the difference lying in that the raw material used in step 5 is the raw material B in the following table instead of 3,5-difluoro-4-methoxy-benzaldehyde to obtain trifluoroacetate of the corresponding compounds. The obtained trifluoroacetate of the compounds were respectively added to sodium bicarbonate solutions, the obtained solutions were extracted with ethyl acetate, and organic phases were dried with anhydrous sodium sulfate and concentrated under reduced pressure to obtain the corresponding compounds.

TABLE 2

| NO. | Product Structure | Raw Material B | Product LCMS m/z [M + 1]+ | Product ¹H NMR |
|---|---|---|---|---|
| Ex. 12 | | | 551.1 | Trifluoroacetate of compound 12 ¹H NMR (400 MHz, CD₃OD) δ ppm 8.23-8.55 (m, 4 H) 7.72-8.04 (m, 2 H) 7.46 (s, 1 H) 6.89-7.09 (m, 1 H) 6.84 (d, J = 8.53 Hz, 1 H) 5.25-5.39 (m, 1 H) 4.55-4.75 (m, 3 H) 4.19-4.33 (m, 4 H) 4.03 (d, J = 12.30 Hz, 1 H) 3.89 (br s, 4 H) 3.60 (s, 1 H) 3.23 (s, 4 H) 2.21 (d, J = 11.29 Hz, 1 H) 1.36 (d, J = 6.02 Hz, 6 H). |
| Ex. 13 | | | 537.1 | Trifluoroacetate of compound 13 ¹H NMR (400 MHz, CD₃OD) δ ppm 8.39 (s, 1 H) 8.30 (s, 1 H) 8.23 (s, 1 H) 7.99-7.88 (m, 1H) 7.86-7.67 (m, 1 H) 7.45 (s, 1 H) 7.32 (s, 1 H) 7.07-6.89 (m, 1 H) 6.18 (s, 2 H) 4.80-4.48 (m, 3 H) 4.28-4.18 (m, 3 H) 4.10-3.99 (m, 1 H) 3.92-3.83 (m, 4 H) 3.71-3.46 (m, 1 H) 3.24-3.18 (m, 4 H) 3.17-3.00 (m, 1 H) 2.18 (d, J = 10.54 Hz, 1 H). |
| Ex. 14 | | | 532.1 | Trifluoroacetate of compound 14 ¹H NMR (400 MHz, CD₃OD) δ ppm 8.52-8.35 (m, 2 H) 8.34-8.21 (m, 3 H) 7.96 (s, 1 H) 7.54 (d, J = 3.54 Hz, 1 H) 7.46 (s, 1 H) 7.16-6.89 (m, 1 H) 6.62 (d, J = 3.26 Hz, 1 H) 4.81-4.31 (m, 4 H) 4.24 (d, J = 13.30 Hz, 2 H) 4.05 (s, 1 H) 3.91-3.82 (m, 4 H) 3.66 (s, 1 H) 3.20 (s, 4 H) 3.07 (s, 1 H) 2.21 (d, J = 9.02 Hz, 1 H). |
| Ex. 15 | | | 541.2 | Trifluoroacetate of compound 15 ¹H NMR (400 MHz, CD₃OD) δ ppm 8.43 (s, 1 H) 8.33 (s, 1 H) 8.27 (d, J = 2.01 Hz, 1 H) 8.06 (d, J = 5.27 Hz, 1 H) 7.94 (d, J = 10.04 Hz, 1 H) 7.47 (d, J = 2.01 Hz, 1 H) 7.09 (t, J = 4.77 Hz, 1 H) 6.97 (d, J = 9.03 Hz, 1 H) 4.70 (s, 3 H) 4.23 (s, 2 H) 4.06 (s, 3 H) 3.85-3.92 (m, 6 H) 3.20-3.27 (m, 6 H) 2.23 (d, J = 11.04 Hz, 1 H). |

TABLE 2-continued

| NO. | Product Structure | Raw Material B | Product LCMS m/z [M + 1]+ | Product 1H NMR |
|---|---|---|---|---|
| Ex. 16 | | | 566.1 | Compound 16 1H NMR (400 MHz, CD3OD) δ ppm 8.33-8.39 (m, 3 H) 8.24 (d, J = 1.63 Hz, 1 H) 7.88 (dd, J = 9.07, 2.31 Hz, 1 H) 7.44-7.48 (m, 2 H) 6.93 (d, J = 8.63 Hz, 1 H) 6.56 (d, J = 3.50 Hz, 1 H) 3.94-4.05 (m, 4 H) 3.87-3.92 (m, 6 H) 3.69 (d, J = 11.51 Hz, 2 H) 3.50 (s, 1 H) 3.39 (s, 1 H) 3.21-3.26 (m, 4 H) |

Example 22

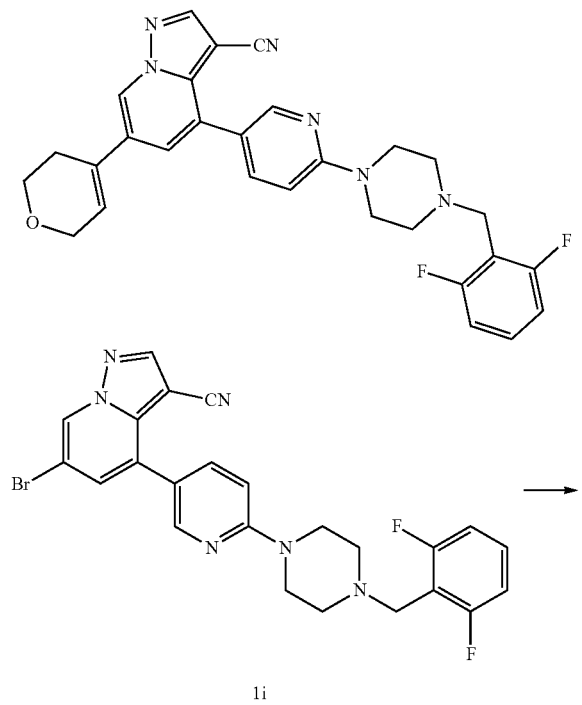

Step 1

Compound 1i (100 mg, 196.33 μmol) 3,6-dihydro-2H-pyran-4-boronic acid pinacol ester (49.49 mg, 235.60 μmol), K₃PO₄ (208.37 mg, 981.65 μmol) and Pd(dppf)Cl₂CH₂Cl₂ (16.03 mg, 19.63 μmol) were added to DMF (10 mL), the air in the reaction system was evacuated and nitrogen was added for protection, the reaction was conducted at 100° C. under microwave for 30 min under stirring. Water was added to the reaction solution, and then the reaction solution was extracted with ethyl acetate (20 mL×2) and dried by a spinning method to obtain a crude product. The crude product was purified by a preparative chromatography column (chromatography column: Boston Green ODS 150×30 mm 5 μm; mobile phase: [water (0.075% trifluoroacetic acid)-acetonitrile]; B %: 31%-51%, 8 min) to obtain a trifluoroacetate of compound 22. The trifluoroacetate of compound 22 was added to a sodium bicarbonate solution, and the obtained solution was extracted with ethyl acetate. Organic phases were dried with anhydrous sodium sulfate, and concentrated under reduced pressure to obtain compound 22.

LCMS (ESI) m/z: 513.4 [M+1]⁺

1H NMR (400 MHz, CDCl₃) δ 8.44 (s, 1H), 8.28 (d, J=2.0 MHz, 1H), 8.18 (s, 1H), 7.71 (dd, J=8.40 Hz, 1H), 7.38-7.48 (m, 1H), 7.36 (d, J=1.25 Hz, 1H), 6.98 (t, J=8.0 Hz, 2H), 6.75 (d, J=8.80 MHz, 1H), 6.25 (s, 1H), 4.28-4.34 (m, 4H), 3.90-3.96 (m, 6H), 3.91 (br s, 4H), 2.43-2.47 (m, 2H).

Example 24

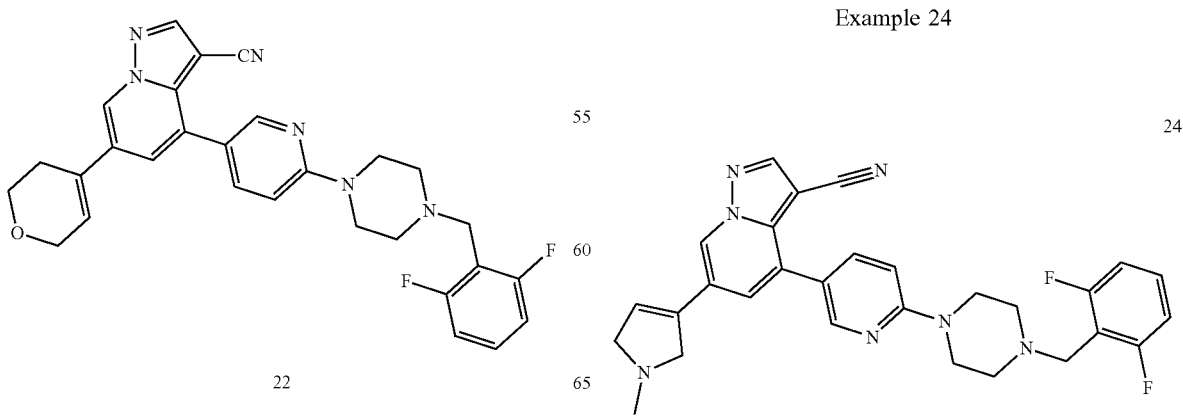

-continued

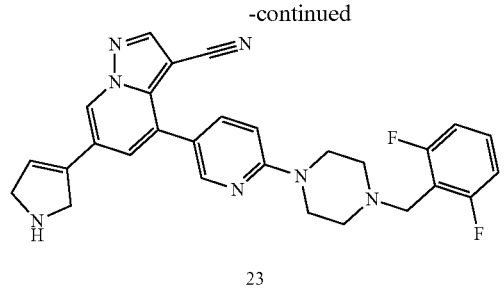

23

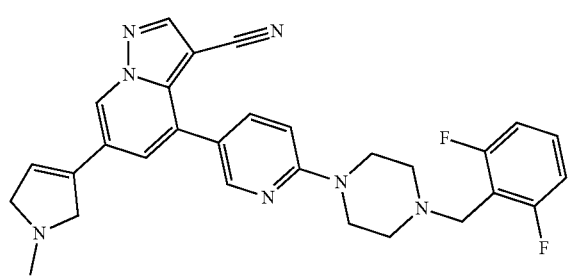

24

Step 1

The compound (0.04 g, 80.40 μmol) obtained in example 23 was dissolved in a mixed solution of anhydrous methanol (1 mL) and anhydrous dichloromethane (2 mL), N,N-diisopropylethylamine (31.17 mg, 241.19 μmol, 42.01 μL) was added at 25° C., stirring was conducted for 10 minutes, acetic acid (38.62 mg, 643.16 μmol, 36.78 μL) and a aqueous formaldehyde (4.83 mg, 160.79 μmol, 40%) solution were added, stirring was conducted for 30 minutes, then sodium triacetoxyborohydride (51.12 mg, 241.19 μmol) was added, stirring was conducted at 25° C. for 20) minutes. The reaction solution was directly concentrated to obtain a crude product. The crude product was purified by a preparative chromatography column (chromatography column: Boston Green ODS 150×30 5μ; mobile phase: [water (0.075% trifluoroacetic acid)-acetonitrile]; B %: 22%-52%, 7 min) to obtain a trifluoroacetate of compound 24. The trifluoroacetate of compound 24 was added to a sodium bicarbonate solution, extracted with ethyl acetate. Organic phases were dried with anhydrous sodium sulfate, and concentrated under reduced pressure to obtain compound 24.

LCMS (ESI) m/z: 512.1 [M+1]$^+$ $^1$H NMR (400 MHz, CD$_3$OD) δ 8.85 (s, 1H), 8.49 (s, 1H), 8.43 (d, J=1.6 Hz, 1H), 7.92 (dd, J=1.9.8.8 Hz, 1H), 7.77 (s, 1H), 7.69-7.61 (m, 1H), 7.22 (t, J=8.4 Hz, 2H), 7.13 (d, J=8.8 Hz, 1H), 6.64 (br s, 1H), 4.57 (s, 2H), 4.27-3.88 (m, 3H), 4.27-3.88 (m, 1H), 3.54 (br s, 4H), 3.33 (br s, 3H), 3.17 (s, 3H).

Example 25

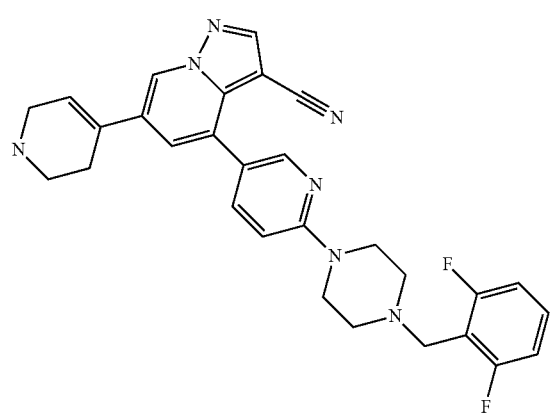

25

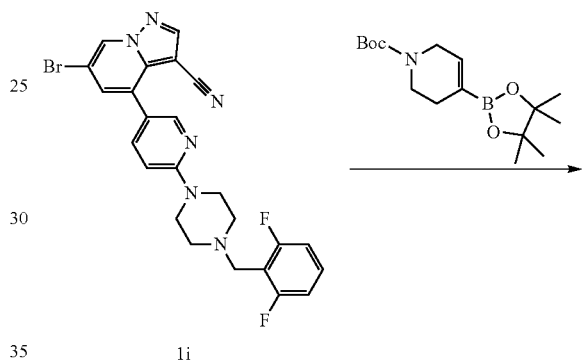

1i

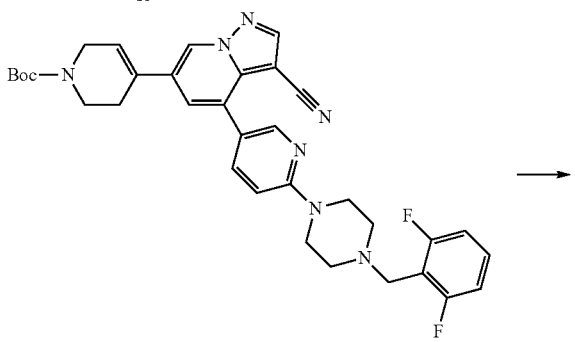

25a

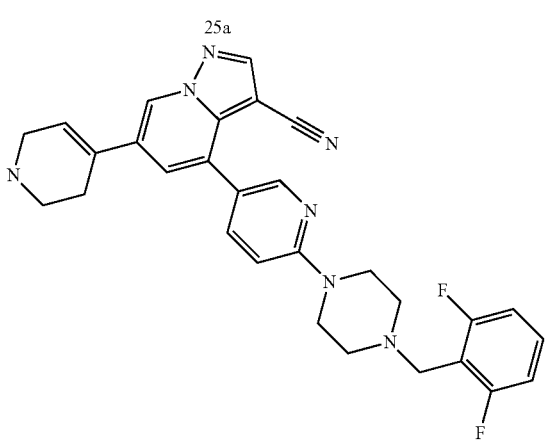

25

Step 1

Compound 1i (150) mg, 294.49 µmol) was dissolved in N,N-dimethylformamide (2 mL). N-Boc-1,2,5,6-tetrahydropyridine-4-boronic acid pinacol ester (100.17 mg, 323.94 mmol), [1,1-bis(diphenylphosphino)ferrocene]dichloropalladium dichloromethane (24.05 mg, 29.45 µmol) and potassium carbonate (203.50 mg, 1.47 mmol) were added, and stirring was conducted at 100° C. for 5 hours under protection of $N_2$. The insoluble material was removed by filtration, and the solvent was spin dried to obtain a crude product. The crude product was purified by an automatic column passing machine (PE:EA=1:1, Rf=0.37) to obtain compound 25a.

LCMS (ESI) m/z: 612.1 [M+1]$^+$ $^1$H NMR (400 MHz, $CDCl_3$) 5.8.46 (s, 1H), 8.31 (d, J=2.40 Hz, 1H), 8.24 (s, 1H) 7.70 (dd, J=8.78, 2.40 Hz, 1H), 7.37 (d, J=1.60 Hz, 1H), 6.91 (t, J=7.64 Hz, 2H), 6.73 (d, J=8.78 Hz, 1H), 6.20 (s, 1H), 3.78 (s, 2H), 3.71-3.62 (m, 6H), 2.64 (s, 4H), 2.53 (s, 2H), 2.04 (s, 2H), 1.48-1.47 (m, 1H), 1.50 (s, 9H).

Step 2

HCl/EtOAc (4 M, 4 mL) was added to compound 25a (150 mg, 245.23 µmol), and stirring was conducted at 25° C. for 20 min. The reaction solution was dried by a spinning method to obtain a crude product. The crude product was separated and purified by a preparative HPLC (chromatography column: Boston Green ODS 150'30-5 µm; mobile phase: [water (0.075% trifluoroacetic acid)-acetonitrile]; B %: 15%-35%, 7 min) to obtain a trifluoroacetate of compound 25. The trifluoroacetate of compound 25 was added to a sodium bicarbonate solution, and the obtained solution was extracted with ethyl acetate. Organic phases were dried with anhydrous sodium sulfate, and concentrated under reduced pressure to obtain compound 25.

LCMS (ESI) m/z: 512.3 [M+1]$^+$ $^1$H NMR (400 MHz, $CDCl_3$) δ 8.55 (s, 1H), 8.30 (d, J=2.26 Hz, 1H), 8.25 (s, 1H), 7.73 (dd, J=8.78, 2.51 Hz, 1H), 7.54-7.42 (m, 1H), 7.37 (d, J=1.00 Hz, 1H), 7.03 (t, J=8.16 Hz, 2H), 6.80 (d, J=8.78H, 1H), 6.21 (s, 1H), 4.38 (s, 2H), 4.00 (s, 4H), 3.88 (s, 2H), 3.47 (t, J=5.90 Hz, 2H), 2.88-2.77 (m, 2H) 3.31 (s, 4H).

Example 26

26

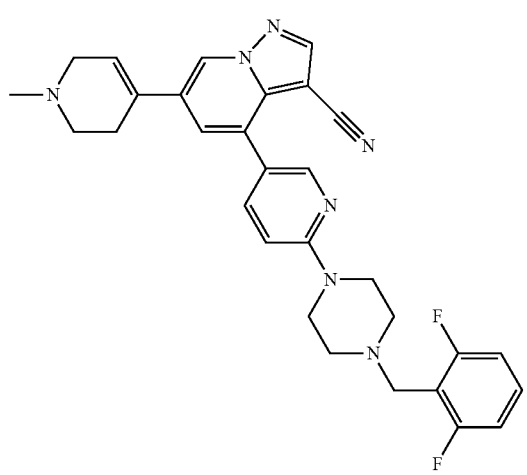

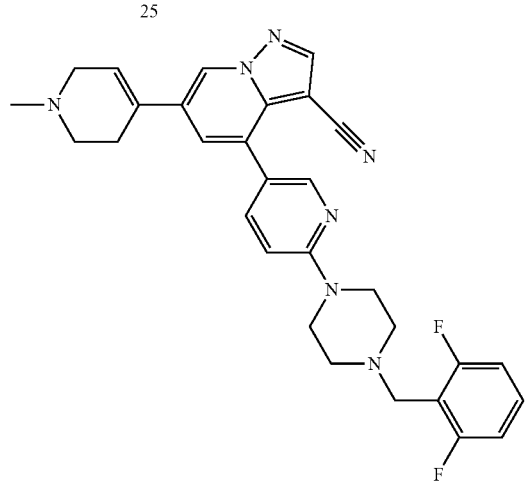

25

26

Step 1

Compound 25 (50 mg, 97.74 µmol) was added to a methanol (0.5 mL)/dichloromethane (1 mL) solution, formaldehyde (47.59 mg, 586.43 µmol, 43.66 µL) and glacial acetic acid (46.96 mg, 781.91 µmol, 44.72 L) were added, stirring was conducted at 20° C. for 1 hour. NaBH(OAc)$_3$ (31.07 mg, 146.61 µmol) was then added, and stirring was conducted for 1 hour. The reaction solution was dried by a spinning method to obtain a crude product. The crude product was separated by a preparative chromatography column (chromatography column: Boston Green ODS150× 30×5 µm; mobile phase. [water (0.075% trifluoroacetic acid)-acetonitrile]; B % 18%-38%, 7 min) to obtain a trifluoroacetate of compound 26. The trifluoroacetate of compound 26 was added to a sodium bicarbonate solution, and the obtained solution was extracted with ethyl acetate. Organic phases were dried with anhydrous sodium sulfate, and concentrated under reduced pressure to obtain compound 26.

LCMS (ESI) m/z: 526.1 [M+1]$^+$ $^1$H NMR (400 MHz, $CD_3OD$) δ8.88 (s, 1H), 8.5137-8.37 (m, 2H), 7.89 (dd, J=8.66, 2.38 Hz, 1H), 7.73-7.60 (m, 2H), 7.22 (t, J=8.16 Hz, 2H), 7.10 (d, J=8.78 Hz, 1H), 6.43 (s, 1H), 4.56 (s, 2H), 4.23-3.71 (m, 6H), 3.52 (s, 3H), 3.04 (s, 2H), 2.99 (s, 1H).

Example 27

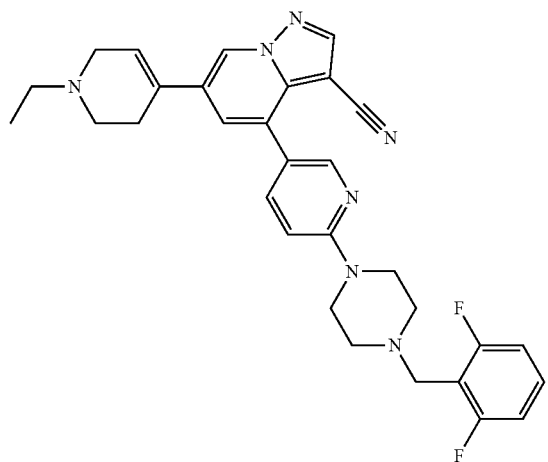

Step 1

Compound 26 (10 mg, 19.55 μmol, 1 eq) was added to a methanol (0.5 mL)/dichloromethane (1 mL) solution, acetaldehyde (12.92 mg, 117.29 μmol, 16.45 μL, 6 eq), glacial acetic acid (9.39 mg, 156.38 μmol, 8.94 μL, 8 eq) were added, stirring was conducted at 20° C. NaBH(OAc)₃ (6.21 mg, 29.32 μmol, 1.5 eq) was then added, and stirring was conducted for 1 hour. The reaction solution was dried by a spinning method to obtain a crude product. The crude product was separated by a preparative chromatography column (chromatography column: Boston Green ODS 150× 30×5 μm mobile phase. [water (0.075% trifluoroacetic acid)-acetonitrile]; B %: 21%-41%, 7 min) to obtain a trifluoroacetate of compound 27. The trifluoroacetate of compound 27 was added to a sodium bicarbonate solution, and the obtained solution was extracted with ethyl acetate. Organic phases were dried with anhydrous sodium sulfate, and concentrated wider reduced pressure to obtain compound 27.

LCMS (ESI) m/z: 540.1 [M+1]⁺

¹H NMR (400 MHz, CD₃OD) δ 8.87 (s, 1H), 8.51-8.36 (m, 2H), 7.98 (s, 2H), 7.88 (dd, J=8.78, 2.40 Hz, 1H), 7.69 (s. H), 7.21 (t, J=8.16 Hz, 2H), 7.10 (d, J=9.04 Hz, 1H), 4.54 (s, 2H), 6.44 (s, 1H), 3.80-3.67 (m, 3H), 3.35 (s, 2H), 3.00 (s, 6H), 2.86 (s, 5H), 1.36-1.34 (m, 3H).

Example 28

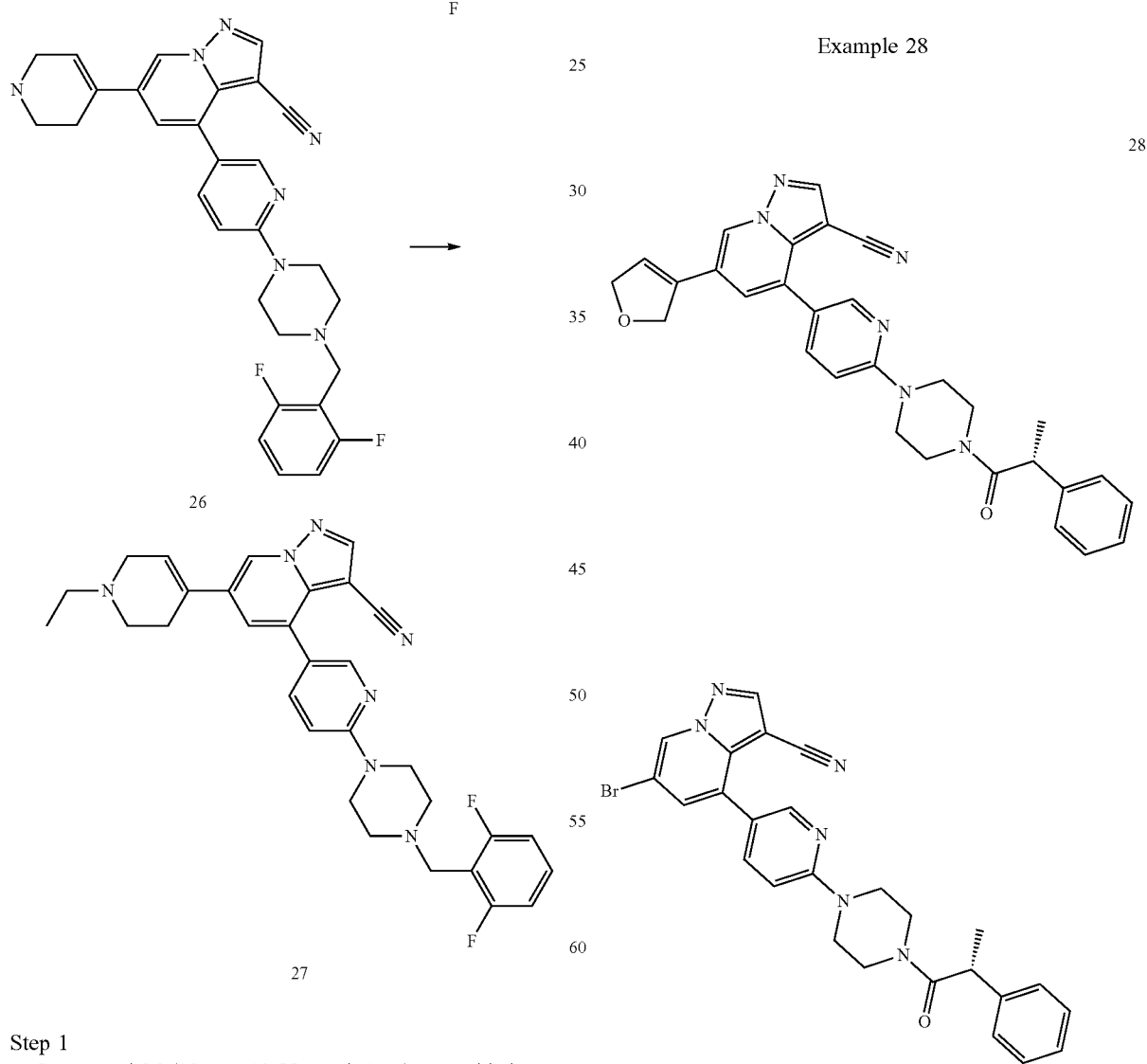

-continued

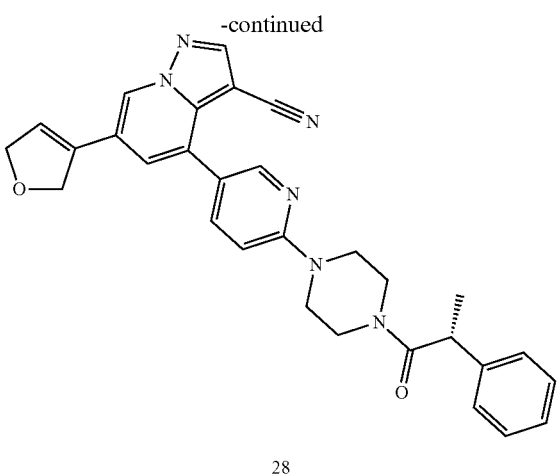

28

Step 1

3,6-dihydro-2H-pyran-4-boronic acid pinacol ester (22.82 mg, 116.41 μmol) and compound 4c (0.04 g, 77.61 μmol) were added to a mixed solution of 1,4-dioxane (4 mL) and H₂O (1 mL), K₃PO₄ (49.42 mg, 232.83 μmol) and Pd(dppf)Cl₂ (5.68 mg, 7.76 μmol) were then added, and stirring was conducted at 90° C. for 2 hours under N₂ protection. The reaction solution was directly concentrated, and purified by a preparative chromatography column (chromatography column: Boston Green ODS150×30 5μ; mobile phase: [water (0.075% TFA)-ACN]; B % 38%-58%, 8 min) to obtain a trifluoroacetate of compound 28. The trifluoroacetate of compound 28 was added to a sodium bicarbonate solution, and the obtained solution was extracted with ethyl acetate. Organic phases were dried with anhydrous sodium sulfate, and concentrated under reduced pressure to obtain compound 28

LCMS (ESI) m/z: 505.0 [M+1]⁺

¹H NMR (400 MHz, CD₃OD) δ 8.70 (s, 1H), 8.46 (s, 1H), 8.31 (d, J=1.5 MHz, 1H), 8.10 (br d, J=9.0 Hz, H), 7.79 (s, 1H), 7.42-7.30 (m, 4H), 7.30-7.24 (m, 2H), 6.67 (br s, 1H), 5.05 (br s, 4H), 4.17 (q, J=6.7 Hz, 1H), 4.02-3.52 (m, 8H), 1.45 (d, J=6.6 Hz, 3H).

Example 29

29

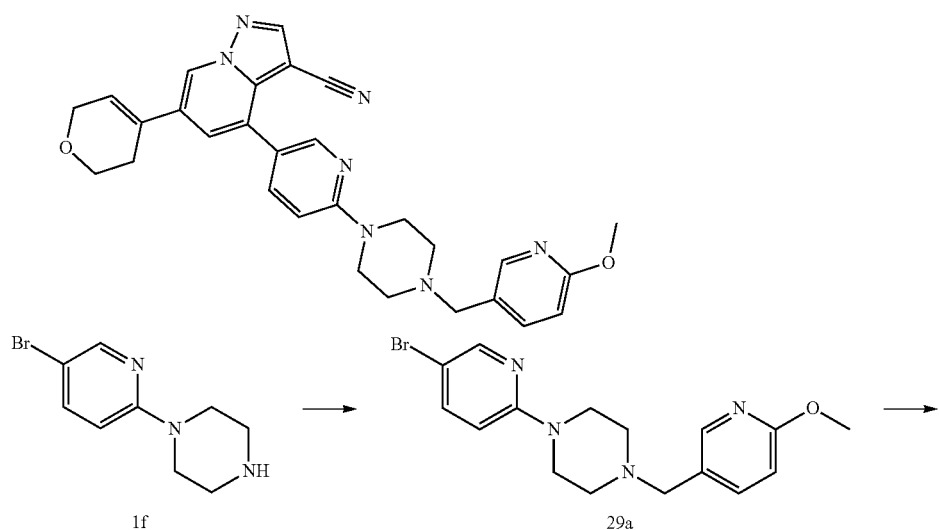

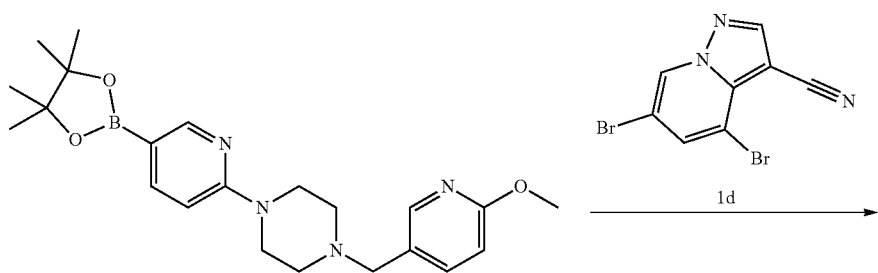

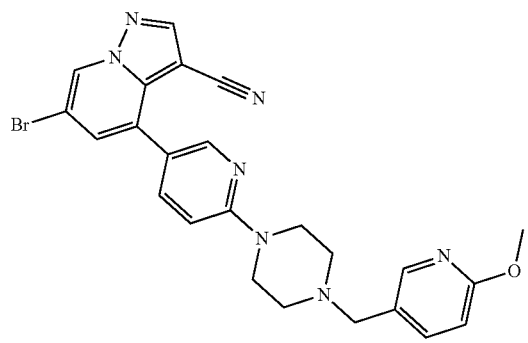

29c

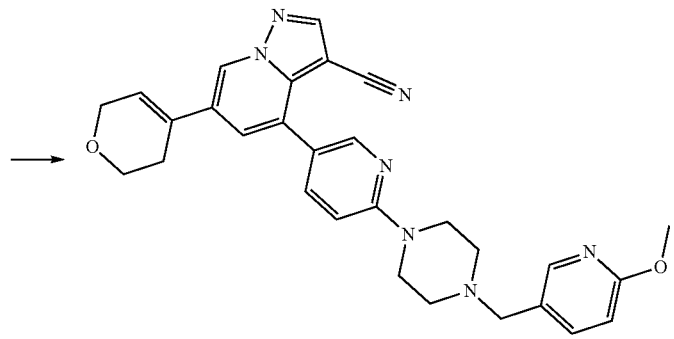

29

Step 1

6-methoxy-3-pyridinecarbaldehyde (4.81 g, 35.10 mmol) was dissolved in 1,2-dichloroethane (200 mL), DIPEA (22.68 g, 175.49 mmol) was added, stirring was conducted for 30 min, compound 1f (30 g, 42.12 mmol, trifluoroacetate) was added to adjust pH to 5-6, stirring was conducted for 2 hours. NaBH(OAc)$_3$ (18.60 g, 87.75 mmol) was added in portions, and stirring was added at 25° C. for 16 hours. 200 mL of water was added, and the reaction solution was extracted with dichloromethane (200 mL×2). Organic phases were combined, washed with water (100 mL×2), washed with a saturated sodium chloride solution (100 mL×2), dried with anhydrous sodium sulfate, and dried by a spinning method to obtain a crude product. The crude product was purified by an automatic column passing machine (petroleum ether:ethyl acetate=3:1) to obtain compound 29a.

LCMS (ESI) m/z: 363.2 [M+1]$^+$, 365.2[M+3]$^+$ $^1$H NMR (400 MHz, CDCl$_3$) δ 8.17 (t, J=4.2 Hz, 1H), 8.05 (d, J=1.6 Hz, 1H), 7.58 (t, J=4.2 Hz, 1H), 7.51 (d, J=2.8 Hz, 1H), 7.49 (d, J=2.8 Hz, 1H), 6.72 (d, J=8.0 Hz, 1H), 6.51 (d, J=8.4 Hz, 2H), 3.93 (s, 3H), 3.46-3.50 (m, 6H), 2.51 (t, J=6.4 Hz, 4H).

Step 2

Compound 29a (3 g, 8.26 mmol) was dissolved in 1,4-dioxane (35 mL), bis(pinacolato)diboron (2.52 g, 9.91 mmol), Pd(dppf)Cl$_2$ (604.30 mg, 825.87 μmmol) and AcOK (1.62 g, 16.52 mmol) were added, and stirring was conducted at 100° C. for 8 hours under N$_2$ protection ne reaction solution filtrated to collect a filtrate, and the filter residue was washed with ethyl acetate to collect a filtrate. Filtrates were combined, and dried by a spinning method to obtain a crude product. The crude product was purified by a silica gel column chromatography (petroleum ether:ethyl acetate=3:1 to 1:1) to obtain compound 29b.

LCMS (ESI) m/z: 411.2 [M+1]$^+$ $^1$H NMR (400 MHz, CDCl$_3$) δ8.52 (s, 1H), 8.05 (d, J=1.6H, 1H), 7.62-7.50 (m, 1H), 6.72 (d, J=8.0 Hz, H), 6.53 (d, J=8.4 Hz, 2H), 3.92 (s, 3H), 3.46-3.51 (m, 6H), 2.49-2.54 (m, 4H), 1.24 (s, 12H).

Step 3

Compound 1 d (0.05 g, 166.15 μmol) was added to a mixed solution of DMF (4 mL) and H$_2$O (1 mL), compound 29b (81.81 mg, 199.38 μmol), Pd(PPh$_3$)$_4$ (19.20 mg, 16.61 μmol) and NaCO$_3$ (41.37 mg, 498.44 μmol) were then added, and the reaction was conducted at 80° C. for 16 hours under N$_2$ protection. The reaction solution was added to 50 mL of water, a solid was precipitated out, and then the reaction solution was filtrated and dried by a spinning method to obtain compound 29c.

LCMS (ESI) m/z: 503.8[M+1]$^+$, 505.8[M+3]$^+$

Step 4

Compound 29c and 3,6-dihydro-2H-pyran-4-boronic acid pinacol ester (16.66 mg, 79.31 μmol) were added to a mixed solution of 1,4-dioxane (4 mL) and 1-20 (1 mL), Pd(dppf)Cl$_2$ (5.80 mg, 7.93 μmol) and K$_3$PO$_4$ (50.50 mg, 237.92 μmol) was added, and the reaction was conducted at 90° C. for 2 hours under N$_2$ protection. The reaction solution was directly concentrated to obtain a crude product. The crude product was purified with a chromatography column (chromatography column: Venusil ASB Phenyl 250-50.10 μm; mobile phase. [water (0.05% HCl)-ACN]; B %: 23%-53%, 10 min) to obtain a hydrochloride of compound 29. The hydrochloride of compound 29 was added to a sodium bicarbonate solution, and the obtained solution was extracted with ethyl acetate. Organic phases were dried with anhydrous sodium sulfate, and concentrated under reduced pressure to obtain compound 29.

$^1$H NMR (400 MHz, CD$_3$OD) δ=8.87 (s, 1H), 8.48 (s, 2H), 8.45 (d, J=2.0 Hz, 1H), 8.36 (br d, J=10.0 Hz, 1H), 8.15 (br s, 1H), 7.85 (s, 1H), 7.61 (br d, J=8.8 Hz, 1H), 7.14 (br d, J=8.3 Hz, 1H), 6.53 (br s, 1H), 4.52 (s, 2H), 4.37 (br d, J=2.6 Hz, 2H), 4.06 (s, 3H), 3.99 (t, J=5.5 Hz, 2H), 3.63 (br d, J=6.9 Hz, 4H), 3.31-3.32 (m, 4H), 2.62 (br s, 2H).

Example 30

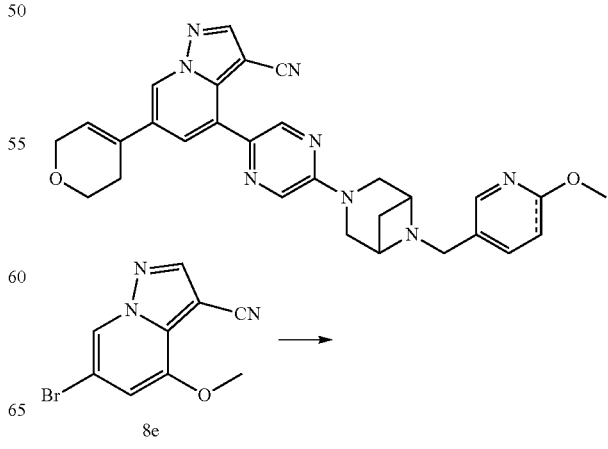

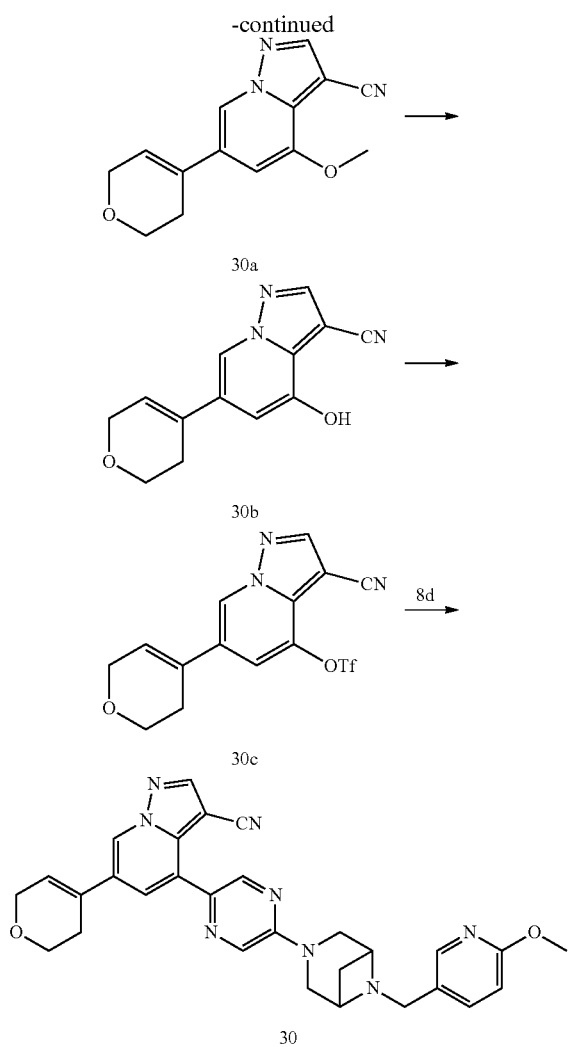

Step 1

3,6-dihydro-2H-pyran-4-boronic acid pinacol ester (1.5 g, 7.14 mmol), compound 8e (1.80 g, 7.14 mmol). Pd(dppf)Cl₂ (261.23 mg, 357.01 µmol) and K₃PO₄ (4.55 g, 21.42 mmol) were added to a mixed solution of 1,4-dioxane (12 mL) and H₂O (6 mL), heated to 100° C. with a microwave synthesizer under nitrogen protection, and reacted for 30 minutes under stirring. The reaction solution was extracted by adding 20 mL of water and 20 mL of ethyl acetate and separated, and an aqueous phase was extracted with 20 mL of ethyl acetate. Organic phases were combined, dried with anhydrous sodium sulfate, and subjected to rotary evaporation to remove the solvent to obtain a crude product.

The crude product was purified by a flash silica gel column (petroleum ether/ethyl acetate=1/1) to obtain compound 30a.

LCMS (ESI) m/z: 255.9 [M+1]

Step 2

Pyridine hydrochloride (4.53 g, 39.17 mmol) was added to compound 30a (1 g, 3.92 mmol), heated to 180° C. with microwave under nitrogen protection, and reacted for 20 minutes under stirring. A saturated sodium bicarbonate aqueous solution was added to the reaction solution until the pH value was 7. The reaction solution was extracted by adding 50 mL ethyl acetate, and separated, and an aqueous phase was extracted with 50l mL ethyl acetate. Organic phases were combined, dried with anhydrous sodium sulfate, and subjected to rotary evaporation to remove the solvent to obtain crude product 30b which was directly used in the next step without further purification.

Step 3

Compound 30b (460 mg, 1.91 mmol). N-phenylbis(trifluoromethanesulfonyl) imine (1.02 g, 2.86 mmol) and DIPEA (739.31 mg, 5.72 mmol) were added together to DMF (10 mL), and the reaction was conducted at 10-20° C. for 16 hours wider nitrogen protection under stirring. The reaction solution was directly added to 50 mL of water, and the reaction solution was extracted by adding 20 mL of ethyl acetate, and separated, and an aqueous phase was extracted with 20 mL of ethyl acetate. Organic phases were combined, dried with anhydrous sodium sulfate, and subjected to rotary evaporation to remove the solvent to obtain crude product 30c.

Step 4

Compound 30c (560 mg, 1.50 mmol), compound 8d (511.79 mg, 1.50 mmol). Pd(dppf)Cl₂ (54.88 mg, 75.01 µmol) and K₃PO₄ (955.27 mg, 4.50 mmol) were added together to a mixed solution of 1,4-dioxane (12 mL) and H₂O (6 mL), heated to 90° C. with a microwave synthesizer under nitrogen protection, and reacted for 0.5 hour under stirring. The reaction solution was extracted by adding 20 mL of water and 20 mL of ethyl acetate, and separated, and an aqueous phase was extracted with 20 mL of ethyl acetate. Organic phases were combined, dried with anhydrous sodium sulfate, and subjected to rotary evaporation to obtain a crude product. The crude product was separated and purified by a preparative chromatography column (chromatography column. YMC-Triart Prep C18 150×40 mm×7 µm, mobile phase: [water (0.1% TFA)-ACN]; B %: 30%-40%, 10 min) to obtain a trifluoroacetate of compound 30. The trifluoroacetate of compound 30 was added to a sodium bicarbonate solution, and the obtained solution was extracted with ethyl acetate. Organic phases were dried with anhydrous sodium sulfate, and concentrated under reduced pressure to obtain compound 30.

LCMS (ESI) m/z: 521.1 [M+1]⁺

¹H NMR (400 MHz, CD₃OD) δ 8.81-8.80 (m, 1H), 8.71-8.65 (m, 1H), 8.48-8.45 (m, 1H), 8.40-8.30 (m, 2H), 8.00~7.92 (m, 1H), 7.90~7.92 (m, 1H), 6.95~6.92 (m, 2H), 6.53 (s, 1H), 4.74~4.71 (m, 2H), 4.63~4.61 (d, J=8 Hz, 1H), 4.39-4.37 (m, 2H), 4.43-4.30 (m, 3H), 4.10~4.06 (m, 1H), 4.00) 3.96 (m, 6H), 3.65~3.62 (m, 1H), 2.62 (s, 2H), 2.25~2.21 (m, 1H).

Examples 31 and 34

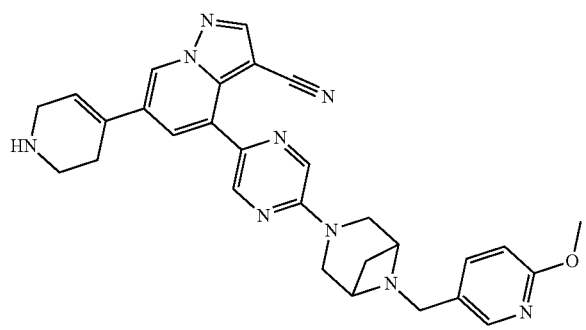

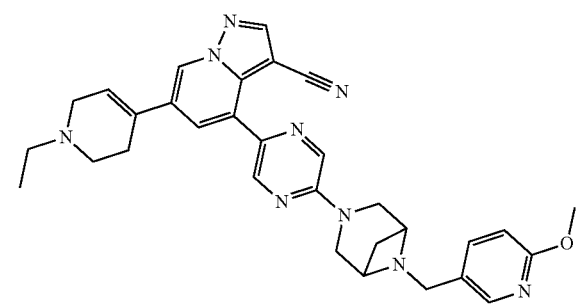

34

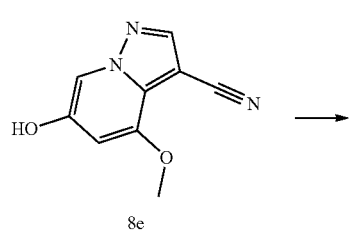

8e

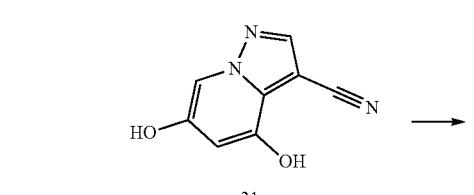

31a

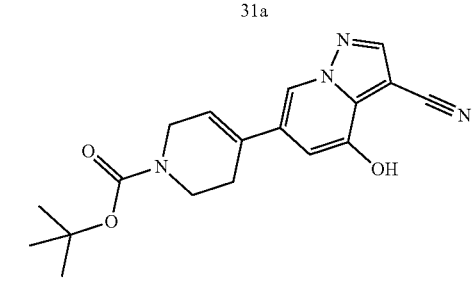

31b

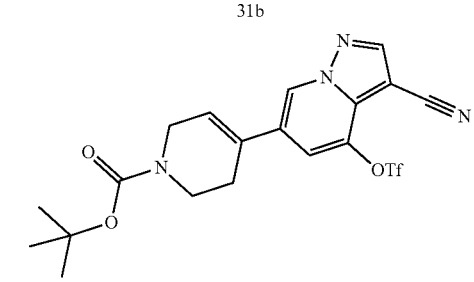

31c

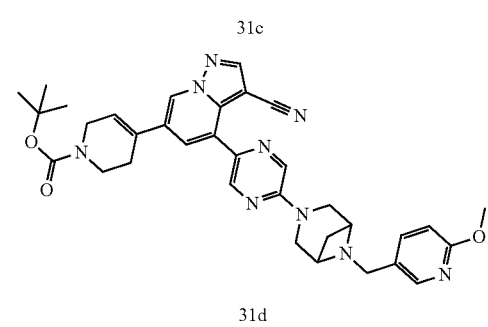

31d

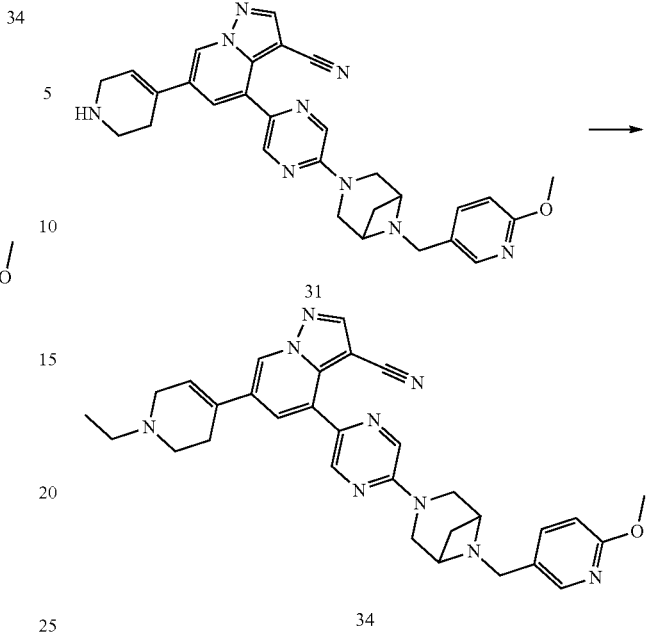

31

34

Step 1

Compound 8e (0.5 g, 1.98 mmol) was added to a microwave tube containing pyridine hydrochloride (2.46 g, 19.84 mmol), and the reaction was conducted for half an hour under the microwave condition of 180° C. 30 mL of a sodium bicarbonate aqueous solution was slowly added to the reaction solution, and then the reaction solution was extracted with ethyl acetate (20 mL) for three times. Organic phases were combined, dried with anhydrous sodium sulfate, filtrated, and concentrated to obtain product 31a.

Step 2

Compound 31a (0.5 g, 2.10 mmol) and N-Boc-1,2,5,6-tetrahydropyridine-4-boronic acid pinacol ester (974.23 mg, 3.15 mmol) were added to a mixed solution of 1,4-dioxane (2 mL) and H$_2$O (0.5 mL), Pd(dppf)Cl$_2$ (153.69 mg, 210.05 µmol) and K$_2$PO$_4$ (1.34 g, 6.30 mmol) were then added, and the reaction was conducted for 2 hours at 90° C. The reaction solution was added to 20 mL of water, extracted with 10 mL of ethyl acetate for three times, dried with anhydrous sodium sulfate, filtrated and concentrated to obtain a crude product. The crude product was purified by column chromatography (SiO$_2$, petroleum ether/ethyl acetate=10/1 to 1/1) to obtain compound 31b.

LCMS (ESI) m/z: 284.9 [M−56]$^+$

Step 3

N-phenylbis(trifluoromethanesulfonyl) imine (362.10 mg, 1.01 mmol, 1.5 eq) was added to DMF (1 mL), compound 31b (0.23 g, 675.72 µmol) and diisopropylethylamine (261.99 mg, 2.03 mmol) were then added, and the reaction was conducted for 1 hour at 20° C. Water (20 mL) was added the reaction solution, and then the reaction solution was extracted with ethyl acetate (20 ml) for three times. Organic phases were combined, dried with anhydrous sodium sulfate, filtrated and concentrated to obtain crude product 31c which was directly used in the next step.

LCMS (ESI) m/z: 417.2 [M−56]$^+$

Step 4

Compound 31c (0.1 g, 211.67 µmol) and compound 8d (108.32 mg, 317.50 µmol) were added to a mixed solution of 1,4-dioxane (2 mL) and H$_2$O (0.5 mL), Pd(dppf)Cl$_2$ (15.49 mg, 21.17 μmol) and K$_3$PO$_4$ (134.79 mg, 635.00 μmol) were then added, and the reaction was conducted for 2 hours at 90° C. under N$_2$ protection. The reaction solution was directly separated and concentrated to obtain a crude product. The crude product was separated and purified by a preparative chromatography column (chromatography column: Boston Green ODS 150×30 mm×5 μm; mobile phase: [water (0.075% TFA)-ACN]; B %: 40%-70%, 9 min) to obtain compound 31d.

LCMS (ESI) m/z: 620.3 [M+1]$^+$

Step 5

Compound 31d (0.06 g, 96.82 μmol) was added to DCM (1 mL). TFA (110.39 mg, 968.19 μmol, 71.68 μL, 10 eq) was then added, and the reaction was conducted for 1 hour at 20° C. The reaction solution was directly dried by a spinning method to obtain a trifluoroacetate of compound 31. The trifluoroacetate of compound 31 was added to a sodium bicarbonate solution, and the obtained solution was extracted with ethyl acetate. Organic phases were dried with anhydrous sodium sulfate, and concentrated under reduced pressure to obtain compound 31.

LCMS (ESI) m/z: 520.3 [M+1]$^+$ $^1$H NMR (400 MHz, CD$_3$OD) δ=8.91 (br d, J=70 Hz, 1H), 8.75-8.63 (m, 1H), 8.55-8.45 (m, 1H), 8.41-822 (m, 2H), 7.95 (br d, J=2.8 Hz, 1H), 7.91-7.77 (m, 1H), 7.42-7.24 (m, 1H), 6.97-6.85 (m, 1H), 6.49 (br s, 1H), 4.76-4.68 (m, 2H), 4.62 (br d, J=6.3 Hz, 1H), 4.38-4.27 (m, 3H), 4.09 (br d, J=13.3 Hz, 1H), 3.96 (br d, J=5.8 Hz, 4H), 3.64 (br dd, J=5.5, 12.3 Hz, 1H), 3.59-3.5 (m, 2H), 2.92 (br s, 2H), 2.28-2.13 (m, 2H).

Step 6

A trifluoroacetate of compound 31 (0.01 g, 15.78 μmol) was added to a mixed solution of DCM (1 mL) and MeOH (0.5 mL), anhydrous acetaldehyde (5.21 mg, 47.35 μmol, 6.64 μL) was added, stirring was conducted at 20° C. for 0.5 hour, then sodium triacetoxyborohydride (3.34 mg, 15.78 μmol) was added, and the reaction was conducted for 0.5 hour at 20° C. The reaction solution was directly dried by a spinning method, and purified by a preparative chromatography column (chromatography column. Welch Xtimate C18 150×25 mm×5 μm, mobile phase: [water (0.075% trifluoroacetic acid)-acetonitrile]; B %: 11%-41%, 10 min) to obtain a trifluoroacetate of compound 34. The trifluoroacetate of compound 34 was added to a sodium bicarbonate solution, and extracted with ethyl acetate. Organic phases were dried with anhydrous sodium sulfate, and concentrated under reduced pressure to obtain compound 34.

1H NMR (400 MHz, DMSO-d$_6$) δ 8.10 (br s, 1), 7.95-7.81 (m, 1H), 7.76-7.47 (m, 3H), 7.21-7.12 (m, 1H), 7.11-6.99 (m, 1H), 6.12 (br d, J=8.5 Hz, 1H), 5.68 (br s, 1H), 3.91 (br s, 2H), 3.81 (br d, J=4.3 Hz, 1H), 3.61-3.40 (m, 4H), 3.39-3.24 (m, 3H), 3.16 (br s, 3H), 3.06 (br s, 1H), 2.83 (br s, 1), 2.58 (br s, 2H), 2.33-2.14 (m, 3H), 1.47-1.33 (m, 1H), 0.65 (br t, J=7.0 Hz, 3H).

Example 32

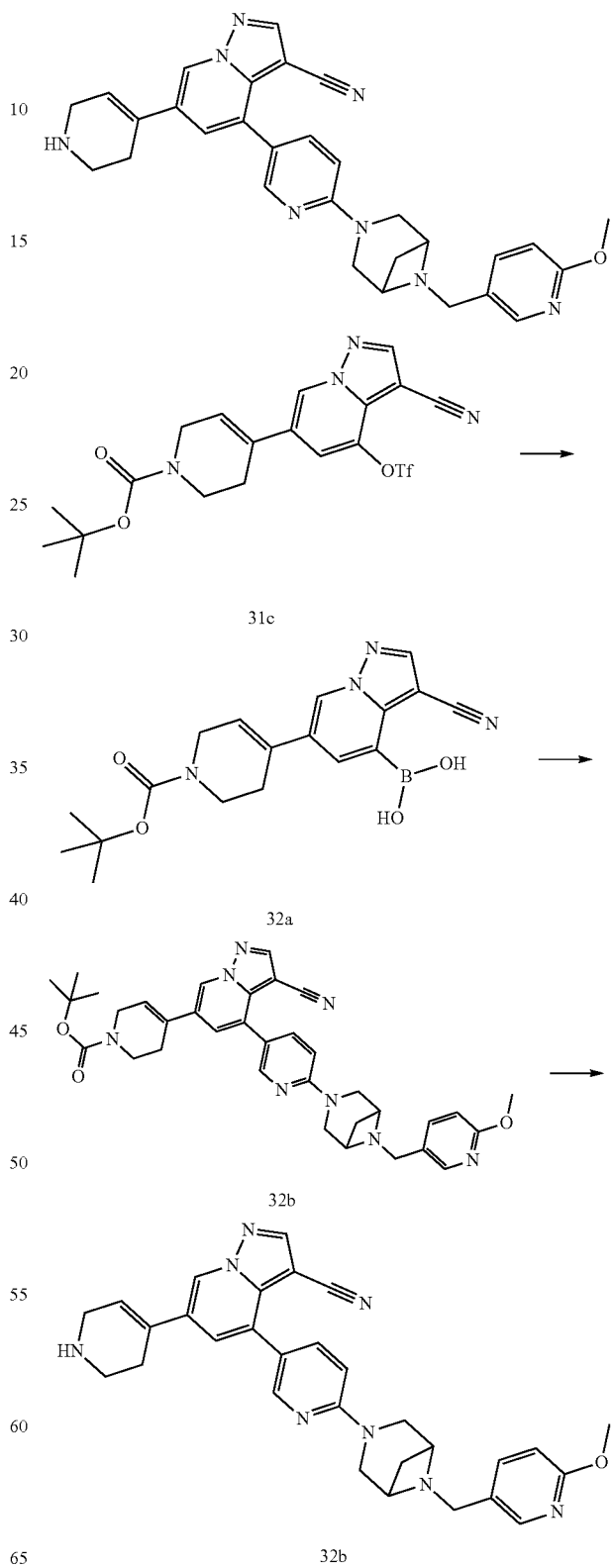

Step 1

Compound 31c and bis(pinacolato)diboron (193.50 mg, 762.01 µmol) were added to 1,4-dioxane (2 mL). Pd(dppf)Cl₂ (18.59 mg, 25.40 mmol) and KOAc (74.78 mg, 762.01 µmol) were then added, and the reaction was conducted for 2 hours at 80° C. The reaction solution was filtrated to obtain a filtrate, and the filtrate was concentrated to obtain crude product 32a which was directly used in the next step.

LCMS (ESI) m/z: 312.9 [M−56]⁺

Step 2

Compound 32a (68.68 mg, 186.54 µmol) and compound 9c (0.07 g, 186.54 µmol) were added to a mixed solution of 1,4-dioxane (2 mL) and H₂O (0.5 mL), Pd(dppf)Cl₂ (13.65 mg, 18.65 µmol) and K₃PO₄ (118.79 mg, 559.61 µmol) were then added, and the reaction was conducted for 1.5 hours at 90° C. The reaction solution was directly concentrated, separated and purified by a preparative chromatography column (chromatography column: Boston Green ODS 150× 30 mm×5 µm, mobile phase: [water (0.075% trifluoroacetic acid)-acetonitrile]; B %: 40%-70%, 7 min) to obtain compound 32b.

LCMS (ESI) m/z: 619.3 [M+1]⁺

Step 3

Compound 32b (0.03 g, 48.49 µmol) was added to DCM (1 mL), TFA (55.28 mg, 484.87 mol, 35.90 µL) was then added, and the reaction was conducted for 0.5 hour at 20° C. The reaction solution was directly dried by a spinning method to obtain a trifluoroacetate of compound 32. The trifluoroacetate of compound 32 was added to a sodium bicarbonate solution, and the obtained solution was extracted with ethyl acetate Organic phases were dried with anhydrous sodium sulfate, and concentrated under reduced pressure to obtain compound 32 LCMS (ESI) m/z: 519.1 [M+1]⁺

¹H NMR (400 MHz, CD₃OD) δ8.87 (br s, 1H), 8.56-8.26 (m, 3H), 8.08-7.80 (m, 2H), 7.69 (br s, 1H), 7.11-6.88 (m, 2I), 6.47 (br s, 1H), 4.73-4.53 (m, 3H), 4.24 (br d, J=13.1 Hz, 3H), 4.03 (br d, J=13.6 Hz, 1H), 3.99-3.90 (m, 4H), 3.67-3.49 (m, 4H), 2.92-3.02 (m, 3H), 2.22 (br d, J=9.8 Hz, 1H).

Example 33

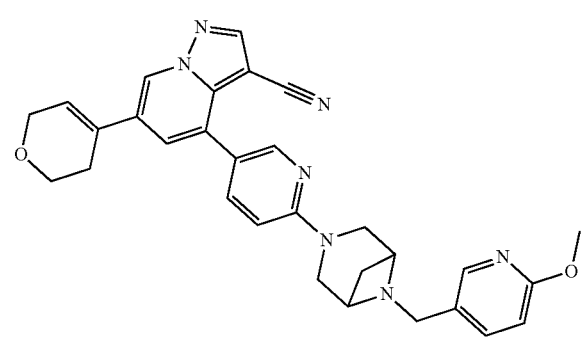

33

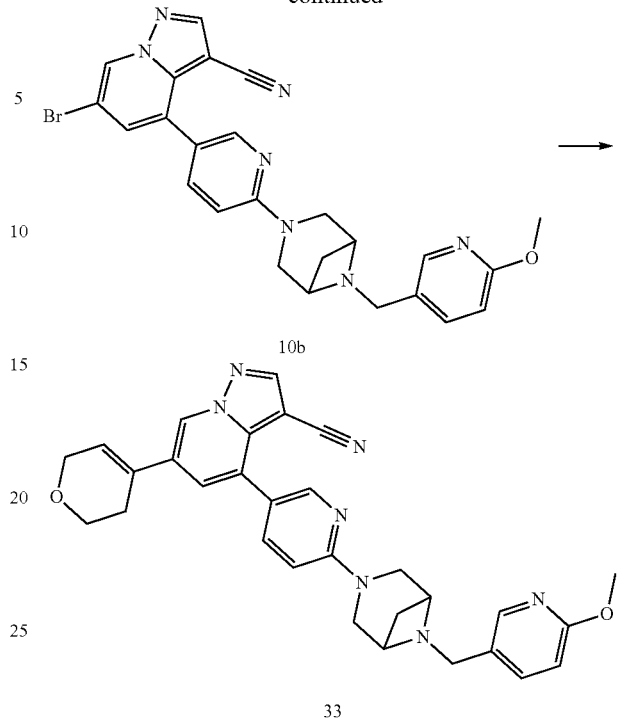

Step 1

Compound 10b (50 mg, 96.83 µmol) and 3,6-dihydro-2H-pyran-4-boronic acid pinacol ester (30.51 mg, 145.24 µmol) were dissolved in a 1,4-dioxane (1 mL)/water (0.5 mL) solution, Pd(dppf)Cl₂ (7.08 mg, 9.68 µmol) and anhydrous potassium phosphate (61.66 mg, 290.48 µmol) were added, and stirring was conducted at 90° C. for 16 hours under nitrogen protection. The reaction solution was dried by a spinning method, dissolved with ethyl acetate, filtrated to remove the insoluble material and obtain a filtrate. The filter residue was washed to obtain a filtrate. Filtrates were combined, and dried by a spinning method to obtain a crude product. The crude product was separated and purified by a preparative chromatography column (chromatography column: Boston Green ODS 150×30 mm×5 µm, mobile phase: [water (0.075% trifluoroacetic acid)-acetonitrile]; B %: 25%-55%, 8 min) to obtain a trifluoroacetate of compound 33 The trifluoroacetate of compound 33 was added to a sodium bicarbonate solution, and the obtained solution was extracted with ethyl acetate. Organic phases were dried with anhydrous sodium sulfate, and concentrated wider reduced pressure to obtain compound 33.

LCMS (ESI) m/z: 520.1 [M+1]⁺

¹H NMR (400 MHz, CD₃OD) δ8.87 (brs, 1H), 8.51-8.18 (m, 4H), 7.89 (s, 1H), 7.75 (s, 1H), 7.28-7.21 (m, 1H), 6.91 (d, J=4.8 Hz, 1H), 6.49 (s, 1H), 4.71-4.63 (m, 3H), 4.38-4.4.32 (m, 6H), 4.28-4.17 (m, 1H), 3.98-3.95 (m, 5H), 3.65-3.61 (m, 1H), 2.58 (t, J=7.2 Hz, 2H), 2.25-2.22 (m, 1H).

Compounds in the examples in Table 3 can be prepared by referring to steps similar to a preparation route of the aforementioned Example 33, with the difference lying in that the raw material used in step 3 is the raw material B in the following table instead of 3,6-dihydro-2H-pyran-4-boronic acid pinacol ester to obtain trifluoroacetate of the corresponding compounds. The obtained trifluoroacetate of the compounds were added to sodium bicarbonate solutions, the obtained solutions were extracted with ethyl acetate, and organic phases were dried with anhydrous sodium sulfate and concentrated under reduced pressure to obtain the corresponding compounds.

TABLE 3

| NO. | Product Structure | Raw Material B | LCMS m/z [M + 1]⁺ | Product ¹H NMR |
|---|---|---|---|---|
| Ex. 39 | | | 534.1 | Trifluoroacetate of compound 39 ¹H NMR (400 MHz, CD₃OD) δ ppm 8.72 (s, 1 H) 8.22-8.49 (m, 3 H) 7.76-8.07 (m, 2 H) 7.64 (s, 1 H) 6.88-7.11 (m, 2 H) 6.32 (s, 1 H) 4.51-4.76 (m, 3 H) 4.24 (d, J = 13.05 Hz, 4 H) 3.99-4.13 (m, 2 H) 3.97 (s, 3 H) 3.62 (s, 1 H) 2.50-2.75 (m, 3 H) 1.99-2.34 (m, 3 H) 1.74-1.91 (m, 1 H). |
| Ex. 54 | | | 506.1 | Trifluoroacetate of compound 54 ¹H NMR (400 MHz, CD₃OD) δ ppm 8.55 (s, 1 H) 8.22-8.42 (m, 3 H) 7.83 (s, 1 H) 7.55-7.75 (m, 2 H) 6.81 (d, J = 8.78 Hz, 2 H) 6.56 (s, 1 H) 4.94 (s, 2 H) 4.37-4.64 (m, 4 H) 4.13 (d, J = 13.30 Hz, 4 H) 3.91 (d, J = 13.05 Hz, 1 H) 3.85 (s, 3 H) 2.10 (d, J = 10.79 Hz, 1 H) 1.19 (d, J = 3.76 Hz, 2 H) |

Examples 35 and 55

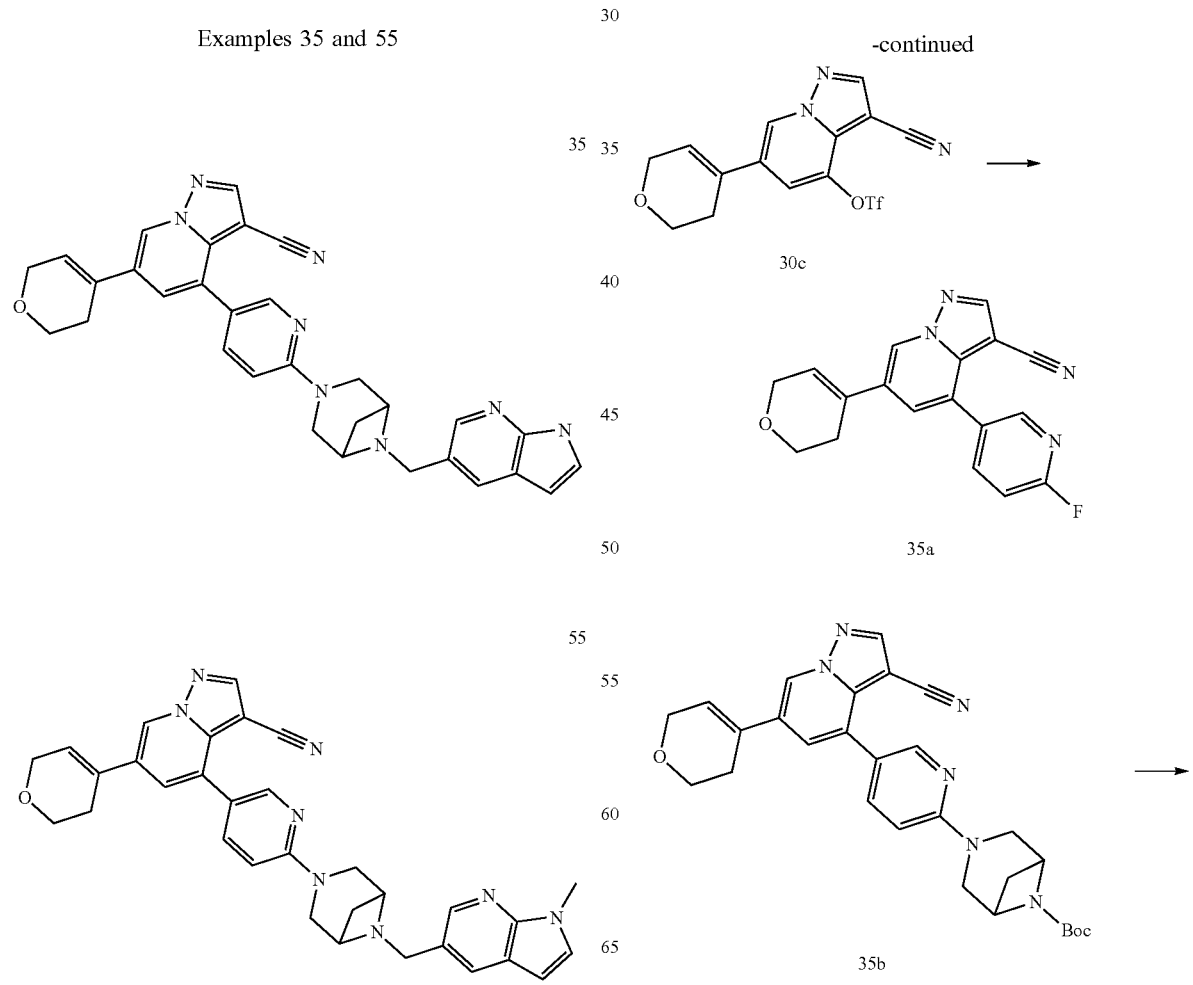

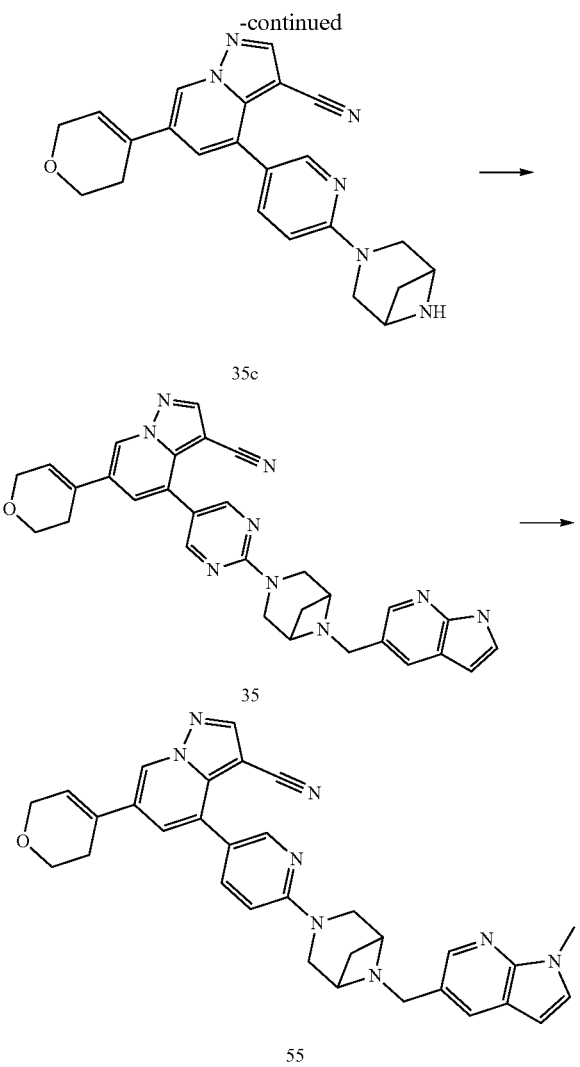

Step 1

Compound 30c (250 mg, 669.69 μmol) and 6-fluoro-3-boronic acid pyridine (94.36 mg, 669.69 μmol) were dissolved in a mixed solution of H₂O (0.4 mL) and THF (2 mL), Pd(dppf)Cl₂CH₂Cl₂ (16.41 mg, 20.09 μmol) and potassium acetate (84.12 mg, 857.16 μmol) were added, and stirring was conducted at 50° C. for 16 hours under nitrogen protection. The reaction solution was filtered and dried by a spinning method to obtain a crude product. The crude product was purified by an automatic column passing machine (PE:EA=1:1) to obtain compound 35a.

LCMS (ESI) m/z: 320.9[M+1]⁺

¹H NMR (400 MHz, CDCl₁) δ 8.58 (s, 1H), 8.41 (s, 1H), 8.29 (s, 1H), 8.05-8.03 (m, 1H), 7.49 (s, 1H), 7.16-7.13 (m, 1H), 6.35 (br s, 1H), 4.39-4.36 (m, 2H), 3.99-3.98 (m, 2H), 2.57-2.56 (m, 2H).

Step 2

Compound 35a (120 mg, 374.63 μmol) and 6-Boc-3,6-diazabicyclo[3.1.1]-heptane (111.41 mg, 561.94 μmol) were dissolved in DMSO (1.5 mL), KOAc (73.53 mg, 749.25 μmol) was added, and stirring was conducted at 75° C. for 16 hours, 10 mL of water was added to the reaction solution, and then the reaction solution was extracted with ethyl acetate (10 mL×3). Organic phases were combined, washed with a saturated sodium chloride solution (15 mL×1), dried with anhydrous sodium sulfate, and finally dried by a spinning method to obtain a crude product. The crude product was purified by an automatic column passing machine (PE:EA=1:1) to obtain compound 35b.

LCMS (ESI) m/z: 499.2 [M+1]⁺

Step 3

Compound 35b (200 mg, 401.14 μmol) was dissolved in dichloromethane (1 ml), HCl/EtOAc (4 M, 4 mL) was added, and stirring was conducted at room temperature of 20° C. for 1 hour. The reaction solution was dried by a spinning method to obtain a crude product. The crude product was directly used in the next step without purification. The reaction was conducted successfully, and compound 35c was obtained.

LCMS (ESI) m/z: 399.2 [M+1]⁺

Step 4

Compound 35c (20 mg, 42.43 μmol) was added to DCM (1 mL) under stirring, triethylamine (8.59 mg, 84.86 μmol, 11.81 μL) was added, stirring was conducted for 5 min. 1H-pyrrolo[2,3-b]pyridine-5-formaldehyde (9.30 mg, 63.64 μmol) was added, stirring was conducted at room temperature of 20° C. for 20 min. sodium triacetoxyborohydride (26.98 mg, 127.29 μmol) was added, and stirring was conducted at room temperature for 2 hours. The reaction solution was dried by a spinning method, dissolved with methanol, and filtered to obtain a filtrate. The filtrate was separated and purified by preparative HPLC (chromatography column: Boston Green ODS 150×30 mm×5 m; mobile phase: [water-acetonitrile]; B %: 16%-46%, 10 min) to obtain compound 35. Compound 35 was placed in DCM, an equivalent amount of TFA was added dropwise, and the obtained solution was concentrated to obtain a trifluoroacetate of compound 35.

LCMS (ESI) m/z: 529.1 [M+1]⁺

¹H NMR (400 MHz, CD₃OD) δ ppm 8.76 (br s, 1H) 8.55-8.34 (m, 3H) 8.31-8.18 (m, 1H) 8.05-7.88 (m, 1H) 7.77-7.62 (m, 1H) 7.54 (d, J=3.38 Hz, 1H) 7.11-6.86 (m, 1H) 6.62 (d, J=3.24 Hz, 1H) 6.49 (s, 1H) 4.75-4.59 (m, 2H) 4.46 (s, 1H) 4.36 (s, 3H) 4.29-4.20 (m, 2H) 4.10-3.92 (m, 4H) 3.66 (s, 1H) 2.61 (s, 2H) 2.32-2.18 (m, 1H).

Step 5

The trifluoroacetate of compound 35 (50 mg, 77.81 μmol) was dissolved in DMF (1 μL), sodium hydride (4.67 mg, 116.71 μmol, 60% purity) was added at 0° C., stirring was conducted for 10 min, methyl iodide was added (13.25 mg, 93.37 μmol), and stirring was conducted at room temperature of 25° C. for 2 hours. The reaction solution was quenched by adding 2 mL of water, and extracted with ethyl acetate (2 mL×3). Organic phases were combined, washed with water (2 mL×2), washed with a saturated sodium chloride solution (2 mL), dried with anhydrous sodium sulfate, and finally dried by a spinning method to obtain a crude product. The crude product was separated and purified by a preparative HPLC (chromatography column: Boston Green ODS 150×30 mm×5 μm; mobile phase: [water (0.075% trifluoroacetic acid)-acetonitrile]; B %: 18%-48%, 7 min) to obtain a trifluoroacetate of compound 55. The trifluoroacetate of compound 55 was added to a sodium bicarbonate solution, and the the obtained solution was extracted with ethyl acetate. Organic phases were dried with anhydrous sodium sulfate, and concentrated under reduced pressure to obtain compound 55.

LCMS (ESI) m/z: 543.1 [M+1]⁺

¹H NMR (400 MHz, CD₃OD) δ ppm 8.81-8.70 (m, 1H) 8.55-8.34 (m, 3H) 8.28-8.12 (m, 1H) 8.05-7.86 (m, 1H) 7.75-7.62 (m, 1H) 7.49 (s, 1H) 7.12-6.89 (m, 1H) 6.58 (s, 1H) 6.47 (s, 1H) 4.74-4.57 (m, 2H) 4.45 (s, 1H) 4.34 (s, 3H) 4.29-4.17 (m, 2H) 4.05-3.93 (m, 3H) 3.90 (s, 3H) 3.65 (s, 1H) 3.05 (s, 1H) 2.59 (s, 2H) 2.24-2.13 (m, 1H).

Compounds in the examples in Table 4 can be prepared by referring to steps similar to a preparation route of the aforementioned Example 35, with the difference lying in that a raw material used in step 7 is the raw material B in the following table instead of 1H-pyrrolo[2,3-b]pyridine-5-formaldehyde to obtain the corresponding compounds.

TABLE 4

| NO. | Product Structure | Raw Material B | Product LCMS m/z: [M + 1]+ | Product ¹H NMR |
|---|---|---|---|---|
| Ex. 37 | | | 529.1 | Compound 37 ¹H NMR (400 MHz, CD₃OD) δ ppm 8.76 (s, 1 H), 8.55-8.34 (m, 3 H), 8.31-8.18 (m, 1 H), 8.05-7.88 (m, 1 H), 7.77-7.62 (m, 1 H), 7.54 (d, J = 3.38 Hz, 1 H), 7.11-6.86 (m, 1 H), 6.62 (d, J = 3.24 Hz, 1 H), 6.49 (s, 1 H), 4.76-4.59 (m, 2 H) 4.46 (s, 1 H), 4.36 (s, 3 H), 4.31-4.20 (m, 2 H), 3.92-4.10 (m, 4 H), 3.66 (s, 1 H), 2.61 (s, 2 H), 2.23 (d, J = 10.76 Hz, 1 H). |
| Ex. 38 | | | 528.1 | Compound 38 ¹H NMR (400 MHz, CD₃OD) δ ppm 8.74 (d, J = 1.12 Hz, 1H) 8.44 (s, 1H) 8.40 (d, J = 2.14 Hz, 1H) 7.90 (dd, J = 8.82, 2.44 Hz, 1H) 7.69 (d, J = 1.50 Hz, 1H) 7.54 (s, 1H) 7.36 (d, J = 8.38 Hz, 1H) 7.23 (d, J = 3.13 Hz, 1H) 7.15 (dd, J = 8.38, 1.38 Hz, 1H) 6.92 (d, J = 8.64 Hz, 1H) 6.51 (s, 1H) 6.42 (d, J = 2.64 Hz, 1H) 4.37 (d, J = 2.72 Hz, 2H) 4.07-3.95 (m, 4H) 3.93-3.76 (m, 4H) 3.68 (d, J = 12.00 Hz, 2H) 2.76 (s, 1H) 2.62 (d, J = 1.64 Hz, 2H) 1.74 (d, J = 8.88 Hz, 1H). |
| Ex. 56 | | | 558.1 | Trifluoroacetate of compound 56 ¹H NMR (400 MHz, CD₃OD) δ ppm 8.92 (s, 1 H) 8.73 (s, 1 H) 8.44 (s, 1 H) 8.40 (s, 1 H) 8.27 (d, J = 7.52 Hz, 1 H) 8.03 (d, J = 7.28 Hz, 1 H) 7.95 (d, J = 8.04 Hz, 1 H) 7.69 (d, J = 0.74 Hz, 1 H) 7.09 (d, J = 7.04 Hz, 1 H) 6.48 (s, 1 H) 4.85-4.43 (m, 4 H) 4.39-4.06 (m, 5 H) 3.83-3.38 (m, 1 H) 3.96 (t, J = 5.40 Hz, 2 H) 2.57 (s, 2 H) 2.24 (d, J = 11.04 Hz, 1 H) |

Example 36

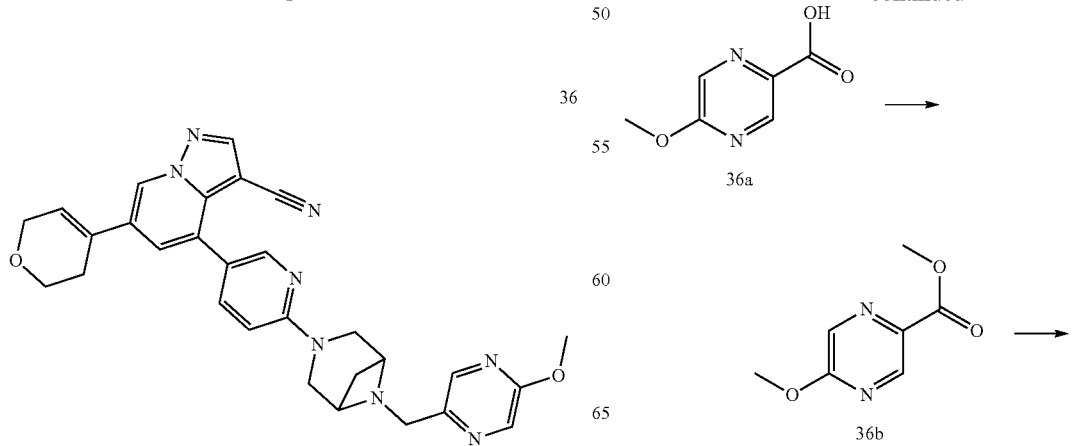

-continued

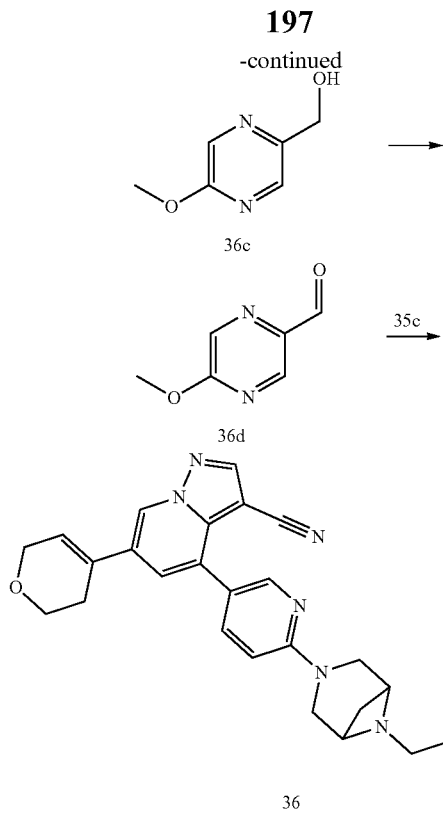

Step 1

Compound 36a (5 g, 32.44 mmol) was dissolved in methanol (20 mL), thionyl chloride (4.63 g, 38.93 mmol, 2.82 mL) was then slowly added to the reaction solution, and the reaction solution was stirred at 60° C. for 2 hours under nitrogen protection. The reaction solution was directly concentrated by rotary evaporation to obtain crude product 36b which was directly used in the next step.

$^1$H NMR (400 MHz, DMSO-d$_6$) δ8.88 (d, J=0.8 Hz, 1H), 8.28 (d, J=1.2 Hz, 1H), 4.08 (s, 3H), 3.98 (s, 3H).

Step 2

Sodium borohydride (337.49 mg, 8.92 mmol) was added to THF (10 mL) containing compound 36b (500 mg, 2.97 mmol), the obtained solution was heated by oil bath to 65° C. for reaction for 1 hour under stirring, then MeOH (2 mL) was added to the reaction solution under stirring, and the reaction was conducted at 65° C. for 2 hours under stirring, 0.5 mL of water was added dropwise to the reaction solution to quench the reaction, 5 mL of water and 10 mL of ethyl acetate were then added, and the the reaction solution was separated and extracted. The aqueous phase was extracted with 10 mL of ethyl acetate twice Organic phases were combined, dried with anhydrous sodium sulfate, and concentrated by rotary evaporation to obtain crude product compound 36c.

$^1$H NMR (400 MHz, CD$_3$OD) δ8.12 (s, 1H), 8.04 (s, 1H), 4.56 (s, 2H) 3.86 (s, 3H).

Step 3

Manganese dioxide (465.27 mg, 5.35 mmol) was added to dichloromethane (5 mL) containing compound 36c (150 mg, 1.07 mmol), and the reaction solution was stirred at 15-20° C. for 16 hours under nitrogen protection. The reaction solution was directly filtered to collect the filtrate, and the solid was washed with 10 ml of dichloromethane. The filtrates collected during filtration were combined, and subjected to rotary evaporation to obtain crude product 36d.

$^1$H NMR (400 MHz, CD$_3$OD) δ9.92-9.83 (m, 1H), 8.64 (d, J=1.2 Hz, 1H), 8.11 (s, 1H), 3.97 (s, 3H).

Step 4

Compound 35c (20 mg, 42.43 μmol) and triethylamine (12.88 mg, 127.29 μmol) were added together to dichloromethane (2 mL), stirring was conducted for 10 minutes, then compound 36d (17.58 mg, 127.29 μmol) was added to the reaction solution, stirring was continued for 1 hour, then sodium triacetoxyborohydride (17.98 mg, 84.86 μmol) was added to the reaction solution, and the reaction solution was stirred at 15-20° C. for reaction for 16 hours under nitrogen protection. The reaction solution was directly subjected to rotary evaporation at low temperature to obtain a crude product. The crude product was separated by a preparative chromatography column (chromatography column: Boston Green ODS 150×30 mm×5 μm; mobile phase: [water-acetonitrile]; B %: 18%-48%, 10 min) to finally obtain compound 36.

LCMS (ESI) m/z: 521.1[M+1]$^+$ $^1$H NMR (400 MHz, CD$_3$OD) δ8 74 (s, 1H), 8.46-8.37 (m, 2H), 8.36-8.20 (m, 2H), 7.93 (br s, 1H), 7.66 (s, 1H), 7.02-6.88 (m, 1H), 6.48 (brs, 1H), 4.74 (brd, J=3.21 Hz, 2H), 4.40 (brs, 1H), 4.34 (brd, J=2.4 Hz, 2H), 4.24 (br s, 3H), 4.11 (br d, J=12.4 Hz, 1H), 4.05-3.89 (m, 5H), 3.71-3.47 (m, 1H), 3.11 (br s, 1H), 2.59 (br s, 2H), 2.21 (br d, J=10.8 Hz, 1H).

Examples 40 and 41

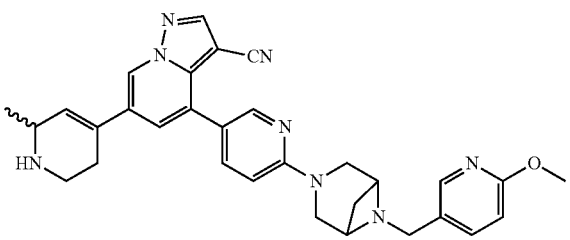

40

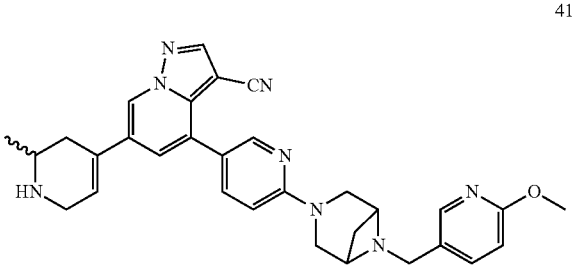

41

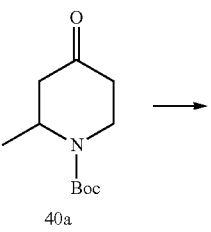

40a

-continued

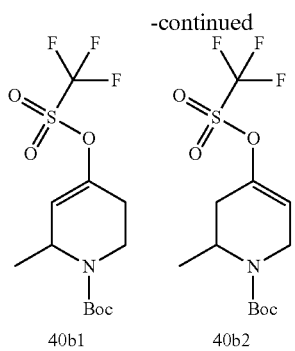

40b1    40b2

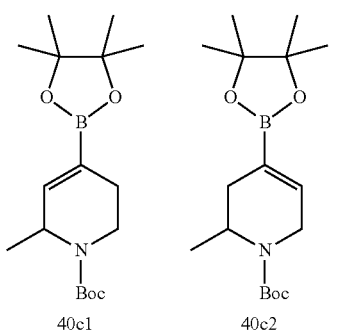

40c1    40c2

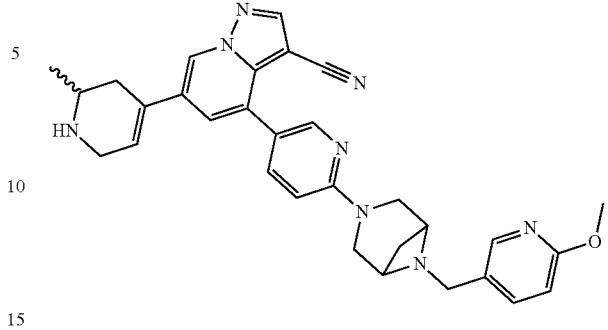

-continued

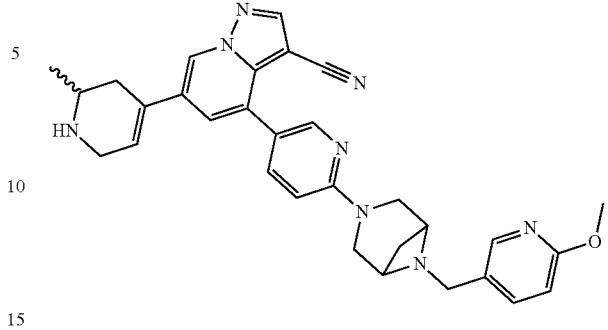

Step 1

Compound 40a (1 g, 4.69 mmol) was dissolved in TH F (10 mL), LDA (2 M, 2.81 mL) was added dropwise at −78° C., stirring was conducted for 30 minutes. N-phenylbis(trifluoromethanesulfonyl) imine (2.01 g, 5.63 mmol) was then dissolved in 5 mL of THF and added dropwise to the above reaction solution at −78° C., after the dropwise addition, the temperature of the reaction solution was slowly risen to 20° C. (1.5 h), and stirring was conducted overnight (10 h). Saturated ammonium chloride (20 mL) was added to the reaction solution, and then the reaction solution was extracted with ethyl acetate (30 mL) twice. Organic phases were combined, dried with anhydrous sodium sulfate, and titrated to obtain a filtrate. The filtrate was concentrated to obtain a crude product. The crude product was purified by a rapid column passing machine (PE:EA=5:1 to 1:1) to obtain a mixture of compounds 40b1 and 40b2.

Step 2

The mixture of 40b1 and 40b2 (1 g, 2.90 mmol) was dissolved in 1,4-dioxane (15 mL), bis(pinacolato)diboron (882.41 mg, 3.47 mmol), KOAc (568.39 mg, 5.79 mmol) and Pd(dppf)Cl$_2$ (211.88 mg, 289.57 µmol) were added, and stirring was conducted at 90° C. for 16 hours under nitrogen protection. The reactant was filtered and dried by a spinning method under reduced pressure to obtain a crude product. The crude product was purified by an automatic column passing machine (PE:EA=5:1) to obtain a mixture of compounds 40c1 and 40c2.

Step 3

Compound 10b (150 mg, 290.48 µmol) was dissolved in 1,4-dioxane (9 mL), the mixture of compounds 40c1 and 40c2 (187.78 mg, 580.95 µmol), K$_3$PO$_4$ (123.32 mg, 580.95 µmol) and H$_2$O (3 mL) were added under stirring, Pd(dppf)Cl$_2$ (21.25 mg, 29.05 µmol) was added, and stirring was conducted at 90° C. for 3 hours under nitrogen protection. 30 mL of water was added to the reaction solution, and then the reaction solution was extracted with ethyl acetate (30 mL×3). Organic phases were combined, washed with a saturated salt solution (30 mL×5), dried with anhydrous sodium sulfate, and dried by a spinning method to obtain a crude product. The crude product was separated and purified by a preparative HPLC (chromatography column: Boston Green ODS150×30 mm×5 µm; mobile phase [H$_2$O-ACN], B %: 31%-61%, 10 min) to obtain a mixture of compounds 40d1 and 40d2.

LCMS (ESI) m/z 633.6[M+1]

Step 4

Compound 40d (100 mg, 158.04 µmol) was dissolved in DCM (1 mL), TFA (360.39 mg, 3.16 mmol, 234.02 µL) was added, and stirring was conducted at 20° C. for 3 hours. The reaction solution was dried by a spinning method under reduced pressure to obtain a crude product. The crude product was purified by SFC (chromatography column: DAICEL CHIRALPAK AD (251) mm×30 mm, 10 μm); mobile phase: [0.1% NH₃H₂O IPA]; B %: 60%-60%, min) to obtain compound 40 and compound 41.

Compound 40 (a mixture, relative retention time: 1.068-1.333 min)

LCMS (ESI) m/z 533.1[M+1]⁺

Compound 41 (relative retention time, 2.675 min)

LCMS (ESI) m/z 533.1 [M+1]⁺

¹H NMR (400 MHz, CD₃OD) δ8.25 (s, 1H), 7.90-7.77 (m, 2H) 7.60-7.48 (m, 11H), 7.29 (dd, J=8.78, 2.26 Hz, 1H), 7.21-7.1 (m, 2H), 6.31 (br d, J=8.78 Hz, 1H), 6.23 (d, J=8.54 Hz, 1H), 5.80 (s, 1H), 3.43-3.32 (m, 5H), 3.25 (br s, 3H), 3.06 (br d, J=12.04 Hz, 1H), 2.87-2.77 (m, 1H), 2.41-2.21 (m, 4H), 2.06 (s, 1H), 1.33-1.16 (m, 2H).

Example 42

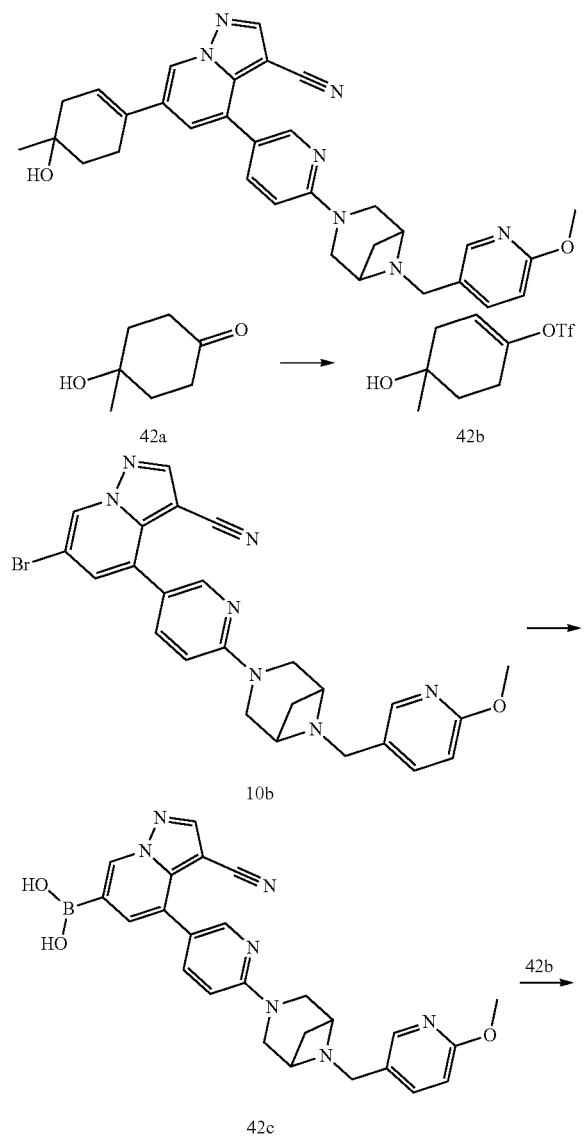

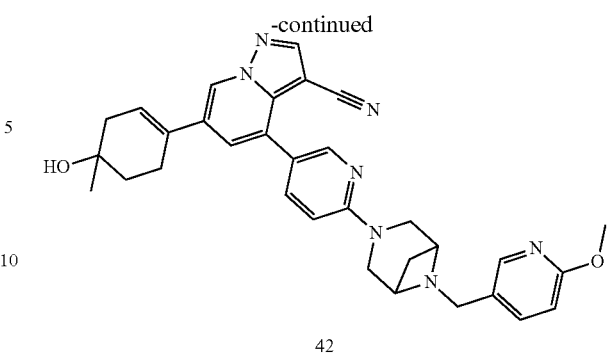

Step 1

2-isopropylamine (47.37 mg, 468.13 μmol, 66.16 μL) was added to a THF (4 mL) solution, the reaction temperature was decreased to −78° C., n-BuLi (2.5 M, 187.25 μL) was added to the reaction solution, the reaction temperature was risen to ° C. stirring was conducted at this temperature for 0.5 hour, then the reaction temperature was decreased to −78° C., compound 42a (0.05 g, 390.11 μmol) was added to the reaction solution, the reaction was conducted at −78° C. for 1 hour under stirring, N-phenylbis(trifluoromethane-sulfonyl)imine (153.30 mg, 429.12 μmol) was added to the reaction solution, the reaction temperature was risen to 20-30° C., and the reaction was conducted at this temperature for 2 hours. 10 mL of water was added to the reaction solution, and then the reaction solution was extracted with ethyl acetate (10 mL 2). Organic phases were combined, dried with anhydrous sodium sulfate, and dried by a spinning method at 40-50° C. under reduced pressure to obtain a crude product. The crude product was purified by a preparative thin layer chromatography plate (PE/EA=1/1) to obtain compound 42b.

Step 2

Compound 42b (0.1 g, 193.65 μmol), bis(pinacolato)diboron (49.18 mg, 193.65 μmol) and potassium acetate (19.01 ng, 193.65 μmol) were added to 1,4-dioxane (2 mL), Pd(dppf)Cl₂ (7.08 mg, 9.68 μmol) was then added to the reaction solution, replacement with nitrogen was conducted for three times, and reaction was conducted at 100° C. for 20 minutes in microwave. 5 mL of water was added to the reaction solution, and then the reaction solution was extracted with ethyl acetate (10 mL×2). Organic phases were combined, dried with anhydrous sodium sulfate, and dried by a spinning method under reduced pressure at 40-50° C. to obtain 81 mg of a crude product. The crude product was purified by a pre-TLC to obtain compound 42c.

LCMS (ESI) m/z: 482.1[M+1]⁺

Step 3

Compound 42c (50 mg, 103.88 μmol), compound 42b (27.03 mg, 103.88 μmol) and K₃PO₄ (66.15 mg, 311.65 μmol) were added to a mixed solution of 1,4-dioxane (4 mL) and H₂O (1 mL), Pd(dppf)Cl₂ (3.80 mg, 5.19 μmol) was then added to the reaction solution, replacement with nitrogen was conducted for three times, and the reaction was conducted at 100° C. for 20 minutes in microwave. 5 mL of water was added to the reaction solution, and then the reaction solution was extracted with ethyl acetate (10 mL×2). Organic phases were combined, dried with anhydrous sodium sulfate, and dried by a spinning method wider reduced pressure at 40-50° C. to obtain a crude product. The crude product was purified by a preparative chromatography column (chromatography column: Welch Xtimate C18 150×

25 mm×5 μm; mobile phase: [H$_2$O (0.05% ammonia v/v)-ACN]; B %: 33%-63%, 12 min) to obtain compound 42.

LCMS (ESI) m/z: 548.1[M+1]$^+$;

$^1$H NMR (400 MHz, CD$_3$OD) δ ppm 8.71 (s, 1H) 8.36-8.44 (m, 2H) 8.12 (s, 1H) 7.88 (br d, J=6.02 Hz, 1H) 7.75 (d, J=8.53 Hz, 1H) 7.65 (s, 1H) 6.91 (d, J=8.53 Hz, 1H) 6.81 (d, J=8.28 Hz, 1H) 6.33 (s, 1H) 4.61 (s, 2H) 3.89-3.95 (m, 5H) 3.82 (d, J=5.52 Hz, 2H) 3.64-3.72 (m, 4H) 2.73 (s, 2H) 2.38 (s, 2H) 1.76-1.98 (m, 2H) 1.33 (s, 3H).

Example 43

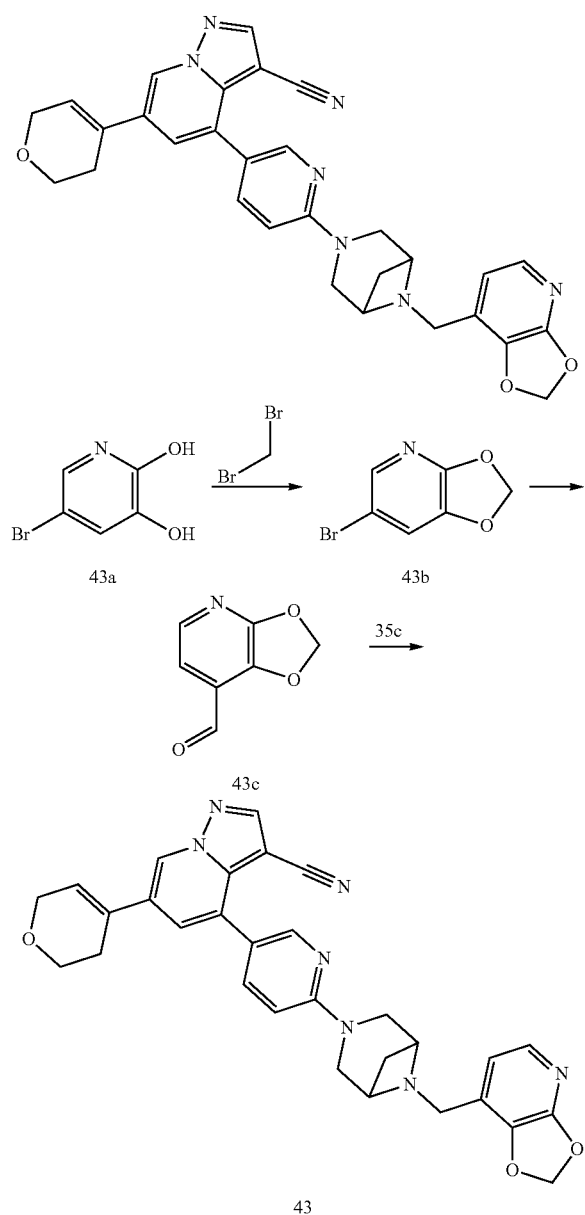

Step 1

Compound 43a (385 mg, 2.03 mmol) was dissolved in NMP (5 mL), dibromonmethane (422.70 mg, 2.43 mmol) and K$_2$CO$_3$ (840.17 mg, 6.08 mmol) were added, and stirring was conducted at 90° C. for 16 hours. The reaction solution was diluted with ethyl acetate, and filtered to remove the insoluble material 15 mL of water was then added to the reaction solution, and then the reaction solution was extracted with ethyl acetate (15 mL×3). Organic phases were combined, washed with water (15 mL×3), washed with a saturated sodium chloride solution (15 mL×1), dried with anhydrous sodium sulfate, and finally t dried by a spinning method to obtain a crude product. The crude product was purified by an automatic column passing machine (PE:EA=3:1) to obtain compound 43b.

LCMS (ESI) m/z: 203.7[M+1]$^+$

Step 2

Compound 43b (20 mg, 99.01 μmol) was dissolved in THF (1 mL), n-BuLi (2.5 M, 79.21 μL) was added at −78° C., the reaction temperature was maintained, stirring was conducted for 1 hour, then DMF (21.71 mg, 297.02 μmol) was added, the reaction temperature was risen to 25° C., and stirring was continued for another 1 hour. 5 mL of a saturated ammonium chloride solution was added to the reaction solution for quenching, and then the reaction solution was extracted with ethyl acetate (5 mL×3). Organic phases were combined, washed with a saturated sodium chloride solution, dried with anhydrous sodium sulfate, and finally dried by a spinning method to obtain a crude product. The crude product was separated and purified by a preparative thin layer chromatography plate (PE:EA=2:1) to obtain compound 43c.

$^1$H NMR (400 MHz, CDCl$_3$) δ ppm 10.26-10.10 (m, 1H) 7.77 (d, J=5.52 Hz, 1H) 7.13 (d, J=5.76 Hz, 1H) 6.25 (s, 2H).

Step 3

Compound 35c (20 mg, 42.43 μmol) was dissolved in DCM (1 mL), triethylamine (12.88 mg, 127.29 μmol, 17.72 μL) was added, stirring was conducted at room temperature of 20° C. for 15 min, compound 43c (7.69 mg, 50.91 μmol) was added, stirring was conducted at room temperature for 1 hour. NaBH(OAc) (26.98 mg, 127.29 μmol) was then added, and stirring was continued for 16 hours. 5 mL of water was added to the reaction solution, and then the reaction solution was extracted with DCM (5 mL×3). Organic phases were combined, washed with a saturated sodium chloride solution (5 mL×1), dried with anhydrous sodium sulfate, filtrated, and finally dried by a spinning method to obtain a crude product. The crude product was separated and purified by a preparative HPLC (chromatography column: Boston Green ODS 150×30 mm×5 μm; mobile phase: [H$_2$O (0.075% TFA)-ACN]; B %: 20%-50%, 10 min) to obtain a trifluoroacetate of compound 43. The trifluoroacetate of compound 43 was added to a sodium bicarbonate solution, and the obtained solution was extracted with ethyl acetate. Organic phases were dried with anhydrous sodium sulfate, and concentrated under reduced pressure to obtain compound 43.

LCMS (ESI) m/z: 534.1[M+1]$^+$ $^1$H NMR (400 MHz, CD$_3$OD) δ ppm 8.77 (s, 1H) 8.55-8.39 (m, 2H) 7.96 (d, J=7.52 Hz, 1H) 7.69 (d, J=5.52 Hz, 2H) 7.03-6.88 (m, 2H) 6.50 (s, 1H) 6.24 (s, 2H) 4.84-4.64 (m, 3H) 4.37 (d, J=2.50 Hz, 3H) 4.23 (s, 4H) 3.99 (t, J=5.40 Hz, 2H) 2.61 (s, 2H) 2.23 (d, J=1.04 Hz, 1H) 1.41-4.21 (m, 1H).

Example 44

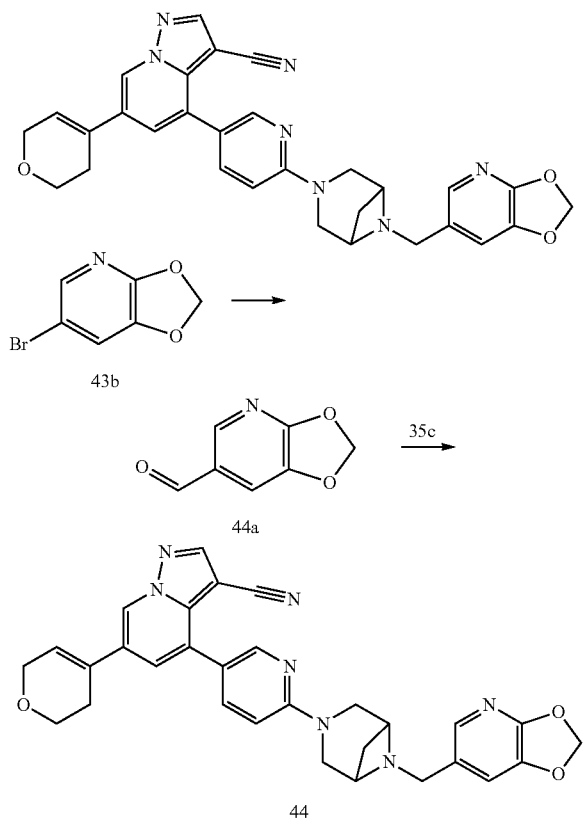

Step 1

Compound 43b (500 mg, 2.48 mmol), Et₃SiH (575.61 mg, 4.95 mmol), triethylamine (751.39 mg, 7.43 mmol, 1.03 mL), Pd(dppf)Cl² (90.56 mg, 123.76 μmol) were added to DMF (5 mL), replacement with carbon monoxide was conducted for three times, and under the air flow of the carbon monoxide (69.33 mg, 2.48 mmol) (50 Psi), the reaction solution was heated to 50° C., and stirred for 24 hours. The reaction solution was dried by a spinning method to obtain a crude product. The crude product was purified by an automatic column passing machine (PE:EA=3:1) to obtain compound 44a.

¹H NMR (400 MHz, CDCl₃) δ ppm 991 (d, J=0.72 Hz, 1H) 8.19 (d, J==: 1.52 Hz, 1H) 7.43 (d, J=1.52 Hz, 1H) 6.19 (d, J=1.00 Hz, 2H)

Step 2

Compound 44a (50 mg, 106.07 μmol) was dissolved in DCM (1 mL), triethylamine (32.20 mg, 318.21 μmol, 44.29 μL) was added, stirring was conducted at room temperature of 20° C. for 15 min, compound 35c (19.24 mg, 127.29 μmol) was added, stirring was conducted at room temperature for 1 hour, then NaBH(OAc)₃ (67.44 mg, 318.21 μmol) was added, and stirring was continued for 16 hours. 5 mL of water was added to the reaction solution, and then the reaction solution was extracted with DCM (5 mL×3). Organic phases were combined, washed with a saturated sodium chloride solution (5 mL×1), dried with anhydrous sodium sulfate, and finally dried by a spinning method to obtain a crude product. The crude product was separated and purified by a preparative HPLC (chromatography column: Boston Green ODS 150×30 mm×5 μm; mobile phase: [H₂O (0.075% TFA)-ACN]; B %: 20%-50%, 12 min) to obtain a trifluoroacetate of compound 44. The trifluoroacetate of compound 44 was added to a sodium bicarbonate solution, and the obtained solution was extracted with ethyl acetate. Organic phases were dried with anhydrous sodium sulfate, and concentrated under reduced pressure to obtain compound 44.

LCMS (ESI) m/z: 534.1 [M+1]⁺

¹H NMR (400 MHz, CD₃OD) δ ppm 8.76 (s, 1H) 8.42 (s, 2H) 8.00-7.63 (m, 3H) 7.31 (s, 1H) 6.93 s, 1H) 6.48 (s, 1H) 6.19 (s, 2H) 4.74-4.51 (m, 4H) 4.35 (d, J=2.64 Hz, 2H) 4.30-4.20 (m, 3H) 4.11-3.89 (m, 3H) 3.68-3.48 (m, 1H) 2.60 (s, 2H) 2.20 (d, J=11.26 Hz, 1H).

Example 45

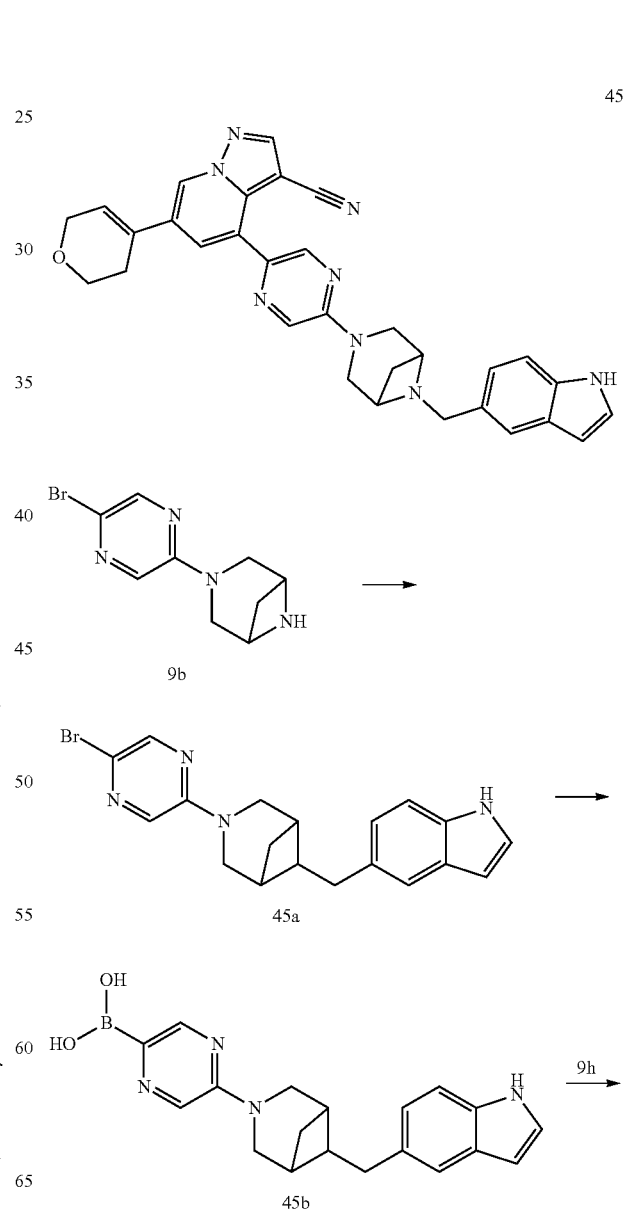

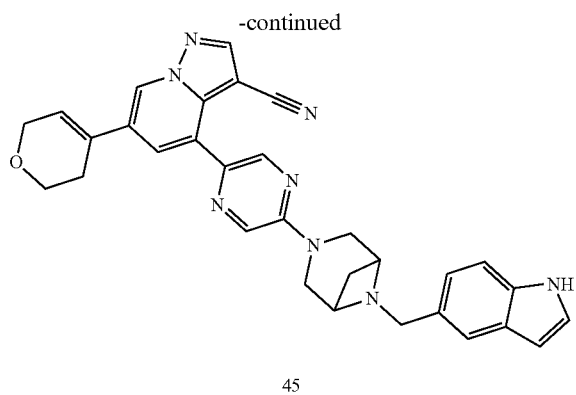

45

Step 1

Compound 9b (200 mg, 783.96 μmol) and 1H-indole-5-carbaldehyde (227.60 mg, 1.57 mmol) were added to 1,2-dichloroethane (5 mL), acetic acid (315.00 mg, 5.25 mmol, 0.3 mL) was added dropwise to adjust the pH value to 5-6, sodium triacetoxyborohydride (830.77 mg, 3.92 mmol) was added, and stirring was conducted at 16° C. for 4 hours. 10 mL of water was added to the reaction solution, and then the reaction solution was extracted with dichloromethane (15 mL×4). Organic phases were combined, washed with a saturated sodium chloride solution (15 mL×1), dried with anhydrous sodium sulfate, and finally dried by a spinning method to obtain a crude product. The crude product was purified by an automatic column passing machine (PE: EA=0:1, Rf=0.11) to obtain compound 45a.

LCMS (ESI) m/z: 385.9 [M+1]⁺

Step 2

Compound 45a (50 mg, 130.12 μmol) and bis(pinacolato)diboron (49.56 mg, 195.17 μmol) were dissolved in 1,4-dioxane (1 mL). Pd(dppf)Cl$_2$ (9.52 mg), 13.01 μmol) and potassium acetate (38.31 mg, 390.35 μmol) were added, and stirring was conducted at 80° C. for 16 hours under nitrogen protection. The reaction solution was filtered to obtain a filtrate, the filter residue was washed with ethyl acetate, and the filtrate was spin dried to obtain crude product of 45b. The crude product of 45b was directly used in the next step without purification.

LCMS (ESI) m/z: 349.9 [M+1]⁺

Step 3

Compound 45b (80 mg, 37.09 μmol) and compound 9h (9.23 mg, 24.73 μmol) were dissolved in a mixed solution of 1,4-dioxane (1 mL) and H$_2$O (0.5 mL), Pd(dppf)Cl$_2$ (1.81 mg, 2.47 μmol) and potassium phosphate (15.75 mg, 74.19 μmol) were added, and stirring was conducted at 90° C. for 16 hours under nitrogen protection. The reaction solution was filtered, and dried by a spinning method to obtain a crude product. The crude product was separated and purified by a preparative HPLC (chromatography column: Boston Green ODS150×30 mm×5 μm; mobile phase: [water-acetonitrile]; B %: 23%-53%, 10 min) to obtain compound 45.

LCMS (ESI) m/z: 529.2 [M+1]⁺

$^1$H NMR (400 MHz, CD$_3$OD) δ ppm 8.73-8.66 (m, 1H), 8.51 (s, 1H), 8.39-8.31 (m, 1H), 8.21 (s, 1H), 7.80 (s, 1H), 7.70 (s, 1H), 7.41 (t, J=7.94 Hz, 2H), 7.27-7.08 (m, 3H), 6.47-6.38 (m, 2H), 4.68-4.63 (m, 2H), 4.56 (d, J=5.24 Hz, 1H), 4.49 (d, J=6.24 Hz, 1H), 4.32-4.14 (m, 6H), 3.96-3.83 (m, 41H), 3.51 (d, J=7.00 Hz, 1H), 2.51 (s, 2H), 2.13-2.05 (m, 1H).

Example 46

46

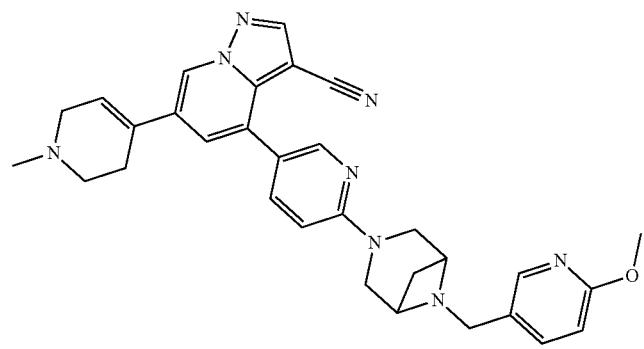

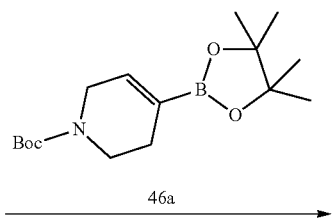

10b

-continued

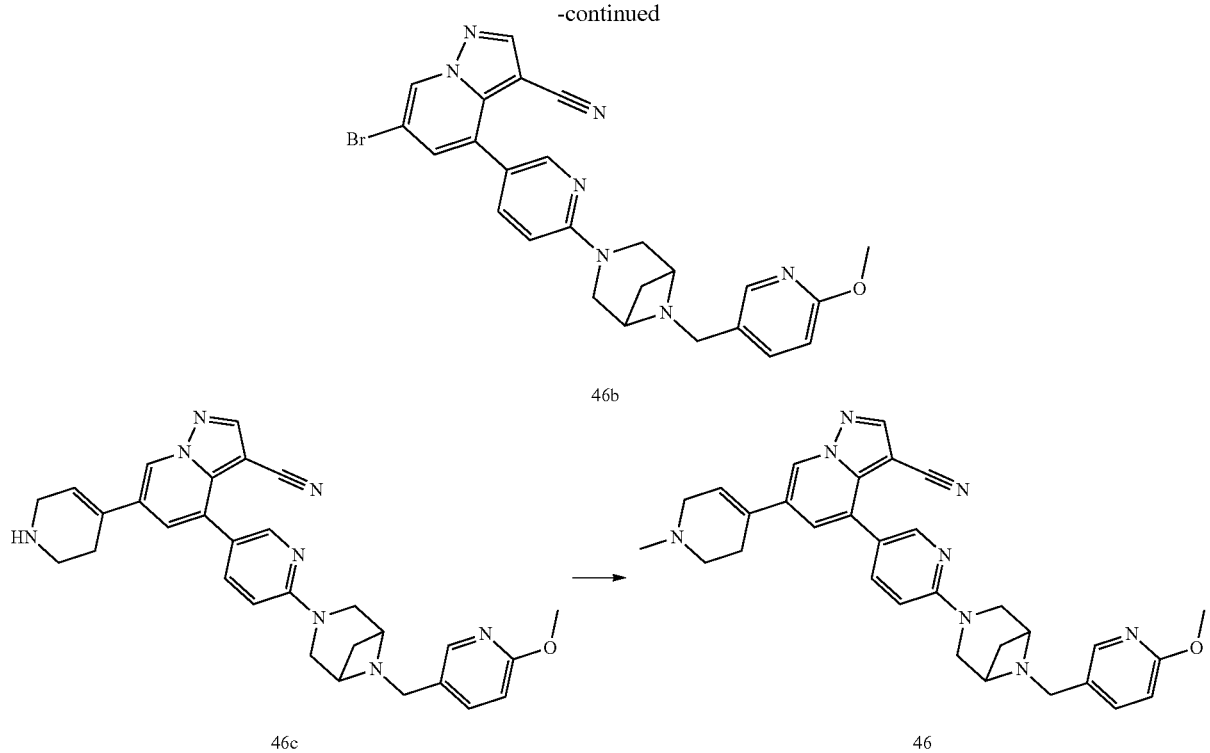

46b

46c

46

Step 1

Compound 10b (5001 mg, 968.26 μmol) was dissolved in 1,4-dioxane (30 mL), compound 46a (598.79 m, 1.94 mmol), K₃PO₄ (411.06 mg, 1.94 mmol) and H₂O (10 mL) were added under stirring. Pd(dppf)Cl₂ (70.85 mg, 96.83 μmol) was added, and stirring was conducted at 90° C. for 3 hours under nitrogen protection 20 mL of water was added to the reactant, and then the reaction solution was extracted with ethyl acetate (30 mL×3). Organic phases were combined, washed with a saturated salt solution (30 mL×3), dried with anhydrous sodium sulfate, and dried by a spinning method to obtain a crude product. The crude product was separated and purified by a preparative chromatography column (chromatography column: Boston Green ODS 150× 30 mm×5 μm; mobile phase: [H₂O (0.075% TFA)-ACN]; B %: 33%-53%, 12 min) to obtain compound 46b.

LCMS (ESI) m/z: 619.1[M+1]⁺

Step 2

Compound 46b (100 mg, 161.62 μmol) was dissolved in DCM (1 mL). TFA (552.85 mg, 4.85 mmol, 358.99 μL) was added, and stirring was conducted at 20° C. for 5 hours. The reaction solution was dried by a spinning method to obtain compound 46c which was directly used in the next step.

Step 3

Compound 46c (40 mg, 77.13 μmol) was dissolved in a mixed solution of MeOH (0.5 mL), and DCM (1 mL), triethylamine (78.05 mg, 771.29 μmol, 107.35 μL) was added to adjust the pH to 9, a formaldehyde aqueous solution (93.89 mg, 1.16 mmol) was added, stirring was conducted for 1 hour, acetic acid (46.32 mg, 771.29 μmol, 44.11 μL) was added to adjust the pH to 5-6, then NaBH(OAc)₃ (24.52 mg, 115.69 μmol) was added, and stirring was conducted at 20° C. for 5 hours. The reaction solution was dried by a spinning method to obtain a crude product. The crude product was purified by a preparative chromatography column (chromatography column: Boston Green ODS 150× 30 mm-5 μm; mobile phase: [H₂O (0.075% TFA)-ACN]; B %: 6%-36%, 10 min) to obtain a trifluoroacetate of compound 46. The trifluoroacetate of compound 46 was added to a sodium bicarbonate solution, and the obtained solution was extracted with ethyl acetate. Organic phases were dried with anhydrous sodium sulfate, and concentrated under reduced pressure to obtain compound 46.

LCMS (ESI) m/z: 533.1[M+1]⁺

¹H NMR (400 MHz, CD₃OD) δ 9.13 (br s, 1H), 8.62-8.78 (m, 3H), 8.05-8.28 (m, 2H), 7.94 (br s, 1H), 7.13-7.33 (m, 2H), 6.70 (br s, 1H), 4.78-5.01 (m, 4H), 4.49 (br d, J=13.20 Hz, 4H), 4.28 (br d, J=13.4 Hz, 2H), 4.22 (s, 5H), 4.03 (br s, 1H), 3.76-3.92 (m, 1H), 3.12-3.30 (m, 3H), 2.45 (br s, 1H), 1.51-1.67 (m, 1H).

Example 47

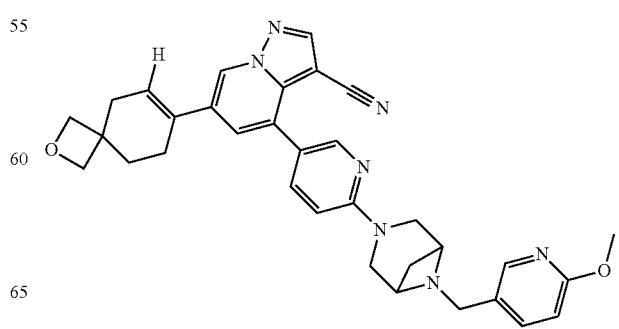

47

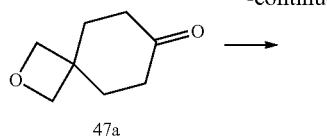

47a

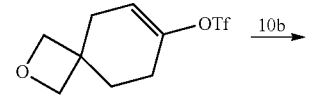

47b

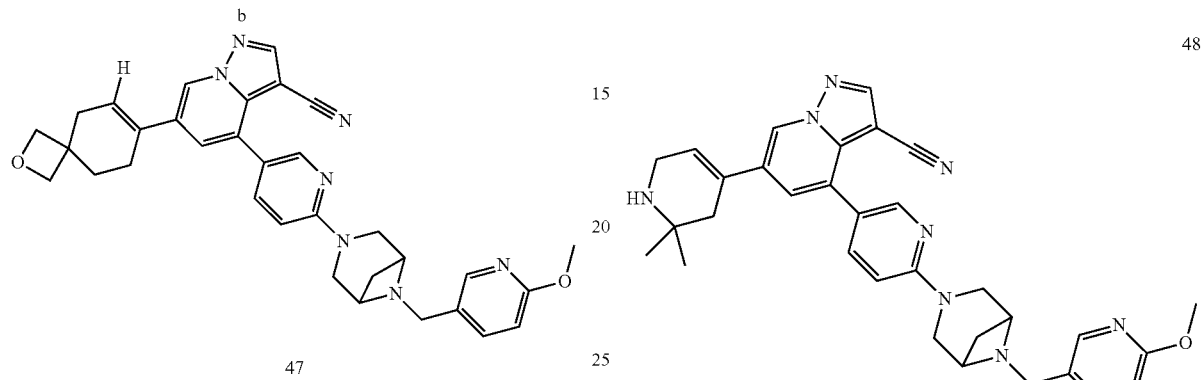

47

Step 1

Compound 47a (40 mg, 285.35 μmol) was dissolved in THF (1 mL), LiHMDS (1 M, 570.70 μL) was added at −78° C., and stirring was conducted for 1 hour, N-phenylbis(trifluoromethanesulfonyl)imine (203.88 mg, 570.70 μmol) was dissolved in THF (0.5 mL), and added dropwise to the reaction solution, and stirring was conducted at −78° C. for 1 hour. 5 mL of water was added to the reaction solution, and then the reaction solution was extracted with ethyl acetate (5 mL×3). Organic phases were combined, washed with water (10 mL×3), washed with a saturated sodium chloride solution (10 mL×1), dried with anhydrous sodium sulfate, and finally dried by a spinning method to obtain compound 47b.

$^1$H NMR (400 MHz, CD$_3$OD) δ ppm 5.81-5.71 (m, 1H), 4.51-4.46 (m, 2H), 4.42 (d, J=5.72 Hz, 2H), 2.57-2.53 (m, 2H), 2.46-2.41 (m, 2H), 2.09 (t, J=6.40 Hz, 2H).

Step 2

Compound 47b (67.87 mg, 124.66 μmol), compound 10b (50 mg, 103.88 μmol) were dissolved in a mixed solution of 1,4-dioxane (1 mL) and 1H$_2$O (0.5 mL), Pd(dppf)Cl$_2$ (7.60 mg, 10.39 μmol, 0.1 eq) and K$_3$PO$_4$ (66.15 mg, 311.65 μmol) were added, and stirring was conducted at 90° C. for 16 hours under nitrogen protection. The reaction solution was diluted with ethyl acetate, and filtered to remove the insoluble material 0.5 mL of water was added to the reaction solution, and then the reaction solution was extracted with ethyl acetate (6 mL×3). Organic phases were combined, washed with a saturated sodium chloride solution (10 mL×1), dried with anhydrous sodium sulfate, and finally dried by a spinning method to obtain a crude product. The crude product was separated and purified by a preparative HPLC (chromatography column: Boston Green ODS 150× 30 mm×5 μm; n mobile phase: [H$_2$O (0.075% TFA)-ACN]; B %: 25%-45%, 12 min) to obtain a trifluoroacetate of compound 47. The trifluoroacetate of compound 47 was added to a sodium bicarbonate solution, and the obtained solution was extracted with ethyl acetate. Organic phases were dried with anhydrous sodium sulfate, and concentrated under reduced pressure to obtain compound 47.

LCMS (ESI) m/z: 560.1[M+1]$^+$ $^1$H NMR (400 MHz, CD$_3$OD) δ 8.72 (br s, 1H), 8.47-8.38 (m, 3H), 7.94-7.86 (m, 2H), 7.61 (s, 1H), 7.01-6.90 (m, 2H), 6.37 (br s, 1H), 4.69-4.50 (m, 9H), 4.29-4.21 (m, 4H), 4.04-4.01 (m, 1H), 3.97 (s, 3H), 2.65-2.51 (m, 4H), 2.35-2.14 (m, 2H).

Example 48

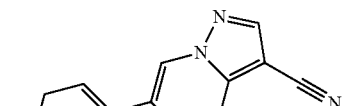

48

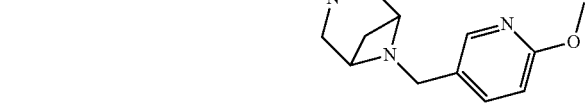

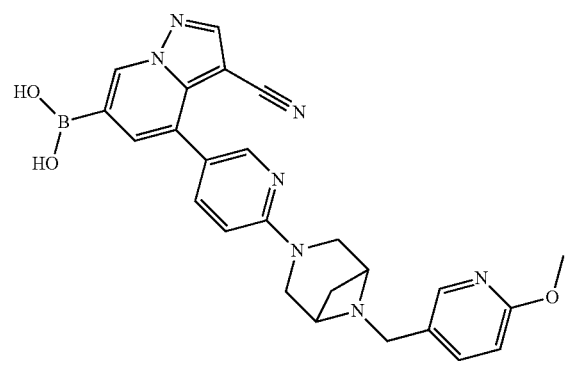

10b

48a

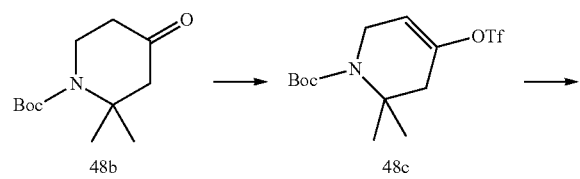

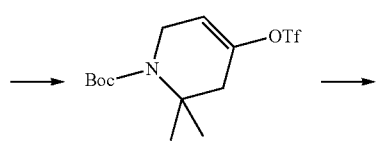

48b    48c

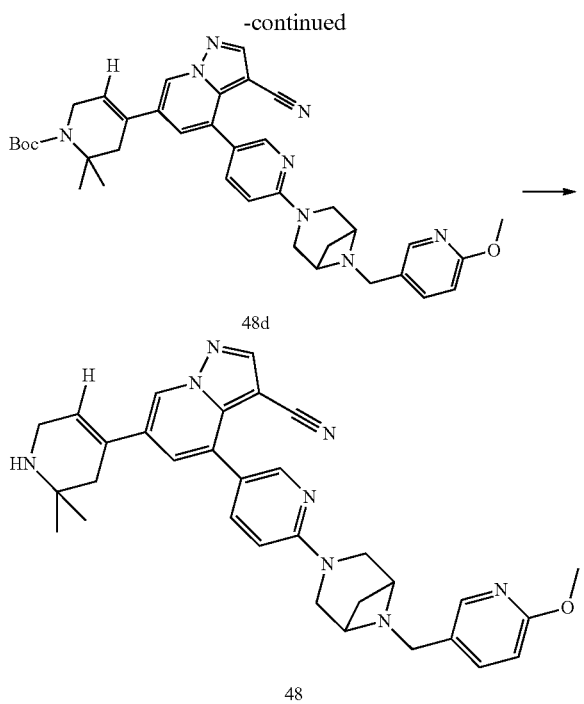

Step 2

Compound 10b (0.3 g, 580.95 μmol), bis(pinacolato) diboron (147.53 mg, 580.95 μmol) and potassium acetate (57.02 ng, 580.95 μmol) were added to 1,4-dioxane (15 mL), then Pd(dppf)Cl$_2$ (21.25 mg, 29.05 μmol) was added to the reaction solution, replacement with nitrogen was conducted for three times, and the reaction was conducted at 100° C. for 50 min in microwave. The reaction solution was directly filtered through diatomaceous earth to obtain a filtrate, and the filtrate was dried by a spinning method under reduced pressure at 40-50° C. to obtain crude product 48a which was directly used in the next step.

LCMS (ESI) m/z: 482.0[M+1]

Step 2

Compound 48b (0.2 g, 879.89 μmol) was dissolved in THF (10 mL). LDA (2 M, 527.94 μL) was added dropwise at −78° C., and stirring was conducted for 30 minutes. N-phenylbis(trifluoromethanesulfonyl) imine (377.21 mg, 1.06 mmol) was dissolved in 5 mL of THF and added dropwise to the reaction solution at −78° C. After the dropwise addition, the temperature of the reaction solution was slowly heated to 20° C. (1.5 h), and stirring was conducted for 10 hours. Saturated ammonium chloride (20 mL) was added to the reaction solution, and the obtained solution was extracted with ethyl acetate (30 mL) twice Organic phases were combined, dried with anhydrous sodium sulfate, filtrated to obtain a filtrate. The filtrate was concentrated to obtain compound 48c which was directly used in the next step.

Step 3

Compound 48c (76.53 mg, 212.97 μmol) and compound 48a (51.25 mg, 106.49 mol) were dissolved in a mixed solution of 1,4-dioxane (1 mL) and H$_2$O (0.3 mL). Pd (dppf) Cl$_2$ (7.79 mg, 10.65 μmol) and K$_3$PO$_4$ (45.21 mg, 212.97 μmol) were added, and stirring was conducted at 95° C. for 12 hours under N$_2$ protection. 5 mL of water was added to the reaction solution, and then the reaction solution was extracted by adding ethyl acetate (5 mL×2). Organic phases were combined, dried with sodium sulfate, and concentrated to obtain a crude product. The crude product was separated by a preparative chromatography column (chromatography column: Boston Green ODS 150×30 mm×5 μm; mobile phase: [H$_2$O (0.075% TFA)-ACN]; B %: 38%-68%, 12 min) to obtain compound 48d.

LCMS (ESI) m/z: 647.3[M+1]$^+$

Step 4

Compound 48d (25 mg, 38.65 μmol) was dissolved in DCM (2 mL), trifluoroacetic acid (0.5 mL) was added, and stirring was conducted at 20° C. for 5 hours. The reaction solution was dried by a spinning method to obtain a trifluoroacetate of compound 48. The trifluoroacetate of compound 48 was added to a sodium bicarbonate solution, and the obtained solution was extracted with ethyl acetate. Organic phases were dried with anhydrous sodium sulfate, and concentrated under reduced pressure to obtain compound 48.

LCMS (ESI) m/z: 547.3[M+1]$^+$ $^1$H NMR (400 MHz, CD$_3$OD) δ 8.88 (br s, 1H), 8.47-8.29 (m, 3H), 7.99-7.64 (m, 3H), 7.06-6.91 (m, 2H), 6.45 (br s, 1H), 4.70 (s, 2H), 4.60 (s, 1H), 4.29-4.23 (m, 4H), 4.06-3.96 (m, 6H), 3.66-3.62 (m, 1H), 2.83-2.80 (m, 2H), 2.23-2.20 (m, 1H), 1.52 (s, 6H).

Example 49

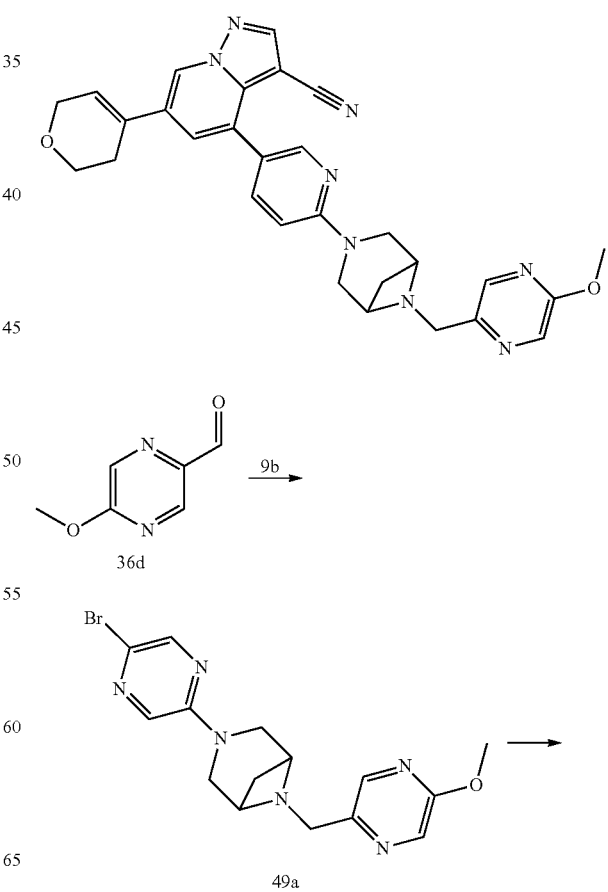

-continued

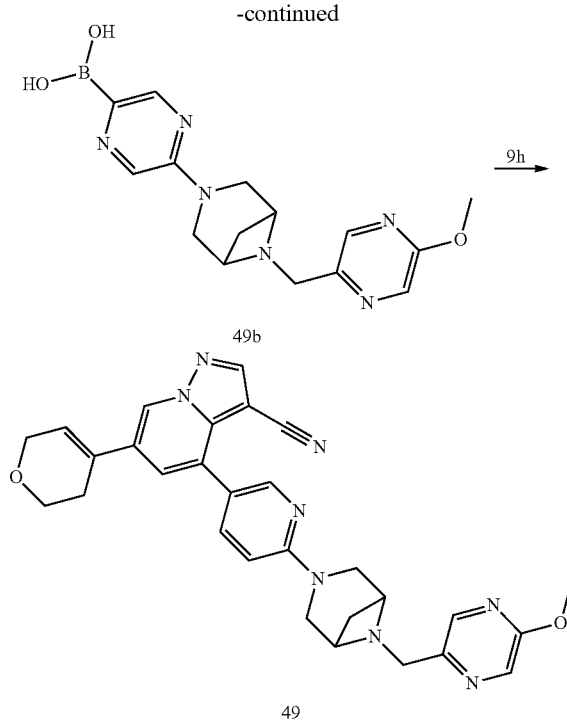

Step 1

Compound 9b (237.49 mg, 723.99 µmol) and trimethylamine (439.56 mg, 4.34 mmol) were added together to DCM (2 mL), stirring was conducted for 10 minutes, then compound 36d (200 mg, 1.45 mmol) was added to the reaction solution, stirring was conducted for 1 hour, then NaBH(OAc); (613.77 mg, 2.90 mmol) was added to the reaction solution, and the reaction solution was reacted at 15-20° C. with stirring under nitrogen protection for 16 hours. The reaction was quenched by adding 10 mL of water, and stirring was conducted for 10 minutes. 10 mL of dichloromethane was added to the reaction solution, and then the reaction solution was extracted and separated. The aqueous phase was extracted with 20 mL of dichloromethane. Organic phases were combined, dried with anhydrous sodium sulfate, and subjected to rotary evaporation to obtain a crude product. The crude product was directly used in the next step without further purification Compound 49a was finally obtained.

LCMS (ESI) m/z: 378.6[M+1]$^+$

Step 2

Compound 49a (100 mg, 265.08 µmol), bis(pinacolato)diboron (67.31 mg, 265.08 µmol), potassium acetate (78.05 mg, 795.25 µmol) and Pd(dppf)Cl$_2$ (19.40 mg, 26.51 µmol) were added together to 1,4-dioxane (2 mL), the obtained solution was heated to 80° C. by an oil bath under nitrogen protection, and the reaction was conducted for 16 hours under stirring. The reaction solution was cooled to room temperature, and filtrated to collect a filtrate. The filtrate was concentrated to obtain crude product 49b which was directly used in the next step Step 3

Compound 9h (43.99 mg, 117.84 µmol), compound 49b (100 mg, 235.68 µmol). Pd(dppf)Cl$_2$ (17.24 mg, 23.57 µmol) and K$_3$PO$_4$ (150.08 mg, 707.04 µmol) were added together to a mixed solution of 1,4-dioxane (1 mL) and H$_2$O (0.5 mL), the obtained solution was heated to 100° C. by a microwave synthesizer under nitrogen protection, and the reaction w as conducted for 30 minutes under stirring, 2 mL of water and 2 mL of ethyl acetate were added to the reaction solution, and then the reaction solution was separated. The aqueous phase was extracted with 2 mL of ethyl acetate. Organic phases were combined, dried with anhydrous sodium sulfate, and filtrated to collect a filtrate. The filtrate was subjected to rotary evaporation to obtain a crude product. The crude product is separated by a preparative chromatography column (chromatography column: Boston Green ODS 150×30 mm×5 µm; mobile phase: [H$_2$O (0.075% TFA)-ACN]; B %: 31%-61%, 10 min) to obtain a trifluoroacetate of compound 49. The trifluoroacetate of compound 49 was added to a sodium bicarbonate solution, and the obtained solution was extracted with ethyl acetate. Organic phases were dried with anhydrous sodium sulfate, and concentrated under reduced pressure to obtain compound 49.

LCMS (ESI) m/z: 522.1[M+1]$^+$ $^1$H NMR (400 MHz, CD$_3$OD) δ 8 8 81 (s, 1H), 8.68 (br s, 1H), 8.47 (s, 1H), 8.34-8.26 (m, 2H), 8.00 (s, 1H), 7.94 (s, 1H), 6.54 (br s, 1H), 4.77 (br d, J=8.8 Hz, 3H), 4.45 (br s, 1H), 4.40-4.30 (m, 6H), 4.05-3.97 (m, 6H), 2.63 (br s, 2H), 2.25 (br d, J=10.8 Hz, 1H).

Examples 50 and 51

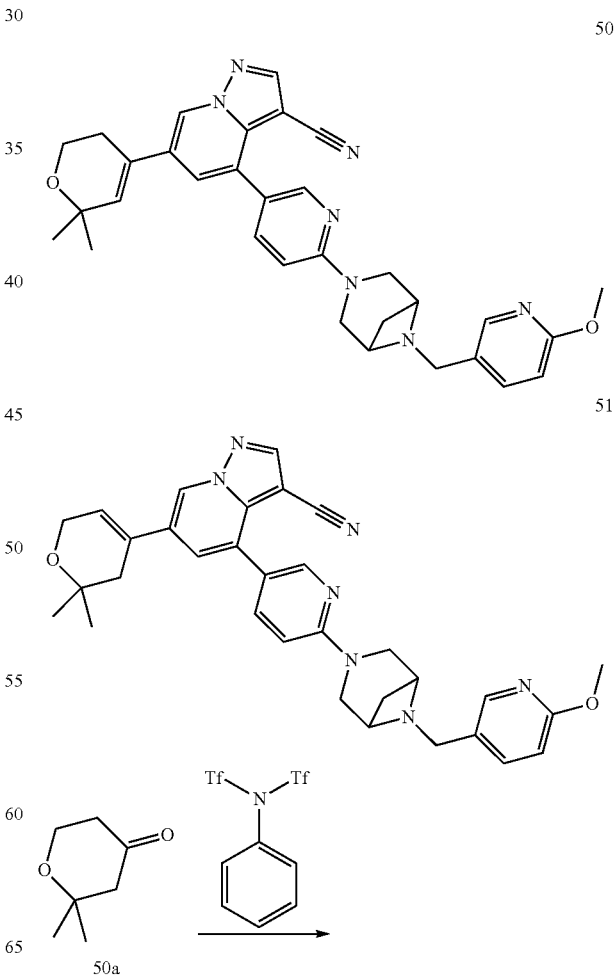

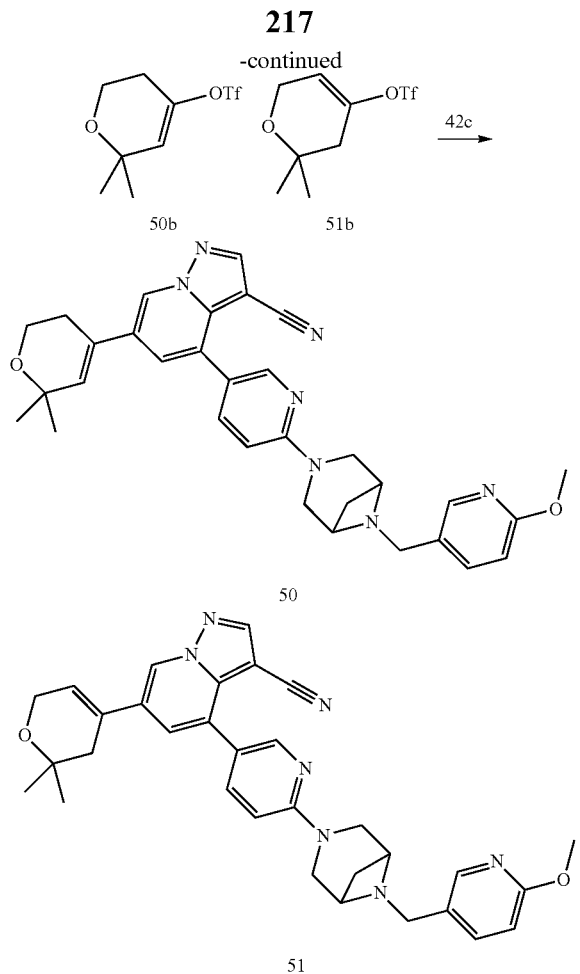

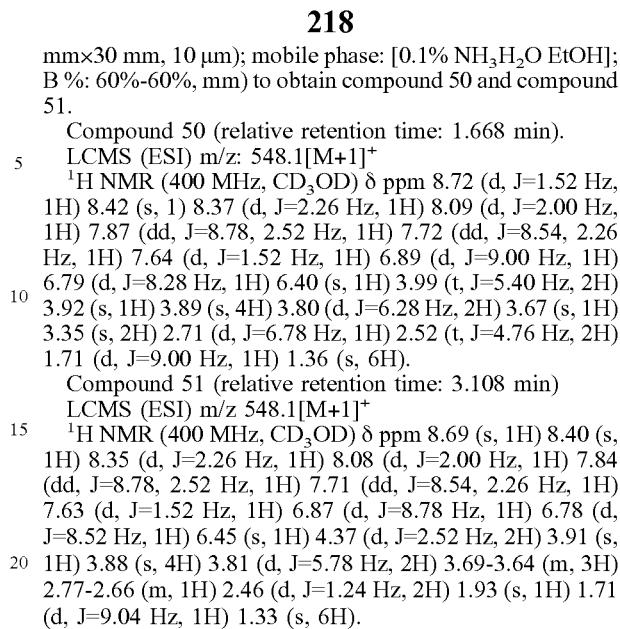

mm×30 mm, 10 μm); mobile phase: [0.1% NH₃H₂O EtOH]; B %: 60%-60%, mm) to obtain compound 50 and compound 51.

Compound 50 (relative retention time: 1.668 min).
LCMS (ESI) m/z: 548.1[M+1]⁺
¹H NMR (400 MHz, CD₃OD) δ ppm 8.72 (d, J=1.52 Hz, 1H) 8.42 (s, 1) 8.37 (d, J=2.26 Hz, 1H) 8.09 (d, J=2.00 Hz, 1H) 7.87 (dd, J=8.78, 2.52 Hz, 1H) 7.72 (dd, J=8.54, 2.26 Hz, 1H) 7.64 (d, J=1.52 Hz, 1H) 6.89 (d, J=9.00 Hz, 1H) 6.79 (d, J=8.28 Hz, 1H) 6.40 (s, 1H) 3.99 (t, J=5.40 Hz, 2H) 3.92 (s, 1H) 3.89 (s, 4H) 3.80 (d, J=6.28 Hz, 2H) 3.67 (s, 1H) 3.35 (s, 2H) 2.71 (d, J=6.78 Hz, 1H) 2.52 (t, J=4.76 Hz, 2H) 1.71 (d, J=9.00 Hz, 1H) 1.36 (s, 6H).

Compound 51 (relative retention time: 3.108 min)
LCMS (ESI) m/z 548.1[M+1]⁺
¹H NMR (400 MHz, CD₃OD) δ ppm 8.69 (s, 1H) 8.40 (s, 1H) 8.35 (d, J=2.26 Hz, 1H) 8.08 (d, J=2.00 Hz, 1H) 7.84 (dd, J=8.78, 2.52 Hz, 1H) 7.71 (dd, J=8.54, 2.26 Hz, 1H) 7.63 (d, J=1.52 Hz, 1H) 6.87 (d, J=8.78 Hz, 1H) 6.78 (d, J=8.52 Hz, 1H) 6.45 (s, 1H) 4.37 (d, J=2.52 Hz, 2H) 3.91 (s, 1H) 3.88 (s, 4H) 3.81 (d, J=5.78 Hz, 2H) 3.69-3.64 (m, 3H) 2.77-2.66 (m, 1H) 2.46 (d, J=1.24 Hz, 2H) 1.93 (s, 1H) 1.71 (d, J=9.04 Hz, 1H) 1.33 (s, 6H).

Examples 52 and 53

Step 1

Compound 50a (200 mg, 1.56 mmol) was dissolved in THF (1 mL), when the internal temperature decreased to −78° C., LiHMDS (1 M, 3.12 mL) was added, stirring was conducted for 1 hour. N-phenylbis(trifluoromethanesulfonyl)imine (668.96 mg, 1.87 mmol) was dissolved in THF (1 mL), then the obtained solution was heated to room temperature of 25° C., and stirring was conducted for 1 hour. 3 mL of water was added to the reaction solution, and then the reaction solution was extracted with ethyl acetate (3 mL×3). Organic phases were combined, washed with a saturated sodium chloride solution (3 mL×1), dried with anhydrous sodium sulfate, and finally dried by a spinning method to obtain a crude product of a mixture of 50b and 51b.

Step 2

The mixture of compound 50b and 51b (194.64 mg, 373.98 μmol) and compound 42c (120 mg, 249.32 μmol) were dissolved in a mixed solution of 1,4-dioxane (3 mL) and H₂O (1 mL), Pd(dppf)Cl₂ (18.24 mg, 24.93 μmol) and K₃PO₄ (158.77 mg, 747.95 μmol) were added, and stirring was conducted at 90° C. in microwave for 30 min under nitrogen protection. The reaction solution was filtered and dried by a spinning method to obtain a crude product. The crude product was separated and purified by a preparative chromatography column (chromatography column: Boston Green ODS 150×30 mm×5 μm; mobile phase: [H₂O (0.075% trifluoroacetic acid)-acetonitrile]; B %: 20%-50%, 12 min), and subjected to freeze drying and SFC resolution (chromatography column DAICEL CHIRALPAK AD (250

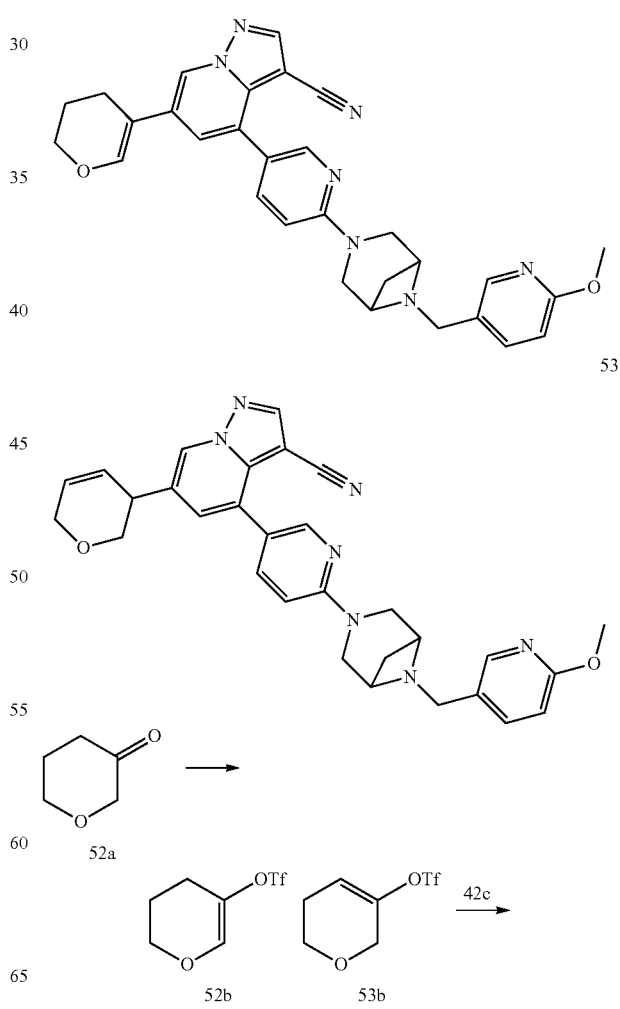

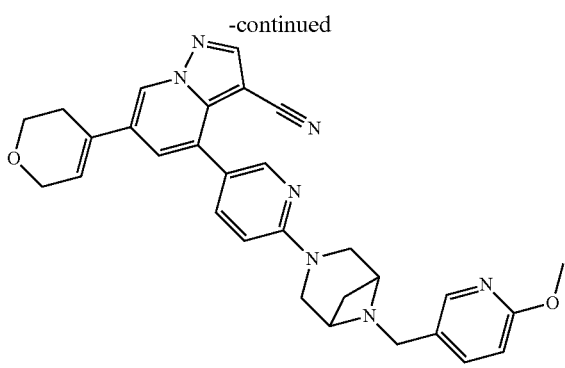

52

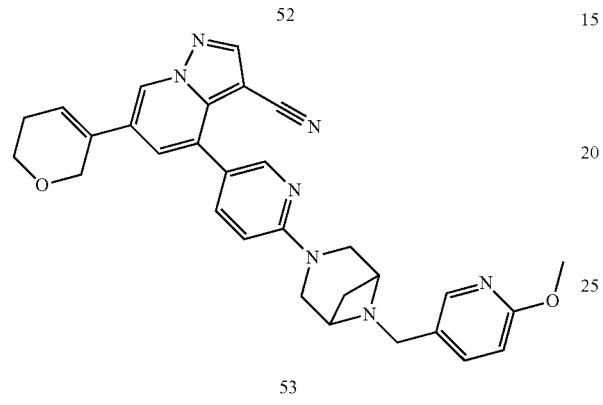

53

Step 1

Compound 52a (100 mg, 998.84 μmol) was dissolved in THF (1 mL), LiHMDS (1 M mL) was added at −78° C., and stirring was conducted at this temperature for 1 hour. N-phenylbis(trifluoromethanesulfonyl)imine (463.89 mg, 1.30 mmol) was then dissolved in THF (1 mL), the obtained solution was added to the reaction solution, the reaction temperature was risen to room temperature of 20° C., and stirring was conducted for 1 hour. 3 mL of water was added to the reaction solution, and then the reaction solution was extracted with ethyl acetate (3 mL×3). Organic phases were combined, washed with a saturated sodium chloride solution (3 mL×1), dried with anhydrous sodium sulfate, and finally dried by a spinning method to obtain a crude product of a mixture of 52b and 53b.

Step 2

A mixture of compounds 52b and 53b (108.54 mg, 186.99 μmol) and compound 42c (60 mg, 124.66 μmol) were dissolved in a mixed solution of 1,4-dioxane (1 mL) and H₂O (0.5 mL) solution. Pd(dppf)Cl₂ (9.12 mg, 12.47 μmol) and K₃PO₄ (79.38 mg, 373.98 μmol) were added, and stirring was conducted at 90° C. for 30 min in microwave under nitrogen protection. The reaction solution was filtered, and dried by a spinning method to obtain a crude product. The crude product was separated and purified by a preparative chromatography column (chromatography column: YMC Triart C18 150×25 mm×5 μm; mobile phase: [H₂O (0.05% HCl)-ACN]; B %: 27%-37%, 9.5 min), dried by a spinning method, and subjected to SFC resolution (chromatography column: Phenomenex-Cellulose-2 (250 mm×30 mm×10 μm); mobile phase: [0.1% NH₃H₂O EtOH]; B %: 55%-55%, min) to obtain compound 52 and compound 53.

Compound 52 (relative retention time 4.094 min)
LCMS (ESI) m/z: 520.1 [M+1]⁺
¹H NMR (400 MHz, CD₃OD) δ ppm 8.63 (d, J=1.00 Hz, 1H) 8.40 (s, 1H) 8.36 (d, J=2.26 Hz, 1H) 8.09 (d, J=1.76 Hz, 1H) 7.85 (dd, J=8.78, 2.26 Hz, 1H) 7.72 (dd, J=8.52, 2.26 Hz, 1H) 7.56 (d, J=1.24 Hz, 1H) 6.89 (s, 1H) 6.78 (d, J=8.54 Hz, 1H) 6.56-6.51 (m, 1H) 4.56 (d, J=2.00 Hz, 2H) 3.90-3.87 (m, 4H) 3.83-3.78 (m, 2H) 3.69-3.64 (m, 3H) 2.38 (d, J=4.28 Hz, 2H) 1.93 (s, 3H) 1.75-1.68 (m, 1H) 1.36 (d, J=7.02 Hz, 1H) 1.28 (s, 1H).

Compound 53 (relative retention time: 5.402 min)
LCMS (ESI) m/z: 520.1[M+1]⁺
¹H NMR (40 MHz, CD₃OD) δppm 8.82 (d, J=1.50 Hz, 1H) 8.41 (d, J=2.381 Mz, 1H) 8.33 (s, 1H) 7.97-7.88 (m, 2H) 7.66-7.55 (m, 2H) 6.80 (d, J=9.00 Hz, 1H) 6.70 (d, J=8.64 Hz, 1H) 6.16 (s, 1H) 3.86 (t, J=5.50 Hz, 2H) 3.79-3.70 (m, 5H) 3.65-3.62 (m, 2H) 3.52-3.42 (m, 5H) 3.07 (s, 3H) 2.34 (s, 2H).

Example 57

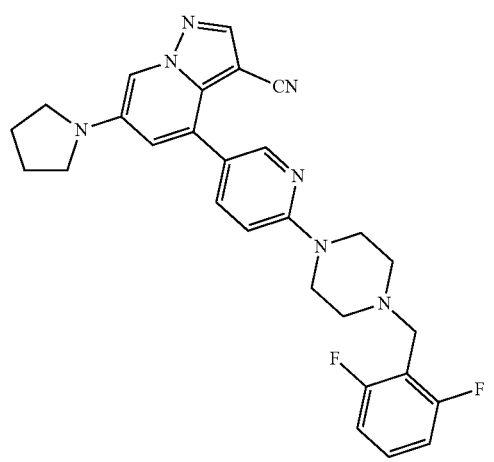

57

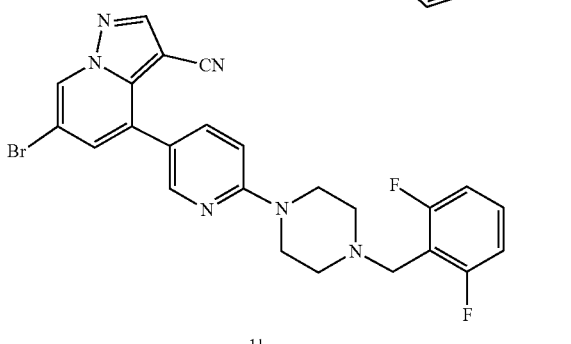

11

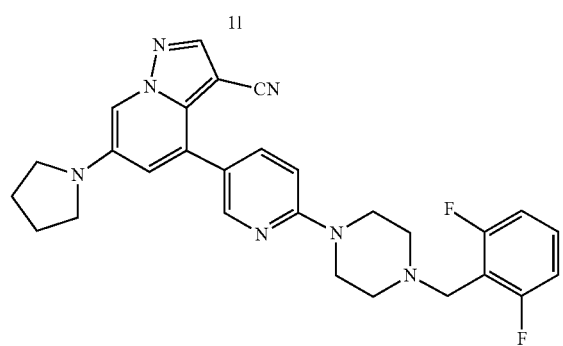

57

Step 1

Compound 1i (100 mg, 196.33 μmol) was added to toluene (3 mL), then tetrahydropyrrole (16.76 mg, 235.60

μmol, 19.67 μL), Pd$_2$(dba)$_3$ (8.99 mg, 9.82 μmol), (±)-2,2-bis(diphenylphosphino)-11-binaphthyl (12.22 mg, 19.63 μmol) and sodium tert-butoxide (56.60 mg, 588.99 μmol) were added, the air in the reaction system was evacuated and nitrogen was filled for protection, and the reaction was conducted at 90° C. for 16 hours under stirring. The reaction solution was cooled, filtrated, and directly dried by a spinning method to obtain a crude product. The crude product was separated by a preparative chromatography column (chromatography column. Boston Green ODS 150×30 mm×5 μm; mobile phase [water (0.075% trifluoroacetic acid)-acetonitrile]; B %: 33%-63%, 7 min) to obtain a trifluoroacetate of compound 57. The trifluoroacetate of compound 57 was added to a sodium bicarbonate solution, and the obtained solution was extracted with ethyl acetate. Organic phases were dried with anhydrous sodium sulfate, and concentrated under reduced pressure to obtain compound 57.

LCMS (ESI) m/z: 500.1 [M+1]$^+$

Trifluoroacetate of compound 57: $^1$H NMR (400 MHz, CDCl$_3$) δ 8.35 (d, J=2.01 Hz, 1H), 8.10 (s, 1H), 7.76-7.90 (m, 2H), 7.44-7.58 (m, 1H), 7.05 (t. J=8.16 Hz, 2H), 6.94 (s, 1H), 6.84 (d, J=8.53 Mz, 1H), 4.39 (s, 2H), 4.04-4.08 (m, 41-H), 3.30-3.33 (m, 8H), 2.01-2.13 (m, 4H).

Example 58

58

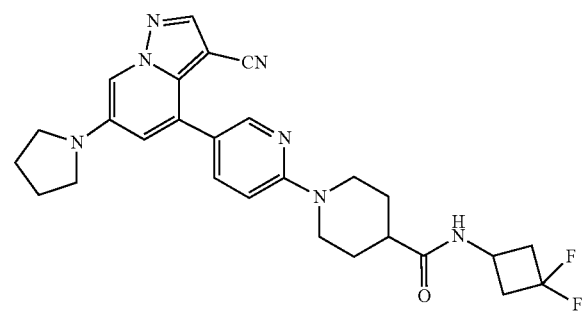

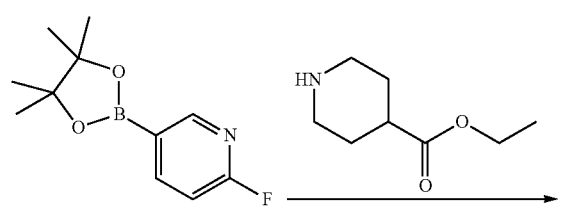

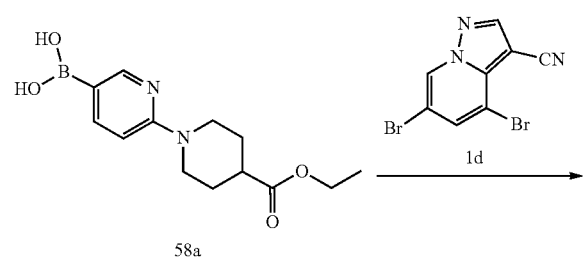

58a

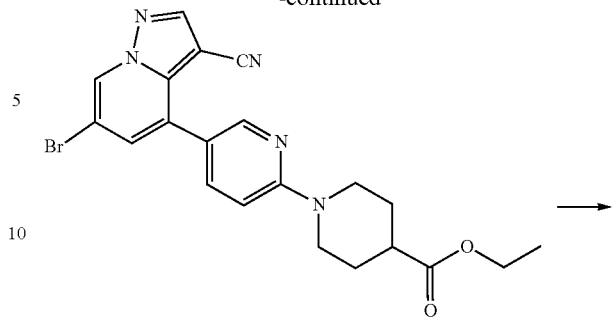

58b

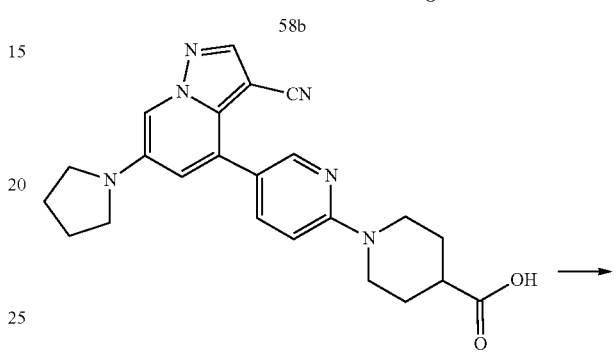

58c

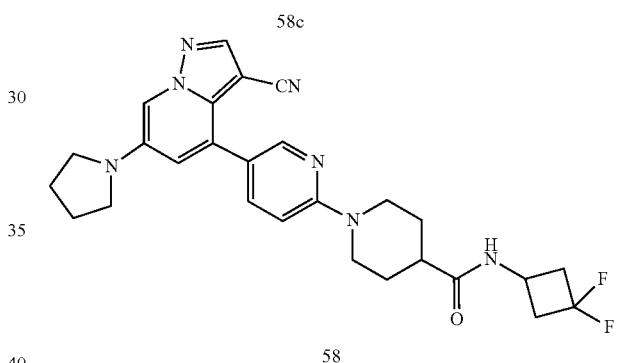

58

Step 1

2-fluoro-5-borate pyridine (0.5 g, 2.24 mmol), 4-ethyl formate piperidine hydrochloride (520.97 mg, 2.69 mmol) and potassium carbonate (929.45 mg, 6.72 mmol) were added together to DMF (10 mL), the reaction solution was then heated to 100° C. by a microwave synthesizer under nitrogen protection, and the reaction was conducted under stirring for 0.5 hour. The reaction solution was directly filtered to collect a filtrate, and the filtrate was subject to rotary evaporation to obtain a crude product. The crude product was purified by a flash silica gel column (PE/EA=1/1, Rf=0.6) to obtain compound 58a.

LCMS (ESI) m/z: 278.7[M+1]$^+$

Step 2

Compound 1d (300 mg, 996.89 μmol), compound 58a (287.31 mg, 797.51 μmol). Pd(PPh$_3$)$_4$ (115.20 mg, 99.69 μmol) and Na$_2$CO$_3$ (316.98 mg, 2.99 mmol) were added together to a mixed solution of DMF (5 mL)) and H$_2$O (2.5 mL), the obtained solution was heated to 60° C. by a microwave synthesizer under nitrogen protection, and the reaction was conducted for 0.5 hour under stirring, 20 mL of water and 20 mL of ethyl acetate were added to the reaction solution solution, and then the reaction solution was extracted, and separated. The aqueous phase was extracted with 20 mL of ethyl acetate. Organic phases were combined, dried with anhydrous sodium sulfate, and subjected to rotary evaporation to obtain a crude product. The crude product was purified by a flash silica gel column (PE/EA=3/1, Rf=0.5) to obtain compound 58b.

LCMS (ESI) m/z: 454.1[M+1]⁺, 456.1 [M+1]⁺

Step 3

Compound 58b (100 mg, 220.11 μmol), tetrahydropyrrole (46.96 mg, 660.33 μmol), Pd₂(dba)₃ (20.16 mg, 22.01 μmol), BINAP (27.41 mg, 44.02 μmol) and sodium tert-butoxide (63.46 mg, 660.33 μmol) were added together to toluene (2 mL), the obtained solution was heated to 90° C. by an oil bath under nitrogen protection, and the reaction was conducted under stirring for 2 hours. The reaction solution was subject to rotary evaporation to obtain a crude product. The crude product was purified by a preparative chromatography plate (PE/EA=1/1, Rf=0.05) to obtain compound 58c.

LCMS (ESI) m/z: 417.2[M+1]⁺

Step 4

Compound 58c (30 mg, 72.03 μmol), 3,3-difluorocyclobutylamine (15.43 mg, 144.07 μmol), HATU (82.17 mg, 216.10 μmol) and DIPEA (27.93 mg, 216.10 μmol) were added together to DMF (5 mL), and the reaction was conducted with stirring at 20° C. under nitrogen protection for 16 hours. The reaction solution was directly subject to rotary evaporation to obtain a crude product. The crude product was separated by a preparative chromatography column (chromatography column: Boston Green ODS 150× 30 mm×5 μm; mobile phase: [water (0.075% trifluoroacetic acid)-acetonitrile]; B %: 33%-63%, 7 min) to obtain a trifluoroacetate of compound 58. The trifluoroacetate of compound 58 was added to a sodium bicarbonate solution, and the obtained solution was extracted with ethyl acetate. Organic phases were dried with anhydrous sodium sulfate, and concentrated under reduced pressure to obtain compound 58.

LCMS (ESI) m/z: 528.4[M+1]⁺

Trifluoroacetate of compound 58: ¹H NMR (400 MHz, CD₃OD) δ 8.27 (s, 1H), 8.23 (d, J=2 Hz, H), 8.18 (dd, J=9.2 Hz, 2 Hz, 1H), 8.00 (d, J=2 Hz, 1H), 7.49 (d, J=9.2 Hz, 1H), 7.28 (d, J=2 Hz, 1H), 4.34~4.31 (m, 2H), 4.16~4.04 (m, 2H), 3.54 (m, 1H), 3.01~2.90 (m, 4H), 2.67~2.50 (m, 4H), 2.13~2.10 (m, 4H), 2.05~2.04 (m, 3H), 1.94~1.85 (m, 2H).

Compounds in the examples in Table 5 can be prepared by referring to steps similar to a preparation route of the aforementioned Example 58, with the difference lying in that the raw material used in step 3 is the raw material A in the following table instead of 3,3-difluorocyclobutylamine to obtain trifluoroacetate of the corresponding compounds. The obtained trifluoroacetate of the compounds were respectively added to sodium bicarbonate solutions, the obtained solutions were extracted with ethyl acetate, and the organic phases were dried with anhydrous sodium sulfate and concentrated under reduced pressure to obtain the corresponding compounds.

TABLE 5

| NO. | Product Structure | Raw Material A | Product LCMS m/z: [M + 1]⁺ | Product ¹H NMR |
|---|---|---|---|---|
| Ex. 59 | | | 502.1 | Trifluoroacetate of compound 59 ¹H NMR (400 MHz, CD₃OD) δ 8.26-8.25 (m, 2H), 8.05-8.03 (d, J = 8 Hz, 1H), 7.95 (s, 1H), 7.32 (d, J = 12 Hz, 1H), 7.22 (s, 1H), 4.38 (d, J = 12 Hz, 1H), 3.67-3.62 (m, 2H), 3.52-3.51 (m, 2H), 3.38-3.36 (m, 4H), 3.12-3.09 (m, 1H), 2.67-2.61 (m, 1H), 2.11 (S, 3H), 2.04-1.96 (m, 4H), 1.89-1.81 (m, 3H), 1.18-1.16 (d, J = 8 Hz, 6H). |
| Ex. 60 | | | 488.1 | Trifluoroacetate of compound 60 ¹H NMR (400 MHz, CD₃OD) δ 8.26 (s, 1H), 8.24 (s, 1H), 8.14-8.11 (dd, J = 8 Hz, 2 Hz, 1H), 7.97-7.96 (d, J = 2 Hz, 1H), 7.43 (d, J = 8 Hz, 1H), 7.25 (d, J = 2 Hz, 1H), 4.35 (d, J = 12 Hz, 1H), 3.38-3.32 (m, 5H), 3.24-3.23 (m, 2H), 3.74-3.70 (m, 1H), 2.13-2.09 (m, 4H), 2.05-2.01 (m, 3H), 1.95-1.84 (m, 2H), 1.20 (s, 6H). |
| Ex. 61 | | | 500.1 | Trifluoroacetate of compound 61 ¹H NMR (400 MHz, CD₃OD) δ 8.26 (s, 1H), 8.24 (d, J = 2 Hz, 1H), 8.12 (dd, J = 2.0, 9.2 Hz, 1H), 7.98 (d, J = 1.8 Hz, 1H), 7.42 (d, J = 9.6 Hz, 1H), 7.25 (d, J = 2.0 Hz, 1H), 4.34 (br d, J = 13.6 Hz, 2H), 3.96-3.88 (m, 1H), 3.72-3.64 (m, 1H), 3.41-3.35 (m, 5H), 3.30 (br d, J = 2.4 Hz, 1H), 3.26 (s, 3H), 2.74-2.67 (m, 2H), 2.63-2.56 (m, 1H), 2.11 (td, J = 3.2, 6.0 Hz, 4H), 2.02-1.95 (m, 2H), 1.91-1.81 (m, 4H) |

TABLE 5-continued

| NO. | Product Structure | Raw Material A | Product LCMS m/z: [M + 1]+ | Product $^1$H NMR |
|---|---|---|---|---|
| Ex. 62 | | H₂N⌒CF₃ | 534.3 | Trifluoroacetate of compound 62 $^1$H NMR (400 MHz, CD$_3$OD) δ 8.26 (s, 2H), 8.05 (br d, J = 8.8 Hz, 1H), 7.96 (s, 1H), 7.32 (br d), J = 9.0 Hz, 1H), 7.25-7.21 (m, 1H), 7.23 (s, 1H), 4.37 (br d, J = 13.2 Hz, 2H), 3.99 (br d, J = 7.2 Hz, 2H), 3.47 (br d, J = 6.0 Hz, 2H), 3.25 (br d, J = 10.8 Hz, 2H), 2.86 (br d, J = 7.6 Hz, 1H), 2.59 (br d, J = 10.4 Hz, 2H), 2.48-2.40 (m, 2H), 2.24-2.13 (m, 2H), 2.02 (br d, J = 18.0 Hz, 2H), 1.85 (br d, J = 12.0 Hz, 2H), 1.70 (br d, J = 13.6 Hz, 2H). |

Example 63

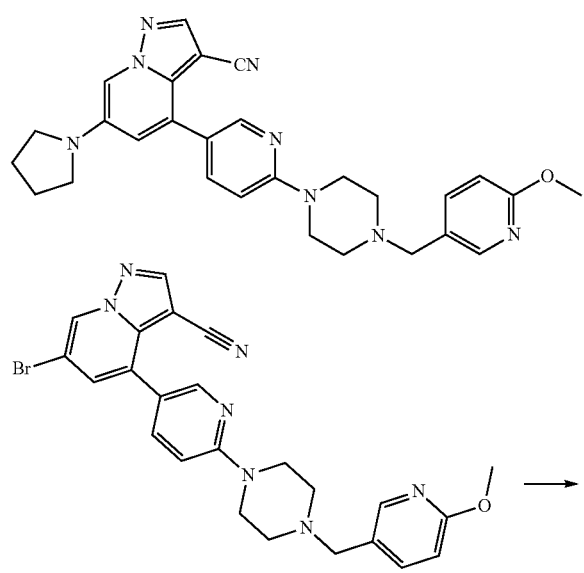

Step 1

Compound 29c (100 mg, 198.26 μmol) was dissolved in toluene (2 mL), tetrahydropyrrole (14.10 mg, 198.26 μmol), sodium tert-butoxide (57.16 mg, 594.79 μmol), BINAP (24.69 mg, 39.65 μmol) and Pd$_2$(dba)$_3$ (36.31 mg, 39.65 μmol) were added, and stirring was conducted at 90° C. for 16 hours under N$_2$ protection. The reaction solution was dried by a spinning method to obtain a crude product. The crude product was purified by a preparative chromatography column to obtain a trifluoroacetate of compound 63. The trifluoroacetate of compound 63 was added to a sodium bicarbonate solution, and the obtained solution was extracted with ethyl acetate. Organic phases were dried with anhydrous sodium sulfate, and concentrated under reduced pressure to obtain compound 63.

Trifluoroacetate of compound 63 $^1$H NMR (400 MHz, CD$_3$OD) δppm 8.41 (d, J=2 Hz, 1H) 8.33 (d, J=2.26 Hz, 1H) 8.24 (s, 1H) 7.93 (d, J=1.76 Hz, 1H) 7.87 (d, J=9, 2.52 Hz, 2H) 7.15 (d, J=2 Hz, 1H) 7.09 (d, J=8.78 Hz, 1H) 6.95 (d, J=8.52 Hz, 1H) 3.98 (s, 3H) 3.35-3.39 (m, 4H) 3.32-3.33 (m, 10H) 2.08-2.14 (m, 4H).

Example 64

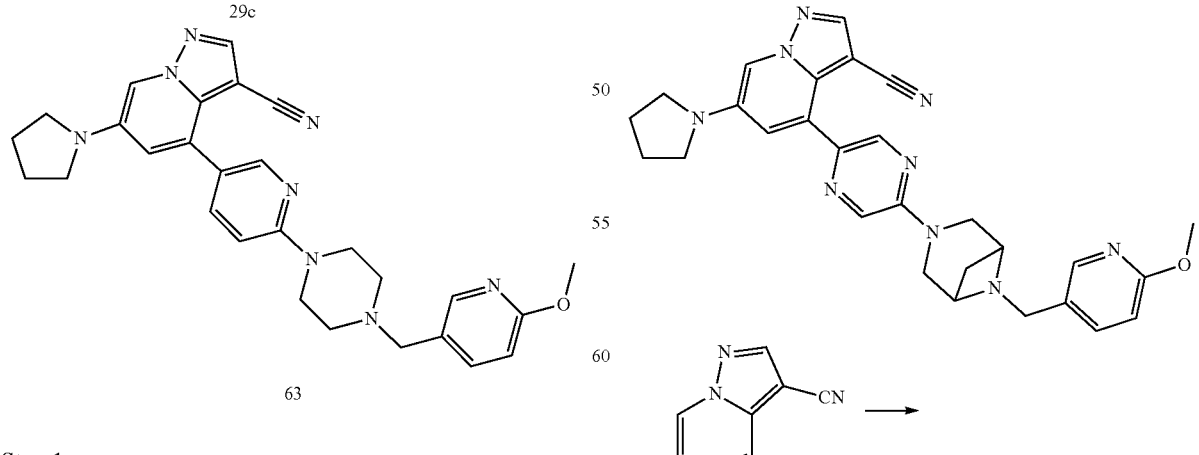

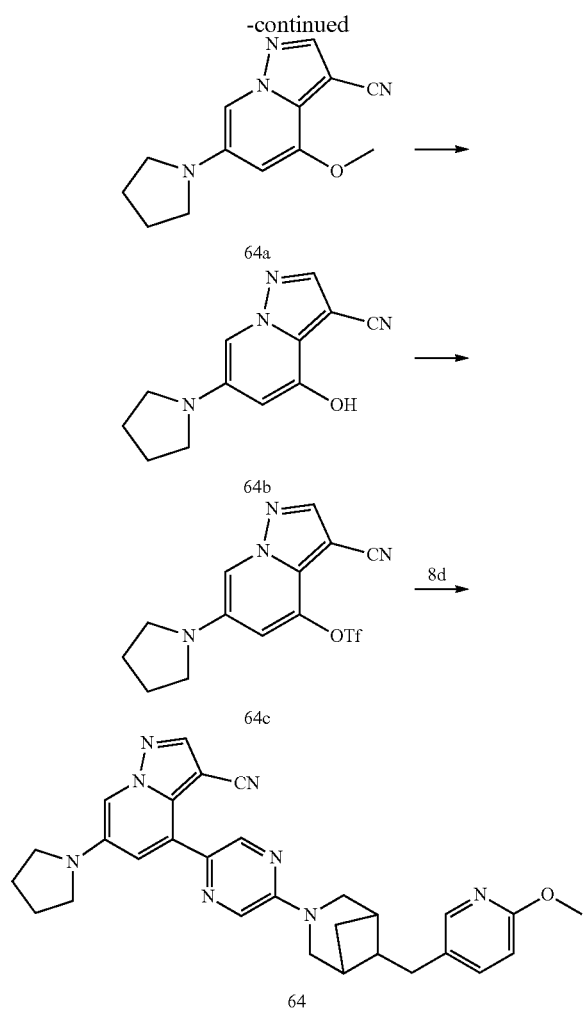

Step 1

Compound 8e (1 g, 3.97 mmol) and tetrahydropyrrole (423.22 mg, 5.95 mmol) were dissolved in toluene (10 mL). $Pd_2(dba)_3$ (363.28 mg, 396.72 μmol), BINAP (494.05 mg, 793.44 μmol) and sodium tert-butoxide (1.14 g, 11.90 mmol) were added, and stirring was conducted at 90° C. for 4 hours under $N_2$ protection. The reaction solution was filtrated to remove the insoluble material to obtain a filtrate, and the filter residue was washed with ethyl acetate to obtain a filtrate. Filtrates were combined, and dried by a spinning method to obtain a crude product. The crude product was purified by an automatic column passing machine (PE:EA=1:1) to obtain compound 64a.

LCMS (ESI) m/z: 242.9[M+1]$^+$

Step 2

Compound 64a (310 mg, 1.28 mmol) and pyridine hydrochloride (1.48 g, 12.80 mmol) were added to a microwave tube, and reaction was conducted at 180° C. for 20 min. The reactant was added to 10 mL of a saturated sodium bicarbonate solution, and the obtained solution was extracted with ethyl acetate (10 mL×3). Organic phases were combined, washed with a saturated sodium chloride solution (20 mL×1), dried with anhydrous sodium sulfate, and finally dried by a spinning method to obtain crude product compound 64b which was directly used in the next step without purification.

Step 3

Compound 64b (250 mg, 1.10 mmol), N-phenylbis(trifluoromethanesulfonyl) imine (586.94 mg, 1.64 mmol) were dissolved in DMF (5 mL). DIPEA (424.68 mg, 3.29 mmol, 572.34 μL) was added, and stirring was conducted at 16° C. for 0.5 hour. The solvent was spin dried to obtain a crude product. The crude product was purified by an automatic column passing machine (PE:EA=3:1) to obtain compound 64c.

Step 4

Compound 64c (200 mg, 555.08 μmol) and compound 8d (1.17 g, 832.62 μmol) were dissolved in a 1,4-dioxane (1 mL)/$H_2O$ (0.5 mL) solution. $Pd(dppf)Cl_2$ (40.62 mg, 55.51 μmol) and $K_3PO_4$ (353.48 mg, 1.67 mmol) were added, and stirring was conducted at 80° C. for 4 hours. The reaction solution was filtrated to remove the insoluble material to obtain a filtrate, and the filter residue was washed with ethyl acetate to obtain a filtrate. Filtrates were combined, and dried by a spinning method to obtain a crude product. The crude product was separated and purified by a preparative chromatography column (chromatography column: Welch Xtimate C18 150×25 mm×5 μm; mobile phase: [water (0.1% trifluoroacetic acid)-acetonitrile]; B %: 22%-52%, 10 min) to obtain a trifluoroacetate of compound 64. The trifluoroacetate of compound 64 was added to a sodium bicarbonate solution, and the obtained solution was extracted with ethyl acetate. Organic phases were dried with anhydrous sodium sulfate, and concentrated under reduced pressure to obtain compound 64.

LCMS (ESI) m/z: 508.1 [M+1]$^+$

Trifluoroacetate of compound 64 $^1$H NMR (400 MHz, $CD_3OD$) δ 8.60 (d, J=12.0 Hz, 1H), 8.39 (d, J=7.6 Hz, 1H), 8.37-8.23 (m, 2H), 8.40~8.30 (m, 2H), 7.92-7.90 (m, 2H), 7.37-7.34 (m, 1H), 6.9-6.89 (m, 1H), 4.70 (d, J=4.8 Hz, 2H), 4.60 (d, J=3.2 Hz, 1H), 4.31-4.27 (m, 3H), 3.95 (d, J=3.2 Hz, 1H), 3.94 (s, 3H), 3.38-3.32 (m, 4H), 2.23-2.18 (m, 1H), 2.11-2.07 (m, 4H).

Compounds in the examples in Table 6 can be prepared by referring to steps similar to a preparation route of the aforementioned Example 64, with the difference lying in that the raw material used in step 3 is the raw material B in the following table instead of tetrahydropyrrole to obtain trifluoroacetate of the corresponding compounds. The obtained trifluoroacetate of the compounds were added to sodium bicarbonate solutions, the obtained solutions were extracted with ethyl acetate, and the organic phases were dried with anhydrous sodium sulfate and concentrated under reduced pressure to obtain the corresponding compounds.

TABLE 6

| NO. | Product Structure | Raw Material B | Product LCMS m/z: [M + 1]⁺ | Product ¹H NMR |
|---|---|---|---|---|
| Ex. 65 | | | 544.1 | Trifluoroacetate of compound 65 ¹H NMR (400 MHz, CD₃OD) δ = 8.73-8.60 (m, 1H), 8.41 (br d, J = 19.3 Hz, 1H), 8.32 (br d, J = 8.5 Hz, 2H), 8.09 (br d, J = 6.3 Hz, 1H), 7.94-7.82 (m, 1H), 7.44 (br d, J = 11.3 Hz, 1H), 6.97-6.88 (m, 1H), 4.76-4.70 (m, 2H), 4.69-4.57 (m, 1H), 4.62 (br d, J = 6.3 Hz, 1H), 4.41-4.25 (m, 4H), 4.14-4.04, (m, 1H), 3.96 (d, J = 5.8 Hz, 3H), 3.87-3.75 (m, 2H), 3.69-3.58 (m, 3H), 2.68-2.52 (m, 2H), 2.27-2.13 (m, 1H). |
| Ex. 66 | | | 526.1 | Trifluoroacetate of compound 66 ¹H NMR (400 MHz, CD₃OD) δ = 8.72-8.61 (m, 1H), 8.42 (br d, J = 17.8 Hz, 1H), 8.35-8.26 (m, 2H), 8.05 (br d, J = 5.5 Hz, 1H), 7.92-7.83 (m, 1H), 7.44 (br d, J = 11.3 Hz, 1H), 6.94 (br d, J = 8.0 Hz, 1H), 4.95 (s, 2H), 4.71 (s, 2H), 4.62 (br d, J = 5.8 Hz, 1H), 4.37-4.28 (m, 3H), 4.08 (br d, J = 13.3 Hz, 1H), 4.00-3.92 (m, 3H), 3.79-3.47 (m, 5H), 2.50-2.14 (m, 4H). |
| Ex. 67 | | | 526.1 | Trifluoroacetate of compound 67 ¹H NMR (400 MHz, CD₃OD) δ = 8.65-8.59 (m, 1H), 8.39 (d, J = 17.2 Hz, 1H), 8.30-8.25 (m, 2H), 8.00 (br d, J = 5.6 Hz, 1H), 7.88-7.81 (m, 1H), 7.39 (br d, J = 11.4 Hz, 1H), 6.89 (br d, J = 8.0 Hz, 1H), 5.42 (d, J = 28.2 Hz, 1H), 4.71 (s, 2H), 4.59 (s, 1H), 4.31-4.27 (m, 3H), 4.03 (br d, J = 13.2 Hz, 1H), 4.00-3.92 (m, 3H), 3.79-3.47 (m, 5H), 3.12-3.07 (m, 1H), 2.50-2.14 (m, 3H). |

Example 73

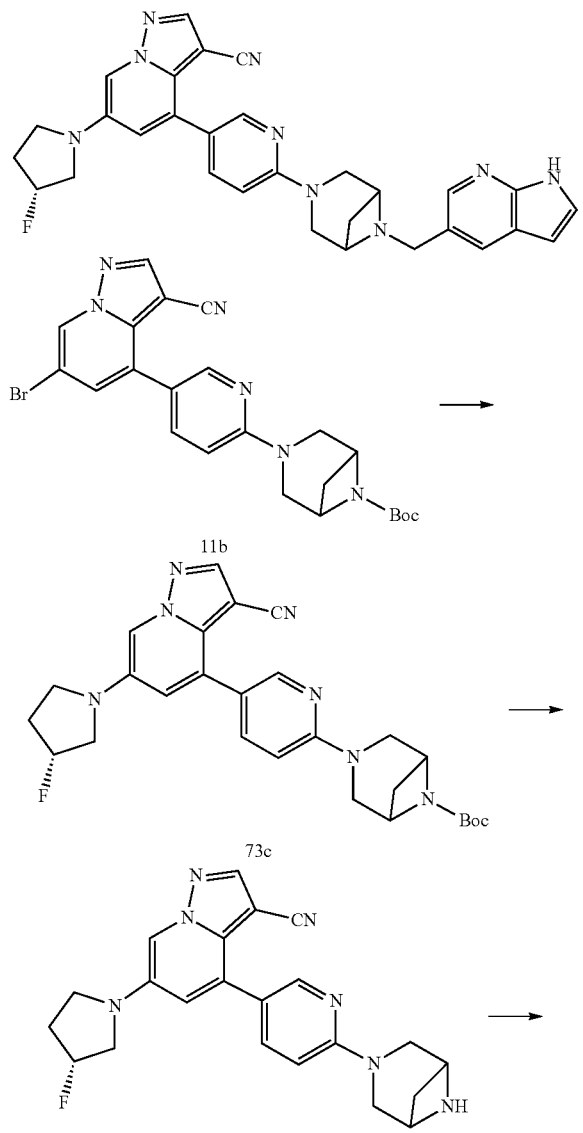

Step 1

Compound 11b (114.07 mg, 908.41 μmol, HCl) was dissolved in toluene (5 mL), triethylamine was added, pH=9, (3R)-3 fluoropyrrole hydrochloride (300 mg, 605.61 μmol), BINAP (75.42 mg, 121.12 μmol). Pd$_2$(dba)$_3$ (55.46 mg, 60.56 μmol) and tBuONa (174.60 mg, 1.82 mmol) were added, and stirring was conducted at 90° C. for 3 hours under nitrogen protection.

The reactant was extracted with ethyl acetate (10 mL/3). Organic phases were combined, dried with anhydrous sodium sulfate, and dried by a spinning method to obtain a crude product. The crude product was purified by an automatic column passing machine (PE:EA=1:1) to obtain compound 73c.

LCMS (ESI) m/i: 504.1[M+1]$^+$

Step 2

Compound 73c (260 mg, 516.31 μmol) was dissolved in EtOAc (10 mL). HCl/EtOAc (4 M, 3.87 mL) was added, and stirring was conducted at 25° C. for 12 hours. The reaction solution was directly concentrated to obtain compound 73d for use in the next step without purification Step 3

Compound 73d (80 mg, 181.85 μmol, HCl) was dissolved in DCM (1 mL), triethylamine (18.40 mg, 181.85 μmol, 25.31 μL) was added, pH=9, stirring was conducted for 10 min, 1H-pyrrole [2,3-b]pyridine-5-carbaldehyde (79.73 mg, 545.56 μmol) was added, stirring was conducted for 1 hour, then NaBH(OAc)$_3$ (192.71 mg, 909.27 μmol) was added, and stirring was conducted at 20° C. for 16 hours. The reactant was filtered, and dried by a spinning method to obtain a crude product. The crude product was purified by a preparative HPLC (chromatography column: Boston Green ODS 150×30 mm×5 μm, mobile phase: [water (0.075% trifluoroacetic acid)-acetonitrile]; B %: 15%-45%, 12 min) to obtain a trifluoroacetate of compound 73. The trifluoroacetate of compound 73 was added to a sodium bicarbonate solution, and the obtained solution was extracted with ethyl acetate. Organic phases were dried with anhydrous sodium sulfate, and concentrated under reduced pressure to obtain compound 73.

LCMS (ESI) m/z: 534.1 [M+1]$^+$ $^1$H NMR (400 MHz, CD$_3$OD) δppm 8.45 (br s, 3H) 8.24 (s, 1H) 8.13 (br s, 1H) 7.99 (br s, 1H) 7.60 (br d, J=3.26 Hz, 1H) 7.22 (br s, 2H) 6.69 (br d, J=3.26 Hz, 1H) 5.31-5.55 (m, 1H) 4.40-4.82 (m, 3H) 4.29 (br d, J=12.04 Hz, 2H) 4.15 (brs, 1H) 3.42-3.79 (m, 5H) 3.24-3.38 (m, 2H) 2.11-2.50 (m, 3H).

Examples 74 and 81

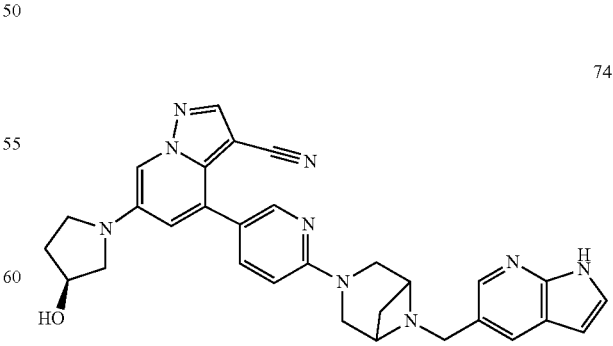

-continued

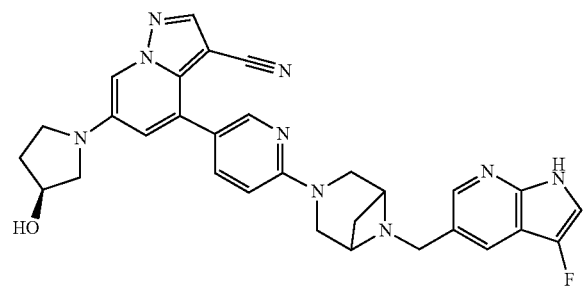
81

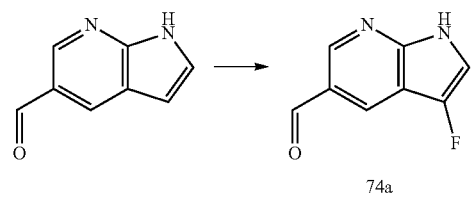
74a

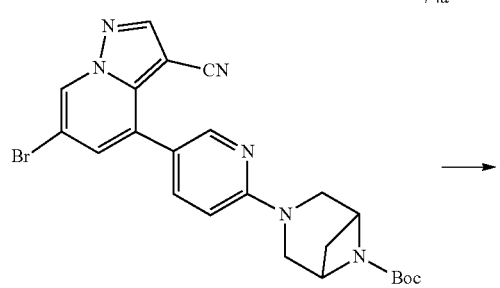
11b

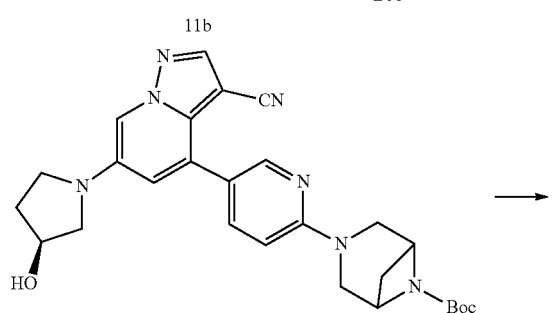
74b

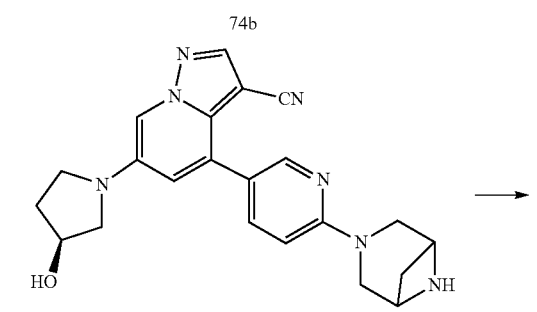
74c

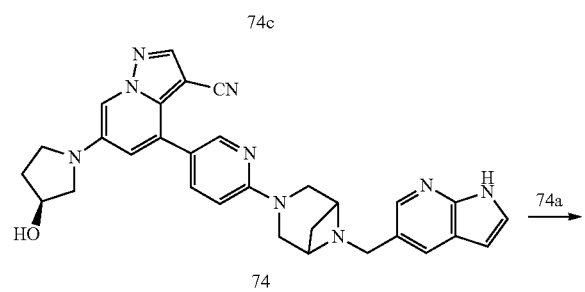
74

-continued

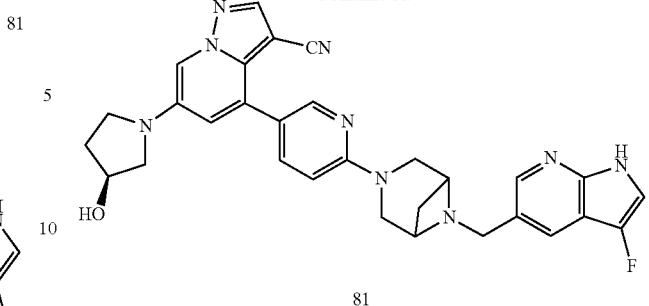
81

Step 1

1H-pyrrolo[2,3-b]pyridine-5-carbaldehyde (300 mg, 2.05 mmol) was dissolved in acetonitrile (3 mL), 1-fluoro-4-methyl-1,4-diazabicyclo[2.2.2]octane tetrafluoroborate (1.09 g, 3.08 mmol) and AcOH (630.00 mg, 10.49 mmol, 0.6 mL) were added, and stirring was conducted at 70° C. for 16 hours THF in the reaction solution was removed by rotation, and then the reaction solution was diluted by adding water and extracted with ethyl acetate (5 mL×3). Organic phases were combined, washed with a saturated sodium chloride solution (5 mL), dried with anhydrous sodium sulfate, and finally dried by a spinning method to obtain a crude product. The crude product was separated and purified by an automatic column passing machine (PE:EA=1:1) to obtain compound 74a.

LCMS (ESI) m/z: 164.8 [M+1]+

Step 2

Compound 11b (1.2 g, 2.42 mmol) was dissolved in toluene (15 mL), (S)-3-hydroxypyrrolidine (422.08 mg, 4.84 mmol, 390.82 μL), Pd$_2$(dba)$_3$ (221.83 mg, 242.24 μmol), BINAP (301.68 mg, 484.49 μmol) and sodium tert-butoxide (698.41 mg, 7.27 mmol) were added, and stirring was conducted at 90° C. for 3 hours under nitrogen protection. Water was added to the reaction solution, and then the reaction solution was extracted with ethyl acetate (20 mL×3). Organic phases were combined, washed with water (20 mL×1), washed with a saturated sodium chloride solution (20 mL×1), dried with anhydrous sodium sulfate, and finally dried by a spinning method to obtain a crude product. The crude product was separated and purified by an automatic column passing machine (PE:EA=1.1 to 0.1) to obtain compound 74b.

LCMS (ESI) m/z: 502.2 [M+1]+

Step 3

Compound 74b (360 mg, 717.73 μmol) was dissolved in DCM (4 mL), trifluoroacetic acid (1.64 g, 14.35 mmol, 1.06 mL) was added, and stirring was conducted at room temperature of 20° C. for 1 hour. The reaction solution was dried by a spinning method to obtain compound 74c.

LCMS (ESI) m/z: 402.2 [M+1]+

Step 4

DCM (2 mL), compound 74c (136 mg, 263.83 μmol), triethylamine (26.70 mg, 263.83 μmol, 36.72 μL) and 1-pyrrolo[2,3-b]pyridine-5-formaldehyde (57.84 mg, 395.74 μmol) were added successively, stirring was conducted at 25° C. for 0.5 hour, then NaBH(OAc); (167.75 mg, 791.49 mol) was added, and stirring was conducted for 16 hours. The reaction solution was dried by a spinning method to obtain a crude product. The crude product was separated by a HPLC (chromatography column. Boston Green ODS 150×30 mm×5 μm; mobile phase: [water (0.075% trifluoroacetic acid)-acetonitrile]; B %: 5%-35%, 9 min) to obtain a trifluoroacetate of compound 74. The trifluoroacetate of compound 74 was added to a sodium bicarbonate solution, and the obtained solution was extracted with ethyl acetate. Organic phases were dried with anhydrous sodium sulfate, and concentrated under reduced pressure to obtain compound 74.

LCMS (ESI) m/z: 532.1 [M+1]+

$^1$H NMR (400 MHz, CD$_3$OD) δ 8.44 (br s, 3H), 8.31-8.19 (m, 2H), 8.03-7.96 (m, 2H), 7.56 (d, J=3.6 Hz, 1H), 7.17 (br s, 1H), 6.64 (d, J=3.6 Hz, 1H), 4.74-4.54 (m, 3H), 4.26 (br d, J=13.3 Hz, 2H), 4.00 (s, 1H), 3.74-3.38 (m, 3H), 3.29 (br s, 1H), 3.23 (br d, J=7.0 Hz, 1H), 3.15 (s, 1H), 2.23 (br d, J=11.0 Hz, 3H), 2.11 (br s, 1H), 1.36-1.30 (n, 1H).

Step 5

Compound 74c (200 mg, 232.79 μmol, TFA) was dissolved in DCM (2 mL), TEA (70.67 mg, 698.37 μmol, 97.20 μL) was added, stirring was conducted at room temperature of 20° C. for 5 min, then compound 31c (57.31 mg, 349.18 μmol) was added, stirring was conducted for 30 min, then NaBH(OAc)$_3$ (148.01 mg, 698.37 μmol) was added, and stirring was continued for 16 hours. The reaction solution was quenched with water, extracted with DCM (5 mL×3). Organic phases were combined, washed with water (5 mL), washed with a saturated sodium chloride solution (5 mL), dried with anhydrous sodium sulfate, and finally dried by a spinning method to obtain a crude product. The crude product was separated and purified by a preparative HPLC (chromatography column: Boston Green ODS 150×30 mm/5 μm, mobile phase: [water (0.075% trifluoroacetic acid)-acetonitrile]; B %: 15%-45%, 8 mm) to obtain a trifluoroacetate of compound 81. The trifluoroacetate of compound 81 was added to a sodium bicarbonate solution, and the obtained solution was extracted with ethyl acetate Organic phases were dried with anhydrous sodium sulfate, and concentrated under reduced pressure to obtain compound 81.

LCMS (ESI) m/z: 550.1 [M+1]+

$^1$H NMR (400 MHz, CD$_3$OD) δ ppm 8.51-8.35 (m, 2H) 8.35-8.17 (m, 2H) 8.03-7.83 (m, 2H) 7.35 (s, 1H) 7.19-6.85 (m, 2H) 4.71 (s, 1H) 4.69-4.55 (m, 3H) 4.47 (s, 1H) 4.40-4.31 (m, 1H) 4.28-4.16 (m, 2H) 4.05-3.94 (m, 1H) 3.73-3.49 (m, 3H) 3.43 (s, 1H) 3.29-3.24 (m, 1H) 3.18-2.98 (m, 1H) 2.32-2.02 (m, 2H).

Examples 75, 76 and 80

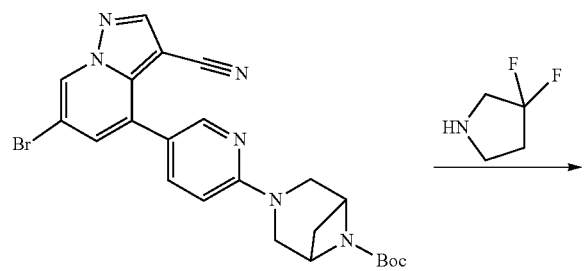

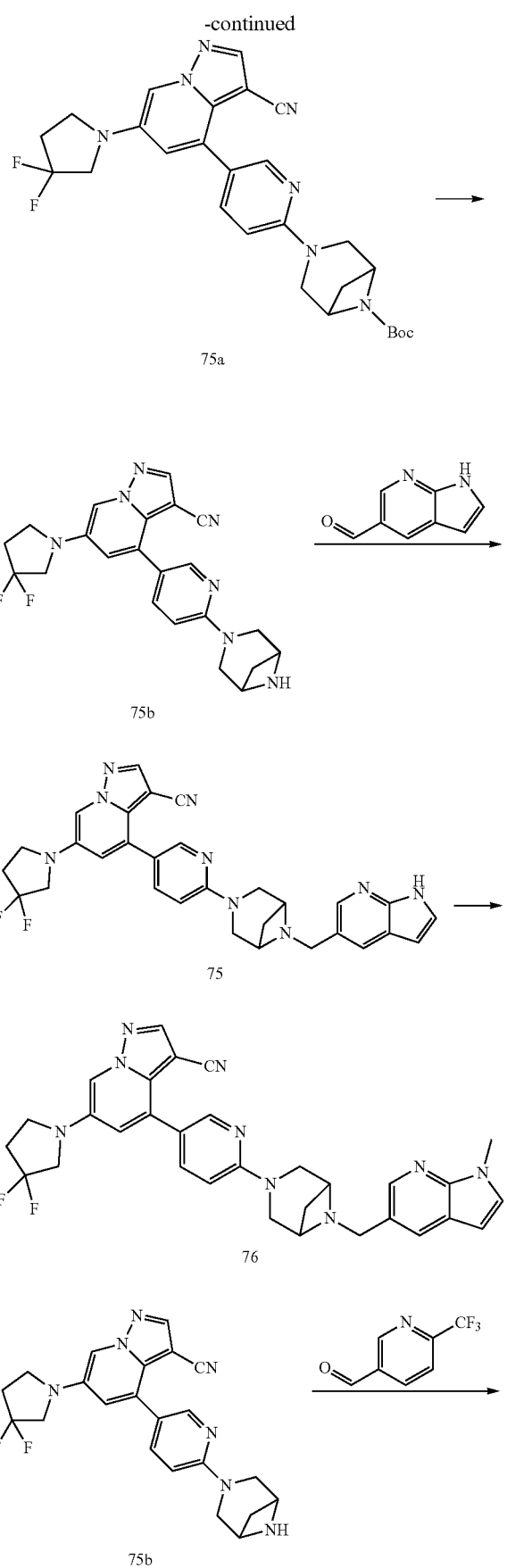

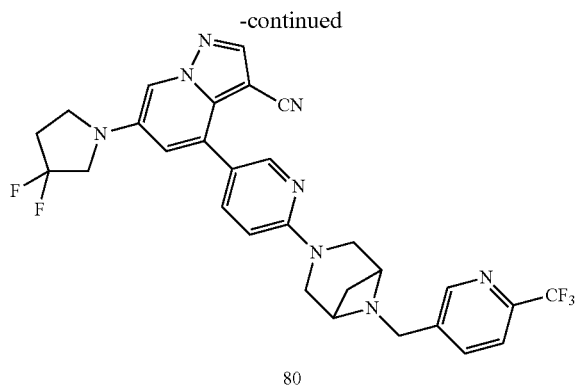

80

Step 1

3,3-difluoropyrrole hydrochloride (956.37 mg, 6.66 mmol) was dissolved in toluene (10 mL), compound 11b (2.2 g, 4.44 mmol), BINAP (553.07 mg, 888.22 μmol), Pd$_2$(dba)$_3$ (406.68 mg, 444.11 μmol) and sodium tert-butoxide (1.28 g, 13.32 mmol) were added, and stirring was conducted at 110° C. for 3 hours under nitrogen protection. The reactant was extracted with ethyl acetate (30 mL×3). Organic phases were combined, dried with anhydrous sodium sulfate, and dried by a spinning method to obtain a crude product. The crude product was purified by an automatic column passing machine (PE:EA=2:1) to obtain compound 75a.

LCMS (ESI) m/z: 522.11[M+1]$^+$

Step 2

Compound 75a (2.1 g, 4.03 mmol) was dissolved in DCM (20 mL), TFA (4.59 g, 40.26 mmol, 2.98 mL) was added, and stirring was conducted at 20° C. for 16 hours. The reaction solution was dried by a spinning method to obtain compound 75b which was used directly in the next step.

LCMS (ESI) m/z: 422.1 [M+1]$^+$

Step 3

Compound 75b (220 mg, 410.86 μmol, TFA) was dissolved in DCM (3 mL), triethylamine (124.72 mg, 1.23 mmol, 171.56 μL) and H-pyrrolo[2,3-b]pyridine-5-carbaldehyde (72.05 mg, 493.03 μmol) were added, stirring was conducted at 25° C. for 1 hour, then NaBH(OAc)$_3$ (261.23 mg, 1.23 mmol) was added, and stirring was continued for 16 hours. The reaction solution was quenched with water, and dried by a spinning method to obtain a crude product. The crude product was purified by an automatic column passing machine (DCM:MeOH=20:1) to obtain a crude product. The crude product was separated and purified by a preparative HPLC (chromatography column: Boston Green ODS 150×30 mm×5 μm; mobile phase: [water (0.075% trifluoroacetic acid))-acetonitrile]; B %: 20%-50%, 7 min) to obtain a trifluoroacetate of compound 75. The trifluoroacetate of compound 75 was added to a sodium bicarbonate solution, and the obtained solution was extracted with ethyl acetate Organic phases were dried with anhydrous sodium sulfate, and concentrated under reduced pressure to obtain compound 75

LCMS (ESI) m/z: 552.2 [M+1]$^+$ $^1$H NMR (400 MHz, CD$_3$OD) δppm 8.73-8.36 (m, 3H) 8.24 (s, 2H) 8.02 (s, 1H) 7.66 (d, J=3.52 Hz, 1H) 7.46-7.19 (m, 2H) 6.77 (d, J=3.52 Hz, 1H) 4.97 (s, 1H) 4.86-4.56 (m, 3H) 4.50-4.16 (m, 4H) 3.75 (t, J=12.92 Hz, 2H) 3.60 (t, J=7.04H, 2H) 2.71-2.46 (m, 2H) 2.25 (d, J=10.04 Hz, 1H)

Step 4

At 0° C., compound 75 (50 mg, 90.65 μmol) was dissolved in DMF (1 mL), NaH (5.44 mg, 135.97 μmol, 60% purity) was added, stirring was conducted at 0° C. for 10 mm, then iodomethane (15.44 mg, 108.78 μmol, 6.77 μL) was added, the reaction temperature was risen to room temperature of 25° C., and stirring was conducted for 2 hours. The reaction solution was diluted with water, and extracted with ethyl acetate (2 mL×3). Organic phases were combined, washed with water (2 mL×2), washed with a saturated sodium chloride solution (2 mL×1), dried with anhydrous sodium sulfate, and finally dried by a spinning method to obtain a crude product. The crude product was separated and purified by a preparative HPLC (chromatography column: Boston Green ODS150×30 mm×5 μm, mobile phase: [water (0.075% trifluoroacetic acid)-acetonitrile]; B % 22%-52%, 8 min) to obtain a trifluoroacetate of compound 76. The trifluoroacetate of compound 76 was added to a sodium bicarbonate solution, and the obtained solution was extracted with ethyl acetate. Organic phases were dried with anhydrous sodium sulfate, and concentrated under reduced pressure to obtain compound 76.

LCMS (ESI) m/z: 566.1[M+1]$^+$ $^1$H NMR (400 MHz, CD$_3$OD) δ ppm 8.55-8.36 (m, 2H) 8.33-8.15 (m, 2H) 8.11-7.85 (m, 2H) 7.56-7.32 (m, 2H) 7.27-7.16 (m, 1H) 6.61 (s, 1H) 4.73-4.58 (m, 2H) 4.46 (s, 1H) 4.23 (d, J=13.04 Hz, 2H) 4.0 (d, J=13.04 Hz, 1H) 3.92 (s, 3H) 3.79 (s, 2H) 3.63 (s, 3H) 3.06 (d, J=6.02 Hz, 1H) 2.59 (s, 2H) 2.27-2.15 (m, 1H) 1.36-1.27 (m, 1H).

Step 5

Compound 75b (197.13 mg, 467.74 μmol, TFA) was dissolved in DCM (3 mL). TEA (141.99 mg, 1.40 mmol, 195.31 μL) was added dropwise, stirring was conducted for 5 min, a white solid was precipitated out, then 2-(trifluoromethyl) pyrimidine-5-carbaldehyde (122.86 mg, 701.62 μmol) was added, stirring was conducted at 25° C. for 30 min, then NaBH(OAc)$_3$ (297.40 mg, 1.40 mmol) was added, and stirring was conducted for 16 hours under this temperature. 5 mL of water was added to the reaction solution, then the reaction solution was extracted with dichloromethane (5 mL×3). Organic phases were combined, washed with a saturated sodium chloride solution (5 mL×1), dried with anhydrous sodium sulfate, and finally dried by a spinning method to obtain a crude product. The crude product was separated and purified by a preparative HPLC (chromatography column: Welch Xtimate C18 150×30 mm×5 μm; mobile phase: [water (0.075% trifluoroacetic acid)-acetonitrile]; B %: 30%-60%, 8 min) to obtain a trifluoroacetate of compound 80. The trifluoroacetate of compound 80 was added to a sodium bicarbonate solution, and the obtained solution was extracted with ethyl acetate. Organic phases were dried with anhydrous sodium sulfate, and concentrated under reduced pressure to obtain compound 80.

LCMS (ESI) m/z: 581.3[M+1]$^+$ $^1$H NMR (400 MHz, CD$_3$OD) δ ppm 8.91 (s, 1H) 8.47-8.40 (m, 1H) 8.30-8.21 (m, 2H) 8.05 (d, J=1.88 Hz, 1H) 8.01-7.92 (m, 2H) 7.24-7.17 (m, 1H) 7.01 (s, 1H) 4.76-4.63 (m, 3H) 4.38-4.00 (m, 5H) 3.83-3.73 (m, 2H) 3.66-3.58 (m, 2H) 2.58 (tt, J=14.06, 7.14 Hz, 2H) 2.23 (d, J=1.00 Hz, 1H) 2.07-2.01 (m, 1H).

Biological Test Data:

Experimental Example 1: In-Vitro Enzyme Activity Tests of Compounds of the Present Disclosure Objective of the Experiment The enzyme activity was detected by a Z'-LYTE™ kinase test, and inhibitory effects of the compounds onRET and RET (V804M) kinases were evaluated with an ICs value of each compound as an index.

Methods of the Experiment

The compounds used for RET and RET (V804M) kinase tests were diluted 3-fold, in 10 concentration gradients ranging from 3 µM to 0.152 nM; and the content of DMSO in detection reaction was 1%.

Reagents:

Basic reaction buffer, 20 mM 4-(2-hydroxyethyl)piperazine-1-ethanesulfonic acid (Hepes) buffer (pH 7.5), 10 mM $MgCl_2$. 1 mM 1,2-bis[2-[bis(carboxymethyl)amino]ethoxy]ethane (EGTA), 0.02% polyoxyethylene lauryl ether (Brij35), 0.02 mg/mL bovine serum albumin, 0.1 mM of $Na_3VO_4$, 2 mM dithiothreitol (DTT) and 1% DMSO.

Compounds:

The compounds to be tested were dissolved in a 100% DMSO system to be diluted to 10 mM for further use. The solution was diluted by using Integra Viaflo Assist.

Universal Enzyme Reaction Process:

Test conditions: concentrations of RET kinase, peptide substrate CHKtide and adenosine triphosphate (ATP) were 3 µM, 1000 µM and 20 µM, respectively, and concentrations of RET (V804M) kinase, substrate peptide and ATP were 80 µM, 1000 µM and 30 µM, respectively.

Reaction process: compound solutions of different concentrations were added to a kinase/peptide solution prepared according to the test conditions, the obtained solution was incubated at room temperature for 20 minutes, and then 33P-ATP of corresponding concentrations were added, and the obtained solution was incubated at room temperature for 120 minutes. The radioactivity was detected by a filter-binding method.

Reaction Detection:

The reaction was terminated by adding phosphoric acid (concentration, 0.5%) into a kinase reaction solution, and plate reading was carried out with an Envision instrument.

Data Analysis

Data were converted into phosphorylation rate and inhibition rate, and the parametric curve was fitted by using GraphPad Software to obtain $IC_{50}$ data of the compounds.

Results of the Experiment Results were Shown in Table 8:

TABLE 8

Test results on the kinase activity $IC_{50}$ of the compounds of the present disclosure.

| | RET kinase $IC_{50}$(nM) | RET V804M $IC_{50}$(nM) |
|---|---|---|
| Compound 1 | 3.66 | 36.1 |
| Hydrochloride of compound 2 | 95.50 | 1410.00 |
| Hydrochloride of compound 4 | 2.42 | 22.67 |
| Hydrochloride of Compound 5 | 146 | 2370.00 |
| Trifluoroacetate of compound 6 | 34.8 | N/A |
| Trifluoroacetate of compound 7 | 239.00 | 1930.00 |
| Trifluoroacetate of compound 8 | 1.15 | 3.14 |
| Trifluoroacetate of compound 9 | 0.97 | 1.8 |
| Trifluoroacetate of compound 10 | 0.69 | 3.79 |
| Trifluoroacetate of compound 11 | 1.30 | 0.61 |
| Trifluoroacetate of compound 12 | 0.61 | 0.51 |
| Trifluoroacetate of compound 13 | 1.57 | 3.49 |
| Trifluoroacetate of compound 14 | 0.72 | 0.48 |
| Trifluoroacetate of compound 15 | 1.21 | N/A |
| Compound 16 | 6.08 | N/A |
| Trifluoroacetate of compound 17 | 5.25 | N/A |
| Trifluoroacetate of compound 18 | 0.46 | N/A |
| Trifluoroacetate of compound 19 | 2.35 | N/A |
| Trifluoroacetate of compound 20 | 0.90 | N/A |
| Trifluoroacetate of compound 21 | 1.98 | N/A |
| Trifluoroacetate of compound 22 | 0.47 | 2.04 |
| Hydrochloride of compound 23 | 0.56 | 5.9 |
| Trifluoroacetate of compound 24 | 1.1 | 8.43 |
| Tfifluoroacetate of compound 25 | 1.62 | 11 |
| Trifluoroacetate of compound 26 | 3.82 | 22 |
| Trifluoroacetate of compound 27 | 4.37 | 33.6 |
| Trifluoroacetate of compound 28 | 1.58 | 11.6 |
| Hydrochloride of compound 29 | 1.04 | 5:75 |
| Trifluoroacetate of compound 30 | 0.72 | 5.86 |
| Trifluoroacetate of compound 31 | 1.24 | 6.15 |
| Trifluoroacetate of compound 32 | 1.10 | 3.15 |
| Trifluoroacetate of compound 33 | 1.47 | 7.43 |
| Trifluoroacetate of compound 34 | 0.92 | 9.89 |
| Compound 35 | 1.57 | 5.47 |
| Compound 36 | 1.22 | 3.79 |
| Compound 37 | 2.30 | 15.60 |
| Compound 38 | 1.21 | 5.93 |
| Trifluoroacetate of compound 39 | 0.67 | 2.27 |
| Compound 40 | 0.29 | 1.83 |
| Compound 41 | 3.09 | 11.30 |
| Compound 42 | 1.13 | N/A |

TABLE 8-continued

Test results on the kinase activity IC$_{50}$ of the compounds of the present disclosure.

| | RET kinase IC$_{50}$(nM) | RET V804M IC$_{50}$(nM) |
|---|---|---|
| Trifluoroacetate of compound 43 | 0.72 | N/A |
| Trifluoroacetate of compound 44 | 2.34 | N/A |
| Compound 45 | 1.83 | 7.53 |
| Trifluoroacetate of compound 46 | 1.16 | N/A |
| Trifluoroacetate of compound 47 | 0.63 | N/A |
| Trifluoroacetate of compound 48 | 2.13 | N/A |
| Trifluoroacetate of compound 49 | 1.22 | N/A |
| Compound 50 | 1.87 | N/A |
| Compound 51 | 1.73 | N/A |
| Compound 52 | 2.00 | N/A |
| Compound 53 | 53.4 | 144 |
| Trifluoroacetate of compound 54 | 2.42 | N/A |
| Trifluoroacetate of compound 55 | 3.90 | N/A |
| Trifluoroacetate of compound 56 | 0.96 | N/A |
| Trifluoroacetate of compound 57 | 1.98 | 8.11 |
| Trifluoroacetate of compound 58 | 1.80 | 7.81 |
| Trifluoroacetate of compound 59 | N/A | N/A |
| Trifluoroacetate of compound 60 | 3.87 | 19.9 |
| Trifluoroacetate of compound 61 | 1.77 | 8.85 |
| Trifluoroacetate of compound 62 | N/A | N/A |
| Trifluoroacetate of compound 63 | 1.60 | 5.68 |
| Trifluoroacetate of compound 64 | 1.23 | 2.67 |
| Trill uoroacetale of compound 65 | 0.66 | 2.60 |
| Trifluoroacetate of compound 66 | 1.62 | 7.53 |
| Trifluoroacetate of compound 67 | 1.09 | 1.60 |
| Trifluoroacetate of compound 68 | 1.53 | 1.47 |
| Trifluoroacetate of compound 69 | 1.44 | 1.57 |
| Compound 70 | 1.09 | N/A |
| Compound 71 | 0.59 | N/A |
| Trifluoroacelate of compound 72 | 6.60 | 12.0 |
| Trifluoroacetate of compound 73 | 0.72 | N/A |
| Trifluoroacetate of compound 74 | 1.97 | N/A |
| Trifluoroacetate of compound 75 | 1.38 | N/A |
| Trifluoroacetate of compound 76 | 8.0 | N/A |
| Trifluoroacetate of compound 77 | 4.39 | N/A |
| compound 78 | 0.77 | N/A |
| compound 79 | 1.39 | N/A |
| Trifluoroacetate of compound 80 | 1.13 | N/A |
| Trifluoroacetate of compound 81 | 1.64 | N/A |
| Trifluoroacetate of compound 82 | 2.34 | N/A |

Note:
N/A, Not Available.

Conclusion: The compounds of the present disclosure exhibited an excellent inhibitor, activity on RET and mutation RET V804M thereof, and may have excellent therapeutic effects in tumor patients with RET abnormalities.

Experimental Example 2: Pharmacokinetic Evaluation on the Compounds of the Present Disclosure Experiment process: 0.1 mg/ml of the clear solution of each test compound in the corresponding solvents (as shown in Table 9) was injected into female Balb/c mice (fasting overnight. 7-9 weeks old) via the tail vein at a dose of 0.2 mg/% kg. Blood samples (30 NL) were collected from the jugular vein or the tail vein at the following time points: 0.0833 hour, 0.25 hour, 0.5 hour, 1.0 hour, 2.0 hours, 4.0 hours. 8.0 hours and 24 hours after intravenous administration. 0.2 mg/ml of the test compounds suspended in the corresponding solvents (as shown in Table 9) were given to the female Balb/c mice (fasting overnight. 7-9 weeks old) by gavage at a dose of 2 mg/kg. The experiment conditions were shown in Table 9 in detail. Blood samples (30 μL) were collected from the jugular vein or the tail vein of the female Balb/c mice at the following time points: 0.0833 hour, 0.25 hour, 0.5 hour, 1.0 hour, 2.0 hours, 4.0 hours, 6.0 hours, 8.0 hours and 24 hours after oral administration. The blood samples were placed in anticoagulant tubes containing EDTA-K2, and centrifuged to separate plasma. The plasma concentration was determined by LC-MS/MS, and a WinNonlin™ Version 6.3 pharmacokinetic software (Pharsight, Mountain View, CA) was used to calculate related pharmacokinetic parameters by a linear-log trapezoidal method in a non-compartmental model.

The experiment results were, shown in Table 10.

TABLE 9

Pharmacokinetic experiment conditions of the compounds in mice.

| | Intravenous injection (IV) | | Peros (PO) | |
|---|---|---|---|---|
| | Does | Solvent | Does | Solvent |
| Trifluoroacetate of compound 30 | 0.2 mg/kg | 0.1 mg/ml 5% DMSO + 10% polyoxyl 15 hydroxystearate (Solutol) + 85% H₂O clear solution | 2 mg/kg | 0.2 ing/tni 5% DMS0 + 10% polyoxyl 15 hydroxystearate (Solutol) + 85% H₂O clear solution |
| cetate of compound 69 | 0.2 mg/kg | 0.1 mg/ml 5% DMS0 + 10% polyoxyl 15 hydroxystearate (Solutol) + 85% H₂O clear solution | 2 mg/kg | 0.2 mg/ml 5% DMS0 + 10% polyoxyl 15 hydroxystearate (Solutol) + 85% H20 clear solution |

TABLE 10

Pharmacokinetic experiment results of the compounds in mice

| | Intravenous injection (IV) 0.2 mg/kg | | | | Peros (PO) 2 mg/kg | | | |
|---|---|---|---|---|---|---|---|---|
| Dose | Cl (mL/min/kg) | $V_{dds}$ (L/kg) | $T_{1/2}$ (h) | $AUC_{0\text{-}last}$ (nM · h) | $C_{max}$ (nM) | $T_{max}$ (h) | $AUC_{0\text{-}last}$ (nM · h) | F (%) |
| Trifluoroacetate of compound 30 | 2.3 | 0.5 | 2.6 | 2794 | 5340 | 2 | 26926 | 96.4 |
| Trifluoroacetate of compound 69 | 1.3 | 0.42 | 3.6 | 3868 | 3630 | 4 | 29614 | 74.7 |

Notes:
Cl, plasma clearance; $V_{dss}$, Volume of distribution at steady state; $T_{1/2}$, half-life of elimination; $AUC_{0\text{-}last}$, area under the plasma concentration-time curve from time zero to last quantifiable time; F, bioavailability; $C_{max}$, concentration peak; and $T_{max}$, time to reach concentration peak Conclusion: According to the experiment results, it is found that: for IV, these two compounds showed low Cl, low $V_{dss}$ and relatively long $T_{1/2}$, with excellent drug exposure; as for PO, these two compounds both showed relatively short $T_{max}$, with excellent oral absorption/exposure and excellent oral absorption/bioavailability in general. In conclusion, the series of compounds had excellent pharmacokinetic properties.

Experimental Example 3: Analysis on Tumor Growth Inhibition (TGI)

Ba/F3-CCDC6-RET cell line was cultured in a 1640 medium (Biological Industries)+10% fetal bovine serum (BI)+1% Penicillin Streptomycin solution (Coring, USA) at 37° C. in a 5% CO₂ incubator, with passage treatment twice a week Cells were collected when the cell saturation was 80%-90%, subjected to cell counting, and then inoculated subcutaneously into the right armpit of each BALB/c nude female mouse (6-8 weeks old). After inoculation, tumor growth was observed day by day. When the average tumor volume reached 165.77 mm³, mice were randomly divided into groups according to the tumor volume, with 6 mice in each group, and then the mice were administrated with drug. Health status and death situation of the mice were checked every day. In addition, the mice were examined regularly, including tumor growth, activity ability, diet, weight, eyes, hair and other abnormal behaviors, and tumor volume and weight were measured twice a week (on Tuesday and Friday).

Inhibitory effects of the compounds on tumor growth were evaluated according to the relationship between tumor volume and time. The tumor volume was measured by a vernier caliper, with the formula being TV=0.5a×b², wherein "a" was the long diameter of the tumor and "b" was the short diameter of the tumor. TGI was calculated by the difference between the median tumor volume of mice in the solvent group and the median tumor volume of mice in the drug group, and expressed as the percentage of median tumor volume in the solvent control group.

TGI was calculated by the following formula:

$$TGI(TGI(\%)=[1-(T_{23}-T_0)/(V_{23}-V_0)]\times 100)$$

Data were expressed by Means±Standard Error (Mean±SE), unless otherwise stated. The one way ANOVA test was used to compare whether the difference between the tumor volume in the treatment group and the tumor volume in the control group is statistically significant. P<0.05 was considered as statistically significant. The 5% DMSO+10% polyoxyl 15 hydroxystearate (Solutol)+85% 120 was used as the negative control. The experiment results were shown in Table 11.

TABLE 11

Results of antitumor activity test in mice

| Ba/F3-CCDC6-RET cell allograft tumor model | | TGI% (tumor volume at Day 23 after drug administration) | P value |
|---|---|---|---|
| Trifluoroacetate of compound 30 | 10 mg/kg$^{(D0-D13)}$/5 mg/kg$^{(D14-D17)}$/2,5 mg/kg$^{(D18-D28)}$ (BID) | 98 | <0.001 |
| Trifluoroacetate of compound 69 | 10 mg/kg$^{(D0-D13)}$/5 mg/kg$^{(D14-D17)}$/2,5 mg/kg$^{(D18-D28)}$ (BID) | 99 | <0.001 |
| Trifluoroacetate of compound 18 | 10 mg/kg$^{(D0-D17)}$/5 mg/kg$^{(D18-D28)}$ (QD) | 91 | <0.001 |

Notes:
BID: twice a day; OD: once a day; and TGI%: tumor growth inhibition rate.

Conclusion: The compounds of the present disclosure exhibit an excellent tumor growth inhibition effect in the Ba/F3-CCDC6-RET tumor model.

The invention claimed is:

1. A compound of formula (I) or a pharmaceutically acceptable salt thereof, (I)

wherein, $T_1$, $T_2$ and $T_3$ are independently selected from the group consisting of CH and N;

structural unit

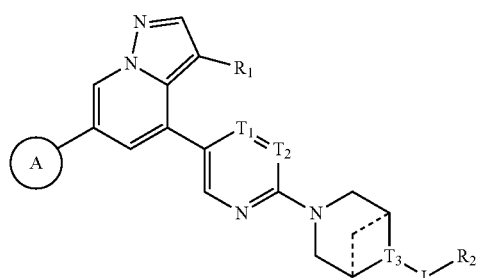

is selected from the group consisting of

L is selected from the group consisting of —CH$_2$—, —C(=O)—C$_{1-3}$ alkyl-, —C(=O)— and and the —CH$_2$ and —C(=O)—C$_{1-3}$ alkyl- are optionally substituted with 1 or 2 R$_a$;

R$_1$ is selected from the group consisting of H, F, Cl, Br, I, OH, NH$_2$ and CN;

R$_2$ is selected from the group consisting of C$_{1-6}$ alkyl, cyclobutyl, phenyl, pyridyl, pyrazinyl, indolyl, each of which is optionally substituted with 1, 2 or 3 R$_b$;

ring A is selected from the group consisting of cyclopropyl, tetrahydropyrrolyl, and the cyclopropyl, tetrahydropyrrolyl,

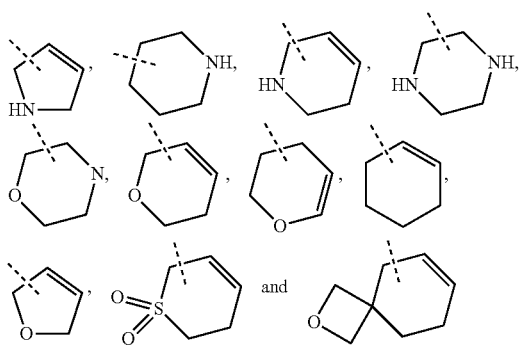

are optionally substituted with 1, 2 or 3 R;

$R_3$ is selected from the group consisting of H, F, Cl, Br, I, OH, $NH_2$, CN, $C_{1-3}$ alkyl, C(=O)—$C_{1-3}$ alkyl, $C_{1-3}$ alkylamino and $C_{1-3}$ alkoxy, and the C(=O)—$C_{1-3}$ alkyl, $C_{1-3}$ alkylamino and $C_{1-3}$ alkoxy are optionally substituted with 1, 2 or 3 $R_c$;

$R_a$ is independently selected from the group consisting of H, F, Cl, Br, I, OH and $CH_3$;

$R_b$ is independently selected from the group consisting of H, F, Cl, Br, I, OH, $NH_2$, CN, $C_{1-3}$ alkyl and $C_{1-3}$ alkoxy, and the $C_{1-3}$ alkyl and $C_{1-3}$ alkoxy are optionally substituted with 1, 2 or 3 R;

$R_c$ is independently selected from the group consisting of H, F, Cl, Br, I, OH and $CH_3$; and R is independently selected from the group consisting of H, F, Cl, Br and I.

2. The compound or the pharmaceutically acceptable salt thereof according to claim 1, wherein structural unit

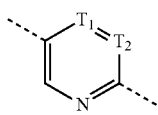

is selected from the group consisting of

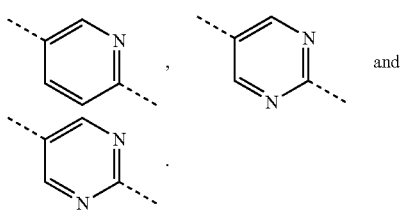

3. The compound or the pharmaceutically acceptable salt thereof according to claim 1, wherein $R_1$ is CN.

4. The compound or the pharmaceutically acceptable salt thereof according to claim 1, wherein L is selected from the group consisting of —$CH_2$—,

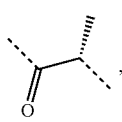

—C(=O)— and

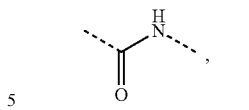

and the —$CH_2$— and

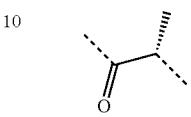

are optionally substituted with 1, 2 or 3 $R_a$.

5. The compound or the pharmaceutically acceptable salt thereof according to claim 4, wherein L is selected from the group consisting of —$CH_2$—, —C(=O)— and

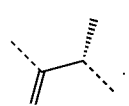

6. The compound or the pharmaceutically acceptable salt thereof according to claim 1, wherein $R_b$ is independently selected from the group consisting of H, F, Cl, Br, I, OH, $NH_2$, CN, $CH_3$ and $C_{1-3}$ alkoxy, and the $CH_3$ and $C_{1-3}$ alkoxy are optionally substituted with 1, 2 or 3 R.

7. The compound or the pharmaceutically acceptable salt thereof according to claim 6, wherein $R_b$ is independently selected from the group consisting of H, F, Cl, Br, OH, $NH_2$, $CH_3$, $CHF_2$, $CF_3$, OCH; and

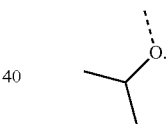

8. The compound or the pharmaceutically acceptable salt thereof according to claim 1, wherein $R_2$ is selected from the group consisting of $C_{1-3}$ alkyl,

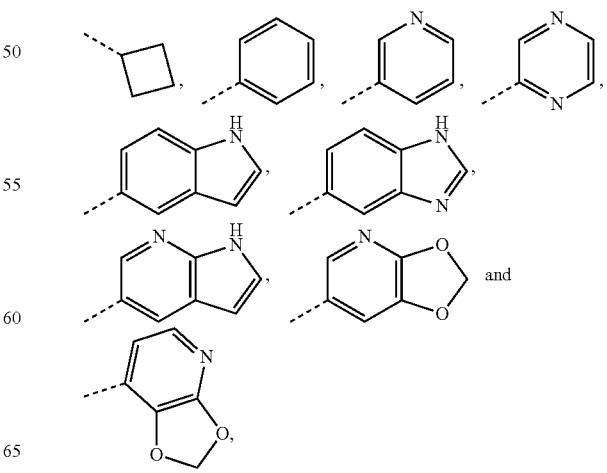

each of which is optionally substituted with 1, 2 or 3 $R_b$.

9. The compound or the pharmaceutically acceptable salt thereof according to claim 8, wherein R₂ is selected from the group consisting of

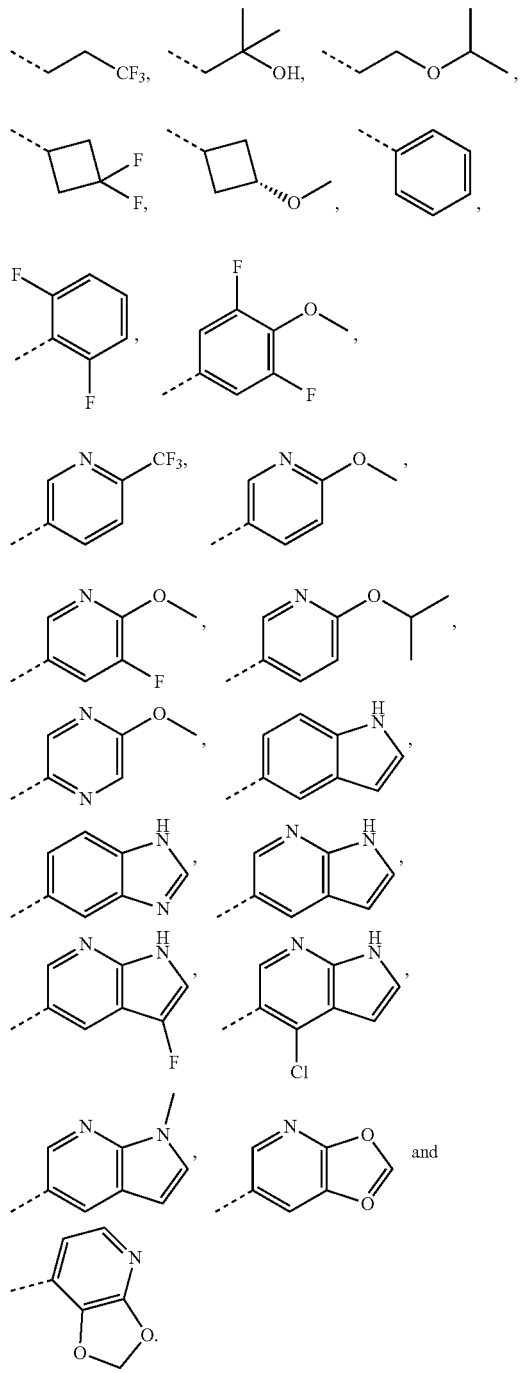

10. The compound or the pharmaceutically acceptable salt thereof according to claim 1, wherein structural unit

is selected from the group consisting of

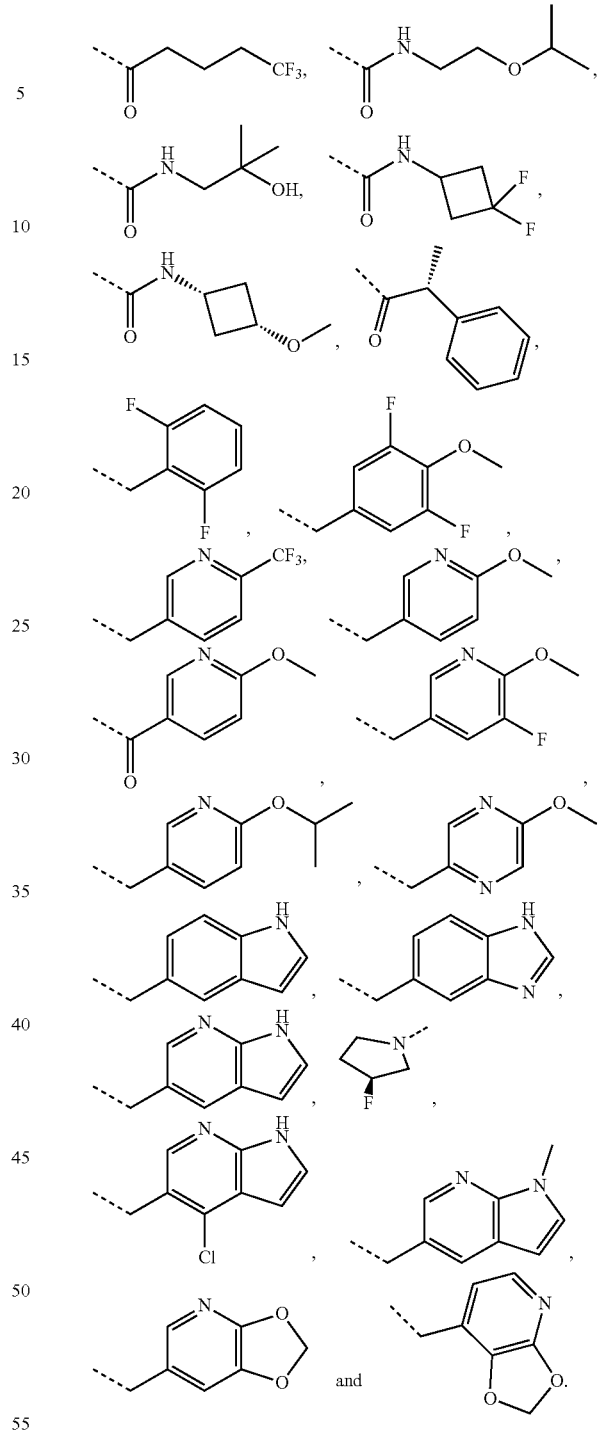

11. The compound or the pharmaceutically acceptable salt thereof according to claim 1, wherein R₃ is selected from the group consisting of H, F, Cl, Br, I, OH, NH₂, CN, CH₃, CH₂CH₃, CH(CH₃)₂, C(=O)CH₃, N(CH₃) and OCH₃, and the CH₃, CH₂CH₃, CH(CH₃)₂, C(=O)CH₃, N(CH₃)₂ and OCH₃ are optionally substituted with 1, 2 or 3 $R_c$.

12. The compound or the pharmaceutically acceptable salt thereof according to claim 11, wherein R₃ is selected from the group consisting of H, F, Cl, Br, I, OH, NH₂, CH₃, CHF₂, CF₃, CH₂CH₃, C(=O)CH₃, N(CH₃)₂, OCH₃ and OCF₃.

13. The compound or the pharmaceutically acceptable salt thereof according to claim 1, wherein ring A is selected from the group consisting of

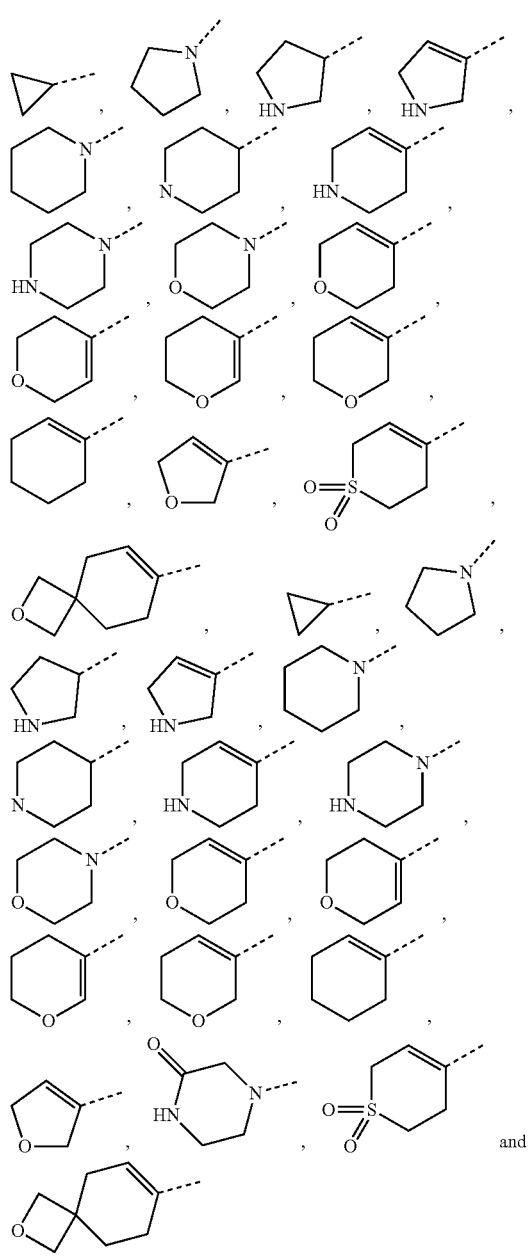

are optionally substituted with 1, 2 or 3 $R_3$.

14. The compound or the pharmaceutically acceptable salt thereof according to claim 12, wherein ring A is selected from the group consisting of

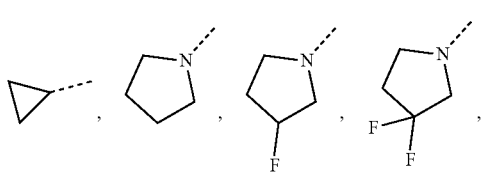

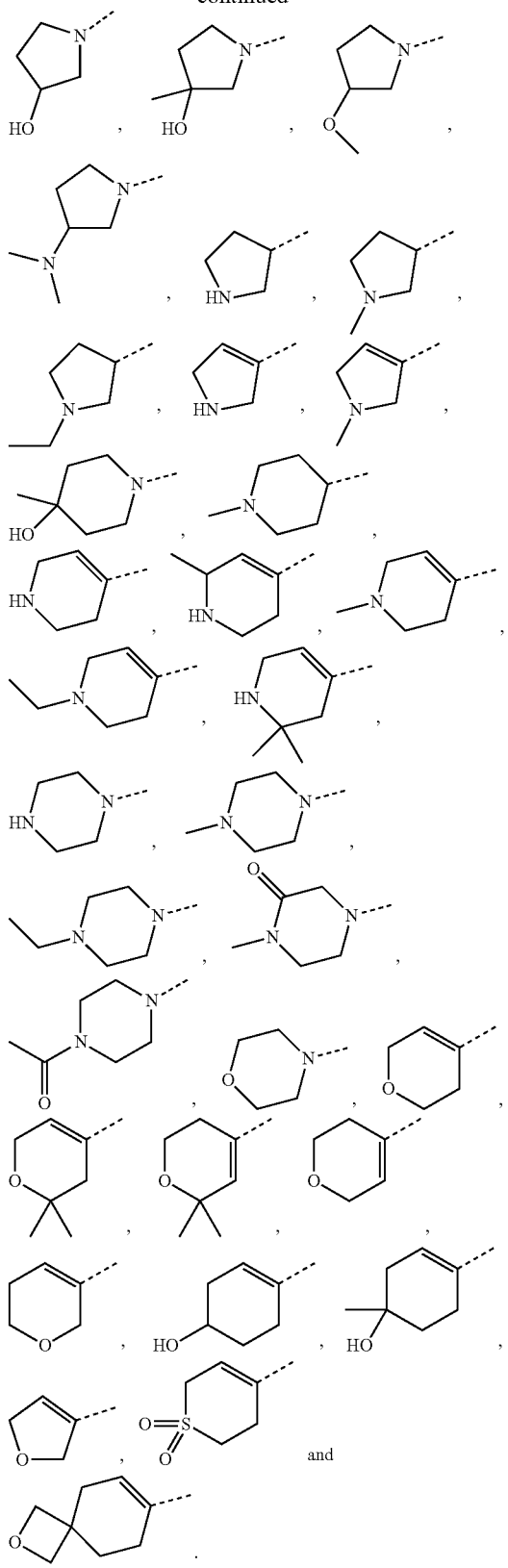

15. The compound or the pharmaceutically acceptable salt thereof according to claim 14, wherein ring A is selected from the group consisting of

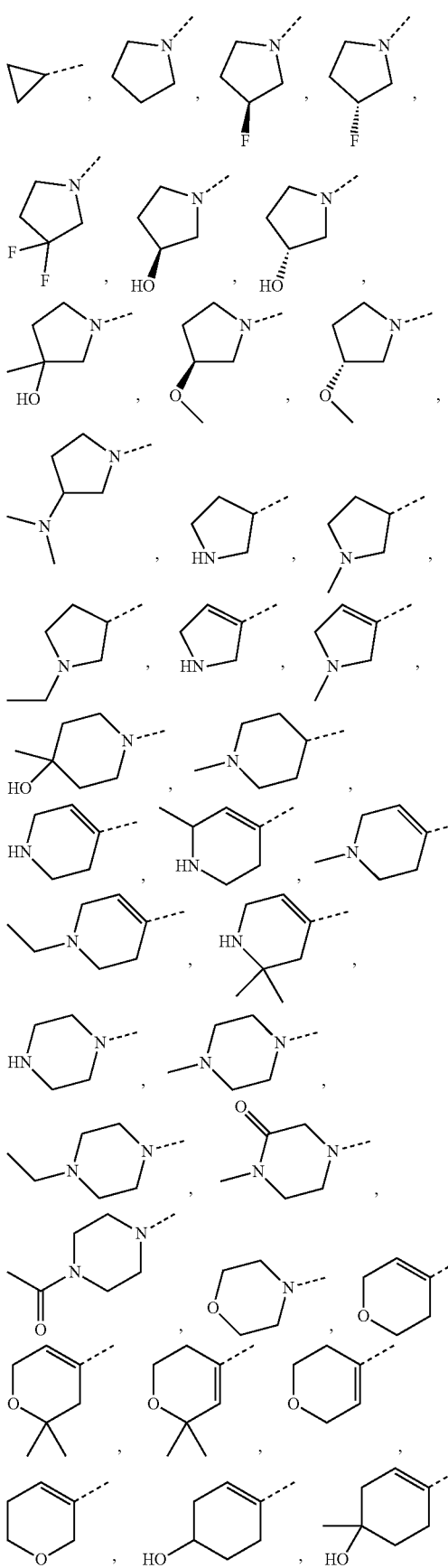
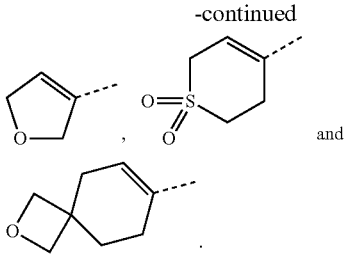
16. The compound or the pharmaceutically acceptable salt thereof according to claim 1, which is selected from the group consisting of:
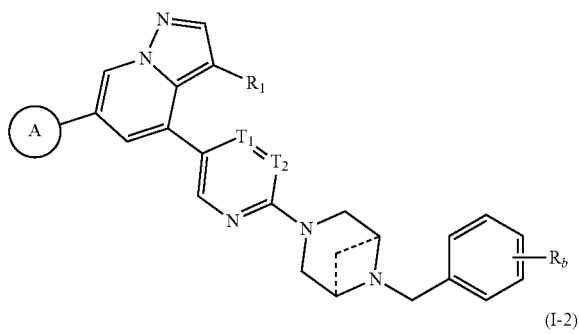

-continued
(I-5)
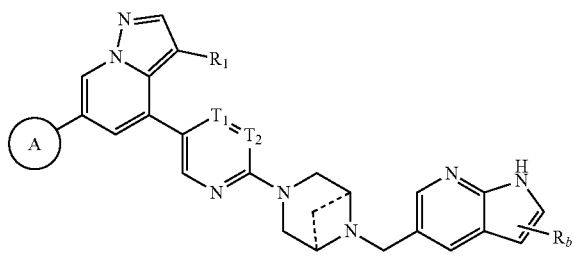
(I-6)
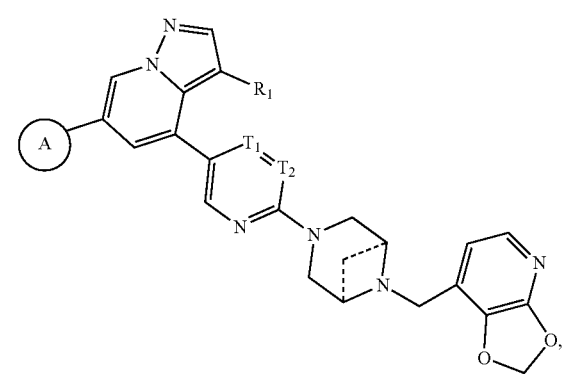
(I-7)
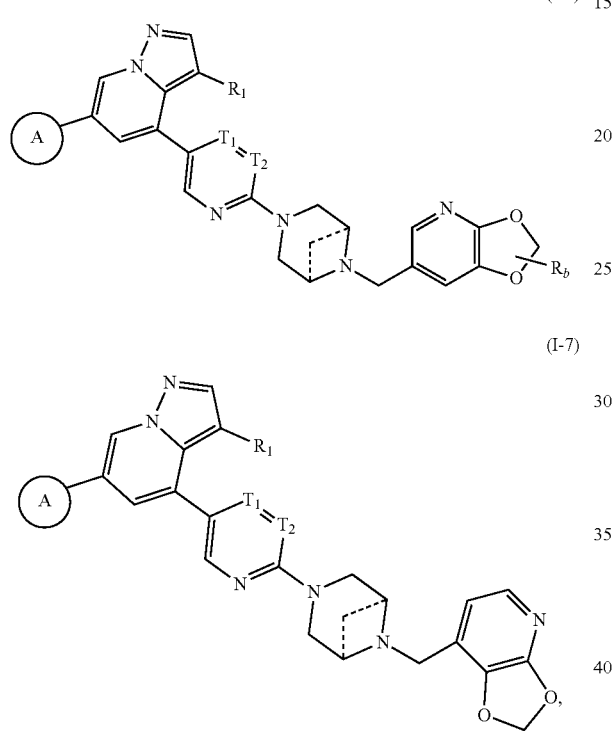
wherein:
structural unit
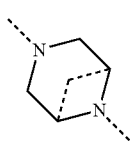
is selected from
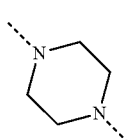 and 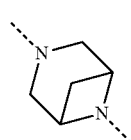.
17. The compound or the pharmaceutically acceptable salt thereof according to claim 1, which is selected from the group consisting of:
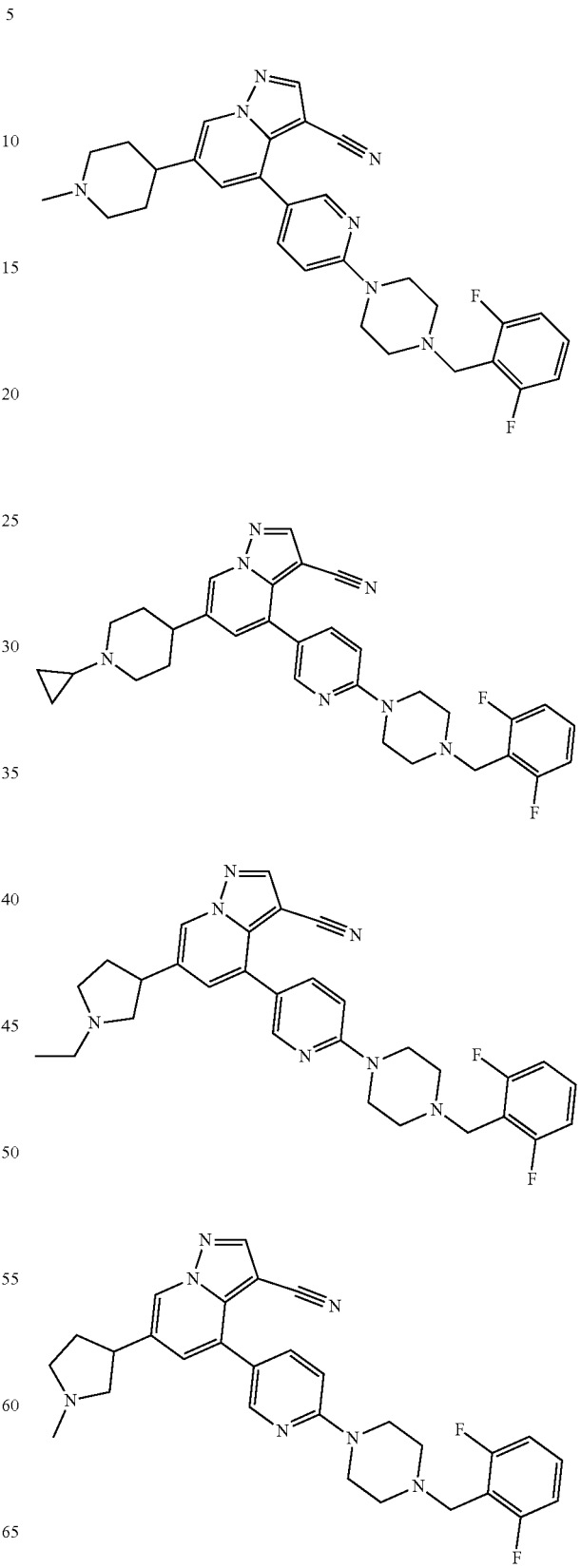

257
-continued
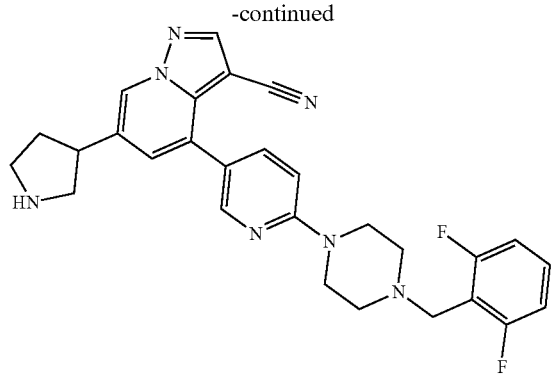
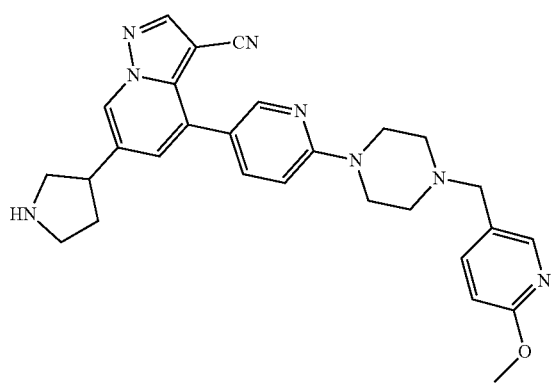
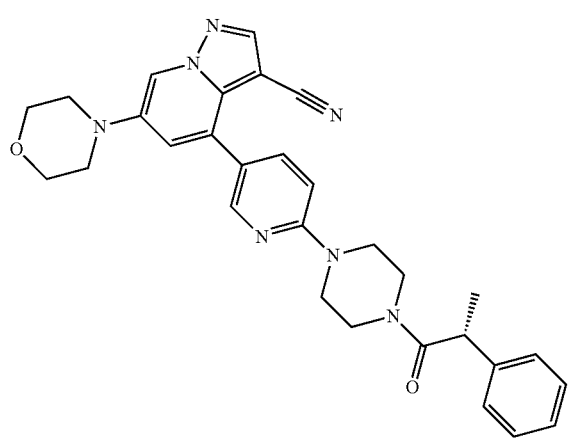
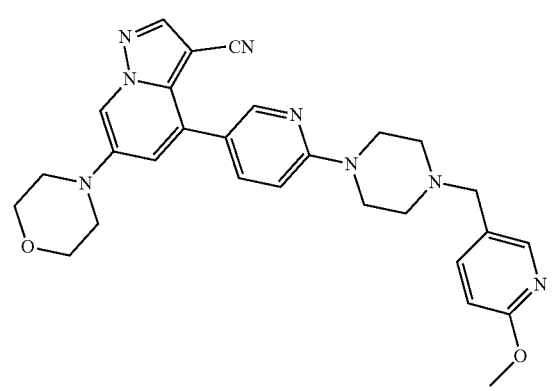
258
-continued
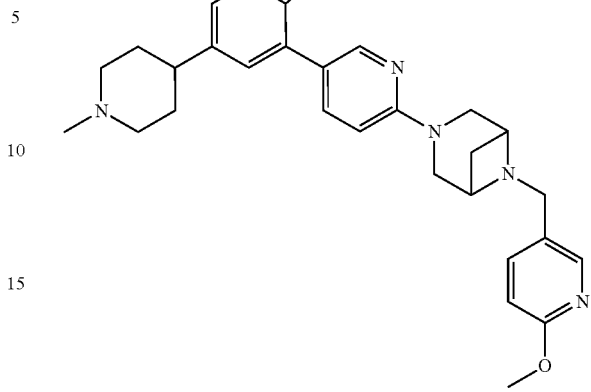
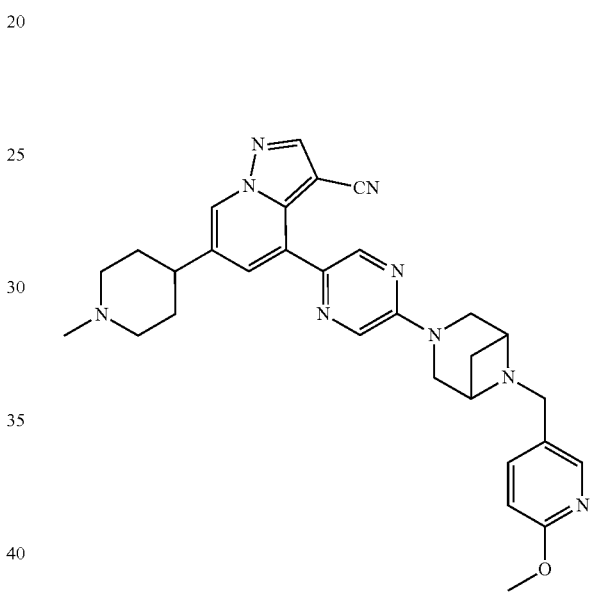
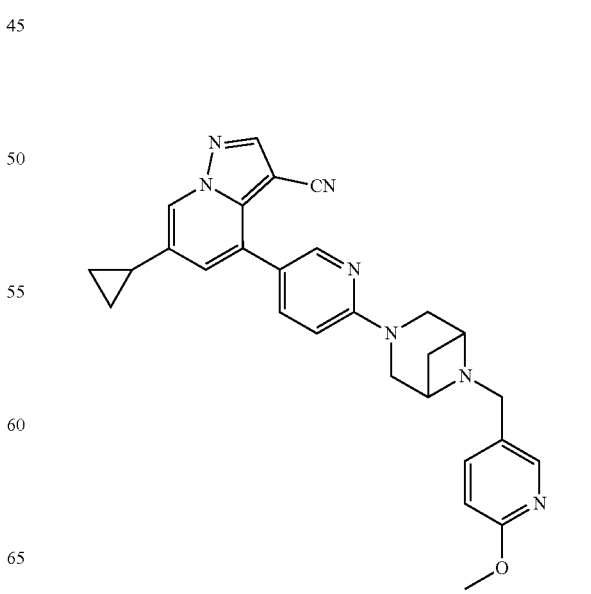

259
-continued
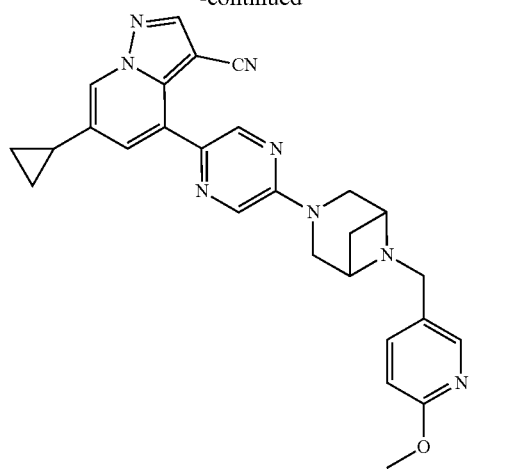
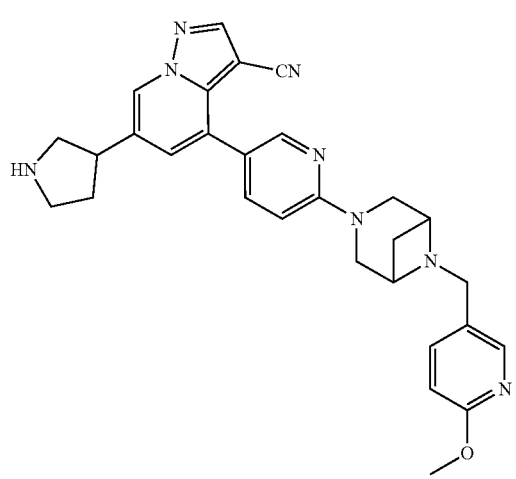
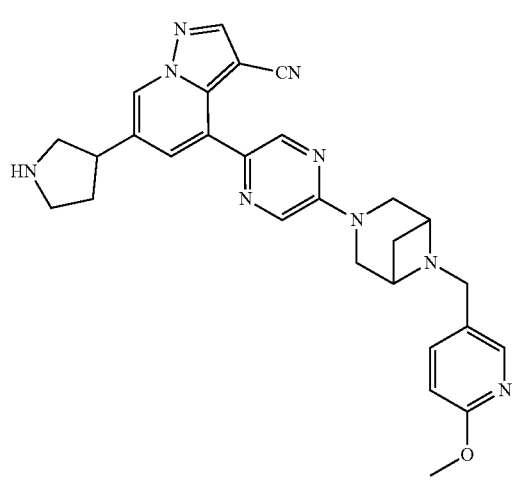
260
-continued
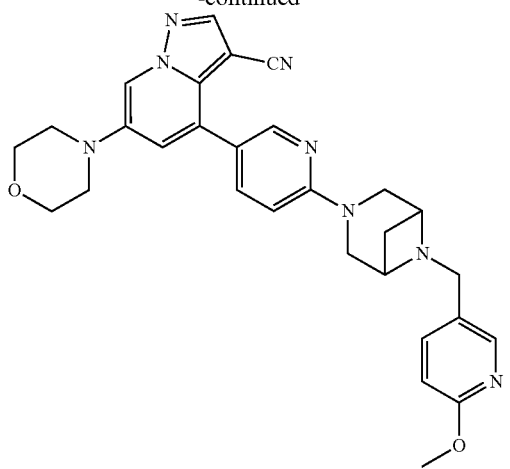
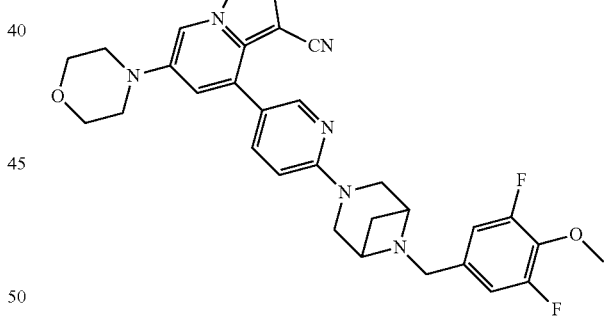
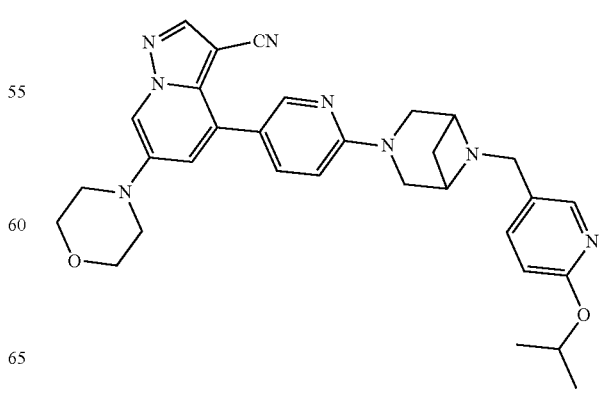

261
-continued
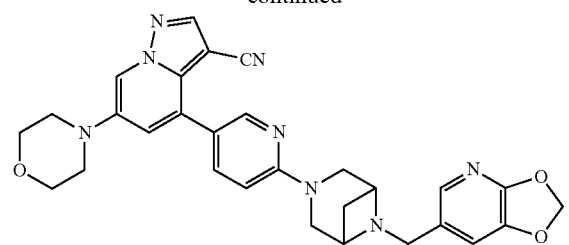
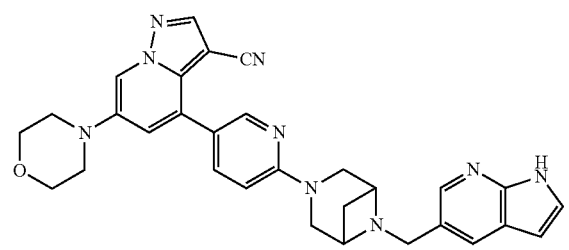
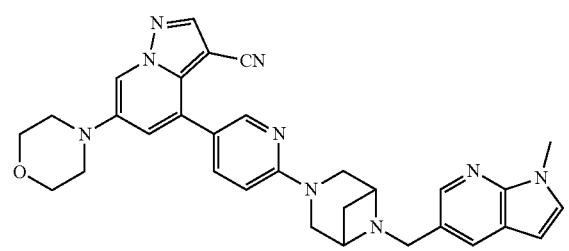
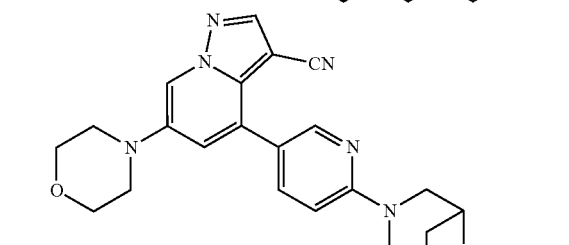
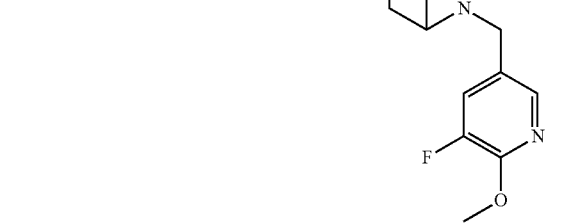
262
-continued
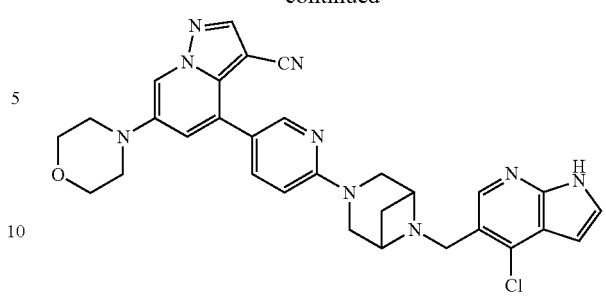
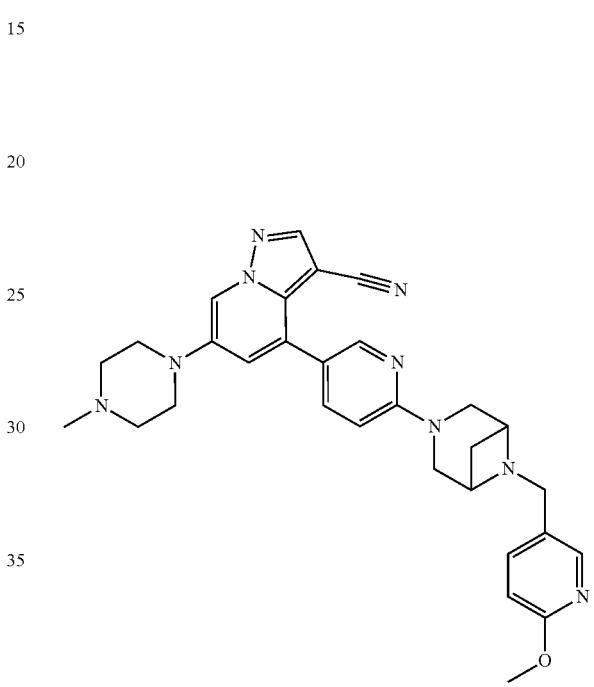
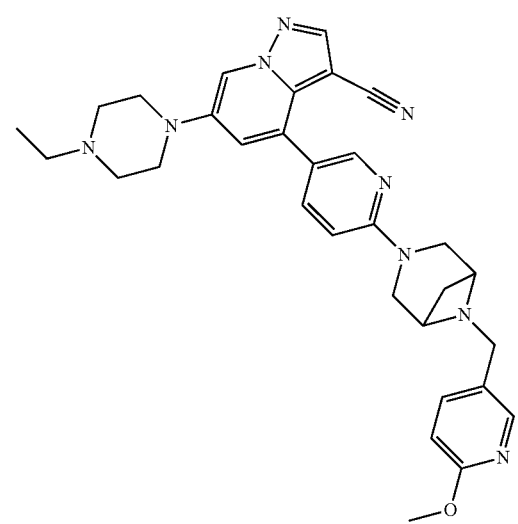

263
-continued
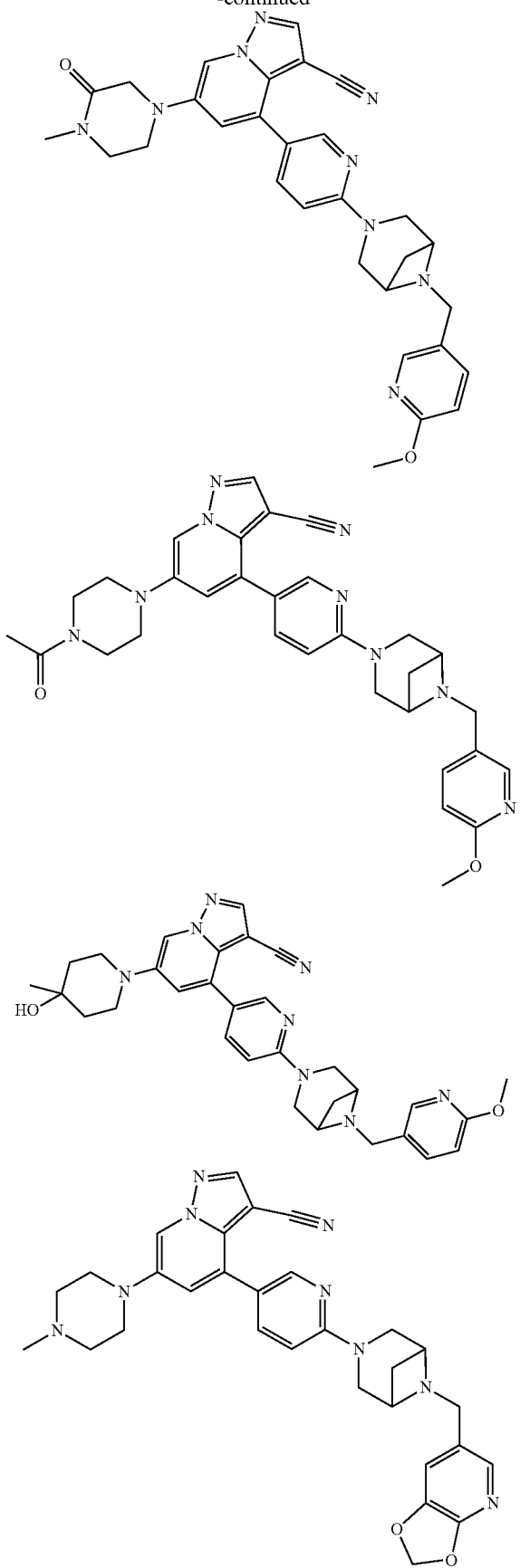
264
-continued
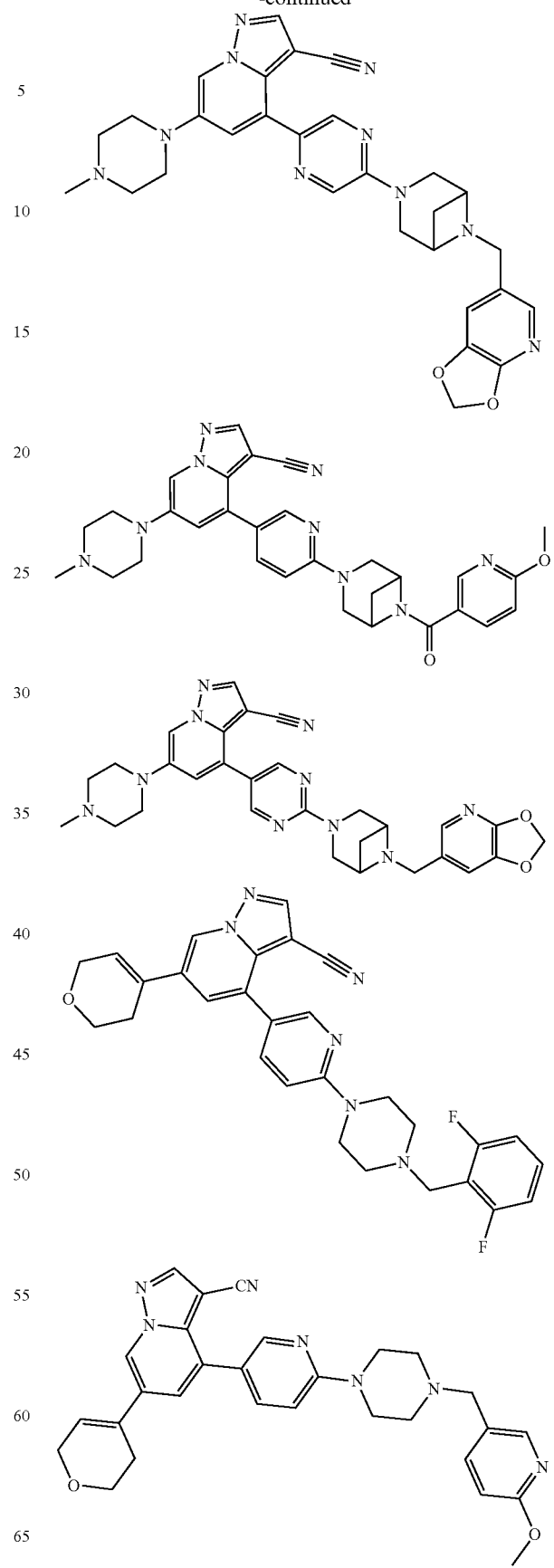

265
-continued
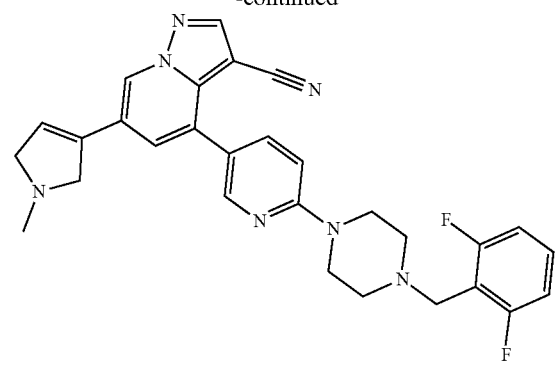
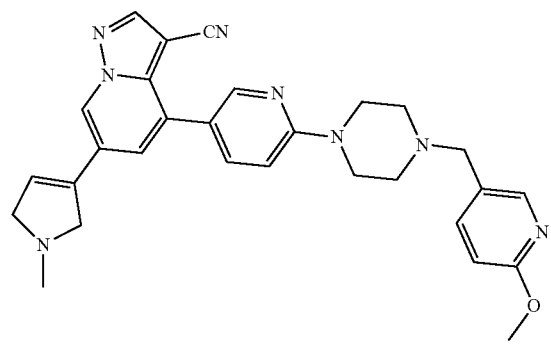
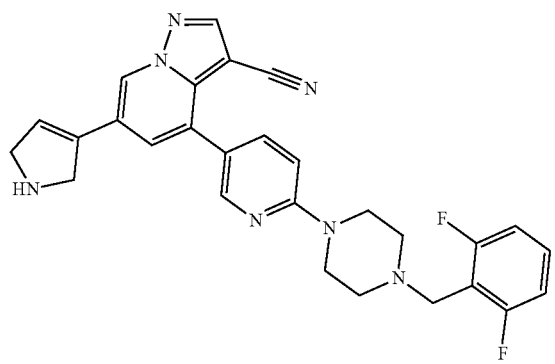
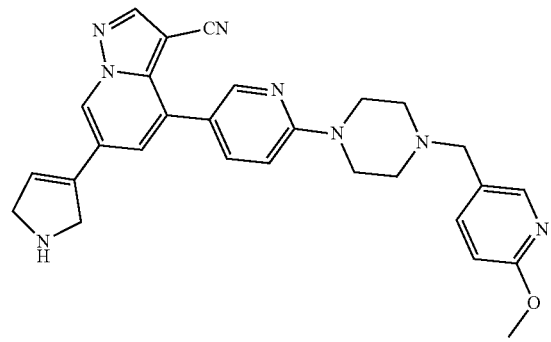
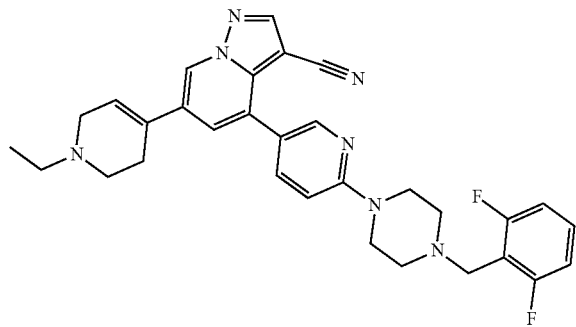
266
-continued
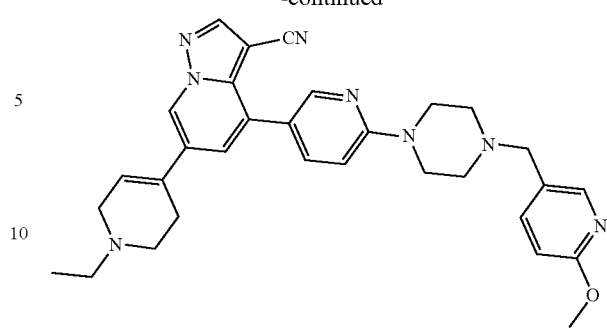
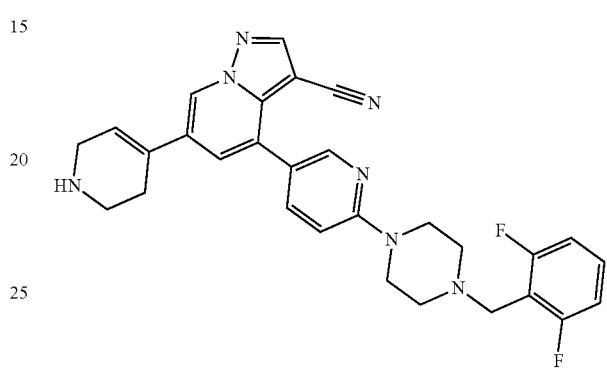
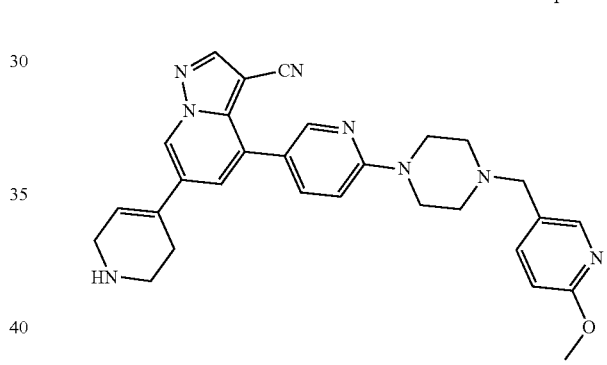
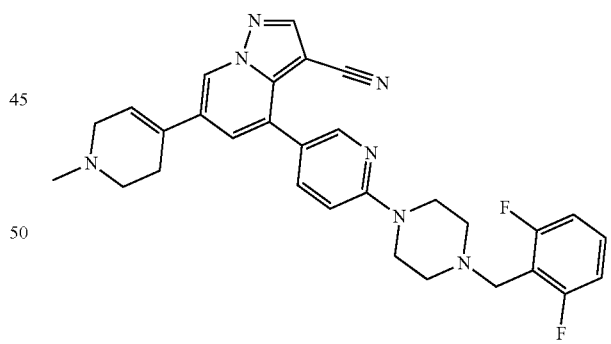
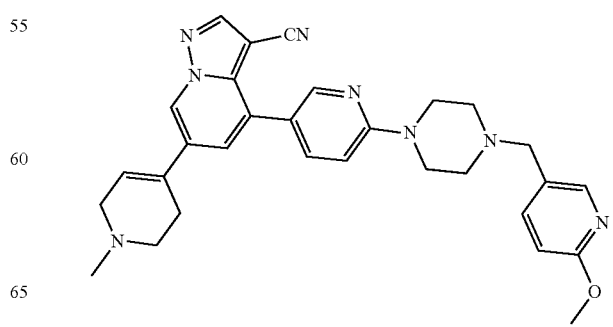

267
-continued
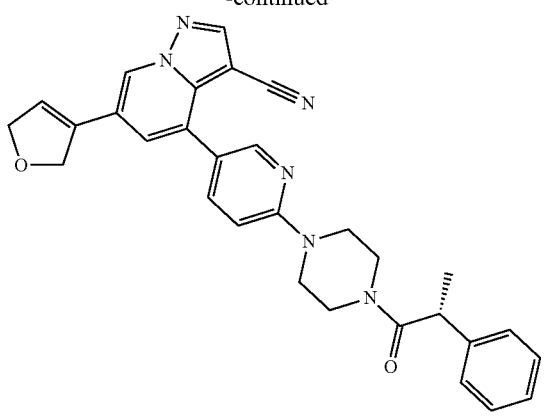
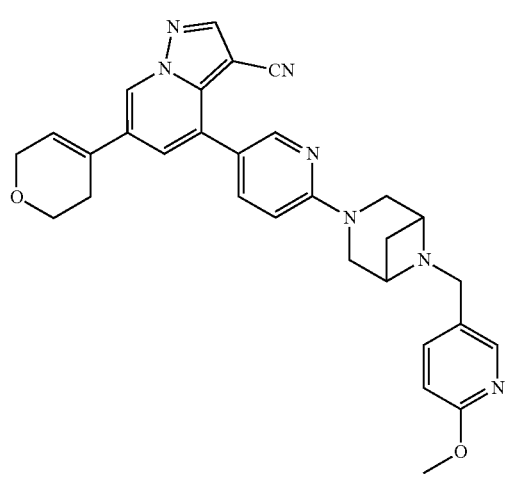
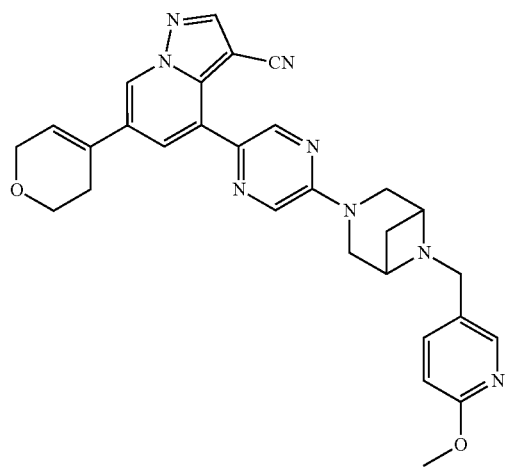
268
-continued
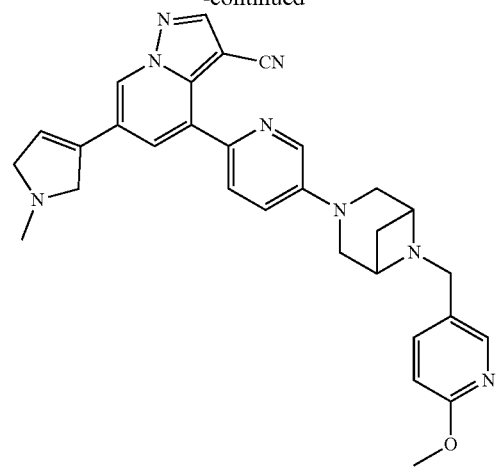
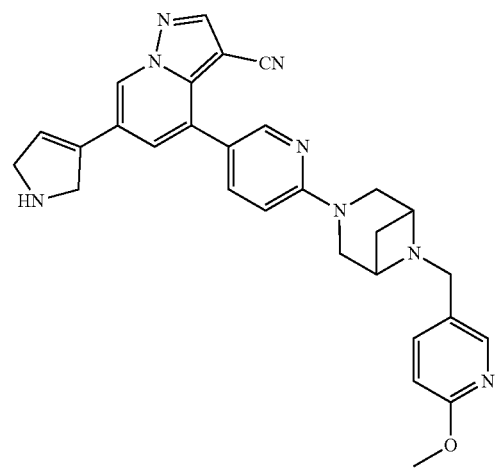

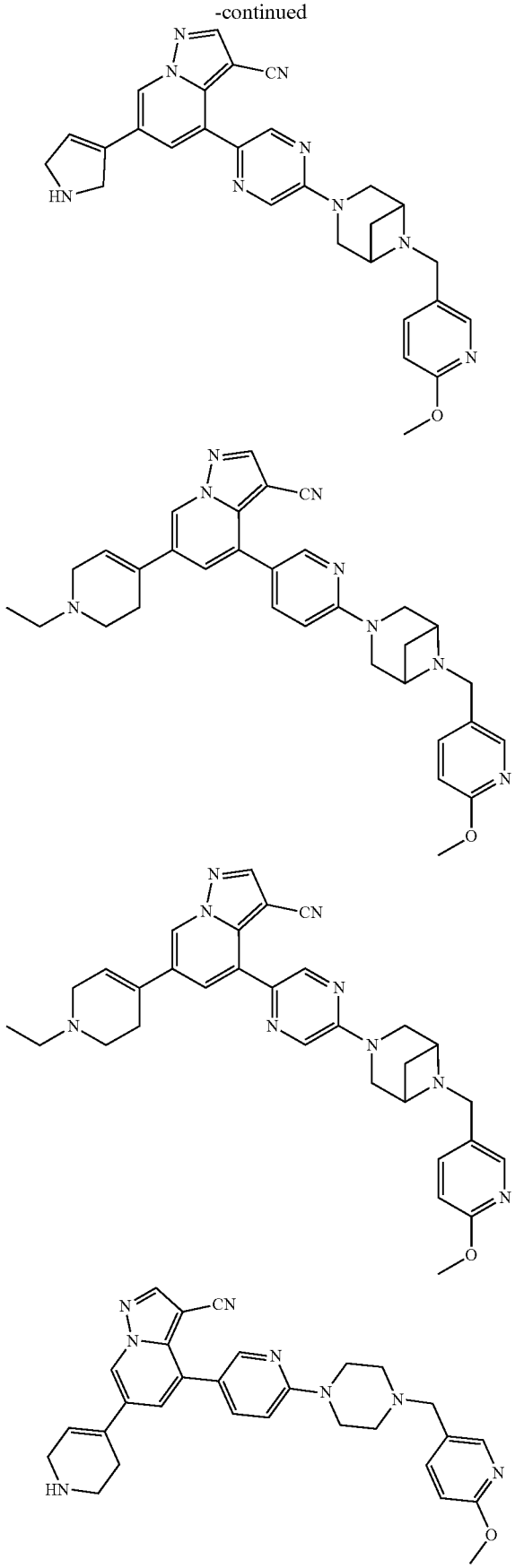
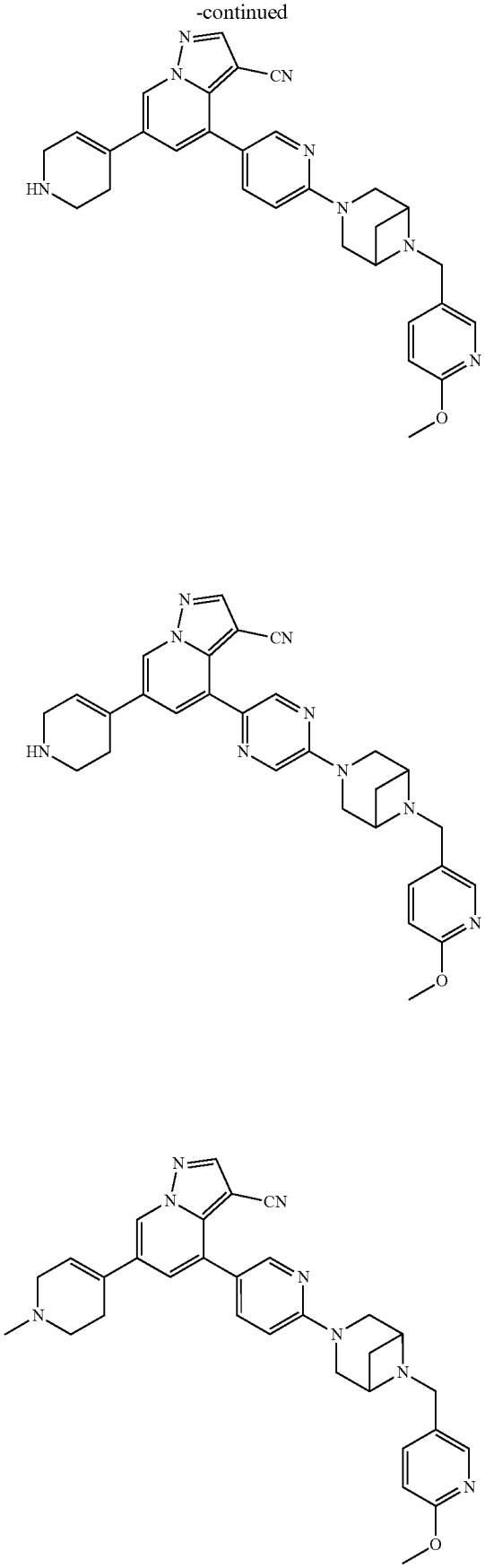

271
-continued
272
-continued
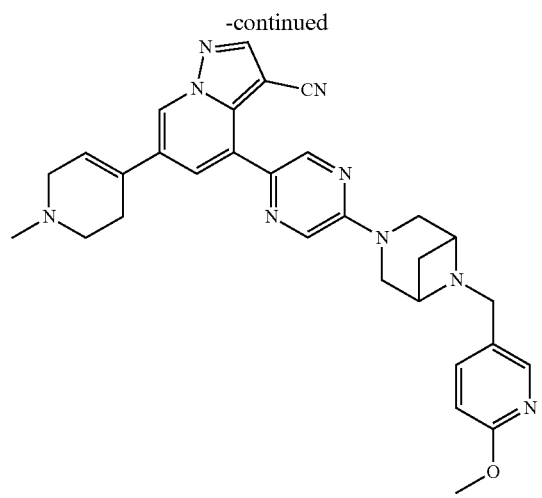
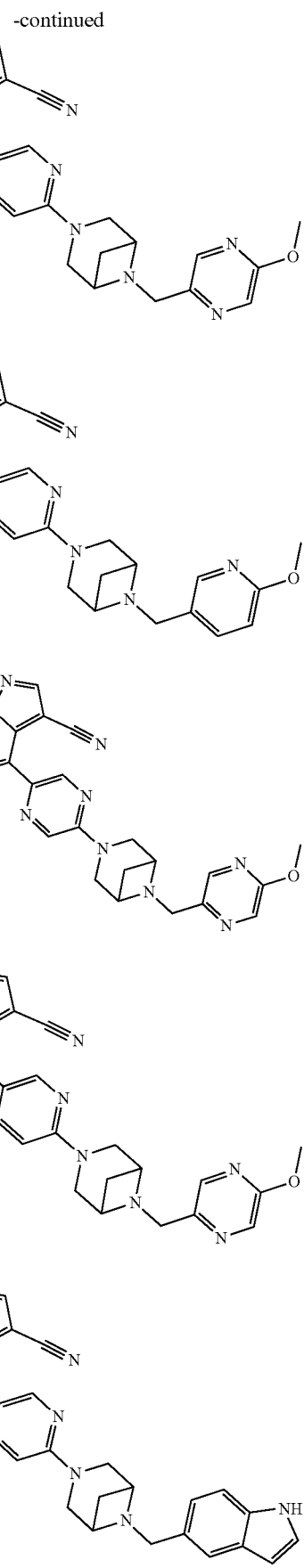

273
-continued
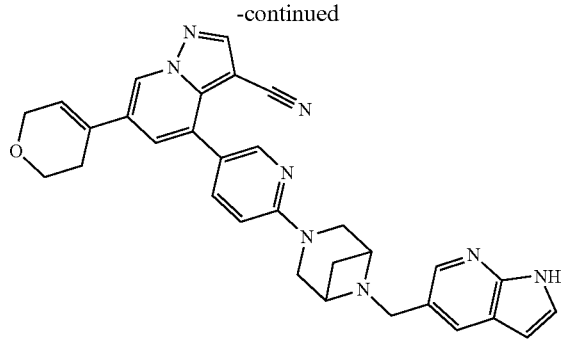
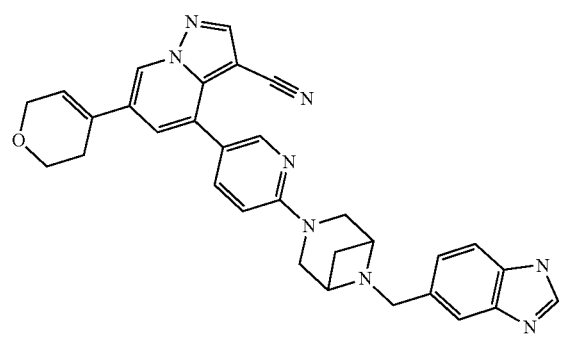
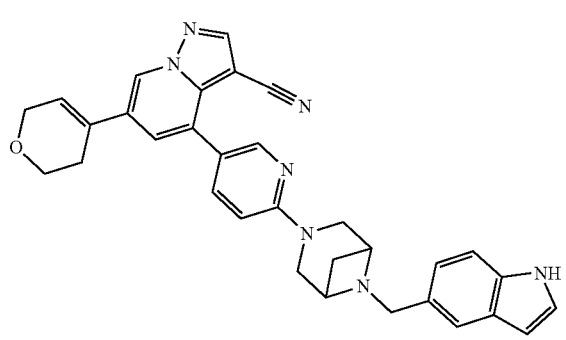
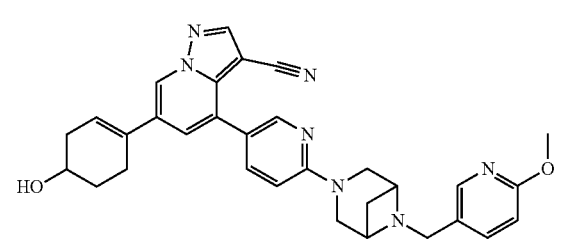
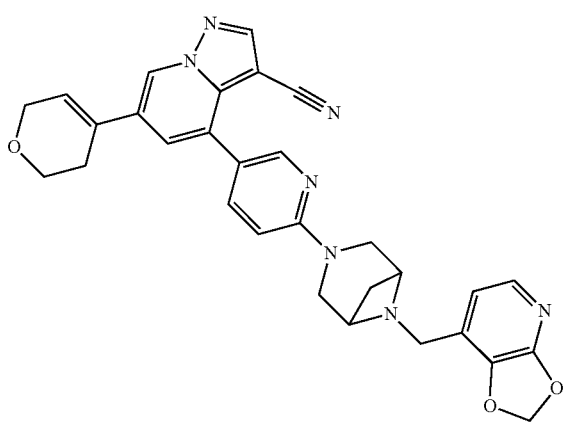
274
-continued
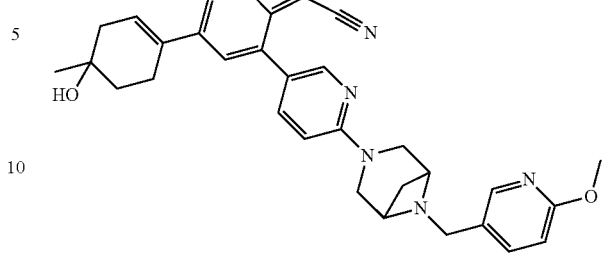
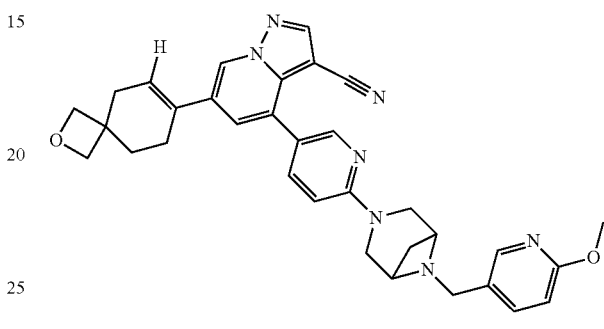
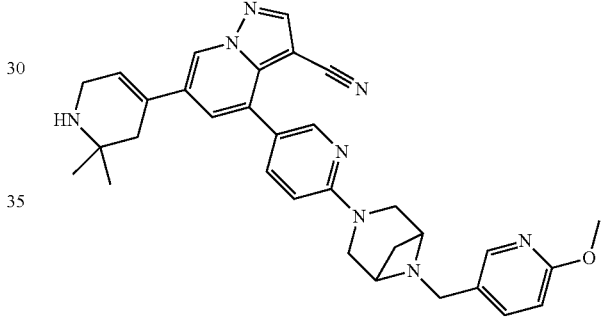
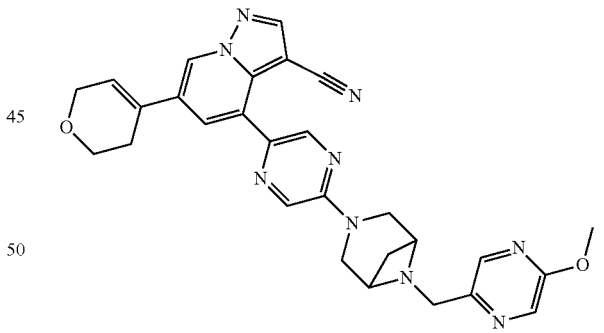
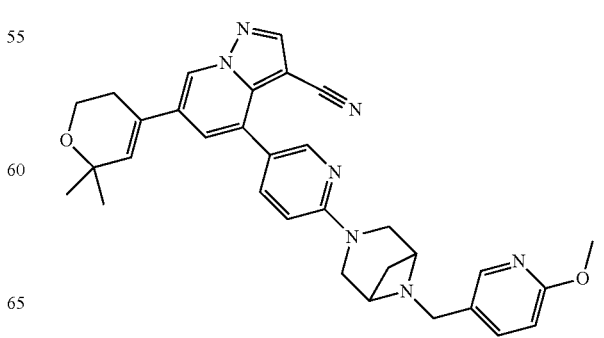

275
-continued
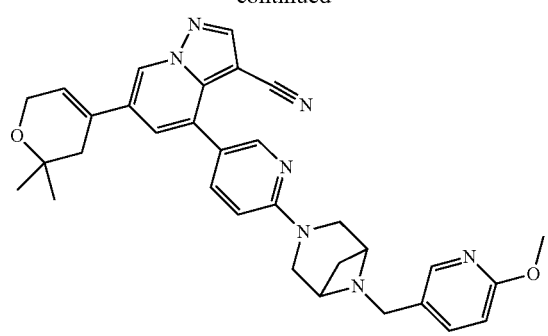
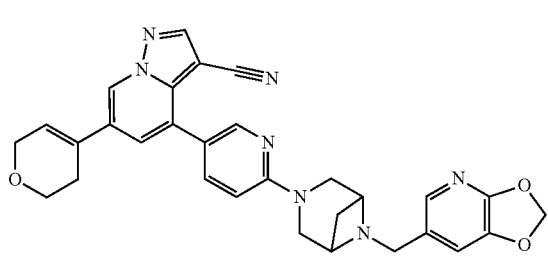
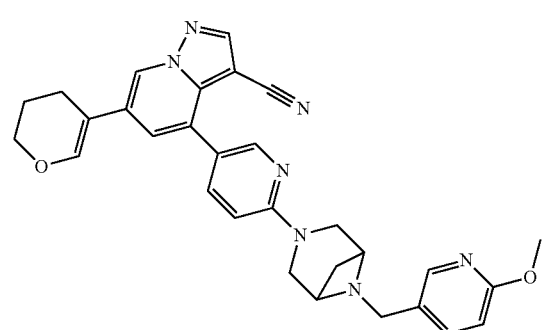
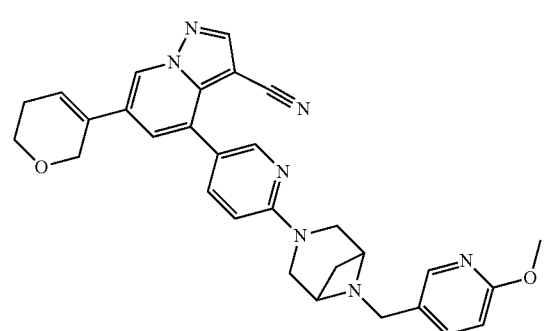
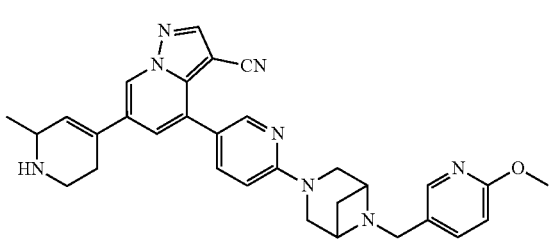
276
-continued
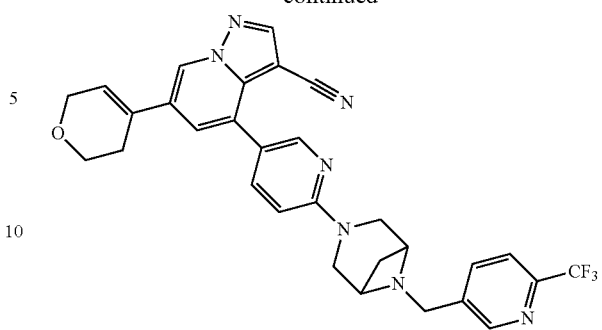
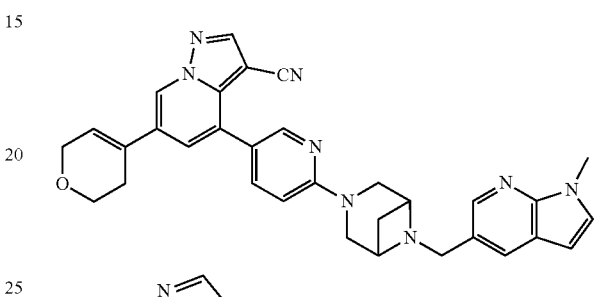
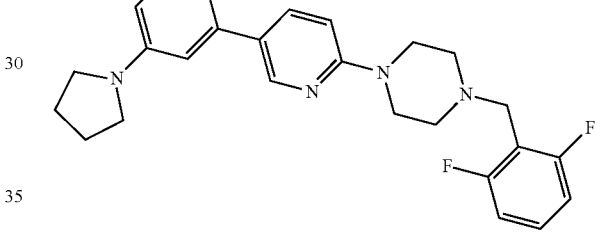
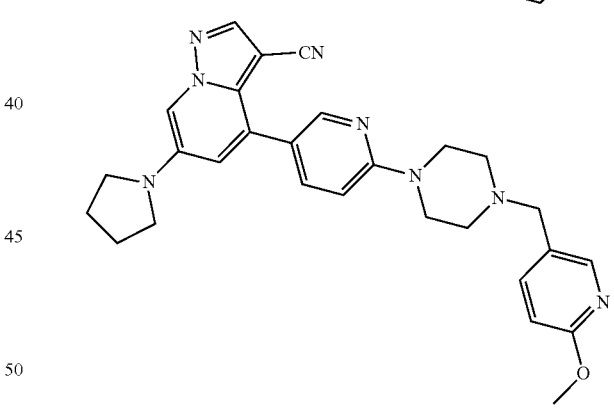
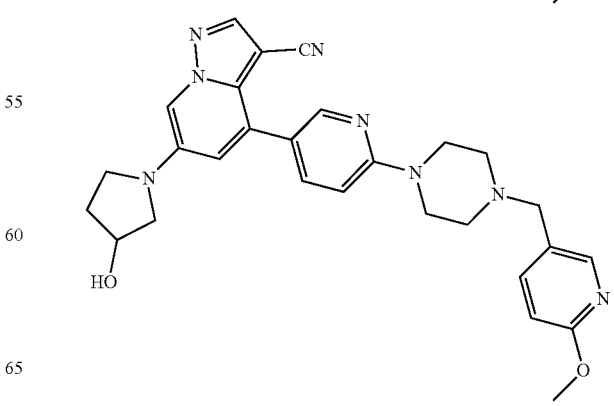

277
-continued
278
-continued
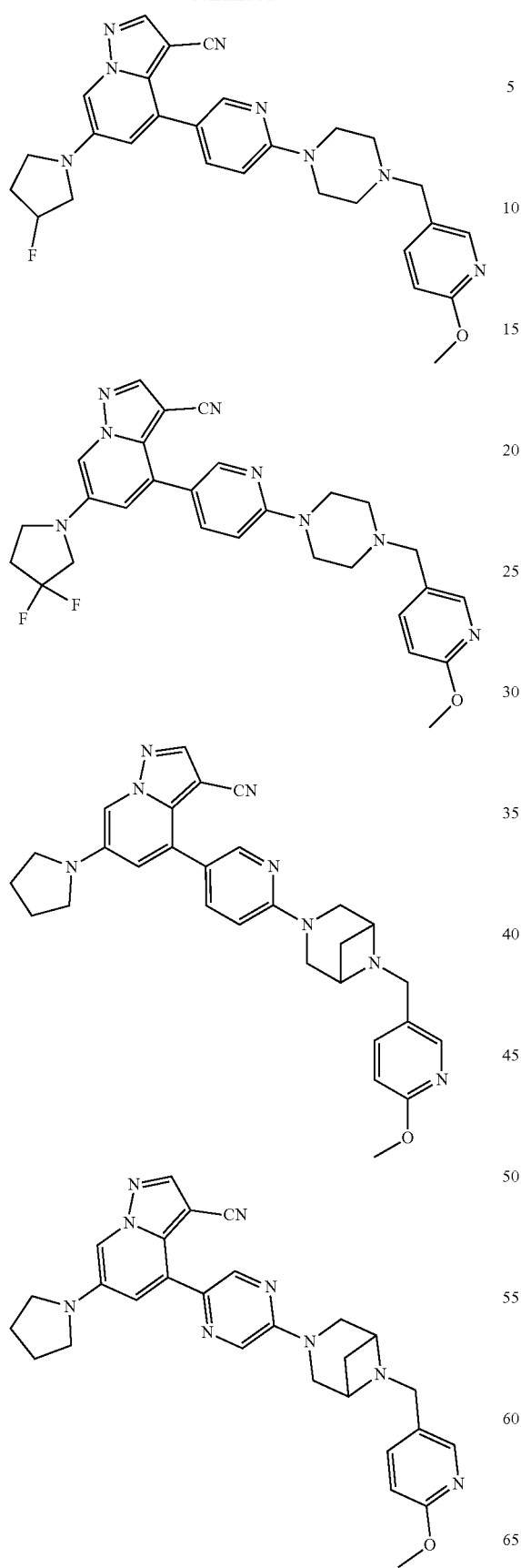
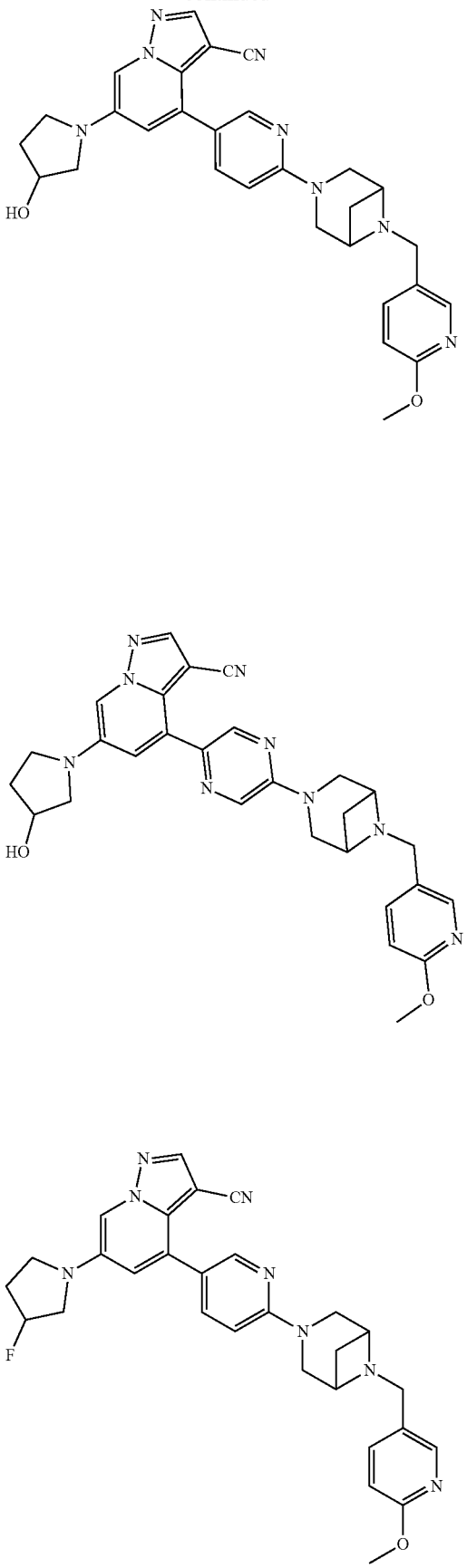

-continued
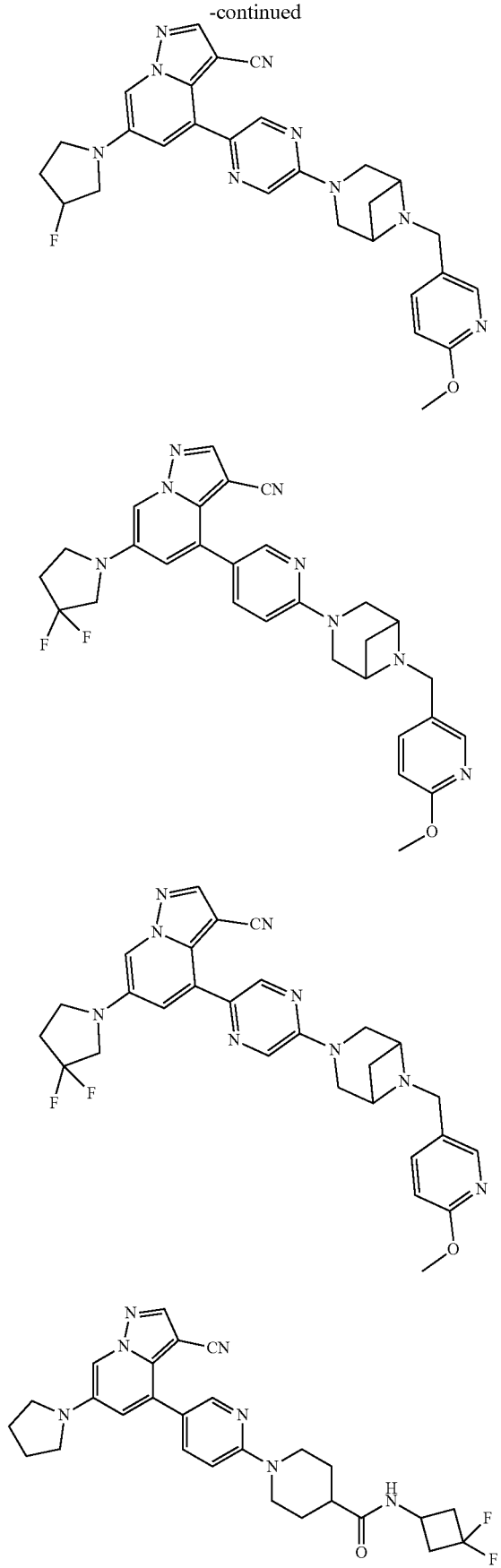
-continued
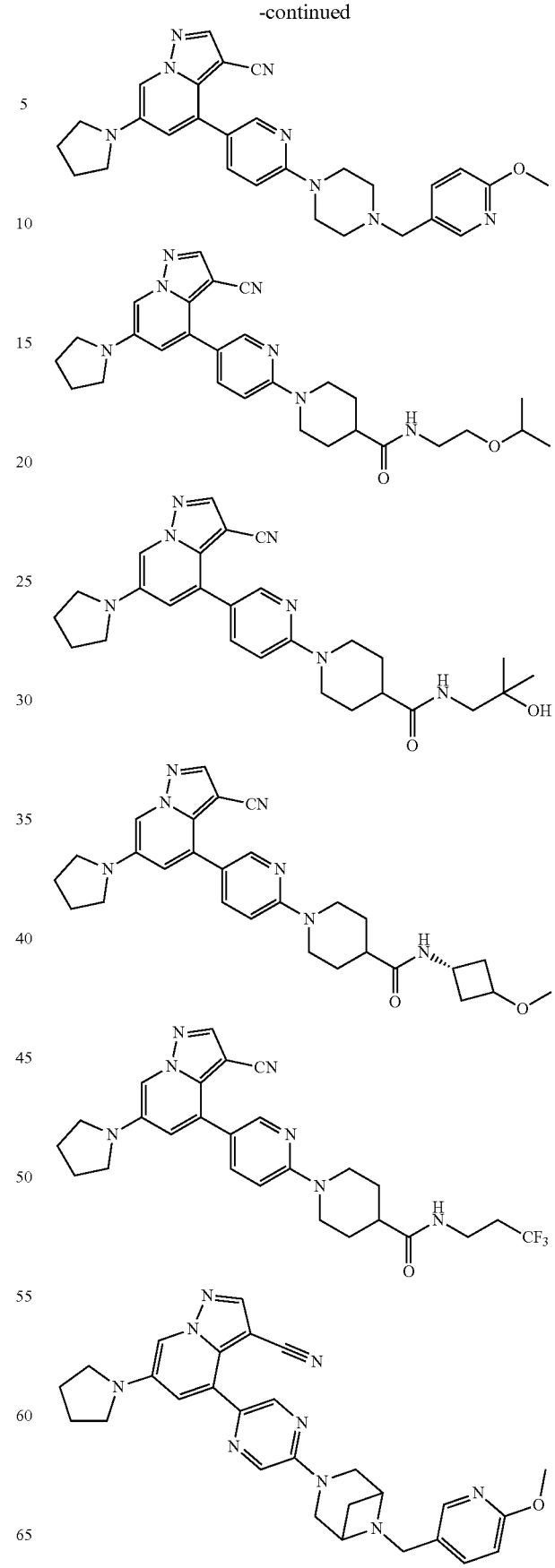

281
-continued
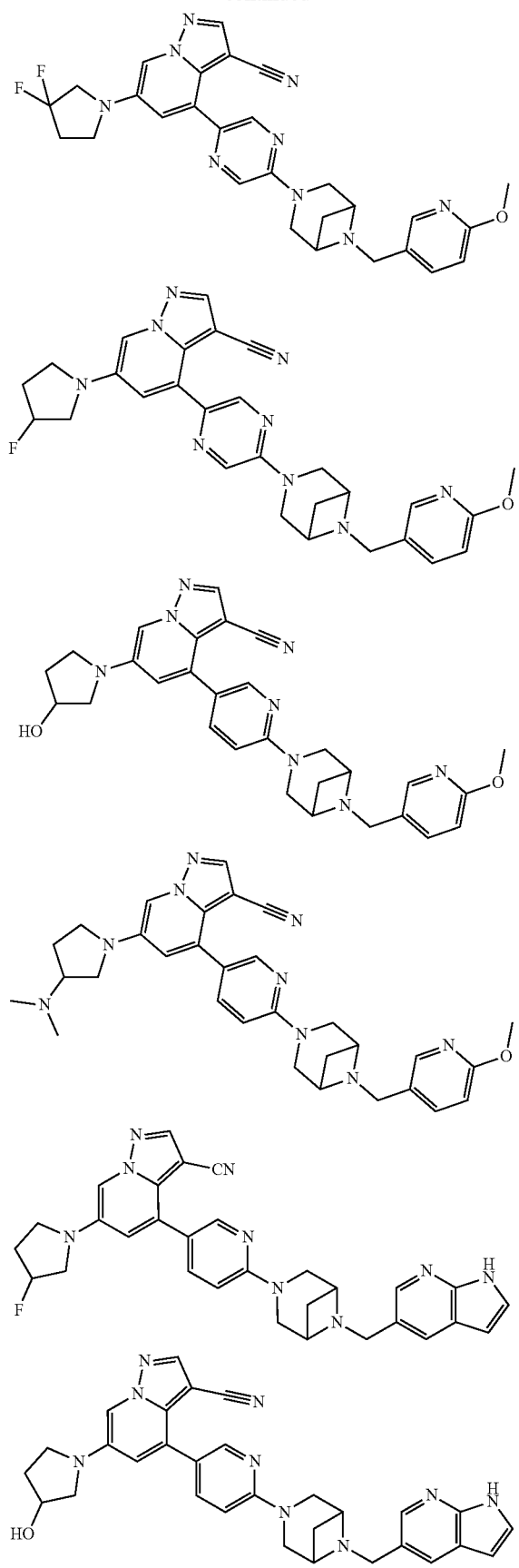
282
-continued
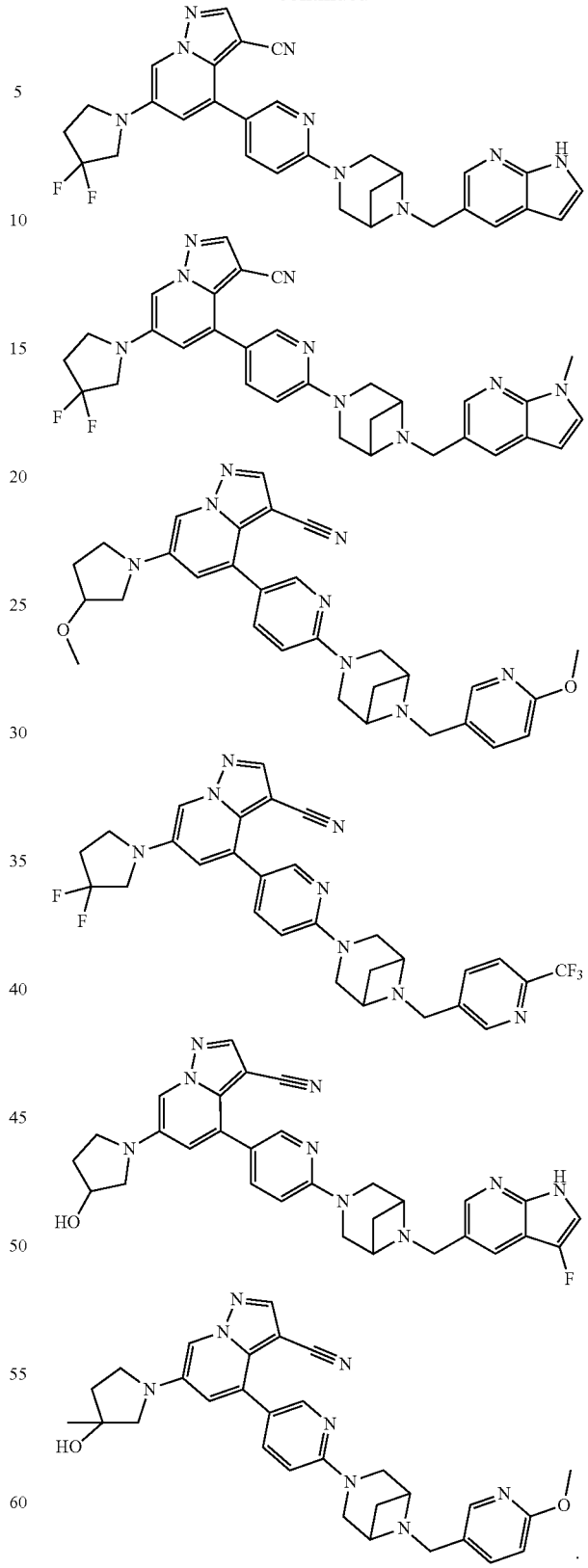
18. The compound or the pharmaceutically acceptable salt thereof according to claim 17, which is selected from the group consisting of:

283
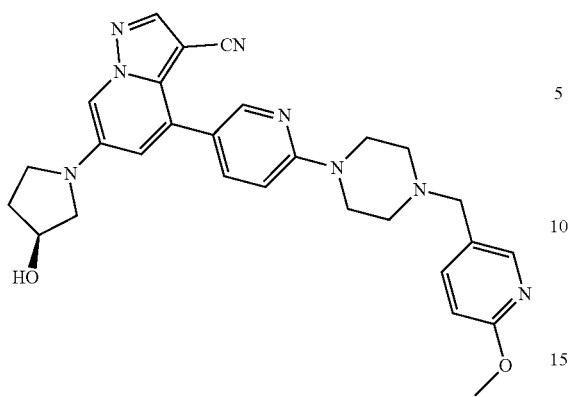
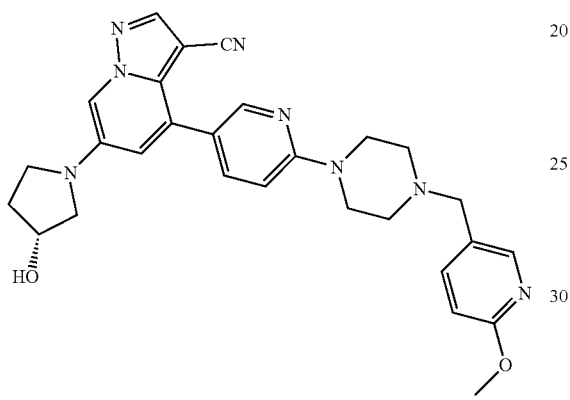
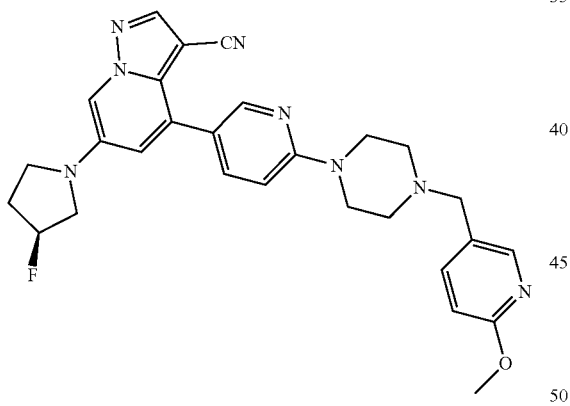
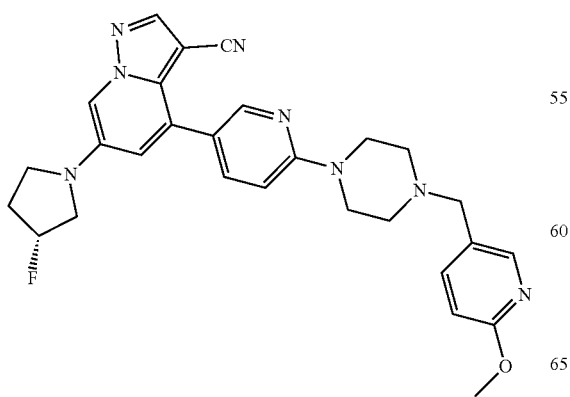
284
-continued
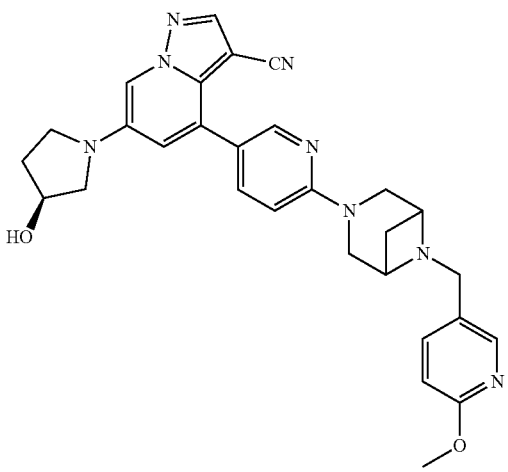
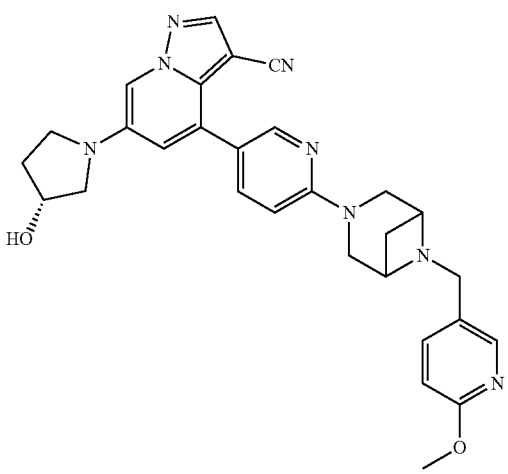
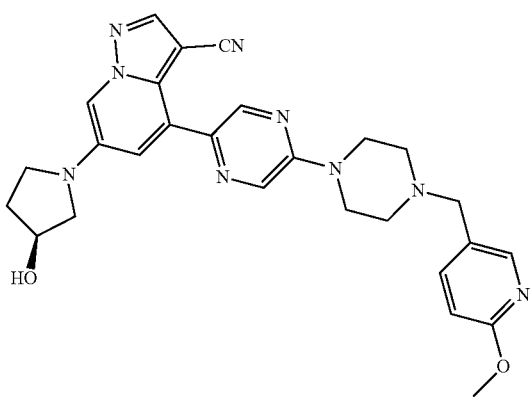

285
-continued
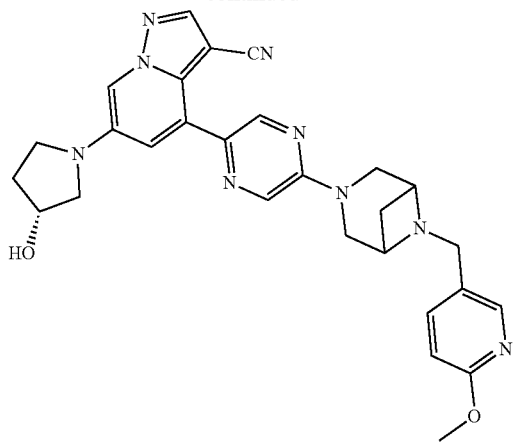
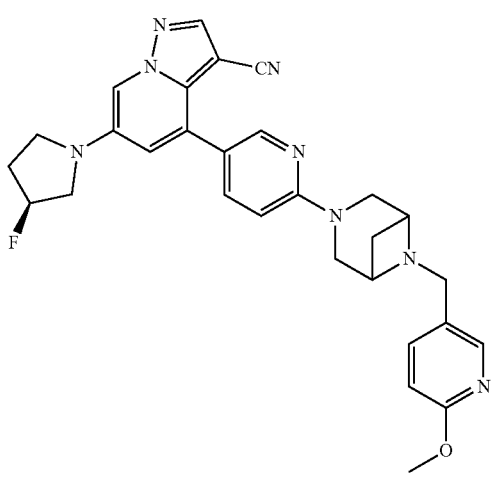
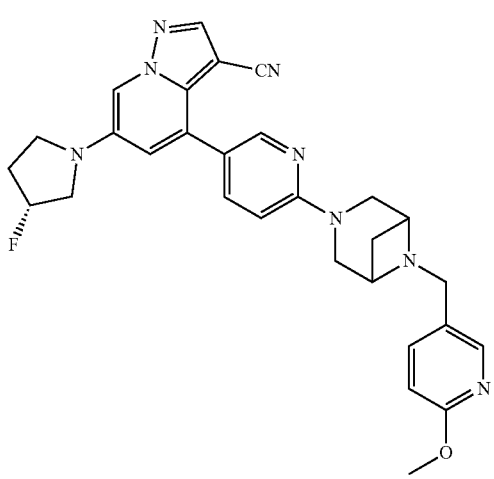
286
-continued
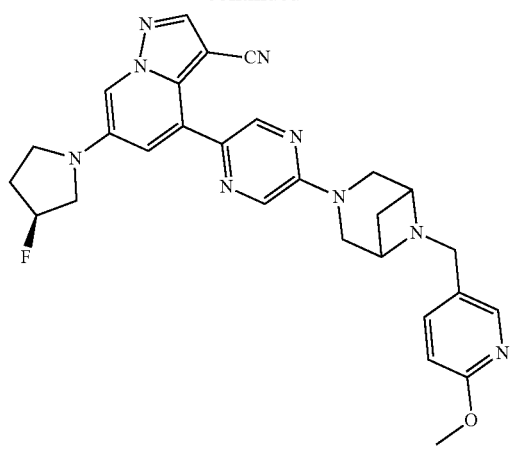
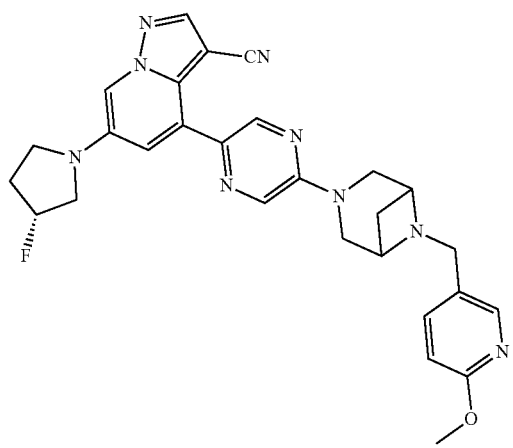
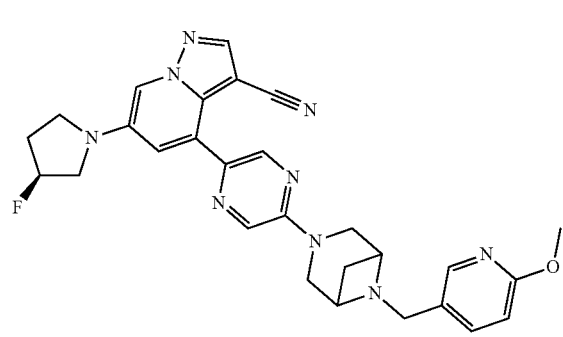
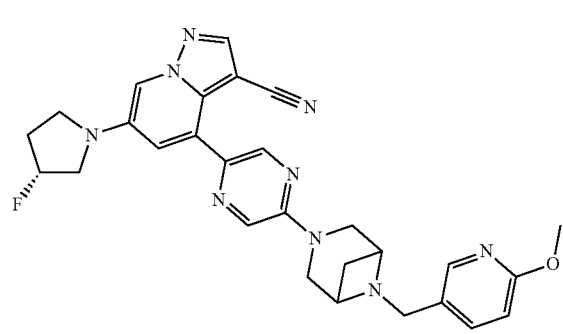

287
-continued
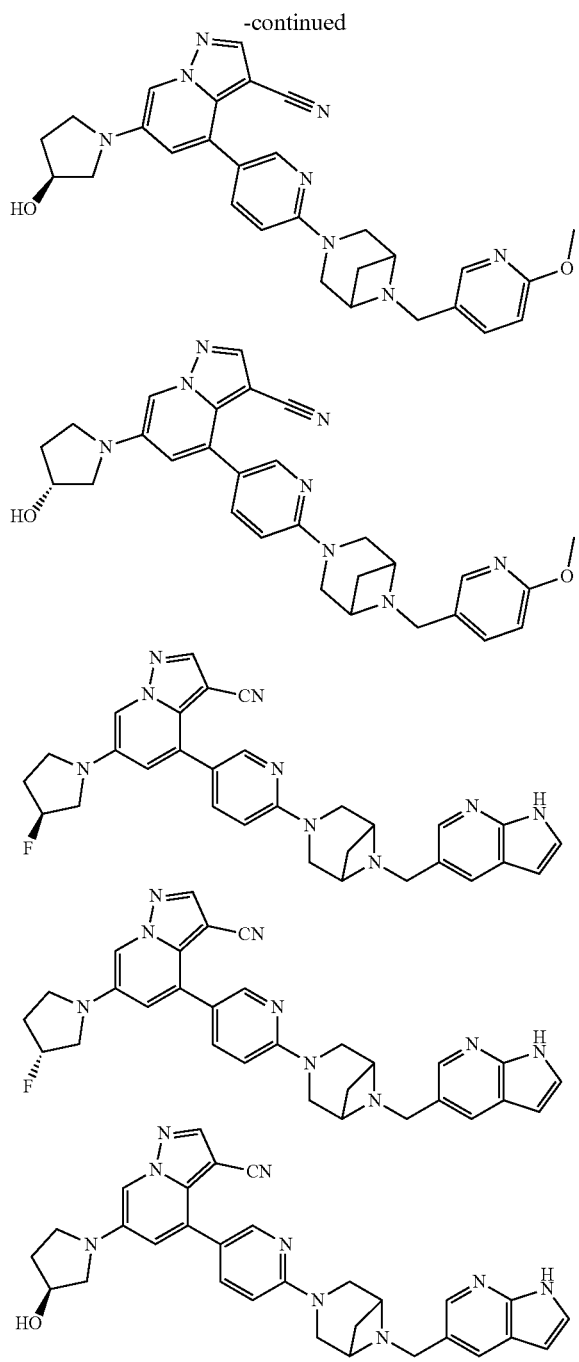
288
-continued
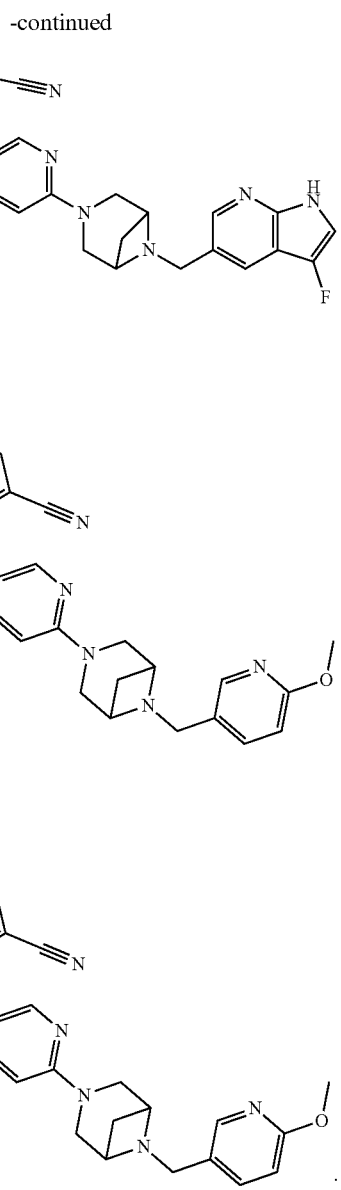
19. A pharmaceutical composition comprising a therapeutically effective amount of the compound or the pharmaceutically acceptable salt thereof according to claim 1 and a pharmaceutically acceptable carrier.
* * * * *